United States Patent
Viguie et al.

(10) Patent No.: US 9,389,233 B2
(45) Date of Patent: Jul. 12, 2016

(54) TET2 AS A DIAGNOSTIC AND PRONOSTIC MARKER IN HEMATOPOIETIC NEOPLASMS

(75) Inventors: Franck Viguie, Deuil la Barre (FR); Olivier Bernard, Vanves (FR); Michaela Fontenay, Paris (FR); Christian Bastard, Ardouval (FR); Francois Delhommeau, Antony (FR); William Vainchenker, Paris (FR)

(73) Assignees: Institute National de la Sante et de la Recherche Medicale (Inserm), Paris (FR); Institut Gustave-Roussy, Villejuif (FR); Assistance Publique-Hopitaux de Paris, Paris (FR); Centre Henri Becquerel, Rouen (FR); Universite Paris Descartes, Paris (FR); Universite Pierre et Marie Curie (PARIS 6), Paris (FR); Universite Paris-Sud, Orsay (FR)

( * ) Notice: Subject to any disclaimer, the term of this patent is extended or adjusted under 35 U.S.C. 154(b) by 692 days.

(21) Appl. No.: 12/997,203

(22) PCT Filed: Jun. 12, 2009

(86) PCT No.: PCT/EP2009/057295
§ 371 (c)(1),
(2), (4) Date: Dec. 9, 2010

(87) PCT Pub. No.: WO2009/150229
PCT Pub. Date: Dec. 17, 2009

(65) Prior Publication Data
US 2011/0263523 A1 Oct. 27, 2011

(30) Foreign Application Priority Data
Jun. 12, 2008 (EP) .................................... 08305255
Mar. 13, 2009 (EP) .................................... 09155169

(51) Int. Cl.
C12Q 1/68 (2006.01)
G01N 33/574 (2006.01)

(52) U.S. Cl.
CPC ........ G01N 33/57426 (2013.01); C12Q 1/6886 (2013.01); C12Q 2600/106 (2013.01); C12Q 2600/118 (2013.01); C12Q 2600/154 (2013.01);
(Continued)

(58) Field of Classification Search
None
See application file for complete search history.

(56) References Cited

U.S. PATENT DOCUMENTS

| 4,683,202 A | 7/1987 | Mullis |
| 5,854,033 A | 12/1998 | Lizardi |

(Continued)

OTHER PUBLICATIONS

NCBI dbSNP entry for submission ss81446742 of cluster rs949681, Build 129, Apr. 2008 (9 pages).*

(Continued)

*Primary Examiner* — Diana B Johannsen
(74) *Attorney, Agent, or Firm* — Foley & Lardner LLP

(57) ABSTRACT

The present invention concerns an in vitro method for diagnosing a myeloid tumor or a lymphoid tumor in a subject, which comprises the step of analyzing a biological sample from said subject by (i) detecting the presence of a mutation in the Ten Eleven Translocation protein family member 2 gene (TET2) coding for the polypeptide having the sequence SEQ ID NO:2, and/or (ii) analyzing the expression of the TET2 gene; wherein the detection of such a TET2 mutation, of the absence of expression of TET2 or of the expression of a truncated TET2 is indicative of a subject developing or predisposed to develop a myeloid tumor or a lymphoid tumor.

10 Claims, 10 Drawing Sheets

(52) U.S. Cl.
CPC ...... *C12Q 2600/156* (2013.01); *C12Q 2600/16* (2013.01)

(56) References Cited

U.S. PATENT DOCUMENTS

2007/0059717 A1* 3/2007 Pascual et al. .................. 435/6
2012/0302517 A1* 11/2012 Viguie et al. .................. 514/43

OTHER PUBLICATIONS

Langemeijer, S.M.C. et al. Nature Genetics 41(7):838 (Jul. 2009; published online May 31, 2009).*
Tefferi, A. et al. Leukemia 23:905 (Mar. 5, 2009).*
Tefferi, A. et al. Leukemia 23:1345 (Mar. 19, 2009).*
Thomas, X. et al. Expert Opin. Drug Discov. 4(2):195 (Feb. 2009).*
International Search Report issued in application No. PCT/EP2009/057295 on Oct. 5, 2009.
Barany, Genetic disease detection and DNA amplification using cloned thermostable ligase, Proc. Natl. Acad. Sci. USA, Jan. 1991, vol. 88, pp. 189-193.
Baxter et al., "Acquired mutation of the tyrosine kinase JAK2 in human myeloproliferative disorders" Lancet, Mar. 2005, vol. 365, pp. 1054-1061.
Bellanné-Chantelot et al., "Genetic and clinical implications of the Val617Phe *JAK2* mutation in 72 families with myeloproliferative disorders," Blood, 2006, vol. 108, No. 1, pp. 346-352.
Braun et al., "NF-kB constitutes a potential therapeutic target in high-risk myelodysplastic syndrome," Blood, 2006, vol. 107(3), pp. 1156-1165.
Campbell et al., "The Myeloproliferactive Disorders," N. Engl. J. Med., 2006, vol. 355(23), pp. 2452-2466.
Chaligne et al., "New mutations of MPL in primitive myelofibrosis: only the MPL W515 mutations promote a $G_1$/S-phase transition," Leukemia, 2008, vol. 22, pp. 1557-1566.
Charbonnier et al., "Detection of Exon Deletions and Duplications of the Mismatch Repair Genes in Hereditary Nonpolyposis Colorectal Cancer Families Using Multiplex Polymerase Chain Reaction of Short Fluorescent Fragments," Cancer Res., Jun. 2000, vol. 60, pp. 2760-2763.
Claessens et al., "In vitro proliferation and differentiation of erythroid progenitors from patients with myelodysplastic syndromes: evidence for Fas-dependent apoptosis," Blood, Mar. 2002, vol. 99, No. 5, pp. 1594-1601.
Clasessens et al., "Rescue of early-stage myelodysplastic syndrome-deriving erythroid precursors by the ectopic expression of a dominant-negative form of FADD," *Blood*, May 2005, vol. 105, No. 10, pp. 4035-4042.
Cole et al., "The EBV-Hybridoma Technique and its Application to Human Lung Cancer," Monoclonal Antibodies and Cancer Therapy, Alan R. Liss, Inc., 1985, pp. 77-96.
Daser A, et al., "The versatile mixed lineage leukaemia gene *MLL* and its many associations in leukaemogenesis", Seminars Cancer Biol., 2005, vol. 15(3), pp. 175-188.
Database Genbank [Online], Apr. 2, 1996, XP002502623 (2 pages), Acc. No. G195650.
Database Uniprot [online], Jun. 10, 2008, XP002502624, Database Accession No. Q6N021, http://www.uniprot.org:uniprot.q6n021.txt? (4 pages).
Database Uniprot [online], Jun. 10, 2008, XP002502625, Database Accession No. Q8NFU7, http://www.uniprot.org:uniprot.q8nfu7.txt? (3 pages).
Database UniProt [Online], Jun. 10, 2008, XP002502625, Database Accession No. Q8NFU7 <URL: http://www.uniprot.org:uniprot.Q8NFU7.txt?> (3 pages).
Delhommeau et al., "LBA-3 TET2 is Novel Tumor Suppressor Gene Inactivated in Myeloproliferative Neoplasm: Identification of a Pre-JAK2 V617F event", Annu Meet Abstr, 2008 (2 pages).
Delhommeau et al., "Oncogenic mechanisms in myeloproliferative disorders," Cell Mol. Life Sci., 2006, vol. 63(24), pp. 2939-2953.

Dupont et al., "The *JAK2* 617V>F mutation triggers erythropoietin hypersensitivity and terminal erythroid amplification in primary cells from patients with polycythemia vera," Blood, Aug. 2007, vol. 110(3), pp. 1013-1021.
Ebert et al., "Identification of *RPS14* as a 5q⁻ syndrome gene by RNA interference screen," Nature, Jan. 2008, vol. 451, No. 17, pp. 335-339.
Fenaux et al., "A multicenter phase 2 study of the farnesyltransferase inhibitor tipifarnib in intermediate-to high-risk myelodysplastic syndrome," Blood, May 2007, vol. 109, No. 10, pp. 4158-4163.
Finazzi et al., "Essential Thrombocythemia," Semin. Hematol., 2005, vol. 42, pp. 230-238.
Gilbert H.S., "Familial Myeloproliferative disease," *Baillieres Clin. Haematol.*, Dec. 1998, vol. 11, No. 4, pp. 849-858.
Guatelli et al., "Isothermal, in vitro amplification of nucleic acids by a multienzyme reaction modeled after retroviral replication," Proc. Natl. Acad. Sci. USA, Mar. 1990, vol. 87, pp. 1874-1878.
Haase D., "Cytogenetic features in myelodysplastic syndromes," Annals of Hematology, 2008, vol. 87, No. 7, pp. 515-526.
Harper, et al., "Chromosomal Rearrangements Leading to MLL Gene Fusions: Clinical and Biological Aspects," Cancer Res, Dec. 2008, vol. 68(24), pp. 10024-10027.
Itzykson et al., "Optimal sequencing of treatments for patients with myelodysplastic syndromes," Current Opinion in Hematology, 2009, vol. 16, pp. 77-83.
Jabbour et al., "Evolution of Decitabine Development: Accomplishments, Ongoing Investigations, and Future Strategies," Cancer, Jun. 2008, vol. 112, No. 11, pp. 2341-2351.
James et al., "The hematopoietic stem cell compartment of JAK2V617F-positive myeloproliferative disorders is a reflection of disease heterogeneity," Blood, Sep. 2008, vol. 112, No. 6, pp. 2429-2438.
James et al., "A unique clonal *JAK2* mutation leading to constitutive signalling causes polycythaemia vera," Nature, Apr. 2005, vol. 434, pp. 1144-1148.
Kiladjian et al., "Pegylated interferon-alfa-2a induces complete hematologic and molecular responses with low toxicity in polycythemia vera," Blood, Oct. 2008, vol. 112, No. 8, pp. 3065-3072.
Köhler et al., "Continuous cultures of fused cells secreting antibody of predefined specificity," Nature, Aug. 1975, vol. 256, pp. 495-497.
Kojima et al., "FLJ10849, a septin family gene, fuses *MLL* in a novel leukemia cell line CNLBC1 derived from chronic neutrophilic leukemia in transformation with t(4;11)(q21;q23)," Leukemia, 2004, vol. 18, No. 5, pp. 998-1005.
Kozbor et al., "The production of monoclonal antibodies from human lymphocytes," Immunol. Today, 1983, vol. 4, No. 3, pp. 72-79.
Kralovics et al., "A Gain-of-Function Mutation of *JAK2* in Myeloproliferative Disorders," N. Engl. J. Med., Apr. 2005, vol. 352, pp. 1779-1790.
Kralovics et al., "Clonal hematopoiesis in familial polycythemia vera suggests the involvement of multiple mutational events in the early pathogenesis of the disease," Blood, Nov. 2003, vol. 102, No. 10, pp. 3793-3796.
Kuendgen et al., "Current status of epigenetic treatment in myelodysplastic syndromes," Ann. Hematol., vol. 87, pp. 601-611, 2008.
Kwoh et al., "Transcription-based amplification system and detection of amplified human immunodeficiency virus type 1 with a bead-based sandwich hybridization format," Proc. Natl. Acad. Sci. USA, Feb. 1989, vol. 86, pp. 1173-1177.
Levine et al., "The JAK2V617F activating mutation occurs in chronic myelomonocytic leukemia and acute myeloid leukemia, but not in acute lymphoblastic leukemia or chronic lymphocytic leukemia," Blood, Nov. 2005, vol. 106, No. 10, pp. 3377-3379.
Lizardi et al., "Exponential Amplification of Recombinant-RNA Hybridization Probes," Bio/Technology, Oct. 1988, vol. 6, pp. 1197-1202.
Lorsbach et al., "TET1, a Member of a Novel Protein Family, is Fused to MLL in Acute Myeloid Leukemia Containing the t(10;11) (q22;q23)," Leukemia, 2003, vol. 17(3), pp. 637-641.
Morgan et al., "A Role for JAK2 Mutations in Myeloproliferactive Diseases," Annu. Rev. Med., 2008, vol. 59, pp. 213-222.

(56) References Cited

OTHER PUBLICATIONS

Ono et al., "Lcx, Leukemia-associated Protein with a CXXC Domain, Is Fused to *MLL* in Acute Myeloid Leukemia with Trilineage Dysplasia Having t(10;11)(q22;q23)," Cancer Research, Jul. 2002, vol. 62(14), pp. 4075-80.

Passamonti et al., "A dynamic prognostic model to predict survival in post-polycythemia vera myelofibrosis," Blood, Apr. 2008, vol. 111, No. 7, pp. 3383-3387.

Passamonti et al., "Prognostic factors for thrombosis, myelofibrosis, and leukemia in essential thrombocythemia: a study of 605 patients," Haematologica, 2008, vol. 93, No. 11, pp. 1645-1651.

Pikman et al., "*MPLW515L* Is a Novel Somatic Activating Mutation in Myelofibrosis with Myeloid Metaplasia," PLoS Med, Jul. 2006, vol. 3, No. 7 (e270), pp. 1140-1151.

Robert-Richard et al., "Human cell engraftment after busulfan or irradiation conditioning of NOD/SCID mice," Haematologica, The Hematology Journal, 2006, vol. 91(10), pp. 1384-1387.

Rumi et al., "*JAK2* (V617F) As an Acquired Somatic Mutation and a Secondary Genetic Event Associated With Disease Progression in Familial Myeloproliferative Disorders," Cancer, Nov. 2006, vol. 107, No. 9, pp. 2206-2211.

Sheils et al., "Nucleic acid microarray: an overview," Current Diagnostic Pathology, 2003, vol. 9, pp. 155-158.

Tahiliani et al., "Conversion of 5-Methylcytosine to 5-Hydroxymethylcytosine in Mammalian DNA by MLL Partner TET1," NIH Public Access Author Manuscript, Science, available in PMC Jul. 2009, pp. 1-11.

Tefferi et al., "Classification and diagnosis of myeloproliferative neoplasms: The 2008 World Health Organization criteria and point-of-care diagnostic algorithms," Leukemia, 2008, vol. 22, pp. 14-22.

Tiu et al., "Clonality of the stem cell compartment during evolution of myelodysplastic syndromes and other bone marrow failure syndromes," *Leukemia*, 2007, vol. 21, pp. 1648-1657.

"Diagnosis"—The Leukemia & Lymphoma Society, www.lls.org, Jun. 24, 2014, 2 pgs.

"Signs and Symptoms" (acute AML), Someday is today—The Leukemia & Lymphoma Society, www.lls.org, Jun. 24, 2014, 1 pg.

"Signs and Symptoms" (early sign of non-Hodgkin lymphoma)—The Leukemia & Lymphoma Society, (Jun. 24, 2014) 1 pg.

"Signs and Symptoms" (no MDS symptoms)—Someday is today—The Leukemia & Lymphoma Society (Jun. 24, 2014), 1 pg.

Acute Myeloid Leukemia—NCCN Clinical Practice Guidelines in Oncology (NCCN Guidelines), Version 2.2014, (Mar. 28, 2014), 89 pages.

Acute Myeloid Leukemia, Practice Guidelines in Oncology—v1.1. 2008 (Dec. 30, 2007), National Comprehensive Cancer Network, Inc., (36 pages)

Buckstein, et al. "Myelodysplastic Syndromes (MDS)",(May 2008), 20 pgs.

Fabre, et al. "Treatment of AML with Azacytidine (AZA): Current Results of the French ATU Program", Blood (ASH Annual Meeting Abstracts) (2007), vol. 110, Abstract 1849 (printed online Jun. 24, 2014), 1 pg.

Fenaux, et al. "Azacitidine prolongs overall survival and reduces infections and hospitalizations in patients with WHO-defined acute myeloid leukaemia compared with conventional care regimens: an update", ecancermedicalscience (2008), vol. 2, No. 121, pp. 1-3.

Garcia-Manero, "Demethylating Agents in Myeloid Malignancies", Curr Opin Oncol. (Nov. 2008), vol. 20, No. 6, pp. 1-11.

Is Lymphoma on Your Radar?, Leukaemia Foundation, downloaded on Jun. 13, 2014, 2 pgs.

Itzykson, et al. "Optimal sequencing of treatments for patients with myelodysplastic syndromes", Current Opinion in Hematology (2009), vol. 16, pp. 77-83.

Leone, et al. "DNA methylation and demethylating drugs in myelodysplastic syndromes and secondary leukemias", Haematologica (2002), vol. 87, pp. 1324-1341.

Myelodysplastic Syndromes—NCCN Clinical Practice Guidelines in Oncology (NCCN Guidelines), Version 2.2014 (May 21, 2013), (65 pages)

* cited by examiner

```
MEQDRTNHVEGNRLSPFLIPSPPICQTEPLATKLQNGSPLPERAHPEVNGDTKWHSFKSYYGIPCM
KGSQNSRVSPDFTQESRGYSKCLQNGGIKRTVSEPSLSGLLQIKKLKQDQKANGERRNFGVSQERN
PGESSQPNVSDLSDKKESVSSVAQENAVKDFTSFSTHNCSGPENPELQILNEQEGKSANYHDKNIV
LLKNKAVLMPNGATVSASSVEHTHGELLEKTLSQYYPDCVSIAVQKTTSHINAINSQATNELSCEI
THPSHTSGQINSAQTSNSELPPKPAAVVSEACDADDADNASKLAAMLNTCSFQKPEQLQQQKSVFE
ICPSPAENNIQGTTKLASGEEFCSGSSSNLQAPGGSSERYLKQNEMNGAYFKQSSVFTKDSFSATT
TPPPPSQLLLSPPPPLPQVPQLPSEGKSTLNGGVLEEHHHYPNQSNTTLLREVKIEGKPEAPPSQS
PNPSTHVCSPSPMLSERPQNNCVNRNDIQTAGTMTVPLCSEKTRPMSEHLKHNPPIFGSSGELQDN
CQQLMRNKEQEILKGRDKEQTRDLVPPTQHYLKPGWIELKAPRFHQAESHLKRNEASLPSILQYQP
NLSNQMTSKQYTGNSNMPGGLPRQAYTQKTTQLEHKSQMYQVEMNQGQSQGTVDQHLQFQKPSHQV
HFSKTDHLPKAHVQSLCGTRFHFQQRADSQTEKLMSPVLKQHLNQQASETEPFSNSHLLQHKPHKQ
AAQTQPSQSSHLPQNQQQQQKLQIKNKEEILQTFPHPQSNNDQQREGSFFGQTKVEECFHGENQYS
KSSEFETHNVQMGLEEVQNINRRNSPYSQTMKSSACKIQVSCSNNTHLVSENKEQTTHPELFAGNK
TQNLHHMQYFPNNVIPKQDLLHRCFQEQEQKSQQASVLQGYKNRNQDMSGQQAAQLAQQRYLIHNH
ANVFPVPDQGGSHTQTPPQKDTQKHAALRWHLLQKQEQQQTQQPQTESCHSQMHRPIKVEPGCKPH
ACMHTAPPENKTWKKVTKQENPPASCDNVQQKSIIETMEQHLKQFHAKSLFDHKALTLKSQKQVKV
EMSGPVTVLTRQTTAAELDSHTPALEQQTTSSEKTPTKRTAASVLNNFIESPSKLLDTPIKNLLDT
PVKTQYDFPSCRCVEQIIEKDEGPFYTHLGAGPNVAAIREIMEERFGQKGKAIRIERVIYTGKEGK
SSQGCPIAKWVVRRSSSEEKLLCLVRERAGHTCEAAVIVILILVWEGIPLSLADKLYSELTETLRK
YGTLTNRRCALNEERTCACQGLDPETCGASFSFGCSWSMYYNGCKFARSKIPRKFKLLGDDPKEEE
KLESHLQNLSTLMAPTYKKLAPDAYNNQIEYEHRAPECRLGLKEGRPFSGVTACLDFCAHAHRDLH
NMQNGSTLVCTLTREDNREFGGKPEDEQLHVLPLYKVSDVDEFGSVEAQEEKKRSGAIQVLSSFRR
KVRMLAEPVKTCRQRKLEAKKAAAEKLSSLENSSNKNEKEKSAPSRTKQTENASQAKQLAELLRLS
GPVMQQSQQPQPLQKQPPQPQQQQRPQQQQPHHPQTESVNSYSASGSTNPYMRRPNPVSPYPNSSH
TSDIYGSTSPMNFYSTSSQAAGSYLNSSNPMNPYPGLLNQNTQYPSYQCNGNLSVDNCSPYLGSYS
PQSQPMDLYRYPSQDPLSKLSLPPIHTLYQPRFGNSQSFTSKYLGYGNQMQGDGFSSCTIRPNVH
HVGKLPPYPTHEMDGHFMGATSRLPPNLSNPNMDYKNGEHHSPSHIIHNYSAAPGMFNSSLHALHL
QNKENDMLSHTANGLSKMLPALNHDRTACVQGGLHKLSDANGQEKQPLALVQGVASGAEDNDEVWS
DSEQSFLDPDIGGVAVAPTHGSILIECAKRELHATTPLKNPNRNHPTRISLVFYQHKSMNEPKHGL
ALWEAKMAEKAREKEEECEKYGPDYVPQKSHGKKVKREPAEPHETSEPTYLRFIKSLAERTMSVTT
DSTVTTSPYAFTRVTGPYNRYI-2002
```

Figure 1

PATIENT nAML2
PATIENT MDS03
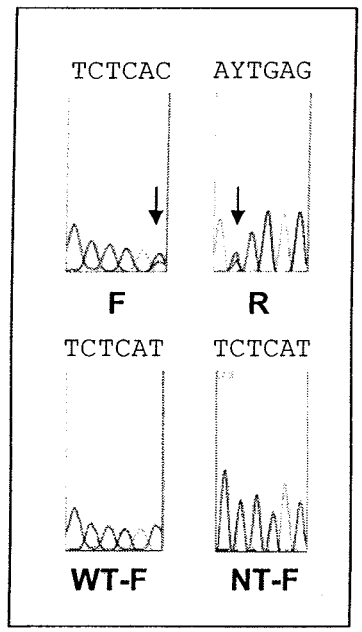
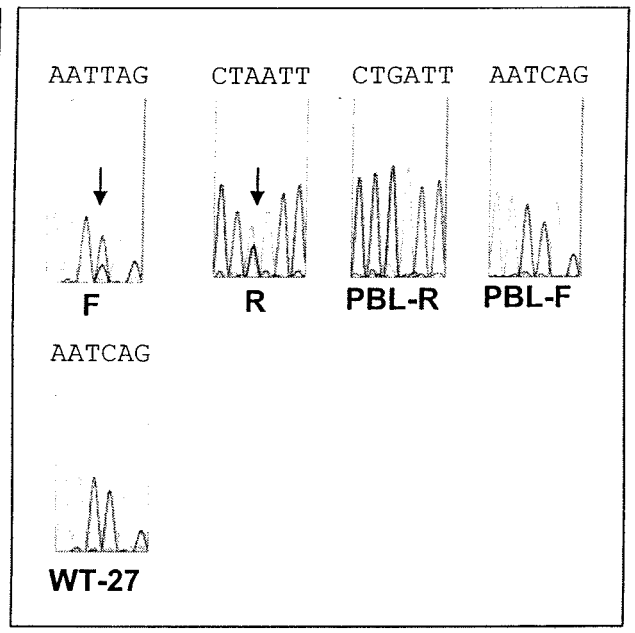
Figure 2

TET2 AS A DIAGNOSTIC AND PRONOSTIC MARKER IN HEMATOPOIETIC NEOPLASMS

This application claims the priority of European patent applications EP 08305255.5 and EP 09155169.7 filed on Jun. 12, 2008 and on Mar. 13, 2009 respectively, which are incorporated herein by reference.

FIELD OF THE INVENTION

The present invention relates to genetic markers to diagnose myeloid neoplasms, more particularly to a new identified tumour suppressor gene, the Ten Eleven Translocation protein family member 2 gene (TET2). Genetic alterations of TET2 are useful to diagnose myeloid tumours, such as myelodysplastic/myeloproliferative syndromes, MDS, AML or MPD, and lymphoid tumours.

BACKGROUND OF THE INVENTION

Hematopoiesis is maintained by a hierarchical system where hematopoietic stem cells (HSCs) give rise to multipotent progenitors, which in turn differentiate into all types of mature blood cells. The molecular mechanisms controlling multipotentiality, self-renewal, quiescence and HSC commitment have been extensively studied. However, numerous issues remain to be addressed and important genes regulating these processes remain to be identified.

Myeloid malignancies include Acute Myeloid leukaemia (AML), Myeloproliferative disorders (MPDs), myelodysplastic syndromes (MDS) and myelodysplastic/myeloproliferative syndromes that are all clonal stem-cell (HSC) or progenitor malignant disorders (TIU et al., *Leukemia*, vol. 21(8), p:1648-57, 2007).

Several genetic mutations have been correlated to AML, and four groups are recognized: (i) the AML with recurrent genetic abnormalities AML t(8;21)(q22;q22) with RUNX1-ETO fusion gene; AML with abnormal bone marrow eosinophils and inv(16)(p13;q22) or t(16;16)(p13;q22) with CBFB/MYH11 rearrangement; acute promyelocytic leukaemia APL with t(15;17)(q22;q12) PML/RARA; AML with 11q23 (MLL) abnormalities); (ii) AML with multilineage dysplasia following MDS or MDS/MPD or without antecedent of MDS or MPD; (iii) AML or MDS therapy related and (iv) other unclassified AML among that comprises the group of AML with normal karyotype which prognosis is based on molecular analysis of oncogenes such as mutations of FLT3-ITD or NPM1.

Myelodysplastic/myeloproliferative syndromes include four myeloid diseases grouped in 1999 by the WHO: chronic myelomonocytic leukemia (CMML), juvenile myelomonocytic leukemia (JMML), atypical chronic myeloid leukemia (aCML) and unclassified myelodysplastic/myeloproliferative syndromes (U-MDS/MPS).

MDS include refractory anemia (RA), and refractory cytopenia with multilineage dysplasia (RCMD). MDS are characterized by ineffective hematopoiesis in one or more of the lineage of the bone marrow. Early MDS mostly demonstrate excessive apoptosis and hematopoietic cell dysplasia (CLAESSENS et al., *Blood*, vol. 99, p:1594-601, 2002; CLASESSENS et al., *Blood*, vol. 105, p:4035-42, 2005). In about a third of MDS patients, this ineffective hematopoiesis precedes progression to secondary AML (sAML). Although some molecular events associated with specific MDS subtypes (ELBERT et al., *Nature*, vol. 451(7176), p:335-9, 2008) or disease transformation (BRAUN et al., *Blood*, vol. 107(3), p:1156-65, 2006) have been identified, the underlying molecular defects are still poorly understood. No biological markers, except morphological features, are currently available for early diagnosis and prognosis.

MPDs, referred now as myeloproliferative neoplasms (MPN; TEFFERI & VARDIMAN, *Leukemia*, vol. 22, p:14-22, 2008), are chronic myeloid diseases including chronic myelogenous leukaemia (CML), polycythemia vera (PV), essential thrombocythemia (ET), primary myelofibrosis (PMF) and idiopathic myelofibrosis (IMF). MPDs are characterized by an increased proliferation of one or several myeloid lineages. If most MPDs are sporadic diseases, familial cases of MPDs, for which the exact prevalence is unknown, have been reported (GILBERT, *Baillieres Clin. Haematol.*, vol. 11, p:849-858, 1998; KRALOVICS et al., *Blood*, vol. 102, p:3793-3796, 2003; BELLANNE-CHANTELOT et al., *Blood*, vol. 108, p:346-352, 2006). The clinical analysis of these familial cases has shown that they are phenotypically identical to sporadic cases. Nevertheless, MPD families are characterized by a clinical and genetic heterogeneity. First, MPD cases from a single family can either display the same subtype or different types of MPD (GILBERT, abovementioned, 1998; BELLANNE-CHANTELOT et al., abovementioned, 2006; RUMI et al., *Cancer*, vol. 107, p:2206-2211, 2006). Second, about 6-15% of patients with PV and 3-5% of patients with ET are at risk of developing hematological complication after 15 years of evolution (FINAZZI & HARRISON, *Semin. Hematol.*, vol. 42, p:230-238, 2005; KILADJIAN et al., *Blood*, vol. 112, p:1746, 2008; PASSAMONTI et al., *Blood*, vol. 111, p:3383-3387, 2008; PASSAMONTI et al., *Haematologica*, vol. 93, p:1645-1651, 2008).

MPDs, in both sporadic and familial cases, are commonly associated with an acquired constitutive kinase activity, as exemplified by the $JAK2^{V617F}$ mutation in Polycythemia Vera, in most PV cases and in half of ET and PMF cases (MORGAN & GILLIGAND, *Annu. Rev. Med.*, vol. 59, p:213-22, 2008; DELHOMMEAU et al., *Cell Mol. Life. Sci.*, vol. 63(24), p:2939-53, 2006, CAMPBELL & GREEN, *N. Engl. J. Med.*, vol. 355(23), p:2452-66, 2006; BELLANNE-CHANTELOT et al., abovementioned, 2006; JAMES et al., *Nature*, vol. 434, p:1144-1148, 2005; BAXTER et al., *Lancet*, vol. 365, p:1054-1061, 2005; LEVINE et al., *Blood*, vol. 106, p:3377-3379, 2005; KRALOVICS et al., *N. Engl. J. Med.*, vol. 352, p:1779-1790, 2005). MPDs frequently result from the expression of a constitutive tyrosine kinase protein:

Through a fusion like BCR-ABL in CML, FIP1L1-PDGFRA in HES, TEL-PDGFRB in CMML with hypereosinophilia, ZNF198-FGFR1 in rare MPD coupled to lymphoid proliferation and PCM1-JAK2 in rare MPDs, AML and T cell lymphomas A limited or single nucleotide mutation i.e. JAK2 V617F (1849G>T), which recent discovery of in PV (98%), ET (75%), IMF (50%) and a few percent of CMML, MDS/MPD and U-MPD allows for a new MPD classification and diagnosis criteria and perspectives for treatment. In addition, KIT mutations are recurrent in systemic mast cell proliferation.

Through activating mutations in the receptor for thrombopoietin receptor (MPL), especially of the tryptophan 515 ($MPLW515^{K/L/A}$) (PIKMAN et al., *PLoS Med*, vol. 3(e270), 2006; CHALIGNÉ et al., *Leukemia*, vol. 22, p1557-66, 2008).

Marginal cases of CML presented with BCR/JAK2 rearrangement due to t(9;22)(p24;q11).

The JAK2 gene on chromosome 9p encodes a tyrosine kinase that associates with type 1 cytokine receptors. The V617F mutation is predicted to disrupt the auto-inhibitory effect of the JH2 domain to constitutive activation of the kinase. Wild type JAK2 exerts a dominant negative effect on the activity of the mutated protein. Therefore the loss of WT JAK2 associated to the duplication of the mutated gene by mitotic recombination observed in most of MPD samples allows for a higher expression and activity of the mutated kinase.

However, several observations, such as the Polycythemia Vera co expressing the WT and mutated JAK2 and the characterization of secondary AML emerging from mutated MPD but lacking of JAK2 mutation in the blast phases indicate oncogenetic events earlier occurring before JAK2 mutation. Moreover, and as discussed previously, the MPD disease evolution is indeed highly variable within and between families. Thus, there is some evidence that there is at least one other mutation than JAK2 implicated in MPDs and, more specifically, their progression.

Lymphoid tumours consist of expansion of cells with lymphoid features. Acute lymphoblastic leukaemia/lymphoma are proliferation of cells blocked in lymphoid differentiation, from either T (T-cell acute lymphoblastic leukaemia; T-ALL) or B (B-cell precursor acute lymphoblastic leukaemia; BCP-ALL) origin. Some leukaemia lymphoma are from Natural Killer (NK) origin. Lymphoma involve expansion of more mature lymphoid cells (B or T). Some neoplasms are chronic, and can involve T cell (prolymphocytic leukaemia) or B cells (Chronic Lymphocytic Leukaemia). The classification of lymphoid neoplasm is based on anatomopathological analyses, differentiation markers and pathogenesis data (Swerdllow S. H., Campo E., Harris N. L., Jaffe E. S., Pileri S. A., Stein H., Thiele J. W., Vardiman J. W. (Eds): WHO classification of tumors of haematopoietc and lymphoid tissues. IARC: Lyon 2008). For example, Anaplasic large T-cell lymphoma are associated with NPM-ALK fusion oncogene (and variant thereof), follicular lymphoma are associated with BCL2 activation following t(14;18)(q32;q21) chromosomal translocation, mantle cell lymphoma are associated with CCND1 activation following t(11;14)(q13;q32) chromosomal translocation. Many lymphoma however lack any reliable molecular marker suggesting a pathophysiological mechanism. This is the case, In particular, for more than 50% of diffuse large B cell lymphomas (DLBCL), for most peripheral T-cell lymphomas (PTCL) and for a majority of non-follicular low grade lymphomas.

Therefore, there was an urgent need of a reliable diagnostic marker that allows to identify lymphoid and myeloid neoplasms, in particular MDS and MPD, and eventually to prognosticate their progression.

The Ten Eleven Translocation protein family contains three recently identified members, with unknown functions, characterized in that they share two highly conserved domains at their C-terminal end. As used herein, the expression "gene of the TET family" refers to members of the Ten Eleven Translocation family, TET1, TET2 or TET3, which have been recently identified (Lorsbach et al, *Leukemia* 2003).

Among them, TET1 is the only studied member, because it has been identified as a fusion partner with the protein mixed lineage leukemia (MLL) in two different and independent studies (ONO et al., *Cancer Research*, vol. 62(14), p:4075-80, 2002 and LORSBACH et al., *Leukemia*, vol. 17(3), p:637-41, 2003). This protein, also called LCX, or "leukemia associated protein with a CXXC domain in N-terminal region", contains an α-helical coiled-coil region in its C-terminal region, region which is retained in the fusion MLL-TET1. On the contrary, the N-terminus CXXC domain of TET1 is not present in this protein fusion (Ono R, Cancer Research 2002).

The two highly conserved carboxy terminal regions are included in the MLL-TET1 fusion (Lorsbach et al, Leukemia 2003). One conserved region is disrupted by the translocation; the other one is fused to MLL. Despite its description as an MLL fusion partner 7 years ago, functional and sequence analysis of the TET1 gene have been reported recently, after the priority date of the present application.

The MLL gene is located at human chromosome 11q23 and is found to be rearranged in a heterogenous group of lymphoid, myeloid and mixed lineage human leukemias. More than 70 loci have been described to be rearranged with the 11q23 chromosomal band and at least 50 of these have been cloned and characterized on a molecular level. Most of the MLL rearrangements map to a 8.3 kb base of the genes. The partners genes are always fused in frame to the 5' part MLL and may include MLL itself. Amplifications of MLL have also been reported. The partner genes code for proteins with disparate functions. In the MLL fusion, they may provide transcriptional activation domains, chromatin modifier complex recruitment or dimerization/oligomerization motif. Indeed, the expression of an MLL-Beta-galactosidase (a bacterial protein able to tetramerize) or to dimerization domain is sufficient to induce leukemia in mouse models. Therefore, it is not possible to infer the function of a protein or its independent involvement in cellular transformation from its fusion to MLL (The versatile mixed lineage leukaemia gene MLL and its many associations in leukaemogenesis. Daser A, Rabbitts T H. Semin Cancer Biol. 2005 June; 15(3):175-88. Review. Chromosomal rearrangements leading to MLL gene fusions: clinical and biological aspects. Harper D P, Aplan P D. Cancer Res. 2008 Dec. 15; 68(24):10024-7.)

On the contrary, little is known about the TET2 protein, which is encoded by a gene located on the 4q24 chromosomal region, and the TET3 protein, which is encoded by a gene located on the 2p12 chromosomal region.

More specifically, the Ten Eleven Translocation oncogene number 2 (TET2) has been designated recently (Lorsbach et al, *Leukemia* 2003). The TET2 gene located on the chromosomal region 4q24, comprises 11 exons spread over >130 Kb and is normally widely expressed. This gene is referenced with the accession number ID 57790, and its cDNA (Accession number NM_001127208, SEQ ID NO:1) is encoding a protein of 2002 amino acids (Accession number NP_001120680, SEQ ID NO:2).

The TET2 protein shares two highly conserved regions with a single orthologous *Drosophila* predicted protein. These regions are i) a 310 amino acid region located near the center of the protein TET2 (amino acids 1134 to amino acid 1444), and ii) a second 80 amino acid region located near the carboxyterminal end of the protein TET2 (corresponding to amino acid 1843 until amino acid 1922) (these regions are highlighted in FIG. 1). The predicted sequence of TET2 did not reveal any motif corresponding to an identified function.

Applicants report herein that one or both copies of the Ten Eleven Translocation 2 (TET2) gene are often inactivated/modified by acquired mutations in MPD, MDS and CMML but also in lymphoma. These events target the hematopoietic stem cell and indicate an important function for TET2 as a tumor suppressor gene in myeloid or lymphoid neoplasms.

SUMMARY OF THE INVENTION

In a first aspect, the present invention provides an in vitro method for diagnosing a myeloid tumour or a lymphoid tumour in a subject, which comprises the step of analyzing a biological sample from said subject by:

(i) detecting the presence of a mutation in the Ten Eleven Translocation protein family member 2 gene (TET2) coding for the polypeptide having the sequence SEQ ID NO:2, and/or (ii) analyzing the expression of the TET 2 gene;

wherein the detection of such a TET2 mutation, of the absence of expression of TET2 or of the expression of a truncated TET2 is indicative of a subject developing or predisposed to develop a myeloid tumour or a lymphoid tumour.

In a preferred embodiment, said subject is a mammal, preferably a human.

In another preferred embodiment, said myeloid cancer is selected in the group consisting of myelodysplastic syndrome (MDS), acute myeloid leukemia (AML), myeloproliferative disease (MPD) and myelodysplatic/myeloproliferative syndrome.

In still another preferred embodiment, said lymphoid tumour is selected in the group consisting of lymphoma and more preferentially of T cell lymphoma Preferably, said mutation is detected on each copy of the TET2 gene coding for the polypeptide having the sequence SEQ ID NO:2 (encoded by the cDNA having the sequence SEQ ID NO:39) and is included in the group consisting of deletions, insertions and point mutations such as mutations affecting splice sites, missense mutation and nonsense mutations, preferably missense mutation and nonsense mutations.

In a more preferred aspect of the invention, the mutation is a deletion or an insertion which results in the absence of expression of the TET2 protein or in the expression of a truncated TET2 protein.

Even more preferably, this truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4), preferably the 80 amino acid region located near the carboxyterminal end of the protein TET2 (corresponding to amino acid 1843 until amino acid 1922, SEQ ID NO:4).

For example, these deletions or insertions can be selected in the group comprising or consisting of those disclosed in Table I in reference to SEQ ID NO:39 for nucleic acid position and to SEQ ID NO:2 for amino acid position.

TABLE I

| Nucleotide Change | Consequence |
|---|---|
| del1264_1666 | p.Glu135 FS |
| delC 1642 | p.Ser261 FS |
| del1893_1896 | p.Lys345FS |
| delC 2448 | p.Gln530 FS |
| delA 2505 | p.Thr549 FS |
| delC 2524 | p. Pro555 FS |
| Ins 2540_2544 | p.Leu560FS |
| delT 2685 | p.Ser609 FS |
| delA 2815 | p.Gln652FS |
| del 2834_2835 | p.His658 FS |
| delA 2935 | p.Glu692 FS |
| delT 2944 | p.Leu699 STOP |
| delG 2994 | p.Glu711 FS |
| delC 3009 | p.His717 FS |
| insA 3009 | p.His717 FS |
| del 3131_3137 | p. Leu757 FS |
| insC 3151 | p.Gln764 FS |
| delA 3166 | p.Gln769 FS |
| delT3215 | p.Phe785 FS |

TABLE I-continued

| Nucleotide Change | Consequence |
|---|---|
| insA3350 | p.Gln831FS |
| insT3995 | p.Glu846 FS |
| delA3430 | p.Asn857FS |
| insT 3465 | p.Pro869 FS |
| insA 5757 | p.Gln891 STOP |
| insCT 3581 | pGly 908 FS |
| del CA 3756_3757 | p.Gln966 FS |
| dupT 3914 | p.Glu1026 STOP |
| delT 3998 | p.Leu1046FS |
| delA 4130 | p.Lys1090 FS |
| delG 4271 | p.Glu1137 FS |
| delA4327 | p.Asn1156 FS |
| delG 4527 | p.Ala1223 FS |
| — | p.del 1237-1239 |
| delG 4932 | p.Glu1357 FS |
| insG 5119 | p.Leu 1420 FS |
| delG 5133 | p.Asp 1425 FS |
| insA 5177 | p.Arg1440FS |
| dupA 5177 | p.Arg1440FS |
| delC 5222 | p.Leu1457 STOP |
| del5521_5524 | pThr1554 FS |
| insA 5540 | p.Tyr1560 FS |
| del 5583_5605 | p.Pro1575FS |
| delT 5570 | p.Leu1637 FS |
| del5828_5843 | p.Met1656 FS |
| del6049_6050 | p.Asp1830 FS |
| delC 6360 | p.Gln1834 FS |
| del6396_6531 | p.Val1846 FS |
| delA 6507 | p.Thr1883 FS |
| insC 6507 | p.Thr1883 FS |
| del6511_6512 | p.Pro1885FS |
| DelC 6555 | p.Leu1889FS |
| insC splice site | mutation of splice site exon 8 |

Del: deletion;
ins: insertion;
FS: frame shift

In another more preferred aspect of the invention, the mutation is a missense mutation, which is located in the open reading frame of the TET2 protein, preferably in at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), and more preferably in the 80 amino acid region located near the carboxyterminal end of the protein TET2 (corresponding to amino acid 1843 until amino acid 1922, SEQ ID NO:4). For example, these missense mutations can be selected in the group comprising or consisting of I1175V, L1197N, H1219Y, E1235V, C1271W, K1299E, L1340P, R1302G, G1370E, A1344E, N1387S, V1417F, H1868R, G1869W, L1872P, I1873T, R1896M, and S1898F, preferably can be selected in the group comprising or consisting of L1197N, H1219Y, E1235V, C1271W, K1299E, L1340P, R1302G, G1370E, A1344E, N1387S, H1868R, G1869W, L1872P, I1873T, R1896M, and S1898F, and more preferably in the group comprising or consisting of H1868R, G1869W, L1872P, I1873T, R1896M, and S1898F.

In another more preferred aspect of the invention, the mutation is a nonsense mutation, which is located in the open reading frame of the TET2 protein, preferably before or inside at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), and more preferably before or inside the 80 amino acid region located near the carboxyterminal end of the protein TET2 (corresponding to amino acid 1843 until amino acid 1922, SEQ ID NO:4). For example, said nonsense mutations can be selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, Q1834Stop and W1847Stop.

In another aspect of the invention, the mutation in the TET2 gene induces absence of expression or under-expression of the polypeptide having the sequence SEQ ID NO:2 and more preferably the absence of expression or under-expression of at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4), more preferably of the 80 amino acid region located near the carboxyterminal end of the protein TET2 (corresponding to amino acid 1843 until amino acid 1922, SEQ ID NO:4).

In a second aspect, the present invention provides a kit for diagnosing myeloid cancer in a subject comprising at least one nucleic acid probe or oligonucleotide or at least one antibody, which can be used in a method as defined previously for detecting the presence of a mutation in the TET2 gene and/or analysing the expression of the TET2 gene.

In a preferred embodiment of the invention, said oligonucleotide is at least one PCR primer, and preferably a set of PCR primers.

More preferably, said set of primers is selected in the group comprising SEQ ID NO: 5 to SEQ ID NO: 38 (see examples).

In a third aspect, the present invention provides the use of a hypomethylating agent for treating a patient suffering from a myeloid or a lymphoid tumour, for which tumour, a TET2 mutation, an absence of TET2 expression or an expression of a truncated TET2 has been detected.

In a final aspect, the present invention provides a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of a hypomethylating agent.

BRIEF DESCRIPTION OF THE DRAWINGS

The FIG. 1 shows the protein sequence of TET2 (SEQ ID NO:2), highlighting the conserved regions between species (bold).

The FIG. 2 shows the sequence traces obtained by sequencing the PCR products obtained for samples obtained from two patients A and E, showing that the mutation only occurs in the tumoral and not in non-tumoral samples (NT), and Peripheral Blood Lymphocytes (PBL). R corresponds to the sequence obtained with the Reverse primer, and F corresponds to the one obtained with the Forward primer. WT corresponds to the sequence obtained in healthy individuals.

Figure 3:
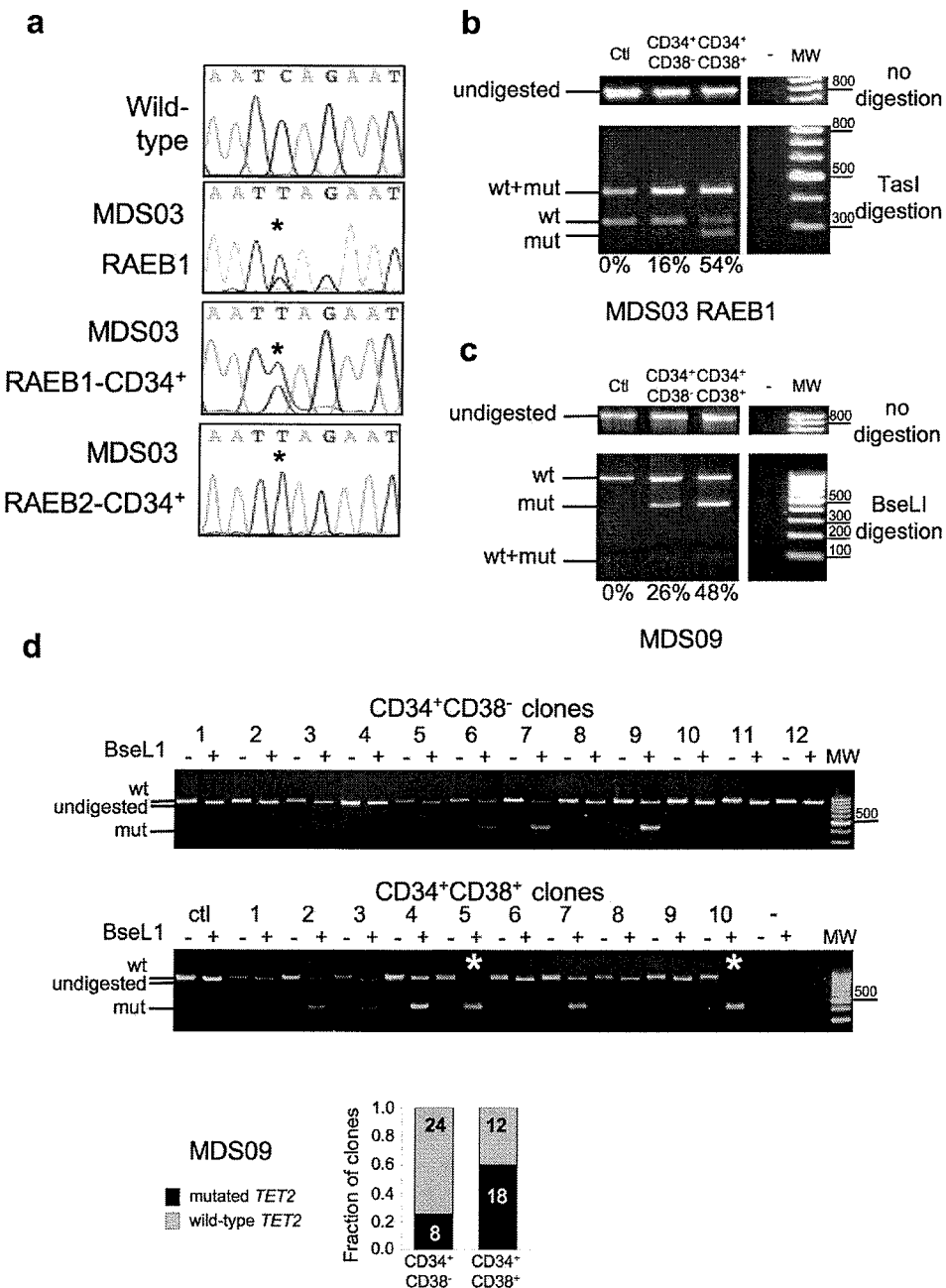

The FIG. 3 shows that in MDS samples, mutated TET2 is observed in immature CD34$^+$ cells and is associated with in vivo expansion of the mutated clone.

Figure 4:
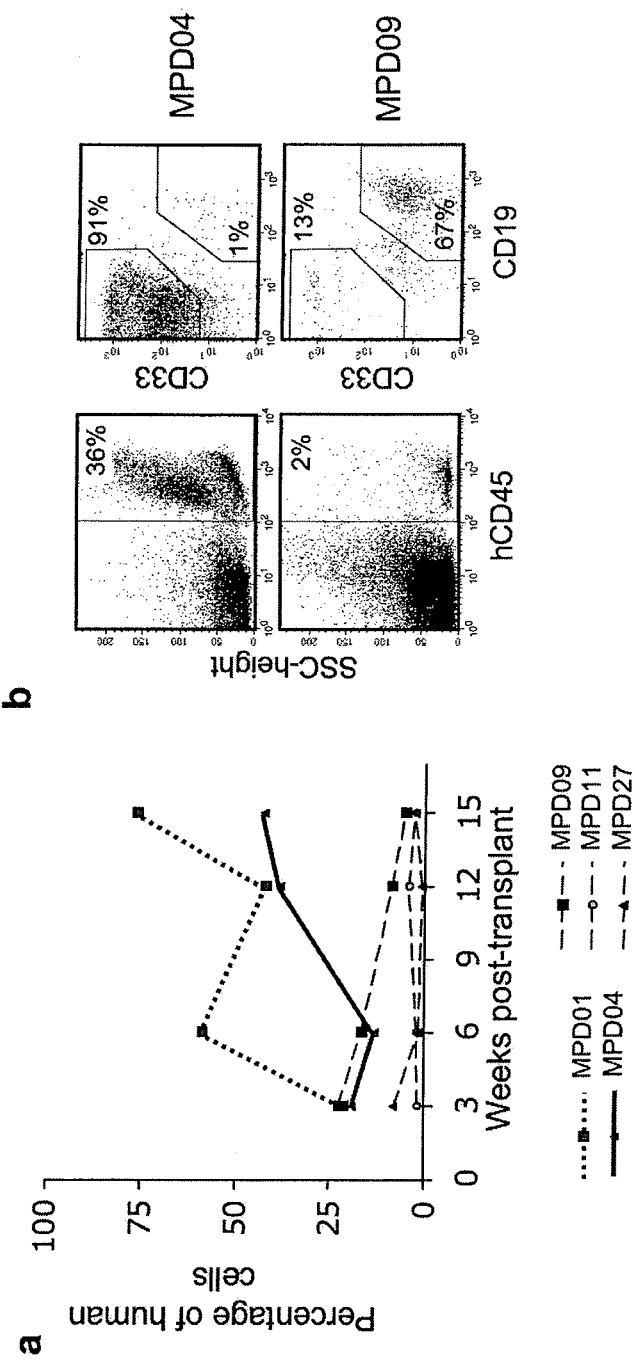
Figure 5:
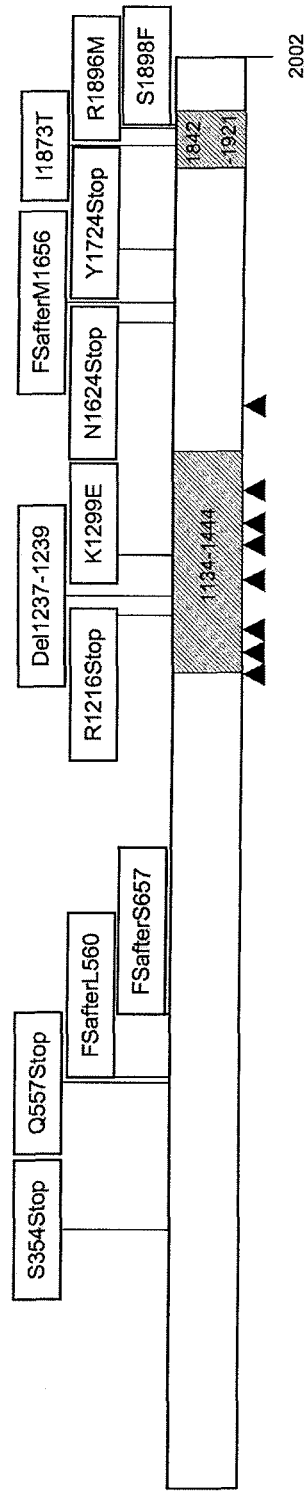

The FIG. 4 shows that JAK2$^{V617F}$-positive MPD hematopoietic stem cells with TET2 defects display enhanced NOD/SCID repopulating capacities The FIG. 5 shows the locations of some of the identified mutations of the TET2 gene distributed along the protein sequence Conserved regions are marked with gray stripes. Arrowheads indicate the location of exon boundaries. FS: Frame shift.

Figure 6:
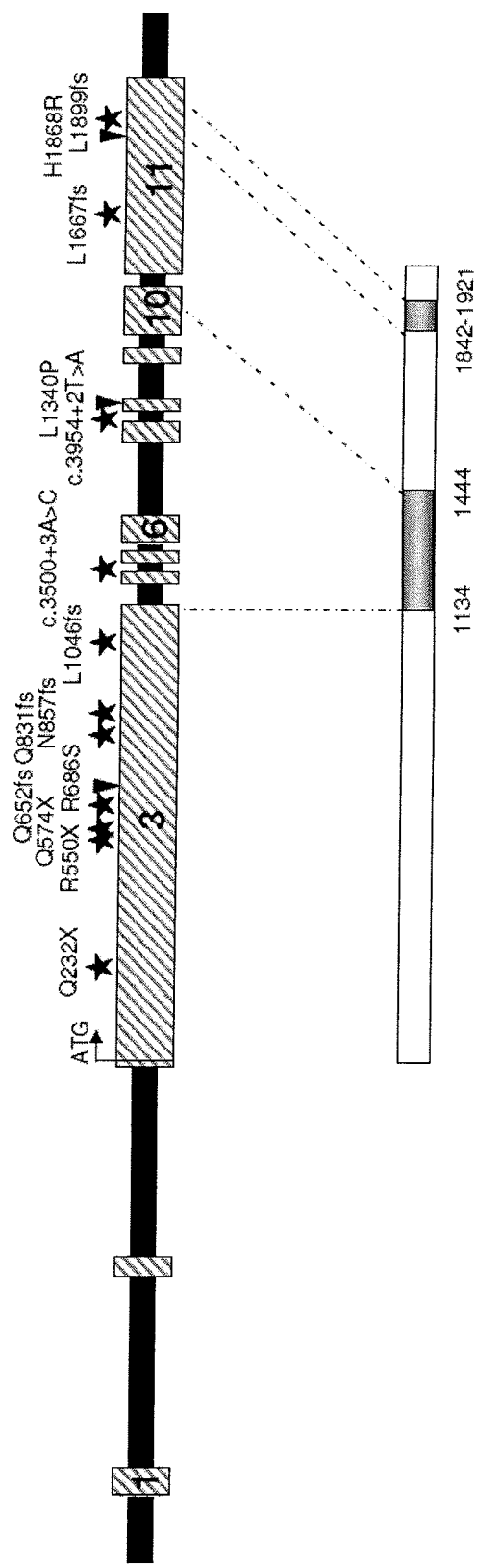

The FIG. 6 shows a schematic representation of the TET2 gene and protein showing the mutations identified in familial myeloproliferative neoplasms. Hatched boxes indicate exons. Truncating mutations are depicted as stars, missense mutations as inverted triangles. Conserved functional domains are depicted as boxes on the protein scheme. fs: frameshift.

Figure 7:
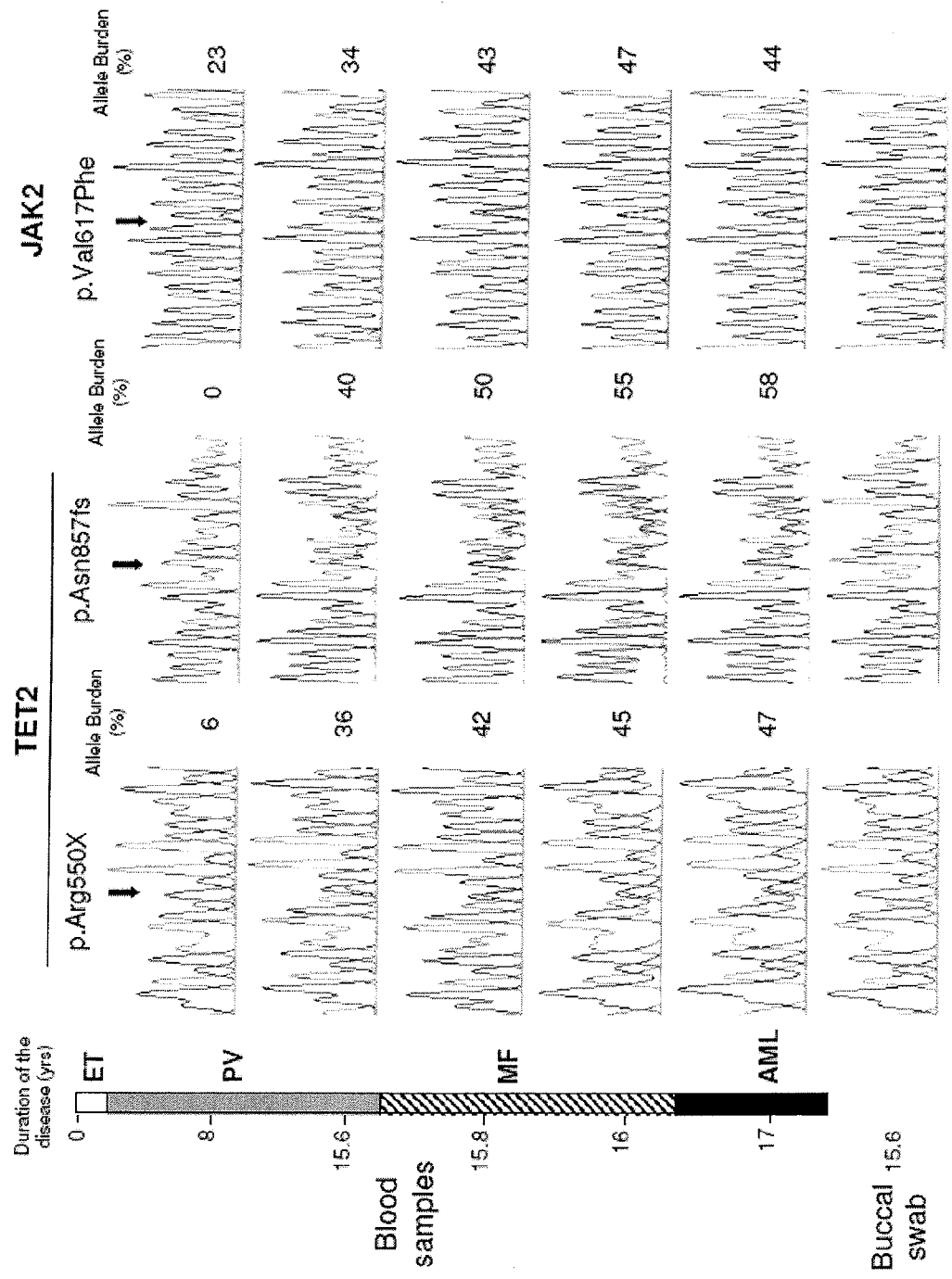

The FIG. 7 shows the sequential study of TET2 and JAK2 in patient P4 (F3). Sequence electrophoregrams are shown for each TET2 mutation and for JAKV617F. The diagram on the left indicates time lapse from diagnosis (in years) and corresponding phenotype for each sample (white: ET; grey: PV; hatched: post-ET MF; black: AML).

Figure 8:
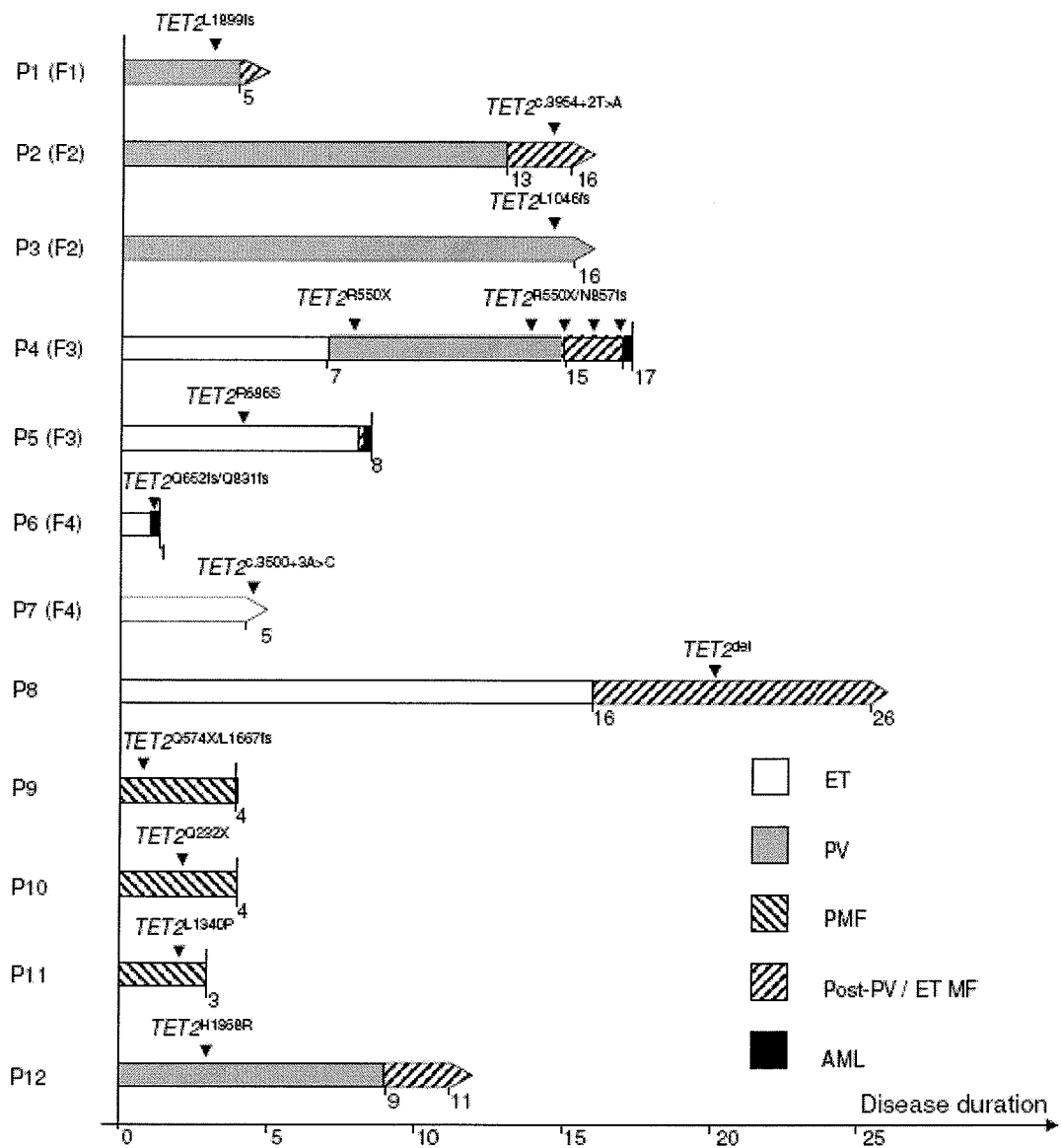

The FIG. 8 shows the schematic representation of the clinical status of the twelve patients with at least one TET2 mutation. White boxes depict ET stages, grey, PV, crosswised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the "zero" point indicating time of diagnosis. Time of death is symbolized as a vertical line, when appropriate, at the right end.

Figure 9:
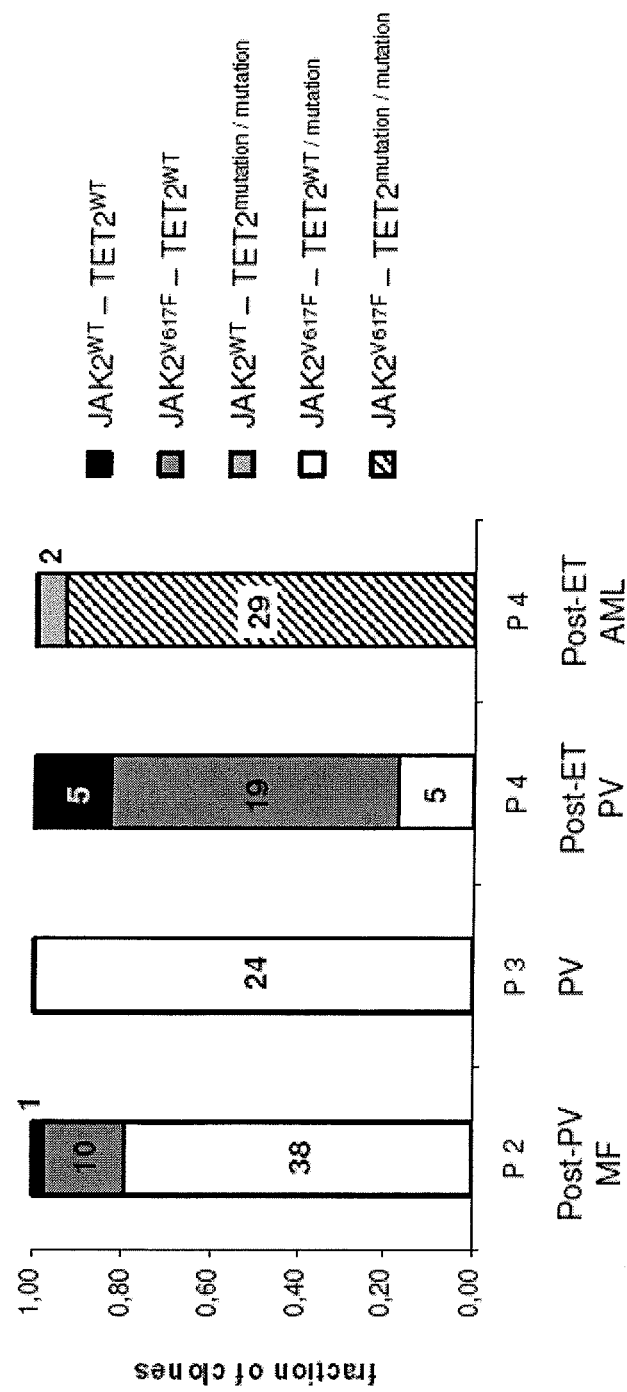

The FIG. 9 shows the TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

Figure 10:
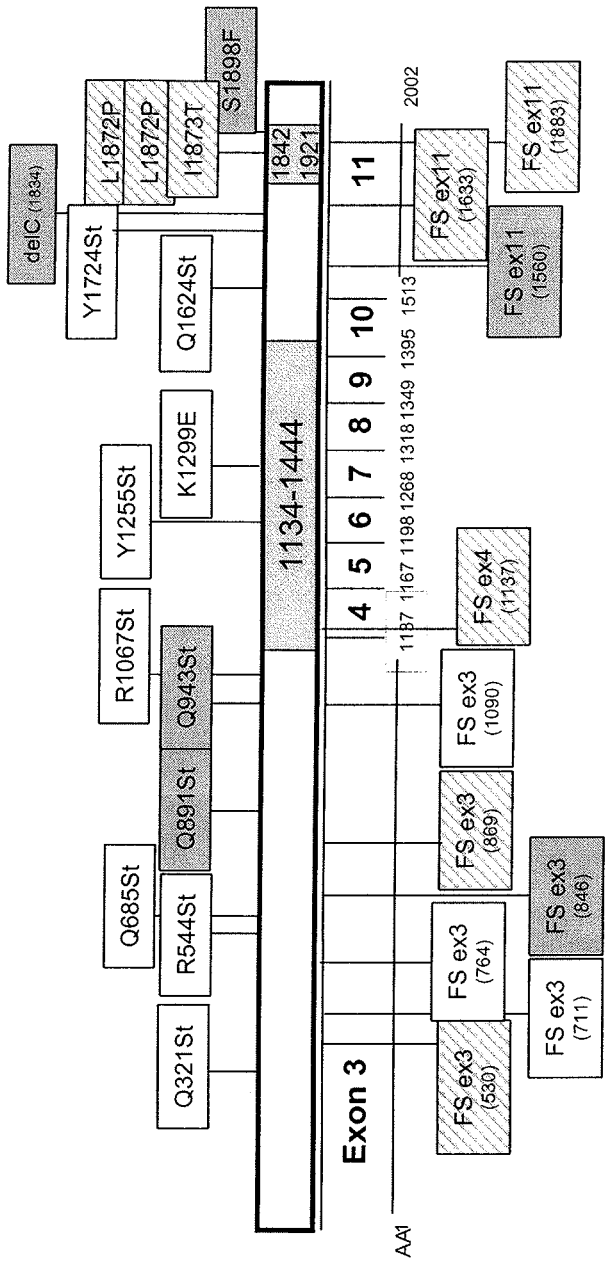

The FIG. 10 shows the clinical status and TET2 genotypes in MDS patients. Whites boxes represent low/int-1 grade MDS, hatched boxes represent int-2/high grade MDS and grey boxes represent secondary AML.

DETAILED DESCRIPTION OF THE INVENTION

The present invention is based on the discovery by the present inventors that the TET2 alleles are often genetically targeted by mutations and/or deletions in tumoral cells in patients suffering from lymphoid tumour or from myeloid tumour such as MPD, AML or MDS and can be considered as a bona fide tumor suppressor gene of human myeloid malignancies.

In a first aspect, the inventors report that, for sporadic cancer, the frequencies of TET2 mutation in unselected patient series were 12% in MPD, 18.5% in MDS, 24% in sAML until 50% in CMML patients. Also, applicants demonstrated that TET2 is a tumor suppressor gene in myeloid malignant disorders, because mutated hematopoietic stem cells are endowed with a growth advantage leading to enhanced proliferation.

In a second aspect, the inventors demonstrated by an analysis of 61 familial MPD cases (i.e. PV, ET, and PMF) that anomalies of TET2 gene are found in 20% of the three major MPD phenotypes (PV, ET and PMF) with a higher prevalence in PMF (42%).

Among the TET2-positive patients diagnosed with PV or ET, 77% developed myelofibrosis (MF) suggesting that the presence of acquired events of TET2 influence the evolution of the disease. In four patients (3 PV and 1 ET), we were able to show that the TET2 defect preceded from one to 7 years the hematological complication. The patients with a defect in TET2 are prone to progress to MF. This highly suggested a possible link between the TET2 acquired mutations and the severity of the disease, more specifically between TET2 and the development of MF.

In a third aspect, the inventors report that, for sporadic cancer, the frequencies of TET2 mutation in patients suffering from T-cell lymphoid tumour was ~20%. Finally, the TET2 rearrangements were observed in patients suffering from B-cell lymphoid tumour.

Thus, in a first aspect of the invention, there is provided an in vitro method for diagnosing a myeloid tumour or a lymphoid tumour in a subject, which comprises the step of analyzing a biological sample from said subject by:
  (i) detecting the presence of a mutation in the Ten Eleven Translocation protein family member 2 gene (TET2) coding for the polypeptide having the sequence SEQ ID NO:2, and/or
  (ii) analyzing the expression of the TET2 gene;
wherein, the detection of a TET2 mutation, of the absence of expression of TET2 or of the expression of a truncated TET2 is indicative of a subject developing or predisposed to develop a myeloid tumour or a lymphoid tumour.

Recent evidence indicate that proteins of the TET family encode enzymes responsible for the conversion of 5-methylcytosine to 5-hydroxymethylcytosine (TAHILIANI et al., *Sciencexpress*, 2009), thus have potential roles in CpG demethylation and epigenetic regulation. Moreover, this reference established that the conserved TET domains, where most TET2 mutations are observed, are implicated in this activity.

Concomitantly, several works have established, in the last years, a role for hypomethylating agents in MDS (ITZYKSON & FENAUX, *Current Opinion in Hematology*, vol. 16, p:77-83, 2009).

The results of the inventors now suggest that the observed efficiency of hypomethylating agent in some MDS potentially results from a demethylation defect in MDS with TET2 mutations.

Thus, the results of the inventors further suggest the use of hypomethylating agent on subjects suffering from lymphoid or myeloid tumour, such as MDS, for which tumour, a TET2 mutation, an absence of TET2 expression or an expression of a truncated TET2 has been detected.

Consequently and according to a preferred embodiment, the detection of a TET2 mutation, of the absence of expression of TET2 or of the expression of a truncated TET2 is indicative of a subject developing a myeloid tumour or a lymphoid tumour suffering from a demethylation defect, which subject can be advantageously treated with a hypomethylating agent, such as azacytidine (AZA).

Preferably, the method of the invention is dedicated to diagnose myeloid tumours.

In fact, the inventors have established that the frequency of TET2 mutations in patients suffering from myeloid tumor or from lymphoid tumour is greater than 10%.

The present invention furthermore provides a method for detection of the presence or absence of cells that have the potential to evolve to invasive myeloid neoplasms or to invasive lymphoid tumours, although those cells are not detectable as a lesion or precursor by conventional means.

As used herein, the term "subject" refers to a mammal, preferably a human.

Said subject may be a healthy, but the method of the invention is particularly useful for testing a subject thought to develop or to be predisposed to developing a myeloid cancer (i.e., myeloid tumour) or a lymphoid tumour. In that case, the method of the invention enables to confirm that said subject develops or is predisposed for developing a myeloid cancer (i.e., a myeloid tumour) or a lymphoid tumour.

More preferably, said lymphoid tumour is selected in the group consisting of lymphoma such as T- or B-cell lymphoma, and more preferentially of T cell lymphoma.

Still more preferably, said myeloid cancer (i.e., myeloid tumour) is selected in the group consisting of myelodysplastic syndrome (MDS), acute myeloid leukemia (AML), myeloproliferative disorders (MPD) and myelodysplatic/myeloproliferative syndrome. Advantageously, said myeloid cancer is a myelodysplatic/myeloproliferative syndrome, and preferably a chronic myelomonocytic leukemia (CMML).

According to a preferred embodiment, the method of the invention is for diagnosing a myelofibrosis (MF) in a subject, wherein said subject is suffering from polycythemia vera (PV) or from thrombocythemia (ET), and wherein the detection of a TET2 mutation or TET2 under-expression is indicative of a subject developing or predisposed to develop a myelofibrosis (MF).

According to still another preferred embodiment, the subject is suffering from myelodysplastic syndrome (MDS), and the detection of a TET2 mutation or TET2 under-expression is indicative of a subject with a good prognosis.

As used herein a good prognosis corresponds to a patient suffering from MDS and having a reduced risk of developing an AML.

In fact, the inventors have established that five-year survival was significantly increased in TET2 mutated patients suffering from MDS compared to unmutated patients ($p<0.05$).

As used herein, the expression "biological sample" refers to solid tissues such as, for example, a lung biopsy; buccal swab, fluids and excretions such as for example, sputum, induced sputum, blood, serum, plasma, urine. Preferably, said biological sample is a bone marrow sample.

In this aspect of the invention, the method comprises the step of detecting the presence of a mutation in the TET2 gene coding for the polypeptide having the sequence SEQ ID NO:2.

As used herein, the term "mutations" correspond to any modification in the sequence of the original nucleic acid sequence. These mutations comprise small-scale mutations, or large scale mutations. Small scale mutations are those affecting a gene in one or a few nucleotides, including point mutations, insertions or deletions of one or more extra nucleotides in the DNA. Point mutations can be silent, missense and nonsense mutation. Large scale mutation in the genomic structure, such as gene duplications, deletions, or mutations whose effect is to juxtapose previously separate pieces of DNA, potentially bringing together separate genes to form functionally distinct fusion genes. These last mutations include chromosomal translocations, interstitial deletions, chromosomal inversions and loss of heterezygosity.

Preferably, only a biological sample containing cells including genomic DNA (or optionally RNA) from the subject to be tested is required.

Preferably, this detecting step is realized on each allele of the TET2 gene. In fact, the diagnosis is more reliable when the mutation is detected on each allele of the TET2 coding for the polypeptide having the sequence SEQ ID NO:2.

In a particular embodiment, the in vitro method of the invention aims to detect mutation included in the group consisting of deletions, insertions and point mutations such as mutations affecting splice sites, missense mutation and nonsense mutations, preferably missense mutation and nonsense mutations.

The inventors have established that the existence of such mutations is associated with myeloid or lymphoid cancer. Moreover, the inventors observed that the polypeptidic C-terminal domain of the TET2 protein is preferentially targeted by the deleterious mutations in the studied patients (see examples).

For deletion or insertion, said deletion or insertion preferably results in the absence of expression of the TET2 protein or in the expression of a truncated TET2 protein, which truncated TET2 protein does not comprise at least one of the two highly conserved regions shared by the other TET proteins and corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4). More preferably, said truncated TET2 protein does not comprise the 80 amino acid region located near the carboxyterminal end of the protein TET2 (corresponding to amino acid 1843 until amino acid 1922, SEQ ID NO:4).

For example, these deletions or insertions can be selected in those disclosed in table 1.

For missense mutation, said missense mutation is preferably located in the open reading frame of the TET2 protein, and preferably in at least one of the two highly conserved regions shared by the TET proteins and corresponding to i) the 310 amino acid region located near the center of the protein TET2 (amino acids 1134 to amino acid 1444, SEQ ID NO:3), and ii) the 80 amino acid region located near the carboxyterminal end of the protein TET2 (corresponding to amino acid 1843 until amino acid 1922, SEQ ID NO:4).

As an example, said missense mutations are selected in the group comprising or consisting of I1175V, L1197N, H1219Y, E1235V, C1271W, K1299E, L1340P, R1302G, G1370E, A1344E, N1387S, V1417F, H1868R, G1869W, L1872P, I1873T, R1896M, and S1898F; preferably in the group comprising or consisting of I1175V, L1197N, H1219Y, E1235V, C1271W, K1299E, L1340P, R1302G, G1370E, A1344E, N1387S, H1868R, G1869W, L1872P, I1873T, R1896M, and S1898F.

More preferably, said missense mutation is located in the 80 amino acid region located near the carboxyterminal end of the protein TET2 (corresponding to amino acid 1843 until amino acid 1922, SEQ ID NO:4). Even more preferably, said missense mutations are selected in the group comprising or consisting of H1868R, G1869W, L1872P, I1873T, R1896M, and S1898F, as an example I1873T, R1896M, and S1898F.

For non sense mutation, said nonsense mutation preferably results in the introduction of a stop mutation in the open reading frame of the TET2 protein, and preferably before at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

As an example, said nonsense mutations are selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, Q1834Stop and W1847Stop; preferably in the group comprising or consisting of Q321Stop, S354Stop, R544Stop, Q557Stop, R1216Stop, and Y1724Stop.

Also, said nonsense mutation can result in the introduction of a stop mutation inside at least one of the two highly conserved regions shared by the TET2 protein corresponding to i) the 310 amino acid region located near the center of the protein TET2 (amino acids 1134 to amino acid 1444, SEQ ID NO:3), or ii) the 80 amino acid region located near the carboxyterminal end of the protein TET2 (corresponding to amino acid 1843 until amino acid 1922, SEQ ID NO:4).

More preferably, said nonsense mutation results in the introduction of a stop mutation in the open reading frame of the TET2 protein before the 80 amino acid region located near the carboxyterminal end of the protein TET2 (corresponding to amino acid 1843 until amino acid 1922, SEQ ID NO:4). As an example, said nonsense mutation is selected in the group comprising or consisting of Q232Stop, Q321Stop, S354Stop, Q417Stop, R544Stop, R550Stop, Q557Stop, Q574Stop, Q635Stop, Q642Stop, Q685Stop, L699Stop, S792Stop, Q891Stop, Q943Stop, E1026Stop R1067Stop, R1216Stop, Y1225Stop, R1404Stop, L1457Stop, R1465Stop, R1516Stop, Q1524Stop, Q1542Stop, N1624Stop, Y1724Stop, Y1751Stop, L1819Stop, and Q1834Stop.

Also, said nonsense mutation can result in the introduction of a stop mutation in the open reading frame of the TET2 protein inside the 80 amino acid region located near the carboxyterminal end of the protein TET2 (corresponding to amino acid 1843 until amino acid 1922, SEQ ID NO:4). As an example, said nonsense mutation is W1847Stop.

Typical techniques for detecting the presence of a mutation may include restriction fragment length polymorphism, hybridization techniques, DNA sequencing, exonuclease resistance, microsequencing, solid phase extension using ddNTPs, extension in solution using ddNTPs, oligonucleotide ligation assays, methods for detecting single nucleotide polymorphisms such as dynamic allele-specific hybridization, ligation chain reaction, mini-sequencing, DNA "chips", allele-specific oligonucleotide hybridization with single or dual-labelled probes merged with PCR or with molecular beacons, and others.

Advantageously, the alteration is detected on the cDNA or DNA of the TET2 gene by either PCR and sequencing, SNP-array or CGH, all of them being well known for the skilled person.

In molecular biology and bioinformatics, a SNP array is a type of DNA microarray which is used to detect polymorphisms within a population. The basic principles of SNP array are the same as the DNA microarray. These are the convergence of DNA hybridization, fluorescence microscopy, and solid surface DNA capture. The three mandatory components of the SNP arrays are: i) the array that contains immobilized nucleic acid sequences or target; ii) one or more labeled Allele specific oligonucleotide (ASO) probes; and iii) a detection system that records and interprets the hybridization signal (see in Sheils, O., Finn, S, and O'Leary J. (2003) "Nucleic acid microarray: an overview." Current Diagnostic Pathology. 9:155-158).

Comparative genomic hybridization (CGH) is a molecular cytogenetic method of screening a tumor for genetic changes. The alterations are classified as DNA gains and losses and reveal a characteristic pattern that includes mutations at chromosomal and subchromosomal levels. The method is based on the hybridization of fluorescently labeled tumor DNA (frequently fluorescein (FITC)) and normal DNA (frequently rhodamine or Texas Red) to normal human metaphase preparations. Using epifluorescence microscopy and quantitative image analysis, regional differences in the fluorescence ratio of gains/losses vs. control DNA can be detected and used for identifying abnormal regions in the genome. CGH will detect only unbalanced chromosomes changes. Structural chromosome aberrations such as balanced reciprocal translocations or inversions can usually not be detected, as they do not systematically change the copy number (Emanuel B S, Saitta S C. From microscopes to microarrays: dissecting recurrent chromosomal rearrangements. *Nat Rev Genet.* 2007 November; 8(11):869-83. *Review*).

In another preferred embodiment of the invention, the method comprises the step of analyzing the expression of the TET family member 2 gene (TET2).

According to the results obtained by the inventors, the absence of expression or the under-expression of the TET2 protein or the expression of a truncated TET2 protein as disclosed previously is associated with myeloid cancer.

Methods for analyzing the expression of a gene are well known for the man skilled in the art.

In a particular embodiment of the invention, the expression of the TET2 gene is assessed by analyzing the expression of mRNA transcript or mRNA precursors, such as nascent RNA, of said gene.

Such analysis can be assessed by preparing mRNA/cDNA from cells in a biological sample from a subject, and hybridizing the mRNA/cDNA with a reference polynucleotide. The prepared mRNA/cDNA can be used in hybridization or amplification assays that include, but are not limited to, Southern or Northern analyses, polymerase chain reaction analyses, such as quantitative PCR (TAQMAN), and probes arrays such as GENECHIP™ DNA Arrays (AFFYMETRIX).

Advantageously, the analysis of the expression level of mRNA transcribed from the TET2 gene involves the process of nucleic acid amplification, e.g., by RT-PCR (the experimental embodiment set forth in U.S. Pat. No. 4,683,202), ligase chain reaction (BARANY, *Proc. Natl. Acad. Sci. USA*, vol. 88, p: 189-193, 1991), self sustained sequence replication (GUATELLI et al., *Proc. Natl. Acad. Sci. USA*, vol. 87, p: 1874-1878, 1990), transcriptional amplification system (KWOH et al., 1989, *Proc. Natl. Acad. Sci. USA*, vol. 86, p: 1173-1177, 1989), Q-Beta Replicase (LIZARDI et al., *Biol. Technology*, vol. 6, p: 1197, 1988), rolling circle replication (U.S. Pat. No. 5,854,033) or any other nucleic acid amplification method, followed by the detection of the amplified molecules using techniques well known to those of skill in the art. These detection schemes are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

In another particular embodiment, the expression of the TET2 gene is assessed by analyzing the expression of the TET2 protein translated from said gene.

Such analysis can be assessed using an antibody (e.g., a radio-labeled, chromophore-labeled, fluorophore-labeled, or enzyme-labeled antibody), an antibody derivative (e.g., an antibody conjugate with a substrate or with the protein or ligand of a protein of a protein/ligand pair (e.g., biotin-streptavidin)), or an antibody fragment (e.g., a single-chain antibody, an isolated antibody hypervariable domain, etc.) which binds specifically to the TET2 protein. Said analysis can be assessed by a variety of techniques well known by one of skill in the art including, but not limited to, enzyme immunoassay (EIA), radioimmunoassay (RIA), Western blot analysis and enzyme linked immunoabsorbant assay (ELISA).

Polyclonal antibodies can be prepared by immunizing a suitable animal, such as mouse, rabbit or goat, with the TET2 protein (SEQ ID NO:2) or a fragment thereof (e.g., at least 10 or 15 amino acids). The antibody titer in the immunized animal can be monitored over time by standard techniques, such as with an ELISA using immobilized polypeptide. At an appropriate time after immunization, e.g., when the specific antibody titers are highest, antibody producing cells can be obtained from the animal and used to prepare monoclonal antibodies (mAb) by standard techniques, such as the hybridoma technique originally described by KOHLER and MILSTEIN (*Nature*, vol. 256, p:495-497, 1975), the human B cell hybridoma technique (KOZBOR et al., *Immunol.*, vol. 4, p: 72, 1983), the EBV-hybridoma technique (COLE et al., *In Monoclonal Antibodies and Cancer Therapy*, Alan R. Liss, Inc., p: 77-96, 1985) or trioma techniques. The technology for producing hybridomas is well known (see generally Current Protocols in Immunology, COLIGAN et al. ed., John Wiley & Sons, New York, 1994). Hybridoma cells producing the desired monoclonal antibody are detected by screening the hybridoma culture supernatants for antibodies that bind the polypeptide of interest, e.g., using a standard ELISA.

As previously mentioned, mutations in the TET2 gene may trigger the absence of expression or the under-expression of the TET2 protein.

As used herein, the "under-expression" of a polypeptide occurs when the transcription and/or the translation of the gene is affected by the mutation, leading to an expression level in a biological sample that is lower than the standard error of the assay employed to assess expression, and is preferably at least 20% inferior to the normal level of expression of said gene, preferably at least 50% inferior to the normal level of expression of said gene, and most preferably at least 100% inferior to the normal level of expression of said gene.

Therefore, the method of the invention may comprise comparing the level of expression of the TET2 gene in a biological sample from a subject with its expression level in a control (i.e., normal expression level). A significantly lower level of expression of said gene in the biological sample of a subject as compared to the normal expression level is an indication that the patient may develop a myeloid neoplasm.

As used herein, a "control" corresponds preferably to a control sample comprising non-tumoral cells. Preferably, said control corresponds to peripheral blood leukocytes (PBL), and most preferably to a peripheral blood leukocyte immortalized with Epstein Barr Virus.

Thus, the "normal" level of expression of the TET2 gene is the level of expression of said gene in a biological sample of non-tumoral cell. Preferably, said normal level of expression is assessed in a control sample and preferably, the average expression level of said gene in several control samples.

Analyzing the normal expression of the TET2 gene may be assessed by any of a wide variety of well-known methods for detecting expression of a transcribed nucleic acid or translated protein as previously described.

In a preferred embodiment of the invention, said mutation in the TET2 gene induces absence of expression or under-expression of the two highly conserved regions shared by the TET proteins and corresponding to i) the 310 amino acid region located near the center of the protein TET (amino acids 1134 to amino acid 1444, SEQ ID NO:3), and ii) the 80 amino acid region located near the carboxy-terminal end of the protein TET2 (corresponding to amino acid 1843 until amino acid 1922, SEQ ID NO:4), and more preferably of the 80 amino acid region located near the carboxy-terminal end of the protein TET2 (corresponding to amino acid 1843 until amino acid 1922, SEQ ID NO:4).

In a second aspect, the present invention refers to a kit for diagnosing myeloid cancer or lymphoid cancer in a subject comprising at least one nucleic acid probe or oligonucleotide or at least one antibody, which can be used in a method as defined in the present in invention, for detecting the presence of a mutation in the TET2 gene and/or analysing the expression of the TET2 gene.

Preferably, the oligonucleotide is at least one PCR primer, preferably a set of PCR primers is provided, which allows to amplify the TET2 gene or a fragment thereof. The skilled person readily provides such an oligonucleotide or set of PCR primers which allows to amplify a region of the TET2 gene, provided that the nucleic acid sequence of TET2 is well known (Accession number NM_001127208, SEQ ID NO:1) (Current Protocols in Molecular Biology; edited by Fred M. Ausubel et al., supra).

In a preferred embodiment, the kit comprises at least one PCR primer selected in the group comprising SEQ ID NO:5 to SEQ ID NO: 38 (see examples and sequence listing) for detecting the presence of a mutation in the TET2 gene and/or analysing the expression of said gene.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a subportion of the total kit components. The containers may be delivered to the intended recipient together or separately. For example, a first container may contain an enzyme for use in an assay, while a second container contains oligonucleotides. The term "fragmented kit" is intended to encompass kits containing Analyte specific reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

The present kits can also include one or more reagents, buffers, hybridization media, nucleic acids, primers, nucleotides, probes, molecular weight markers, enzymes, solid supports, databases, computer programs for calculating dispensation orders and/or disposable lab equipment, such as multi-well plates, in order to readily facilitate implementation of the present methods. Enzymes that can be included in the present kits include nucleotide polymerases and the like. Solid supports can include beads and the like whereas molecular weight markers can include conjugatable markers, for example biotin and streptavidin or the like.

In one embodiment, the kit is made up of instructions for carrying out the method described herein for diagnosing a myeloid cancer or a lymphoid cancer in a subject. The instructions can be provided in any intelligible form through a tangible medium, such as printed on paper, computer readable media, or the like.

Still a further aspect of the present invention refers to the use, for diagnosing myeloid or lymphoid cancer, of the above-mentioned kit comprising at least one nucleic acid probe or oligonucleotide or at least one antibody, which can be used in a method as defined for detecting the presence of a mutation in the TET2 gene and/or analysing the expression of the TET2 gene.

Advantageously, myeloid cancer is selected in the group consisting of myelodysplastic syndrome, acute myeloid leukemia, myeloproliferative disease and myelodysplatic/myeloproliferative syndrome.

Still advantageously, said lymphoid cancer is selected in the group consisting of lymphoma such as T- or B-cell lymphoma, and more preferentially of T-cell lymphoma.

In still another aspect, the invention relates to the use of a hypomethylating agent for treating a patient suffering from a myeloid or a lymphoid tumour, for which tumour, a TET2 mutation, an absence of TET2 expression or an expression of a truncated TET2 has been detected.

Preferably, said myeloid tumour is not a MDS.

Hypomethylating agent are well known from the skilled person and include, as an example, azacytidine.

In a final aspect, the invention relates to a method for treating a subject suffering a myeloid or a lymphoid tumour, for which tumour, a TET2 mutation, an absence of TET2 expression or an expression of a truncated TET2 has been detected, said method comprising the step of administrating to said subject a therapeutically efficient amount of hypomethylating agent.

Preferably, said myeloid tumour is not a MDS.

Preferably said hypomethylating agent is azacytidine.

A therapeutically efficient amount of hypomethylating agent can be simply determined by the skilled person. As an example of therapeutically efficient amount of azacytidine for treating lymphoid or myeloid tumour, one can cite the regimen which is disclosed in FENAUX et al. (*Blood*, vol. 110, 817, 2007) which is incorporated herein by reference.

In the following, the invention is described in more detail with reference to amino acid sequences, nucleic acid sequences and the examples. Yet, no limitation of the invention is intended by the details of the examples. Rather, the invention pertains to any embodiment which comprises details which are not explicitly mentioned in the examples herein, but which the skilled person finds without undue effort.

EXAMPLES

1. Identification of TET2 Gene Mutation in MDS, MPD and in AML

We identified 6 patients suffering from myeloid cancer (AML (nAML1, nAML2, nAML3) or MDS (MDS01, MDS02, and MDS03)) and harboring an acquired chromosomal translocation associated with a genomic deletion in the vicinity of the chromosome 4 breakpoint at 4q24. These deletions were homozygous in one instance and heterozygous in the other cases and could indicate the location of a tumor suppressor gene in that region.

FISH analyses first permit to narrow the commonly deleted region in these patients to a ~500 kb interval (data not shown). Computer and RT-PCR assisted analyses uncovered the structure of a single gene, Ten Eleven Translocation (TET2) lying in this region (FIG. 1).

TET2 gene comprises 11 exons spread over 150 Kb. The predicted TET2 protein, encoded by exons 3 to 11, belongs to a three-member family (TET family) in human and mouse. Proteins of the TET family share two highly conserved regions with a single orthologous Drosophila protein in their central and carboxy-terminal part (FIG. 1).

The FIG. 1 shows the protein sequence of TET2 (SEQ ID NO:2), highlighting the conserved regions between species (bold).

For TET2, a translational initiation codon situated at the 5' end of exon 3 (Nucleotides 862-864 of the cDNA or 27-29 of Exon 3) was predicted to allow for the synthesis of a 2002 amino acids protein (FIG. 1). An alternative ATG situated in exon 2 (nucleotides 798-800 of the cDNA or 111-113 of Exon 2) will direct the synthesis of 21 more amino acids. Additional starts are not excluded.

TET2 transcript is widely expressed (ONO et al., abovementioned, 2002; LORSBACH et al., abovementioned, 2003), and as suggested by available data, the expression of TET2 was confirmed in human bone marrow and blood tissues by RT-PCR (data not shown). More specifically, TET2 transcripts were detected in umbilical cord blood CD34+ cells, in granulocytes from healthy controls, and in hematopoietic cell lines.

Finally, of these six patients, five harbored a deletion on one chromosome 4 whereas both copies were deleted in MDS01.

The involvement of the same 4q24 region was also found by using a different approach in MPD. Analysis of CD34+ CD38− multipotent progenitors, CD34+CD38+ committed progenitors, and mature cells, led us to identify two subsets of JAK2 V617F MPD at diagnosis with distinct kinetics of hematopoietic expansion (DUPONT et al., Blood, vol. 110 (3), p:1013-21, 2007). The first subset is characterized by a late expansion of the malignant clone; i.e. downstream of the committed progenitor. In contrast, the second subset of patients had an early expansion of the clone, upstream of the committed progenitor. We hypothesized that the second subset of patients had a molecular defect able to promote the early expansion of the malignant clone. Five patients from this second subset (MPD01 to MPD05) were analyzed using high-resolution CGH and SNP arrays to compare presumed clonal cells (granulocytes) versus polyclonal cells (peripheral blood mononuclear cells or lymphocytes) DNA. One primary myelofibrosis (PMF) patient (MPD01) and one polycythemia vera (PV) patient (MPD04) exhibited a large acquired loss-of-heterozygosity (LOH) without copy number modification (uniparental disomy; UPD (20)) ranging from q22 to qter of chromosome 4. The third patient (MPD05) demonstrated an acquired deletion located in the 4q24 region. This 325 kb deletion in MPD05 was included in the 4q24 LOH region of patients MPD01 and MPD04 and contained TET2 as a single candidate gene. This region was normal in the two other studied MPD samples (MPD02 and MPD03).

As the 4q24 region is affected in patients suffering from myeloid neoplasms, and as TET2 localized in this region, the integrity of the TET2 gene might be affected in these patients. Moreover, loss of the two copies of TET2 in patient MDS01 and recurrent loss of one copy in 8 other patients with MDS, MPD or AML designated TET2 as a candidate tumor suppressor gene.

PCR on the TET2 gene was thus performed in order to detect alterations of the TET2 gene in these patients. Importantly, both alleles were analysed in order to detect bi-allelic modifications.

2. Experimental Procedure to Detect Alterations of the TET2 Gene

2.1. Primers Used for the Identification of TET2 Mutations or Deletions (Table 2)

TABLE 2

| SEQ ID NO | Tm (° C.) | Sequences | Amplified region | Length of amplicon |
|---|---|---|---|---|
| 5 | 60.9 | TGAACTTCCCACATTAGCTGGT | 106374235- | 955 |
| 6 | 60.7 | GAAACTGTAGCACCATTAGGCATT | 106375189 | |
| 7 | 62.0 | CAAAAGGCTAATGGAGAAAGACGTA | 106374894- | 836 |
| 8 | 62.0 | GCAGAAAAGGAATCCTTAGTGAACA | 106375729 | |
| 9 | 63.0 | GCCAGTAAACTAGCTGCAATGCTAA | 106375458- | 843 |
| 10 | 62.3 | TGCCTCATTACGTTTTAGATGGG | 106376300 | |
| 11 | 60.0 | GACCAATGTCAGAACACCTCAA | 106376065- | 867 |
| 12 | 60.9 | TTGATTTTGAATACTGATTTTCACCA | 106376931 | |
| 13 | 60.5 | TTGCAACATAAGCCTCATAAACAG | 106376703- | 788 |
| 14 | 60.9 | ATTGGCCTGTGCATCTGACTAT | 106377490 | |
| 15 | 62.1 | GCAACTTGCTCAGCAAAGGTACT | 106377284- | 781 |
| 16 | 62.3 | TGCTGCCAGACTCAAGATTTAAAA | 106378064 | |
| 17 | 60.1 | ATACTACATATAATACATTCTAATTCCCTCACTG | 106381631- | 495 |
| 18 | 61.5 | TGTTTACTGCTTTGTGTGTGAAGG | 106382125 | |

TABLE 2-continued

| SEQ ID NO | Tm (° C.) | Sequences | Amplified region | Length of amplicon |
|---|---|---|---|---|
| 19 | 61.7 | CATTTCTCAGGATGTGGTCATAGAAT | 106383324- | 286 |
| 20 | 61.5 | CCCAATTCTCAGGGTCAGATTTA | 106383609 | |
| 21 | 60.1 | AGACTTATGTATCTTTCATCTAGCTCTGG | 106383864- | 599 |
| 22 | 60.1 | ACTCTCTTCCTTTCAACCAAAGATT | 106384462 | |
| 23 | 60.0 | ATGCCACAGCTTAATACAGAGTTAGAT | 106400093- | 362 |
| 24 | 60.9 | TGTCATATTGTTCACTTCATCTAAGCTAAT | 106400454 | |
| 25 | 61.1 | GATGCTTTATTTAGTAATAAAGGCACCA | 106402226- | 354 |
| 26 | 61.5 | TTCAACAATTAAGAGGAAAAGTTAGAATAATATTT | 106402579 | |
| 27 | 61.7 | TGTCATTCCATTTTGTTTCTGGATA | 106410076- | 361 |
| 28 | 60.5 | AAATTACCCAGTCTTGCATATGTCTT | 106410436 | |
| 29 | 63.0 | CTGGATCAACTAGGCCACCAAC | 106413052- | 774 |
| 30 | 63.0 | CCAAAATTAACAATGTTCATTTTACAATAAGAG | 106413825 | |
| 31 | 61.1 | GCTCTTATCTTTGCTTAATGGGTGT | 106415516- | 748 |
| 32 | 60.5 | TGTACATTTGGTCTAATGGTACAACTG | 106416263 | |
| 33 | 60.5 | AATGGAAACCTATCAGTGGACAAC | 106416016- | 1107 |
| 34 | 60.2 | TATATATCTGTTGTAAGGCCCTGTGA | 106417122 | |
| 35 | 62.0 | CAGAGCTTTCTGGATCCTGACAT | 106416670- | 535 |
| 36 | 60.3 | GCCCACGTCATGAGAACTATACTAC | 106417204 | |
| 37 | 66 | TCTAAGCTCAGTCTACCACCCATCCATA | 106416118- | 570 |
| 38 | 66.7 | TGCTCGCTGTCTGACCAGACCTCAT | 106416671 | |

2.2. PCR

PCR were performed in 20 μL starting from 25-50 ng of DNA on APPLIED BIOSYSTEM PCR 9700.

For each sample: 17 PCR were used to detect the mutations/deletions localized on the TET2 gene. The mix was prepared as below:

| | mix *1 |
|---|---|
| 10X | 2 |
| dNTP 25 mM | 0.15 |
| O1 100 pmol/μl | 0.1 |
| O2 100 pmol/μl | 0.1 |
| hot star (5 U/μl) | 0.2 |
| Water | 15.5-16.5 |
| DNA sample (25 ng/μl) | 1-2 |

We use the following PCR cycles conditions:

| 15' | 94° C. | 1 cycle |
|---|---|---|
| 20 s | 94° C. | 2 cycles |
| 20 s | 56° C. | |
| 30 s | 72° C. | |
| 20 s | 94° C. | 2 cycles |
| 20 s | 54° C. | |
| 30 s | 72° C. | |
| 20 s | 94° C. | 2 cycles |
| 20 s | 52° C. | |
| 30 s | 72° C. | |
| 20 s | 94° C. | 37 cycles |
| 20 s | 50° C. | |
| 30 s | 72° C. | |
| 10' | 72° C. | 1 cycle |

2.3. Sequencing of the PCR Products

Finally, the PCR products sequencing was realized by EUROFINS MWG Biotech (France, 9, rue de la Laponie, 91967 Les Ulis cedex) or by "Département des services commun de l'Institut Cochin" (Plate forme transcriptomique, Hôpital Cochin/Bat G. Roussy/3ème étage, 27 rue du Fg St Jacques, 75014 Paris) with the kit Big Dye terminator V1.1 and 3130 XL sequencing machines (both from APPLIED BIOSYSTEMS).

3. Mutations of the TET2 Gene in Patients Suffering from MDS or AML with Heterozygous 4q24 Deletion

3.1. In Tumoral Cells

TET2 gene integrity was checked on the 4q24 "intact" copy of the 8 abovementioned patients harboring the heterozygous acquired chromosomal translocation associated with a genomic deletion in the vicinity of the chromosome 4 breakpoint at 4q24.

To identify potential mutations of the TET2 gene in these alleles, the sequence of the eight coding exons and of their splice sites in the DNA extracted from bone marrow samples of 8 patients having a 4q24 rearrangement was investigated by PCR as described previously.

Table 3 discloses the status of both alleles of the TET2 genes in patients suffering from MPD, MDS or AML and having a 4q24 deletion on one allele:

| Patient | Copy 1 | Copy 2 | Disease |
|---|---|---|---|
| nAML1 | R1896M | Deletion | AML |
| nAML2 | I1873T | Deletion | AML |
| nAML3 | Deletion | Unknown | AML |
| MDS01 | Deletion | Deletion | RA |
| MDS02 | FS after L560 (Exon 3) | Deletion | RA |
| MDS03 | N1624Stop (Exon 11) | Deletion | RA |
| MPD01 | Q557Stop | Q557Stop | PMF |
| MPD04 | Deletion (1237 to 1239) | Deletion (1237 to 1239) | PV |
| MPD05 | Deletion | Wild type | PV |

Comparison of the sequence obtained from the patients with the wild type counterpart identified nucleotide changes in 6 patients (Table 3). Changes were not attributable to identified polymorphisms. Patient nAML1 and nAML2 harbored single nucleotide changes, leading to an I1873T in patient nAML2 and to R1896M in patient nAML1. Patient MDS03 exhibited a CAG to TAG changes, introducing a stop codon instead of N1624. Patient MPD01 exhibited a single nucleotide change, introducing a stop codon instead of NQ557. Patient MDS02 had a 4 base pair insertion, leading to a stop codon 6 amino acids after L560. Patient MPD04 had an in frame 9-nucleotide deletion. No notable nucleotide changes were observed in DNA of patient nAML3. Patient MDS01 harbors a bi-allelic deletion of the TET2 gene.

3.2. In Non-Tumoral Cells of the Patients

To confirm that the observed changes were somatically acquired, we analyzed DNA from non-tumoral samples when available.

In patient nAML2, the T to C change was not observed in DNA from EBV-transformed B cell population (FIG. 2). In patient nAML1, the analyses of a sample obtained after auto-bone marrow transplantation demonstrated an inversed ratio between the wild type G and the mutated T, when compared to the diagnosis sample (data not shown). Similarly, the signal corresponding to the mutated T is almost absent in DNA extracted from stimulated PBL from patient MDS03 (FIG. 2). This analysis has also shown the absence of mutation for MPD04 or of deletion for MPD05 in non-tumoral cells (data not shown). This analysis has further shown that a small amount of residual wild-type sequence is detected in peripheral mononuclear cells from patient MPD01 (data not shown).

The FIG. 2 shows the sequence traces obtained by sequencing of PCR on samples obtained from the two patients nAML2 and MDS03, and showing that the mutation only occurs in the tumoral (R: reverse primer and F: forward primer) and in non-tumoral samples (NT or PBL).

Taken together, these results demonstrate that the two copies of the TET2 gene is targeted in patients suffering from diverse myeloid neoplasm, and this through two different events, a chromosomal translocation associated with a deletion and point mutations, establishing TET2 as a tumor suppressor gene.

4. Alteration of the TET2 Gene in Patients Suffering from MDS or AML without Cytogentically Detectable 4q24 Deletion To establish whether mutation of TET2 could also occurs independently of a chromosomal abnormality, DNA from bone marrow samples of 309 additional patients with different subtypes of MDS (n=81), sAML (n=21), CMML (n=9), $JAK2^{V617F}$ positive MPD (n=181), and $JAK2^{V617F}$ negative MPD (n=17) without known 4q24 abnormality was analyzed by PCR as previously described.

Table 4 discloses the status of the identified TET2 defect in patients suffering from MDS or AML:

| Patient | TET2 defect | Disease |
|---|---|---|
| sAML2 | S1898F | sAMLII |
| sAML4 | FS (Exon3) | sAMLII |
| sAML5 | FS (Exon11) | sAMLII |
| sAML6 | FS (Exon11)/Q891stop | sAMLII |
| sAML7 | Q943Stop | sAMLII |
| MDS04 | K1299E/R544Stop | RA |
| MDS07 | No amplification Ex11 | RA |
| MDS30 | FS (Exon3) | RA |
| MDS09 | FS (Exon3) | RARS |
| MDS35 | Y1225Stop Exon6 | RARS |
| MDS10 | Y1724Stop/Q321Stop | RCMD-RS |
| MDS28 | FS (Exon3) | RCMD-RS |
| MDS18 | FS (Exon11) | RAEB1 |

-continued

| Patient | TET2 defect | Disease |
|---|---|---|
| MDS27 | FS (Exon3)/FS (Exon3) | RAEB1 |
| MDS33 | FS (Exon4) | RAEB1 |
| MDS39 | L1872P | RAEB1 |
| MDS40 | FS (Exon11) | RAEB1 |
| MDS42 | L1872P/I1873T Mutation of splice acceptor | RAEB1 |
| MDS34 | Site Exon5 | RAEB2 |
| MDS41 | FS (Exon11) | RAEB2 |
| CMML01 | Q685Stop | CMML |
| CMML02 | FS (Exon3)/R1067Stop | CMML |

RA, refractory anemia; RARS, refractory anemia with ringed sideroblasts; RARS-T, RARS with thrombocytosis; RAEB, refractory anemia with excess blasts; RAEB1: blasts 5-9%; RAEB2: blasts 10-19%; AML, acute myeloid leukemia; FAB, French American British classification; del, deletion; FS, frame shift; ND, not done. All MDS/AML tested (22/27) were negative for $JAK2^{V617F}$. MDS03 was studied at the RAEB1 and RAEB2 phases. Two successive samples of patient MDS34 were analyzed. Selected patients analyzed during the initial part of the study appear in bold.

Table 5 discloses the status of the identified TET2 defect in patients suffering from MPD:

| Patient | TET2 defect | Disease | JACK2 and MPL status |
|---|---|---|---|
| MPD18 | R1216stop | PV | $JAK2^{V617F}$ |
| MPD20 | FS Ex11 | PV | $JAK2^{V617F}$ |
| MPD35 | S354stop | ET | $JAK2^{V617F}$ |
| MPD43 | FS Ex3/R550stop | post ET MF | $JAK2^{V617F}$ |
| MPD45 | FS Ex3 | PV | $JAK2^{V617F}$ |
| MPD69 | FS Ex7/FS Ex11 | PV | $JAK2^{V617F}$ |
| MPD74 | FS Ex3 | PMF | WT |
| MPD81 | FS Ex6 | ET | $JAK2^{V617F}$ |
| MPD86 | FS Ex5/R1404stop | PV | $JAK2^{V617F}$ |
| MPD89 | FS Ex10 | PV | $JAK2^{V617F}$ |
| MPD92 | R1302G | PMF | $JAK2^{V617F}$ |
| MPD96 | W1847stop | ET | $JAK2^{V617F}$ |
| MPD99 | FS Ex3 | ET | $JAK2^{V617F}$ |
| MPD120 | FS Ex3 | PV | $JAK2^{V617F}$ |
| MPD130 | FS Ex3 | ET | $JAK2^{V617F}$ |
| MPD132 | FS Ex3 | PV | $JAK2^{V617F}$ |
| MPD133 | G1869W | ET | $JAK2^{V617F}$ |
| MPD142 | FS Ex3 | PV | $JAK2^{V617F}$ |
| MPD149 | FS Ex6 | ET | $JAK2^{V617F}$ |
| MPD158 | FS Ex3 | PV | $JAK2^{V617F}$ |
| MPD163 | Q1542stop | ET | $MPL^{W515L}$ |
| MPD164 | FS Ex3 | PMF | $JAK2^{V617F}$ |
| MPD183 | FS Ex7/Q635stop | PV | $JAK2^{V617F}$ |
| MPD200 | FS Ex3/FS Ex11 | ET | WT |

PMF, primary myelofibrosis,
PV, polycythemia vera,
ET, essential thrombocythemia.
WT: negative for $JAK2^{V617F}$ and $MPL^{515}$ mutations.
FS, frame shift.

Obvious abnormalities of TET2 coding sequence were observed in 45 patients, resulting in conserved amino acid substitution, generation of in frame stop codons, or frame shifts (Tables 4 and 5. In one additional patient (MDS07), amplification of the 5' part of exon 11 only resulted in trace amounts of PCR fragment despite the use of several conditions and primers pairs (data not shown), which was attributed to an uncharacterized structural genomic rearrangement affecting this region. Defects of TET2 were observed in all types of MDS (22/111) and BCR-ABL negative MPDs associated with JAK2 V617F (21/181), or MPL W515L/K (1/6) or devoid of these mutations (2/11).

The results demonstrate that TET2 defects can be identified in unselected diverse myeloid disorders with a high prevalence (46/309=17%). As an example, patient MDS04 showed two changes leading to K1299D and R544Stop. Patient MDS10 had two stop mutations, Y1724Stop and Q321Stop. Patient sAML2 had a point mutation leading to S1898F. These observed mutations may result in a partial or total loss of function of the TET2 protein. It can be anticipated that other defects such as deletions of the TET2 gene might have been missed and thus the estimated the frequency of TET2 defects in these malignancies would be underestimated.

Overall, in 19/55 of the patients with TET2 defects, two different mutations were detected, likely targeting both copies of TET2. This point was confirmed by sequencing individual molecules after subcloning of the PCR fragments obtained from patient MDS42. A single defect was observed in 35/55 samples suggesting that TET2 haploinsufficiency may play a role in these malignancies.

5. TET2 Mutations Target Early Progenitors in MDS

MDS are myeloid malignancies originating from a HSC. If the mutations observed in TET2 are causative, they should also be observed in the HSC. To investigate this, we first analyzed the presence of the TET2 defects in CD34$^+$ cells, which include HSC and hematopoietic progenitors, from 4 MDS patients (MDS03, MDS09, MDS28, MDS35).

The FIG. 3a shows the sequencing histograms of sorted CD34$^+$ cells from patient MDS03 at RAEB1 and RAEB2 phases. Sequences observed in unsorted bone marrow sample and of wild-type control are shown for comparison purposes. Asterisks indicate the mutated nucleotide.

The FIG. 3b shows the PCR-RFLP analysis of DNA isolated from sorted MDS03 CD34$^+$CD38$^-$ and CD34$^+$CD38$^+$ cells at RAEB1 phase. Amplified fragments were digested using Tas1 and size-fractionated by agarose migration. The proportion of mutated TET2 mutated was evaluated by measuring the intensities of the mutated (mut) or wild-type (wt) signals relative to that of the signal generated by both alleles (wt+mut). Undigested (−) and digested (+). (ctl) correspond to PCR products from control DNA. MW: molecular weight.

The FIG. 3c shows the PCR-RFLP analysis of TET2 directly performed from sorted CD34$^+$CD38$^-$ and CD34$^+$CD38$^+$ cells from MDS09 patient using BseLI endonuclease.

The FIG. 3d shows the genotyping by PCR-RFLP using BseLI of sorted CD34$^+$CD38$^-$ and CD34$^+$CD38$^+$ cells from patient MDS09 grown at one cell per well. Annotations are as in b. The histograms represent the fraction of clones with wild-type (gray) or mutated (black) TET2. Note the absence of wild-type fragment in CD34$^+$CD38$^+$ clones indicated by asterisks.

In all cases, the mutated TET2 sequence could be detected (FIG. 3). In one of these patients (MDS03), CD34$^+$ cells could be analyzed at refractory anemia with excess of blasts 1 (RAEB1) and RAEB2 phases. Interestingly, the wild-type sequence was detected at the RAEB1 phase, but not at the RAEB2 phase (FIG. 3a), suggesting expansion of TET2 mutated progenitors with the disease progression.

We next fractionated the CD34$^+$ from these four patients into CD34$^+$CD38$^-$ (corresponding to HSC and multipotent progenitors) and CD34$^+$CD38$^+$ (corresponding to more mature progenitors) cell populations using CD34-PeCy5 and CD38-FITC antibodies (IMMUNOTECH) using a FACS-Diva cell sorter (BECTON DICKINSON). In two patients (MDS03 and MDS09), PCR-RFLP analysis was used to distinguish mutated and wild-type TET2 sequences. The mutated TET2 burden increased in both patients from CD34$^+$CD38$^-$ to CD34$^+$CD38$^+$ cells (16% to 54% in MDS03, and 26% to 48% in MDS09) (FIG. 3b, c). Further analysis was performed at the cellular level, by seeding single hematopoietic progenitors from MDS09.

Sorted CD34$^+$CD38$^-$ cells from MDS09 bone marrow were seeded at one cell per well on a confluent layer of the MS5 cell line in MEM alpha medium supplemented with 10% FBS (STEM CELL TECHNOLOGIES), and a cocktail of early cytokines (thrombopoietin (Tpo) interleukin-3 (IL3), FLT3-L, Stem Cell factor (SCF) and interleukin-6 (IL6)). CD34$^+$CD38$^+$ cells were also seeded at one cell per well using the same combination of "late" cytokines (SCF, IL3, erythropoietin (Epo) and granulocyte-colony stimulating factor (G-CSF)) as used in methylcellulose cultures (DUPONT et al., abovementioned, 2007). After three weeks (CD34$^+$CD38$^-$) or 10 days (CD34$^+$CD38$^+$), individual clones were collected for further genotyping.

The results show that TET2 mutation was identified in 8 out of 32 (25%) and 18 out of 30 (60%) clones derived from CD34$^+$CD38$^-$ and CD34$^+$CD38$^+$ cells, respectively (FIG. 3d). Interestingly, the wild-type copy of TET2 was not always amplified from clones bearing a mutated TET2, suggesting its loss in a minority of the cells.

For the two other patients (MDS28, MDS35), the increase in TET2 mutation burden from CD34$^+$CD38$^-$ to CD34$^+$CD38$^+$ samples was evaluated with the sequence graphs. To be more accurate, the amplified fragments from MDS28 samples were subcloned and individual bacterial clones were sequenced. The mutated copy was barely detectable in the CD34$^+$CD38$^-$ population of MDS28 whereas it represented 32% of TET2 sequences in the CD34$^+$CD38$^+$ population (data not shown). These data indicate that TET2 mutations target a CD34$^+$CD38$^-$ cell and that in MDS TET2 mutated burden increases from immature to mature progenitors, suggesting a selective advantage of the mutated cells during early phases of hematopoietic differentiation.

In three sAML samples (sAML2, sAML4, sAML5), TET2 mutations were also found in CD34$^+$ cells (data not shown). When analyzed, in sAML4, sAML5 sorted cells, no marked changes in the mutated TET2 burden were observed between CD34$^+$C38$^-$ and CD34$^+$CD38$^+$ populations.

6. Prevalence and Prognosis Impact of TET2 Mutations in MDS

So as to establish the prevalence and prognosis impact of TET2 mutations in MDS, we retrospectively analyzed TET 2 mutations and their prognosis value, in 204 MDS and AML post MDS enrolled in GFM multicenter trials (41 RA/RCMD/MDS-U/5q-, 18 RCMD, 28 RARS/RCMD-RS/RARS-T, 43 RAEB 1, 32 RAEB 2, 44 AML post MDS). TET2 mutations analysis was realized as described previously and the results are presented in table 6.

Table 6 discloses the status of the identified TET2 defect in patients suffering from MDS or AML:

| Disease | Nucleotide change | Consequence |
| --- | --- | --- |
| MDS02 G04 | delA 3166 | p.Gln769 FS |
| MDS 04 | c.4755A > G + c.2490C > T | p.[Lys1299Glu] + [Arg544X] |

| Disease | Nucleotide change | Consequence |
|---|---|---|
| MDS01 A08 | insT 3465 | p.Pro869 FS |
| MDS01 A11 | c.5071 C > T | p.Arg1404 STOP |
| MDS02 C01 | delT 2685 + insA 3009 | p.Ser609 FS + p.His717 FS |
| MDS01 B03 | insA 5540 | p.Tyr1560 FS |
| MDS01 B11 | c.2913 C > T | p.Gln685 STOP |
| sAML1 | | del/wt |
| MDS 07 | | No amplification of 5' Exon 11 |
| MDS01 C08 | delC 6360 | p.Gln1834 FS |
| MDS01 C09 | c.3532C > T + insA 5757 | p.Cys1633 FS + p.Gln891 STOP |
| MDS01 D01 | c.6475T > C | p.Leu1872Pro |
| MDS02 H02 | c.4384A > G + c.4625C > G | p.Ile1175Val + p.Tyr1255 STOP |
| sAML2 | | Ser1898Phe |
| MDS01 D06 | del 2834_2835 | p.His658 FS |
| MDS 10 | | p.Gln530 FS + p.Tyr1724 STOP |
| MDS02 C12 | delT 2685 + c.6316T > G | p.Ser609 FS + p.Leu1819 STOP |
| MDS02 D01 | delC 3009 | p.His717 FS |
| MDS 01 | | del/del |
| MDS 02 | | del/p.Arg581 FS |
| MDS01 E02 | c.5730C > T | del/Gln1624 STOP |
| MDS02 D04 | delT 2944 | p.Leu699 STOP |
| MDS01 E06 | insC 3151 + p.5406C > T | p.Gln764 FS + Arg1516 STOP |
| MDS01 E07 | c.6475T > C + c.6478T > C | p.Leu1872Pro + p.Ile1873Thr |
| MDS01 E08 | delC 2448 + delA 4130 | p.Gln530 FS + p.Lys1090 FS |
| MDS01 F02 | p.6360C > T | p.Gln1834 STOP |
| MDS01 F04 | delG 2994 | p.Glu711 FS |
| MDS02 E01 | c.6114T > G + insT splice site | p.Tyr1751 STOP + mutation of splice site exon 8 |
| MDS01 F06 | p.3688C > T + delA 6507 | p.Gln943 STOP + p.Thr1883 FS |
| MDS01 G01 | delG 4271 + c.6478T > C | p.Glu1137 FS + p.Ile1873Thr |
| MDS01 G03 | p.3688C > T | p.Gln943 STOP |
| nAML2 | c.6478T > C | del/p.Ile1873Thr |
| MDS01 G05 | delC 5222 | p.Leu1457 STOP |
| MDS01 F11 | dupT 3914 | p.Glu1026 STOP |
| MDS01 G06 | delA 2935 + del5828_5843 | p.Glu692 FS + p.Met1656 FS |
| MDS02 A12 | p.4969G > A + del6396_6531 | p.Gly 1370 Glu + p.Val1846 FS |
| MDS01 G7/8 | g.4366-1G > T | mutation of splice acceptor site exon5 |
| MDS02 E10 | insCT 3581 | pGly 908 FS |
| MDS02 H12 | delG 4932 + del5521_5524 | p.Glu1357 FS + pThr1554 FS |
| MDS02 G03 | insC 3151 + insC 6507 | p.Gln764 FS + p.Thr1883 FS |
| MDS02 G01 | delG 5133 + del6511_6512 | p.Asp 1425 FS + p.Pro1885FS |
| MDS02 G07 | p.5253C > T | p.Arg1465 STOP |
| MDS02 C07 | c.4561A > T | p.Glu1234Val |
| MDS02 B07 | c.2109C > T | p.Gln417 STOP |
| nAML1 | c.6547G > T | del/p.Arg1896Met |
| MDS02 E11 | c.2784C > T + p.5253C > T | p.Gln642 STOP + p.Arg1465 STOP |
| MDS01 H05 | c.4515C > T | p.His1219 Tyr |
| MDS02 H06 | del1264_1666 | p.Glu135 FS |
| MDS02 B08 | delA4327 + c.5020A > G | p.Asn1156 FS + Asn 1387Ser |
| MDS02 D10 | insC 3151 + c.4891C > A | p.Gln764 FS + p.Ala1344 Glu |
| MDS02 B02 | delT 5570 + insC splice site | p.Leu1637 FS + mutation of splice site exon 8 |
| MDS01 F01 | insT3995 + c.4059A > T | p.Glu846 FS + p.Arg1067 STOP |
| MDS02 B11 | c.4673C > G + Del6049_6050 | p.Cys1271 Trp + p.Asp1830 FS |
| MDS01 E09 | insG 5119 | p.Leu 1420 FS |
| MDS | c.5430C > T | p.Gln1524STOP |
| MDS | c.5177dupA | p.Arg1440FS |
| MDS | c.5583_5605 del | p.Pro1575FS |
| MDS | c.5310 A > G | p.Lys1197Arg |
| MDS | c.2375C > A | p.Ser792STOP |

We found 59 mutations of the TET2 gene by direct sequencing of exons 3 to 11 (27 frameshifts, 21 nonsense and 11 missense mutations in conserved domains) in 43/204 pts (Table 6). The frequencies according to the WHO subtypes were 21.8% in RA, 5.2% in RCMD, 21.4% in RARS/RARS-T/RCMD-RS, 34.9% in RAEB 1, 15.6% in RAEB 2, 19% in AML post MDS. Other anomalies of the 4q24 region were found including a deletion in 1/46 pts analyzed by CGH and 3 LOH in 3/22 patients analyzed by SNP arrays and 2 deletions in 5/23 pts analyzed SNP arrays. Thus, the overall prevalence of 4q24 anomalies was 21.6% patients (44/204). 20 patients had two anomalies of TET2 identified by direct sequencing (17 patients), or sequencing plus SNP array (3 patients), indicating that the two copies of the gene were targeted in 43.5% of mutated patients.

Then, univariate and multivariate survival analyses were conducted with Cox hazard proportional model so as to establish the prognosis impact of TET2 mutations. Comparison between the 43 patients with TET2 coding sequence mutations and unmutated patients found no significant differences in initial characteristics for sex, age, previous exposure to chemo or radiotherapy, Hb level, WBC count, ANC, plt count, % bone marrow blasts, multilineage dysplasia, WHO and FAB subtypes, karyotype and IPSS.

The analysis revealed that five-year survival (Kaplan-Meier curve) was significantly increased in TET2 mutated patients compared to unmutated patients (p<0.05).

7. Rearrangement of the TET2 Gene in Patients Suffering from MPD with 4q24 abnormality detected by SNP or CGH arrays analyses Among 35 MPD samples, 4 patients had a LOH by SNP arrays and were analyzed for mutations within TET2 gene on both alleles. In 3 of the 4 samples a clear mutation or deletion was observed.

Table 7 discloses the status of both alleles of the TET2 genes in patients suffering from MPD:

| Patient | Copy 1 | Copy 2 | Disease |
|---|---|---|---|
| IGR-1 | Q557Stop | LOH | PMF |
| IGR-2 | Deletion 1237-1239 | LOH | PV |
| IGR-3 | whole gene deletion | No abnormality | PV |
| IGR-4 | unknown | LOH | ET |

In table 7, "PMF" stands for Primitive Myelofibrosis, "PV" for polycythemia Vera, "EV" for Essential Thrombocytosis. All these diseases are Class II MPDs.

Patient IGR-2 harbored a 9 base pair in frame deletion lead to the loss of three amino acids, P1237, L1238, S1239. As shown by SNP analyses and by the analyses of the sequence traces, patients IGR-1 and IGR-2 had lost the other TET2 copy. None of the mutations were observed in non-tumoral cells of the patients. These data establish that inactivation TET2 participates to the development of MPD.

Systematic sequencing of TET2 genes in 17 other patients revealed two patients with a stop codon on one allele (IGR17: S354Stop, IGR-18:R1216Stop) and one patient with one nucleotide deletion leading to a frameshift in exon 11.

8. Analysis of the Acquisition of the TET2 Rearrangement

Recent evidence indicate that JAK2$^{V617F}$ may not be the initiating event in some MPDs. Therefore we used MPD samples to evaluate the relative roles of TET2 defects and JAK2$^{V617F}$ mutation in these diseases and to gain insight into the sequence of the acquisition of the mutations. We first analyzed hematopoietic progenitors from five MPD patients with mutations in both genes, like the patient IGR2.

For MPD samples, Immature CD34$^+$CD38$^-$ cells were seeded at one cell per well for four to six weeks in conditions permitting simultaneous B, NK and granulocytic differentiations (lympho-myeloid differentiation) as described (DUPONT et al., abovementioned, 2007), whereas more mature CD34$^+$CD38$^+$ cells were grown in erythroid/granulocytic methylcellulose assays. Individual clones were collected for analysis of B, NK, and granulocytic differentiation by flow cytometry, and genotyping. CD34$^+$CD38$^+$ cells were seeded at 1,500 to 3,000 cells per culture dish in 2% standard methylcellulose supplemented with 37% FBS (STEM CELL TECHNOLOGIES), and a cocktail of cytokines as described (DUPONT et al., abovementioned, 2007)). Individual colonies grown from burst-forming units-erythroid (BFU-E) and colony-forming units-granulocyte/macrophage (CFU-GM) were picked on day 14. The obtained clones were analyzed for the presence of both molecular defects.

The results have shown that in all patients tested, sequence analyses revealed that both TET2 and JAK2 defects were present in clones derived from lympho-myeloid progenitors (data not shown). Interestingly the JAK2$^{V617F}$ mutation was not observed in the absence of TET2 defect whereas TET2 mutation could be observed in the absence of JAK2$^{V617F}$. These results demonstrate that, as in MDS, the TET2 mutation is present in immature progenitors of MPD patients and indicate that TET2 defects precede JAK2 mutation during the evolution of the disease.

To further define the role of the TET2 mutations in the amplification of the malignant clone, we compared the genotype of colonies derived from immature (CD34$^+$CD38$^-$) progenitors to that of erythroid and granulocytic colonies derived from committed (CD34$^+$CD38$^+$) progenitors.

The results shown that in three MPD patients (MPD01, MPD04, MPD35), almost all the colonies at different stages of hematopoietic differentiation harbored a TET2 mutation, suggesting that the TET2 mutated clone expanded at early steps of hematopoiesis (data not shown). In 2 other patients (MPD05, MPD20), most immature progenitors were wild-type whereas most committed progenitors were mutated for TET2. Within JAK2 wild-type progenitors from these two patients, we observed an increase in the proportion of clones with TET2 defects from the immature (2/37 and 0/34, respectively) to the committed (10/23 and 9/54, respectively) progenitor stage. Taken together, our results indicate that the selective advantage of the TET2 mutated clone at early differentiation steps is independent of the JAK2$^{V617F}$ mutation.

Overall, these data from MPD samples demonstrate that TET2 defects (i) occur at early steps of hematopoietic differentiation and that (ii) they may precede the occurrence of the JAK2$^{V617F}$ mutation and (iii) they give a selective advantage to the clone as it proceeds to myeloid differentiation.

9. Engraftment and Proliferation of TET2 Mutated Cells In Vivo

We reasoned that loss of function of TET2 could confer a growth advantage to the hematopoietic stem cells. To demonstrate that the TET2 mutations occur in a HSCs with NOD-SCID repopulating capacity, we used a xenotransplantation assay by injecting, into NOD-SCID mice, CD34$^+$ cells isolated from JAK2$^{V617F}$ MPD patients with TET2 mutations.

CD34$^+$ cells (1 to 10×10$^5$ cells) from JAK2$^{V617F}$ MPD patients with TET2 mutations were injected intravenously into sub-lethally irradiated (3.5 Gy) NOD-SCID mice, previously treated with 200 µg of anti-CD122 antibody (JAMES et al., Blood, vol. 112(6), p:2429-36, 2008). Bone marrow was obtained with heparinized syringue from the right femur at 3, 6 and 12 weeks after transplantation and mice were sacrificed at week 15. Human cell engraftment was evaluated by the sum of human leukocytes (CD45$^+$) and erythroid populations (CD45$^-$CD36$^+$ and CD45$^-$CD36$^-$GlycophorinA$^+$), as assessed by flow cytometry. Bone marrow cells were seeded in culture dish and 96-well plates for methylcellulose and long-term culture-initiating cell (LTC-IC) assays, respectively allowing the selective growth of human cells as described in JAMES et al. (abovementioned, 2008). Individual colonies were subsequently picked and genotyped.

We first compared the kinetics of chimerism after transplantation of CD34$^+$ cells from these JAK2$^{V617F}$ MPD patients with TET2 mutations and from three JAK2$^{V617F}$ MPD devoid of TET2 defects (MPD09, MPD11, MPD27).

The FIG. 4a shows the percentage of human CD45-positive cells in mouse bone marrow monitored at 3, 6, 12, and 15 weeks post-transplant. MPD01 and MPD04 are patients with TET2 defects whereas MPD09, MPD11, and MPD27 are control patients devoid of identified TET2 defect.

The FIG. 4b shows the flow cytometric analysis of human cells present in NOD-SCID bone marrow 15 weeks after transplantation with 3×10$^5$ CD34$^+$ cells from patients MPD04 and MPD09. The percentages of human CD45 (hCD45)-positive myeloid and lymphoid cells were determined using anti-CD45-PC7, anti-CD33-APC, and anti-CD19-PE antibodies.

The results show that human cells from the three patients devoid of TET2 mutation disappeared with time (FIG. 4a).

In contrast, the percentage of human cells in the bone marrow of mice engrafted with cells from the two TET2 mutated patients increased with time (FIG. 4a). In these mice, differentiation was skewed toward myeloid progenitor expansion, at the expense of lymphoid progenitors, as judged from CD33 and CD19 antigen flow cytometry analyses (FIG. 4b) unlike what is observed with normal HSCs wherein lymphoid differentiation is favored (ROBERT-RICHARD et al., *Haematologica*, vol. 17(3), p:637-41, 2003).

Human cells present in the mouse bone marrow 15 weeks after transplantation (W15) were tested in in vitro progenitor and LTC-IC assays, and analyzed for the presence of TET2 and JAK2 mutations. The TET2 defects were found in pooled W15 CFU-derived colonies from both MPD01 and MPD04 samples, and in all individual human LTC-IC and progenitors present in the mice (data not shown). The results were compared with progenitor assays performed immediately before engraftment (D0). All colonies arising from patients' committed progenitor cells (D0 CFU) harbored TET2 mutation.

These results demonstrate that TET2 mutation occurs in a HSC. Interestingly, the results have further shown that the proportion of progenitor cells carrying only the TET2 mutation increased upon transplantation at the expense of cells carrying both TET2 and JAK2$^{V617F}$ mutations. These cells are thought to reflect the original HSC population. Therefore, these observations indicate that TET2 mutated HSCs with a wild-type JAK2 are more numerous than the TET2/JAK2 double mutant HSCs, further establishing the mutation of TET2 as a "pre-JAK2$^{V617F}$" event in these patients.

Therefore our data are compatible with the hypothesis that TET2 defects endow the HSC with a selective engraftment advantage independently of JAK2$^{V617F}$.

10. Positions of the Identified Mutations on the TET2 Gene

We report that the inactivation of TET2 is a common early event in human MDS, MPD and sAML and that the frequencies of TET2 mutation in unselected patient series were 15/81=18.5% in MDS, 2/9=22% in CMML, 24/198=12% in MPD and 5/21=24% in sAML. It must be noticed that in these analyses we did not consider amino acid changes occurring outside of the conserved domains. Sequencing of the TET2 gene using the couples of primers identified in table 1 permits to identify a number of mutations in the TET2 gene (FIG. 5).

The FIG. 5 shows the locations of some of the identified mutations of the TET2 gene distributed along the protein sequence.

Mapping of the identified TET2 mutations on the TET2 sequence suggest an essential role for the carboxy terminal conserved region (amino acids in position 1860 to the position 1950) in the function of the protein.

Finally, the detection of acquired genetic defects targeting the two TET2 copies in 19 of the 55 patients with TET2 alteration establishes this gene as a bona fide tumor suppressor gene of human myeloid malignancies. TET2 defects are observed in both MDS and MPD, which are two distinct myeloid diseases. It is therefore likely that their characteristic clinical and biological phenotypes require at least another additional cooperating event. In MPD samples with both TET2 and JAK2 mutations, TET2 mutations likely occur first in the natural history of the disease, preceding the occurrence of JAK2$^{V617F}$ mutation.

11. Identification of TET2 Gene Mutations in Familial MPD

Families with at least 2 affected patients with MPD were collected through a national network as previously described (BELANNE-CHANTELOT et al., abovementioned, 2006). The diagnoses of MPD were reviewed based on the 2008 World Health Organization criteria.1 All participants gave their written informed consent.

In a first step, we analyzed 15 probands of families compatible with an autosomal dominant inheritance, in search for a constitutional event that would account for these familial cases. Elected probands mostly suffered from PV or ET. In a second step, the analysis was extended to patients with hematological complications and to relatives of patients with TET2 variants.

Altogether, we analyzed 61 patients for mutations in the 6009 by coding sequence of the TET2 gene from 42 MPD families (40 European, 2 African: families F3 and F4) including at least two available affected patients with MPDs. Thirty-four patients displayed a simple phenotype consisting of either PV (15), ET (12) or PMF (7) with no observed hematological evolution of the disease after a follow-up period of 12 years. Twenty-seven other patients had experienced an evolution in their MPD phenotype: PV evolving into myelofibrosis (post PV MF, 5) or into AML (12); ET evolving into MF (4) or AML (5), or PMF turning into AML (1).

The analysis was performed by polymerase chain reaction (PCR) on genomic DNA extracted from buccal swabs after heating at 95° C. for 10 minutes to release genomic DNA. Purified PCR products were sequenced using the BIGDYE TERMINATOR chemistry (APPLIED BIOSYSTEMS) and run on an APPLIED BIOSYSTEMS 3100 capillary sequencer.

The JAK2V617F mutational status was determined as previously reported in BELANNE-CHANTELOT et al. (abovementioned, 2006).

The whole coding region of the TET2 gene was sequenced as described previously. Two multiplex PCRs were set up to estimate the copy number of each TET2 exon using the quantitative multiplex PCR of short fluorescent fragments (QMPSF) method (CHARBONNIER et al., *Cancer Res.*, vol. 60, p:2760-2763, 2000). Two additional primer pairs amplifying short sequences of either the F9 or the DSCR1 gene were used as internal controls. PCR products were separated by capillary electrophoresis using a DNA genetic analyzer (ABI 3100). The analysis is based on the comparison of the peak heights generated from the tested DNA sample and the control DNA. The quantitative estimation of the height of peaks was determined using commercially available analysis software (GENEMAPPER VERSION 4.0, APPLIED BIOSYSTEMS).

Table 8 shows the TET2 mutations identified in 12 MPD patients.

| | | | | TET2 | | |
|---|---|---|---|---|---|---|
| Patients | Phenotype | Evolution | JAK2 | Location | Nucleotide change | Proteic change |
| P1 (F1) | PV | MF | 95 | Exon 11 | c.5695delC | p.Leu1899fs |
| P2 (F2) | PV | MF | 63 | Intron 7 | c.3954 + 2T > A | p.? |
| P3 (F2) | PV | | 49-82 | Exon 3 | c.3138delT | pLeu1046fs |

| Patients | Phenotype | Evolution | JAK2 | TET2 Location | Nucleotide change | Proteic change |
|---|---|---|---|---|---|---|
| P4 (F3) | ET | PV > MF > AML | 23-47 | Exon 3 | c.1648C > T | p.Arg550X |
|  |  |  |  | Exon 3 | c.2570delA | p.Asn857fs |
| P5 (F3) | ET | MF > AML | 0 | Exon 3 | C2058A > T | p.Arg686Ser |
| P6 (F4) | ET | AML | 0 | Exon 3 | C1955delA | p.Gln652fs |
|  |  |  |  | Exon 3 | c.2490dupA | p.Gln831fs |
| P7 (F4) | ET |  | 39 | Intron 4 | c.3500 + 3A > C | p.? |
| P8 | ET | MF | 90 | All exons | c.1.4999_5014del16 | p.0 |
| P9 | PMF |  | 36 | Exon 3 | c.694C < T | p.Gln574X |
|  |  |  |  | Exon 11 |  | p.Leu1667fs |
| P10 | PMF |  | 33 | Exon 3 | c.4019T < C | p.Gln232X |
| P11 | PMF |  | 66 | Exon 8 | c.5603A < G | p.Leu1340Pro |
| P12 | PV | MF | 78-96 | Exon 11 |  | p.His1868Arg |

Patients were initially diagnosed with the phenotype indicated in the second column and subsequently had a hematological evolution shown in the third column. When measured in several samples, the JAK2V617F allele burden is indicated as a range.

The FIG. 6 is a schematic representation of the TET2 gene and protein showing the mutations identified in this study. Hatched boxes indicate exons. Truncating mutations are depicted as stars, missense mutations as inverted triangles. Conserved functional domains are depicted as boxes on the protein scheme. fs: frameshift.

Following this analysis, we identified a complete deletion of TET2 in one patient and a total of 39 point variants. Examination of these variants showed that 15 of them, identified in 12 patients, were deleterious heterozygous mutations. They were distributed as one deletion of the entire gene, 11 truncating (3 nonsense mutations, 6 out-of-frame insertions/deletions and 2 splice site mutations) and 3 missense mutations (FIG. 6, Table 8).

Furthermore, all three missense mutations were absent from 165 control individuals of ethnically matched populations, thus confirming their deleterious effect. Two, p.Leu1340Pro and p.His1868Arg, were located in the highly conserved TET2 functional domains (1134-1444 and 1842-1921). Truncating mutations seemed to be randomly distributed along the coding sequence (FIG. 6).

In patients P4, P6 and P9 two TET2 mutations were identified. For the former, multiple allele specific amplifications of the two mutations located in exon 3 showed that these two molecular events occurred on different alleles leading to the biallelic inactivation of TET2 (data not shown). The observation of such a biallelic inactivation of TET2 in these patients meets the criteria of the classical two-hit recessive model of carcinogenesis and supports the hypothesis that TET2 acts as a tumor suppressor gene.

Twenty-five other variants identified on the coding sequence of TET2 and the short nearby intronic regions were polymorphisms. Seven were substitutions in non-coding regions (intronic or 3'UTR), one was a variation in an intronic short tandem repeat, 4 were silent variations in the coding sequence and 13 were missense polymorphisms. They were all classified as polymorphisms on the basis of their presence in public databases, the fact that they were found in asymptomatic family members, or their identification in control populations. It is of interest to note that none of the missense polymorphisms were located in either one of the functional domains.

12. TET2 Mutations were Sequentially Acquired in a Patient with Two Mutations

Seven blood samples were available for patient P4 from family F3, throughout the last three steps of her evolution: PV, MF and AML. Sequencing these samples allowed us to determine the temporality of the clinical and molecular events.

The FIG. 7 shows the sequential study of TET2 and JAK2 in patient P4 (F3). Sequence electrophoregrams are shown for each TET2 mutation and for JAKV617F. The diagram on the left indicates time lapse from diagnosis (in years) and corresponding henotype for each sample (white: ET; grey: PV; hatched: post-ET MF; black: AML).

The results show that JAK2V617F and the TET2 p.Arg550X mutation were already present in the first sample, when the patient suffered from PV. The second mutation, p.Asn857fs was detectable in the second sample, 7 years later and 5 months before the diagnosis of MF. This sequential analysis has shown that the burden of each of these mutations grew in time, concomitantly with the development of the disease.

Finally, TET2 mutations were found in similar proportions in JAK2V617F positive and negative patients suggesting that molecular events in both genes may arise independently of each other.

13. TET2 Molecular Events were Mainly Observed in Patients with PMF or Patients with PV or ET Who Secondarily Evolved Towards a Hematological Transformation Altogether, 12 patients were found carrying at least one TET2 mutation. They account for 20% of all MPD patients tested.

The FIG. 8 shows the schematic representation of the clinical status of these twelve patients with at least one TET2 mutation. White boxes depict ET stages, grey, PV, crosswised hatching indicates myelofibrosis, either primary (left-slanting) or post-PV/ET (right-slanting) and AML are symbolized as black boxes. Above each arrowhead indicating a molecular analysis is annotated the TET2 corresponding mutation. Disease duration (in years) is indicated below the bars, the "zero" point indicating time of diagnosis. Time of death is symbolized as a vertical line, when appropriate, at the right end.

This analysis shows that these TET2 defects were identified in patients diagnosed with the three main MPD phenotypes: PV (4/32), ET (5/21) and PMF (3/8). No TET2 mutation was observed in relatives with rare hematological phenotypes, including de novo AML and systemic mastocytosis (data not shown). All patients with a TET2 defect but two were positive for the JAK2V617F mutation. The allele burden varied from 33 to 95% (Table 6). The negative cases were ET patients who developed very active AML and died rapidly (P5 and P6, data not shown). We should note that the two patients, P3 and P7, who had not developed post-PV or post-ET MF at the time of examination, were characterized by a high level of JAK2V617F allele burden (82 and 39% respectively, Table 6).

Altogether, our results established that 20% of the JAK2V617F positive patients were found mutated for TET2 (10/49) vs. 17% among the JAK2V617F negative patients (2/12).

All patients carrying a TET2 mutation but two had either a myelofibrosis that occurred at onset or was acquired secondarily after PV or ET, or a secondary AML. Hence 29% (10/34) of patients with PMF or hematological complication after PV or ET were found mutated in TET2 compared to 7.4% (2/27) of patients without any diagnosed haematological complications after a mean time of disease duration of 12 years. Both patients with TET2 mutations and presenting PV or ET without hematological transformations had nevertheless an active course of the disease.

No correlation can be done between the clinical presentation, the hematological data or even the course of the disease in patients and the type and location of mutations or between patients with a single heterozygous TET2 mutation and patients with two. As shown on FIG. 8, TET2 mutations were found at different times in the evolution of the disease for each patient from the time of diagnosis (P9) to 20 years later (P8); the time to progression was also variable [1-16 years].

14. TET2 Mutations were Present in Early Hematopoietic Progenitors and were Acquired Independently from JAK2V617F Three patients were available for analysis of their progenitor cells, patient P4 from family F3 and patients P2 and P3 from F2. Blood progenitor cells were available for the former at two different steps of her disease during the PV stage and the blast phase after MF.

The FIG. 9 disclosed TET2 and JAK2 genotypes in committed progenitors of patients P2, P3 and P4. Histograms show the fraction of clones harboring JAKV617F and two TET2 mutations (crosswised hatching), JAK2V617F and one TET2 mutation (white), wild type JAK2 and two TET2 mutations (light grey), JAK2V617F and wild type TET2 (grey) and no mutation in any of the two genes (black). Two samples were analyzed for patient P4, the corresponding stage is indicated below each bar. The numbers of analyzed clones are indicated.

The results show that eight years after diagnosis, during the PV stage, endogenous erythroid colonies already carried the p.Arg550X mutation (5/29) but p.Asn857fs was never observed (0/29, FIG. 9).

Nine years later, after leukemic transformation, all genotyped Burst forming unit-erythroid (BFU-E) and all colony forming unit-granulocyte macrophage (CFU-GM), but 2, carried JAK2V617F and both TET2 mutations (FIG. 9). The progenitor analysis therefore confirmed the temporality of these events: in patient P4, p.Arg550X was first acquired in the earliest stages of the disease; and the latest stages were characterized by the presence of both p.Arg550X and p.Asn857fs. Interestingly, two CFU-GM carried both TET2 mutations in the absence of JAK2V617F. For patient P2, colonies were found with either both JAK2 and TET2 mutations, the sole JAK2V617F or none (FIG. 9). This was an indication that for this patient the TET2 mutation occurred in clones already mutated for JAK2. All BFU-E and CFU-GM from patient P3 diagnosed with PV carried both JAK2 and TET2 mutations and did not allow concluding on the temporality of JAK2 and TET2 events.

15. TET2 Molecular Events were Mainly Observed in Patients with CMML

The nature and frequency of somatic mutations in TET2 was also studied in bone-marrow or peripheral blood collected from 88 patients with CMML1 (n=70) or CMML2 (n=18) according to the WHO criteria and 14 acute blastic transformation of a previously identified CMML. Patients signed their informed consent according to current ethical regulations. Patients with CMML in chronic phase were newly diagnosed (n=43) or known for hematopoietic disease and followed up every 3 months for therapeutic abstention, supportive cares or cytotoxic treatment, in most cases with Hydroxyurea (n=45).

Blood and bone-marrow samples were collected on EDTA and mononuclear cells were selected by Fycoll Hypaque. DNA was extracted using commercial kits (QIAGEN). Polymerase chain reaction (PCR) and direct sequencing reaction were performed using standard conditions with gene-specific primers designed to amplify coding sequences spanning from exon 3 to exon 11 of TET2 gene as described previously. For each PCR reaction, 20 ng of genomic DNA was used for PCR amplification followed by magnetic bead purification and bidirectional sequencing using ABI 3300 capillary sequencers (AGENCOURT BIOSCIENCE). Mutation Surveyor (SOFTGENETICS) was used to detect nonsense and missense mutations located in conserved regions spanning from 1134-1444 and 1842-1921 and sequences were reviewed manually to detect frameshift mutations. TET2 abnormalities were numbered according to FM 992369 EMBL nucleotide sequence database.

The mutations identified in TET2 are listed in table 10.

TABLE 10

| Patient | WHO | Nucleotide change in TET2 | Exon | Consequence |
|---|---|---|---|---|
| 2 | CMML1 | c.4453G > A | 5 | W1198STOP |
| 4 | CMML1 | c.5214C > T; Ins 5537 (A) | 10 & 11 | R1452 STOP; Y1560FS |
| 5 | CMML1 | c.4942G > A | 9 | G1361S |
| 15 | CMML1 | c.4500C > A; Del 5118__21 (TTAT) | 6 & 10 | R1214W; L1420FS |
| 18 | CMML1 | delT 4172; c.5011A > T | 3 & 9 | F1104FS, D1384V |
| 19 | CMML1 | del 5362__5365; c.6441G > A | 10 & 11 | G1501FS; G1860R |
| 20 | CMML1 | c.2631C > T | 3 | Q591 STOP |
| 21 | CMML1 | Del 6507 (A) | 11 | T1883FS |
| 22 | CMML1 | c.2961C > T | 3 | Q701 STOP |
| 23 | CMML1 | c.1818G > T; c.4936G > A | 3 & 9 | E320 STOP; R1359H |
| 24 | CMML1 | c.4515C > T | 6 | H1219Y |

TABLE 10-continued

| Patient | WHO | Nucleotide change in TET2 | Exon | Consequence |
|---|---|---|---|---|
| 25 | CMML1 | c.4663n + 1 G > A; Del 6424__33 | 6 & 11 | Mutation splice donor site exon 6 + L1855FS |
| 26 | CMML1 | ins 2468__9 (AA) | 3 | K536FS |
| 28 | CMML1 | c.1272C > A; c.4814n-1 G > A | 3 & 8 | Q138 STOP, Mutation splice receptor site exon 8 |
| 31 | CMML1 | Ins 3151 (C); c.4390T > G | 3 & 5 | Q764FS; I1175S |
| 32 | CMML1 | c.3675C > T | 3 | Q939 STOP |
| 35 | CMML1 | delG 4754; dup 6569__6573 (GAGA) | 7 & 11 | K1298FS; M1570FS |
| 39 | CMML1 | delA 3874; del 4830__31 (TC) | 3 & 8 | K1008FS; S1324FS |
| 40 | CMML1 | c.2208A > T; del 4347 (A) | 3 & 4 | K450 STOP; I1163FS |
| 41 | CMML1 | c.6478T > C | 11 | I1873T |
| 42 | CMML1 | ins 1921 (A); ins 2703 (G) | 3 & 3 | S354FS; L615FS |
| 44 | CMML1 | ins 3995 (T); c.4059 A > T | 3 & 3 | E846FS; R1067 STOP |
| 17 | CMML2 | c.2814C > T | 3 | Q652 STOP |
| 30 | CMML2 | Ins 4293 (A); c.6510A > G | 4 & 11 | G1145FS; T1884A |
| 34 | CMML2 | delT 4277; c.6598G > T | 4 & 11 | I1139FS; G1913V |
| 38 | CMML2 | c.4936G > C | 9 | R1359S |
| 14 | TA | c.3235C > A | 3 | S792 STOP |
| 29 | TA | c.2490C > T; Del 5334 (G) | 3 & 10 | R544 STOP; E1492FS |
| 1 | CMML1 | c.5043n-1G > A; Dup 6575__6579 (GAGCA) | 10 & 11 | Mutation splice receptor site exon ex10; M1907FS |
| 7 | CMML1 | c.4439T > G | 5 | C1193W |
| 8 | CMML1 | c.4726G > T | 7 | C1289F |
| 9 | CMML1 | c.5100C > T | 10 | Q1414 STOP |
| 11 | CMML1 | Del 6023 (G) | 11 | L1721FS |
| 12 | CMML1 | Del 1921 (C) | 3 | S354 STOP |
| 16 | CMML1 | c.4827G > T; Ins 5178 (A) | 8 & 10 | E1323 STOP; R1440FS |
| 27 | CMML1 | insG 2703; ins 5125__26 (AA) | 3 & 10 | L615FS; K1422FS |
| 33 | CMML1 | Ins of 2950__85 (dup) | 3 | L718FS |
| 36 | CMML1 | c.4638G > A; c.4825T > C | 5 & 8 | C1193Y; L1322P |
| 37 | CMML1 | c.6414C > T; c.6496A > C | 11 & 11 | Q1852 STOP; E1879A |
| 43 | CMML1 | del 3859 (A) | 3 | N1000FS |
| 46 | CMML1 | del 1264__66 (AAA) | 3 | E135FS |
| 3 | CMML2 | c.4431C > T | 5 | Q1191 STOP |
| 6 | CMML2 | c.5070C > T | 10 | R1404 STOP |
| 10 | CMML2 | Del 2655__2658 (CAAA) | 5 | N598FS |
| 13 | CMML2 | Ins 5602__5606 (TCCAA) | 11 | 51582FS |
| 45 | CMML2 | c.2784 C > T; c.5253 C > T | 3 & 10 | Q642 STOP; R1465 STOP |

The results revealed that a mutated status of TET2 gene was detected in 44 out of the 88 (50%) patients. Among the 43 patients studied at diagnostic, a mutated status of TET2 gene was identified in 18 cases (42%). Such a mutated status was identified in 26 of the 45 patients (58%) studies along the course of the disease. These results thus suggest that TET2 mutation prevalence is higher in CMML than in any other studied myeloid disease.

Moreover, it must be noticed that two distinct mutations in TET2 sequence, suggesting a bi-allelic alteration of the gene, were identified in 18 out of the 44 (40%) mutated patients with a chronic phase CMML, including 5 out of the 18 (27%) patients whose mutations was identified at diagnosis, and 13 out of the 26 (50%) mutated patients studied along the course of the disease. Altogether, 69 mutations in TET2 were identified, including 33 frameshift mutations, 19 nonsense mutations, 14 missense mutations and 3 mutations in a splice site. These mutations most frequently involved exon 3 (22 events), exon 10 (9 events) and exon 11(10 events).

An analysis of overall survival was performed in 40 of the 43 patients whose TET2 status was determined at diagnosis with an at least two months follow-up and indicated a lower 1-year overall survival in patients with the 16 patients of this cohort with TET2 mutation, but the difference did not reach significance. When overall survival analysis was limited to the 29 patients with a CMML1 according to the WHO classification and an at least two months follow-up, the difference was then significant (p<0.01). None of the other tested parameters includes age, sex and FAB classification did affect survival. Finally, the results established that TET2 mutation was associated in the 29 patients with CMML1 with a trend to significantly lower survival.

16. Alteration of the TET2 Gene in Patients Suffering from Lymphoid Cancer

CGH analyses of 157 patients suffering from B-cell lymphoma showed the loss of a whole chromosome 4 in 2 cases, a partial deletion of chromosome 4q sequences deleting the TET2 gene in 4 cases and loss of the upstream side of TET2 associated with duplication of the downstream side of TET2 in one case. These rearrangements were found in diffuse large B-cell lymphomas (107 cases), whereas no rearrangement could be found in follicular lymphomas (50 cases).

We have analyzed 93 patients for variation within the coding sequence of TET2. They were 33 T cell lymphoma and 60 B cell lymphoma.

14 mutations were observed in 10 samples from T-cell lymphomas, including 10 frame shifts and 2 non-sense and 2 missense mutations.

Table 9 shows the TET2 mutations identified in 10 T-cell lymphomas patients.

| disease | Nucleotide changes | Amino acid consequences |
| --- | --- | --- |
| T-lymphoma | c.3215delT | p.Phe785FS |
| T-lymphoma | c.[1893_1896delAAGC] + [4527delG] | p.[Lys345FS] + [Ala1223FS] |
| T-lymphoma | c.[2505delA] + [2524delC] | p.[Thr549FS] + [Pro555FS] |
| T-lymphoma | c.6564C > T | p.Tyr1902 |
| T-lymphoma | c.6745C > T | p.Pro1962Leu |
| T-lymphoma | c.5523_5524insA | p.Glu1555fs |
| T-lymphoma | c.[3131_3137delCCAGACT] + [5109G > T] | p.[Leu757FS] + [Val1417Phe] |
| T-lymphoma | c.[3747C > T] + [5331A > T] | p.[Gln963STOP] + [Lys1491STOP] |
| T-lymphoma | c.3756_3757del CA | p.Gln966 FS |
| T-lymphoma (LAI) | c.1642delC | p.Ser261 FS |

Thus, these results established that the frequencies of TET2 mutation in patients suffering from T-cell lymphoid tumour is 30%.

The invention claimed is:

1. A method of treating a subject having a myeloid tumour or a lymphoid tumour, wherein the tumour comprises:
cells having a mutated TET2 gene having a nonsense mutation that encodes R1404Stop, Q321Stop, S354Stop, Q557Stop, or Y1724Stop in the resulting TET2 protein expressed by the tumour;
cells having a mutated TET2 gene having a missense mutation that encodes S1898F, H1868R, G1869W, or L1872P in the resulting TET2 protein expressed by the tumour; or
cells having a mutated TET2 gene encoding a frameshift at Q1834 or L1889 in the resulting TET2 protein expressed by the tumour;
the method comprising:
detecting in a biological sample from the subject the presence of the mutated TET2 gene and/or the resulting TET2 protein expressed by the tumour; and
administering to the subject a therapeutically efficient amount of a hypomethylating agent.

2. The method according to claim 1, wherein said subject is in need of confirmation of having myelodysplastic syndrome (MDS), acute myeloid leukemia (AML), myeloproliferative disease (MPD) or myelodysplastic/myeloproliferative syndrome.

3. The method according to claim 2, wherein said subject is in need of confirmation of having myelodysplastic/myeloproliferative syndrome.

4. The method according to claim 2, wherein said subject has myelodysplastic syndrome (MDS).

5. The method according to claim 1, wherein said subject is in need of confirmation of having lymphoma.

6. The method according to claim 1, wherein said subject is suffering from polycythemia vera (PV) or from thrombocythemia (ET).

7. The method according to claim 1, wherein the detecting comprises using a kit comprising at least one nucleic acid probe, oligonucleotide, or antibody.

8. The method according to claim 7, wherein said at least one oligonucleotide is at least one PCR primer.

9. The method according to claim 1, wherein the biological sample is a blood sample or a bone marrow sample.

10. The method according to claim 1, wherein the hypomethylating agent is azacytidine (AZA).

* * * * *

SEQUENCE LISTING

```
<160> NUMBER OF SEQ ID NOS: 39

<210> SEQ ID NO 1
<211> LENGTH: 132428
<212> TYPE: DNA
<213> ORGANISM: Homo sapiens
<220> FEATURE:
<221> NAME/KEY: Intron
<222> LOCATION: (1)..(100)
<220> FEATURE:
<221> NAME/KEY: exon
<222> LOCATION: (101)..(787)
<220> FEATURE:
<221> NAME/KEY: Intron
<222> LOCATION: (788)..(44167)
<220> FEATURE:
<221> NAME/KEY: exon
<222> LOCATION: (44168)..(44294)
<220> FEATURE:
<221> NAME/KEY: Intron
<222> LOCATION: (44295)..(87704)
<220> FEATURE:
<221> NAME/KEY: exon
<222> LOCATION: (87705)..(91159)
<220> FEATURE:
<221> NAME/KEY: Intron
<222> LOCATION: (91160)..(95146)
<220> FEATURE:
<221> NAME/KEY: exon
<222> LOCATION: (95147)..(95237)
<220> FEATURE:
<221> NAME/KEY: Intron
<222> LOCATION: (95238)..(96641)
<220> FEATURE:
<221> NAME/KEY: exon
<222> LOCATION: (96642)..(96735)
<220> FEATURE:
<221> NAME/KEY: Intron
<222> LOCATION: (96736)..(97377)
<220> FEATURE:
<221> NAME/KEY: exon
<222> LOCATION: (97378)..(97586)
<220> FEATURE:
<221> NAME/KEY: Intron
<222> LOCATION: (97587)..(113426)
<220> FEATURE:
<221> NAME/KEY: exon
<222> LOCATION: (113427)..(113577)
<220> FEATURE:
<221> NAME/KEY: Intron
<222> LOCATION: (113578)..(115566)
<220> FEATURE:
<221> NAME/KEY: exon
<222> LOCATION: (115567)..(115656)
<220> FEATURE:
```

```
<221> NAME/KEY: Intron
<222> LOCATION: (115657)..(123417)
<220> FEATURE:
<221> NAME/KEY: exon
<222> LOCATION: (123418)..(123555)
<220> FEATURE:
<221> NAME/KEY: Intron
<222> LOCATION: (123556)..(126371)
<220> FEATURE:
<221> NAME/KEY: exon
<222> LOCATION: (126372)..(126726)
<220> FEATURE:
<221> NAME/KEY: Intron
<222> LOCATION: (126727)..(128855)
<220> FEATURE:
<221> NAME/KEY: exon
<222> LOCATION: (128856)..(132328)
<220> FEATURE:
<221> NAME/KEY: Intron
<222> LOCATION: (132329)..(132428)

<400> SEQUENCE: 1
```

| | | | | | |
|---|---|---|---|---|---|
| gcgcggggggc | gtgtgcgcgg | gacctcgaag | tggtggtgga | gtgcagacca | gcaaaaagtt | 60 |
| tcaaagggaa | atcttagatg | tcacgtcttt | gtccaggcac | ccgtgccatc | ccaacctccc | 120 |
| acctcgcccc | caaccttcgc | gcttgctctg | cttcttctcc | cagggtgga | gacccgccga | 180 |
| ggtcccccggg | gttcccgagg | gctgcaccct | tccccgcgct | cgccagccct | ggccccctact | 240 |
| ccgcgctggt | ccgggcgcac | cactcccccc | gcgccactgc | acggcgtgag | ggcagcccag | 300 |
| gtctccactg | cgcgccccgc | tgtacggccc | caggtgccgc | cggcctttgt | gctggacgcc | 360 |
| cggtgcgggg | ggctaattcc | ctgggagccg | gggctgaggg | cccagggcg | gcggcgcagg | 420 |
| ccggggcgga | gcgggaggag | gccggggcgg | agcaggagga | ggcccgggcg | gaggaggaga | 480 |
| gccggcggta | gcggcagtgg | cagcggcgag | agcttgggcg | gccgccgccg | cctcctcgcg | 540 |
| agcgccgcgc | gcccgggtcc | cgctcgcatg | caagtcacgt | ccgcccctc | ggcgcggccg | 600 |
| cccccgagacg | ccggccccgc | tgagtgatga | aacagacgc | caaactgcct | tatgaatatt | 660 |
| gatgcggagg | ctaggctgct | ttcgtagaga | agcagaagga | agcaagatgg | ctgcccttta | 720 |
| ggatttgtta | gaaaggagac | ccgactgcaa | ctgctggatt | gctgcaaggc | tgagggacga | 780 |
| gaacgaggtc | agagcgcttc | tcttatgccg | cgaaactctc | cctttcttct | ccccttcgct | 840 |
| ttttctcggg | cttccaggga | ctggggagca | aaccctgtag | tgtcacccac | aaataccaag | 900 |
| agggaagagg | gaagcttcac | aaaattactgg | agcctcttca | acatggctga | caaatatagt | 960 |
| tttaattccc | tctacccctt | ttaaacctgt | agttctgtgt | tctcttctct | cctcctaatg | 1020 |
| ctcgtccccct | catctcccag | aaaacttacc | tttgtgcctc | cgacgagccg | gtttcccggc | 1080 |
| cttttttaat | cctcagaaaa | gtgattttta | aatttgcttt | cctttctaaa | atagttcagc | 1140 |
| tttggggggca | ctactttttcc | ctttaatcct | cttccctgt | ttcttcgtg | taagtgaaac | 1200 |
| gagtctcccg | tttatcctga | acaacctcag | agagaacact | gatagggtgt | ttttcgaccc | 1260 |
| ttttatcagc | tgtagggtct | gggtctgggt | ttgtgtctgc | ctcctcctac | cttcttatcc | 1320 |
| cccctttaggg | ggctgtacga | agtgaatgtc | acagggagtg | gaattggagt | acactgagtg | 1380 |
| ggttttttttt | ttccttaagt | ccgcgcgttt | tgttagcggc | gctgagtgaa | agaggaaaga | 1440 |
| atagtttctc | tggttcccca | aacaagacca | gaactcactt | ttctcaaggt | acataagtca | 1500 |
| gcgctgggct | gagccttcca | gcctggggaa | tgtatgtaag | agaatttatg | gacaaatctg | 1560 |
| tgtcccggct | ttgtgcttct | cccgaatcag | cttcgtttgg | ttccttggta | agtgacaggc | 1620 |
| agacacaaag | gcaggcgcag | gcccggggag | ggggcgggag | ggggtgggga | gcgcagcgtt | 1680 |

-continued

```
ggagttgcaa gactgcaagg tcaggggcgc ctaaagaaat gaaacccaat cccagcaaag    1740
aagtgaagag cagatttata acagtcccat ccaaatttct cttttggcttc tctctttggt   1800 ctttcatctc tctgcctttc tctctgtgtc tcctctctac tctttcttct ctctctctca    1860
tacacataca cacacacaca cacacacaca cctcactcgc atcttgctga atcttttcac    1920
tgggactgct tgtctagttt tattaagcta atagggtttg tatggagagt tttctaccta    1980
tgacataatg aagtgtggcc tggatagact cctggaaagg ccgaaaatga aatataagtg    2040
ttatttgctg gttattcccc tcatgatata cttttaatta cattgaggga gttctccctt    2100
cttcatctaa tgtttaagaa ttgagaaaag gcttattttc cagcggtaaa atttagtgca    2160
taaaatttag tgaaatattt atatatttac gtgtctaggg agtggaatac attcatgaat    2220
ttaatatctc aaatcacaca ttgtgctttt tccccttcag tcaggattaa taatgggaaa    2280
cccaaattca aagatattca tcaacaaatg atccatcata ggaataagat tgtatcttaa    2340
gggaagttgg gattcacaga gaaagacat tggtttggtt tggtgtgata ctgtgggtat     2400
tgttgcctgg ctaatgaaat cattacattt gcatttaat ggaaagttga aatactaagg     2460
ggagttatgt tcttttacat gtttgtatgt gtgcttaata atgtttggaa tagaatataa    2520
atttaaacac aataaatatt gattttttta aatgttaata agcagagaac ggttaatgaa    2580
gtgttggata atcaaactga agtttagaag acaatttata ggattaaaaa atggatagaa    2640
ggaaaaacac aataatagat atttctccat aagtcgaatt tccaaaacta tttgtcctcg    2700
atagttcact ttgtaacttt ctattttgat ctttgttaat ttaatgtagt ttgctttaat    2760
cattgatacg tggggttctt tcacatgatt acaaggaga agcattactc atctctgtgg     2820
aatagaaacg gttcattggt tagttcttat ttgccctaaa attaaaacaa aaattaggat    2880
tttaccatta atgctgttca tggtaaacta tcgagaaaac tatggttaat tattccagca    2940
attcagaatt aaaaacaatt cctttttgcta acaaactaat atttactttt tggggacaac   3000
ttttcaaatg ttgtggtata tactgtcttc aggctactca actaataata gatcaaacat    3060
tttccactca ataaataaga ataactacat tggttaataa ttttgaatac aactatgaag    3120
gcttgttttt tcctgtcatc aaatttagat tcttgttatt ttgtgcatcc tacttttata    3180
ctgaaaatag ctgctaatta atactgtata aagtatttca gtgattataa ggaagagatg    3240
tgtatgttag tcacttatc ctttgttgga aaagagaaat tatttaata agtatggggt      3300 agtttacaat aaaagacata acctcagttc tttctttacc atatatgtga tcatactacc    3360
taggtgctcc aaaaattcca taggactgtc ttgggttatt gaattttagg aacatgataa    3420
tggacaataa caagatagat agcttttctt aactatgaca ttgttttgct tatttctta    3480 ttgaactaat catcaatgag aaattaagtt gcagtgagag aaatcccttg ctttgtttaa    3540
attgtcatat ttgccaaact cttcttaagg ctttaattag gtctgatgtg ccagtttatg    3600
ccagaagccg gaggaattga tatgattttg aggcagtggc acatggtcct actagacatt    3660
ggcaagtgaa tatcacttcc agaacaagtg aagtgcacct gccaaggagt tgttatgaaa    3720
gaattccaaa gtccttattg ggcactggtc ttgtattagg taacaacaac tggagttaat    3780
gttttagttt cacttgttga agttaaaagt tccctatcaa ttcttctaag actccacccc    3840
caaacaatgt tgtaagtcaa atgtcactat tgaaatgtat ttccttaatt actgacctca    3900
ttaagaagcc cttcttatga ttcataggca cacctcacag aaactctatt ttccatcctg    3960
cccaaagtct gagtaggtaa attccttatga attcttatga aattaccttg aaataaaata   4020
tcttcaaaag ttacggatgc tagacattgt ataatgtcaa tatttttagaa tatctaatat   4080
```

```
ttagaaaatc ttagatctac tttttatgct ttaattgctt ctaatgcaag ttaaattgtt   4140
tttgttgtta ttgttttaat agaatttcat agtcttatct agcaatttca aatcgctgga   4200
aagagtcatc tttgttatat aaataaccat gtagactgtt ttaatgttat tgtttcctac   4260
cttgggaaca ggctaaaact ttggaccagc tgtcagtatt tgttcatcag aataacactt   4320
tgtcaatgat tattctacca ttgcacagta gttcttaagg atagtaatgg taccaaagcc   4380
agcagcaata gaatatctcc caagccaact ttacaattgg agccttcact gtgggaaaga   4440
ccagttgcca agtagagctg gtggttatct gggaaactgt gctgaagaac acaaccacaa   4500
atgattttgc caaatataca gtatttactt ggtctagatc tccaatttct atttctactc   4560
actgccaaaa ctgagtgaat actgtgacat tattgaagga ggttatgcag tacatctgtt   4620
ggtttggtat atagtaggag agaagggttc caggagggaa aggggaaagt cagagcatgt   4680
gaatcactgt gactacaatc caaaagaat tatgtatgtc tgctatttcc agcattattt    4740
ttgtcctata ttgtacattg cagagacttg ctgacttaaa atagatatat aatcttttc    4800 tcaaaagaat agatatttgg ttgtccattc caaataacaa attttggatg ggcgtggtga   4860
ctcatgcctg taatcctagc actttgggag gccaaggtga gagatcactt gaggccagga   4920
gtttgaaacc accctgggca acacagtcag gccccagtct ctacaaaaaa tttaaaaagt   4980
tagtggggca tggtggtaca ttcctgtagt cccagctact caggagactg agataggagg   5040
atggattgag ctcaagtgtt ctaacttata gtgagctctg atcacaccac tgcgctccag   5100
cccaggcaag agggagagac cctatctcaa acagcgacaa caacaaaacc aaacaaacaa   5160
aaaagcacat tctatcagct ttgatttatg ttttcttcat ttgtaatgac atgtagttaa   5220
atgtgtcata cttcaaaaag aagaaacaga tagtaggtgg atttttcaata taatatatat  5280 tagatataga taatatatat tttcaatata taatatatgt aaaaataaat tcagtgataa   5340
tatcatccta cctgcagttt taagaattca gaactcaggc caggtgtggt ggctcattct   5400
gggaggggaa ggcaggagga tcacttgagg ccagaagttc tagaccagcc tgggcaacat   5460
agtgagatac ctgtctctat tcaataaaaa taaaaataaa aataattcag aactcaatgc   5520
tttatactca ctgaaagttg ttcctctaaa ctgacttgaa atcatgttcc aaataaactg   5580
agaattaaag taagagacga ggccggttgt ggtggctcat gcctgtaatc ccagcacttt   5640
gggacgacaa ggcaggtgga tgacctgagg tcaggagttt gagaccagcc tggccaacat   5700
ggtgaaaccc tgtctctact aaaaatacaa aaattagccg ggcatggtgg cacacaccag   5760
taatcccagc tactcaggag gctgaggccc gagaatcact tgagcctggg catggtggct   5820
catacctata atcccagcac tttgggaggc cgaggcaggt ggatcacctg acgtcaggaa   5880
ttcgagacca gtctggccaa catggtgaaa ccccatctcc actaaacata caaaattagc   5940
tgggtgtggt ggcacatgcc tgtagtctca gctattctgg aggctgatac aggagaattg   6000
cttgaaccct cccgggaggc agaggctgcg gtgagccgag atggctctgc tgcactccag   6060
cctgggcgag gcagagagac tctgcctcaa aaaagaaaa ataataataa taaataggag    6120
atgaataaat tgggataaag tgttttgaa ggacagtcta ggatataaaa tgaactggtt    6180
gtttgactaa aaatactaca aatgtttctt tcaaattaca tttctttttt gtctattgga   6240
aggtaggcac tgatttctat gtctttctat tccctaatag aacctactgt tgacctctca   6300
gtcaatattt aatggatgat atagaactag tgaaaaacca tgcaatttaa ctagaaaaaa   6360
aaagtataat ctatttctt ttccttttc tttctttctt tctttctttt ttttttttt     6420
```

```
tttgagacgg tatcttgctc tgtcacctag gctggagtgc agtggtgtga tctcggctca    6480
ctgcaacctc tgccttccag gttcaagtga ttctctttct cagccccag agtagctggg    6540 actaggagcg tgccccacca cacctggcta atttttctat ttttattaga cagggtttt    6600 caccatgttg gccaggctga tctcgtactc ctggtctcag gtgatctgcc tgcccgggtc    6660
tcccaaagtg ctgggattac aggcatgagc cactgcacct ggtctaatct attttcaatg    6720
tataagagaa aaatagtgtt aagtgtcttg gtgatggtga tgatggtagg agtaatggtg    6780
tgttttcctt acatttaatt tctacaggct atggcaattg ccctataaaa gccacccatt    6840
ttaagcacaa aagtgaatgg ttttagtaa acttatatgg gatcatatat ttttaattga    6900 aatattttt gagttaatta tagattcata tgccattgta tgaataata cagagagatt    6960 ccacgtatac ttgctcaatt tcccccagtg gcaacacttt gcaaaactat aatatcatat    7020
cacatcacat gcaaaactat aatatcatat cacaaccatg atactgacat tgatgtggcc    7080
tactaatctt attcagatgt cctcagttta acttgtactc atttgtgtgt gttttgtttt    7140
ataccattta gtcacatgat cacatatttt taaaaccttt tttctcaaa cagagaagtt    7200 tagcacaaaa gtttagcaat ttatcaatct tgtgattgtg ctgttatgcc atattaaaat    7260
gtgtgtcaga atgtaagttt ttgttttctt aaaagtcctt tttttgatag aatggccttt    7320
atgttaaaaa tattttaagt tgtttttgtga cagtgtaagt cgatgtcatt taattctcat    7380 cacacccta gagataggta ttattcttat ccctattat gagtgaggaa actgaagccc    7440
agtgaggtta ataacttcc ttaagttcat acagcctata catggcttag cttagccag    7500 catttgagtt aagcagtctg tctctagtgc caaatctttt aatcactata ttatacttca    7560
tcattatcat tgatagctgt aaaagtgtat aatgtggact atgtagagaa agtcataaaa    7620
ggagatttaa aatgcataca gttgttcaca tgaaaacttg tagccaaatg ttcattacag    7680
cattattaat aatggtaaaa aatggaaaca acccagatgt ctatcatgtc atgagtgaat    7740
aaacaaattg tggtatatcc atacagtgaa atattattaa gtagtataaa ggaatggatt    7800
attgataaat gctgtcacat aggtgaatct gagaggcaca agaaaggcca catatgatat    7860
gctttcaatt ttaagtaacg tccagaatag gcaaatctaa ggagacagaa agttggctag    7920
ttattactag gggctaggga tgggagggag gtgactccta ataagtatga gatttcttt    7980 ggtgatgatg aaaatgttct ataattagat agtaatgatt gcccaactct ttgaatatgc    8040
tgaaacccac tgaattatat gctttaaaag gatgaattta ttgtatgtga attatatttc    8100
aaaaagctgt tgttataaaa atgaatgtag ttgagttatt tggtttattt tatgtcagaa    8160
aatgtcttac atctcatgca aagaaatgc aggaactatt tggattgaat gaggctaagc    8220
atatctttct aggaagatgg catcaaggag tttattatg cctgtaatcc tggcactttg    8280
ggaggccaag gcgggagacc agaagtttga gattagtctg gcaacatcc tcttatagat    8340 gagaaggata cttaatcact caaaagttgg cattgtgttt tgtgataaca atagccttta    8400
gagctcatat gggaagattc aatagatagt gataggttat atgacttggt aaagagggct    8460
taatgtatag gtgcaagaaa ctttctcaga tgtctttagt tacctagcca ttcagttcag    8520
gagatgtaac ccaagtgtta aaaggaatgt gactgggtgc ggtggctcac acctgtaatc    8580
ccagcacttt gcgaggcgga agtgggtggg tctcttgagc tcaggagttg agacaagcc    8640 tgggcaacat ggcaaaaccc catccctaca aaaatgcac aaattagctg ggtgtggtgg    8700
cacatccctg tagttccagg tacttgtggg gctgaggcgg gaggatggct cgagcctggg    8760
aagttgaggc tgcagtgagc catgttggtg cccccacact tcagcctggg tgacaaaatg    8820
```

```
agaccctctc tctcaaaaaa aaactataaa aattgctgtt cttgtttaaa ttactacaaa    8880
gtgcagttta atctagaaat aataacaaat tactagattt gggggggttat taatgtctta    8940
tctatgtgaa aacagaaggg caatgcaggg cagagaataa acttcaaaac tttgagtttg    9000
ttaactgttt atatctccac ttgtcatgtt tcagatttta aagttaaaat gacaaagtat    9060
ctcatagggt ttaaacaagt gactcttttc ctgttaactg atactgtggc atgttgaaga    9120
tgtaaaataa ggttgaaaag gaaattgctt tgcagcagtc ttcataatgc caggacaaag    9180
tgagaaacag ggtcagaatg atgatggctc tccatctttg ctacacatgg ctgcaagtat    9240
ttacaaatac cagcagaact tctacaaacc acttacaggt aaaatgagtg cagatttta    9300
acactagtcc ctatggaact atgacttgta gttttggaca cacagggtga attacttggg    9360
gttgattgta tttgaatttc taaccttatg taattctaga taccagacat tcttgttgtg    9420
caatgcttct ctccctttt attctcatga gaatgctggg ttgcagccgg ttggatccca    9480
taccttggga ccatgactga taactggagt ggagaaaatt cactgatctg gaaaggttga    9540
gctttagggt tcagagactt atttaaggta cacatgtgat tgtacccaat aaggaagtat    9600
attggcttta tataattgtt atgatcactt gttcaatgag taactataga attttacttt    9660
ttaagagtat gatcatagca tctacttgta ggtttgttga gtatgtttga caagcccaag    9720
atagatgctc atgttagacc cattaagaag ttggtgtagt gatggttatg gaaagcagta    9780
agatagaatt taggttctgt tctccttact ggagaaatga ctagcttact tgtcttcact    9840
ctctcttgtt tctctcaaaa ctttgtgaac caccctcagct gactataaat ttttgtacta    9900
gtatctccat aattttaaaa aagttgttca caagtttgag tgtagtactt catctttgct    9960
ttttaatgca cttccaaaaa atgtaaatct gttctcgcat attaggaaca ttttgatttg   10020
ttgtttattt ttagctttgc ttttttataag taatttatac agaaggtaca ccatattcaa   10080
aagaagaaaa atgggctgtg aatttttgct gatgtactac tctcttcaaa gggaattgcc   10140
tatgttcagg catagaaatg caggcagtct gacatttagg tatgccatac agagtattga   10200
tattttaat ttgctacttt taacattttg agatttgtca cagtttgttc tgtgggtggg   10260
taaaagtaat ggtaatttta attacagttg tcgtgcctca ttagccattg ctaaaacctg   10320
ccttaccaaa tcacttattt tcttgatgca gtgttaaatc tagcttctat gtccaggtta   10380
tacattaatg agaacattca cccatctctc aaatgggtta ttatagtatt ttctcctgaa   10440
atagatgatg cataaaaaaa agtaaaaaag cttcaatagg gataatgaaa gccagataac   10500
atagcatggt atatgagtta ttcctcccgt ttttcttacc tgtctgcact aagaagggca   10560
cccattaaat accataatta ttagttgtgc tgcctctgaa gtagagcacc agaatgtgag   10620
agtaatacaa tgagaccaca cccagattct atccataaca tactgtcctg gtcttattaa   10680
tttttttaac ctgtttgttc ttttagcact tttcctgctt ttgtttgaag tctcttgctt   10740
tgaagttata gaattttat atttgccatt ggctgtaaag ttatctcagc tctttttataa   10800
cttttcatta tatttgcatt aaaaggatca ctttgagcac cctgtaatta attcagatga   10860
ttattagctt ttttgtttgt tctactgtgc actctcctat atacattata acagaagaaa   10920
aaaccatttc tacaaataca gtgtctgata gttcatcaaa tcagaatgag catcttaaaa   10980
agtgaattat taaaatatta attcatttac attcctattt taatgtacca aatgtaactg   11040
atgaaaagaa gaataccata aatgggtacc tttcaaaaat gaaggaaaaa aaatctcac   11100
aactaaagat tcttaccata taaattattt attttagtaa ataattattt tagtacaaac   11160
```

```
agatacattt tagcaggaaa aaacacactt taaaccttgt tttatagatt ttatctttct    11220
tccaatctag ccactgaaat ggttttttct ccagtgaagt tatattatct acataagttg    11280
aatttaaaac aaggttgtat tttaattttg cagttgtctg ccacattacg cttgtggaaa    11340
aacactggca gaaagcaaag ctaatagaca ttttgctgtt ggctcacctt attaatggct    11400
aagatttaat tatgtatttc tactgaaaag caaacttgaa aaagacgttt ggttactaac    11460
tgtgggaact aaaaatttt atttattttt atttttatt ttttggtaga gtctcactct    11520
cttgcccagg ctggagtgca gtggcatgat cttggctcac tgcagcctcc tccttctggg    11580
ttcaagcgat tctcctgtct cagcctcccg agtagctggg attataggca ccagccacca    11640
tgcctggcta attttttgcat ttttagtaga aacagcgttt cgccatgtag ctaggctgg    11700 tctcgaactc ctgacctcta gtgatccacc cccttctgct tcctaaagtg ctgggattac    11760
aggcatgagc catcggcctg gccaacttat ttactgttac aacttactta ctttgaaaca    11820
acttatttac tgttaaaaaa tgtggttctt atttcaaata agattttatg gacatcaact    11880 aatttttaa acatatattg taattttaaa acattttac caacattttt caagagcatg    11940
ggaaatctag ggtatggcat tttaaagtga cttaaagac acttcttggg ttttgttgaa    12000
gtcagaatat ttttaaaaat acaatgagtt taatttacta ctgacagatt ttctttaatt    12060 tttttttgcat tgttataatt agtcatgcct taatcctcgg ggttttttggg aaactatatt    12120 tagggggttaa aaacttagtt attgacattg taattttttct cagtattggt aagaattcag    12180
gtgtttaagg aatggagttt acttgttttc tgttcacaaa cccattgtaa aagatataat    12240
gaatgtagat gaaggtgaaa tccgagatag gaagagaggg aaaatgctac ttttttttcc    12300
ttcacccaag gaaagccatt gaatactgaa tgggtcatgt tgtaatttaa ttgggtgtaa    12360
attataactt tgtaaatcat ttgcctactt agtgtatatc tctggttttt atgtaattca    12420
tctcccataa tatctcagtt tacactgaag taaataagca agcaggaata agtcctgcaa    12480
atagaggaag tagaaagtgc attcagaatg cattgctgaa attgtaaaac tgatcctaaa    12540
ttgaattagg tagagcagtt aatttagatt acaagaaatg caacaggaaa aaaatattac    12600
agttcttcct ctttttttgga aaaaaaaaaa gaaagaaaag acaaataaat cacccttagt    12660
tagtgataat tccttgacat ctgtatgctc attttttaggg ccaaaaaata gtaggcttct    12720
ctttggaaat tgtagacgct ttctctcctt ccagttacac gcggtcacat caacatttga    12780
cacgtgggta ccgtgcacgt ggcagcagta tttacaaaca ccatcctagg attccagaga    12840
ctcttatgta acagtggaga gagtaagctt tgagtgtctg tgggcggagg aatcaacaca    12900
gtttaattca ttgtccggga gcccttgtct ggctctgata gggtcatgaa ccaaagatca    12960
aggtgtttag gtcaggatat tccctaacgc atggttttcc taccaaagcc tcaaaagctg    13020
tgcctaaata caagattaat ctttttcttt ctttctttct ttttttttt tttttttgag    13080 acggagtttc gctcttgctg ccaaggttgg agtgcagtgg cgccgcgatc tcggctcact    13140
gcaacctccg cctcaccggt tcaagcgatt ctccagcctc agacacccaa gtagctggga    13200
ttataggcat gcgccaccac gcccggctaa ttttgtattt ttagtacaga cggggtttct    13260
ccatgttggt cagcctggtg ttgaactccc gacttaaggt gatccgcttg cttcggcccc    13320
ccaaagtgct gggattacag gcttgagcca ccgcgcccag ctaagattaa tcttttttatg    13380 ccctgcagca acaactagt catgccaaac cattttttgtg atttggggaa acatgagcag    13440
atgatgcttt ggatctgatt ataattcaca gtgctcttgt aatttacgtg agatttgcat    13500
acctgcctcc cagcctcaca aaatgccttt aaaaaattac atcttggcca ggatggctca    13560
```

```
cgcctgtaat cccggcattt tgggaggcca aggcgggtgg caagagatcg agatcatcct   13620
ggccaacacg gtgaaaaccc gtctctgcta aaaatacaaa aattagctgg gcgtggtggc   13680
gggcgcctgt aatcccagct acttgggaga ctgtggcagg agaatcgctt gaccccggga   13740
ggcggaggtt gcagtgagcc gagatcgcgc cactgcactc cagcctggcg acagaacgag   13800
actccgtctc agaaaaaaaa aaaatcttga tatttgtatg catcttaaaa agcaagagaa   13860
ttcatgattg acttcccaaa ctaaacggtc tgaccagaaa acactcaaga aaactcttgg   13920
ttaatcatgc tccttagtat accattatac ctgcctctcc cctttcccca tcctctgtaa   13980
attctctcaa ccttctctca tttttaattt cataccaaga cctagagcta aaacaacaac   14040
aacaaagctt taagtctcta tatttaggga atgtgcctcc tatcccaaat tgattttag    14100 agcttttcat ttatttttat caatacaaag caagttgaaa taaaaaaaaa ggcatcaaaa   14160
atttaaatgt ctaaccacgt atatttggta tatgtatact ggtgctatgt attagctgta   14220
agcagactgg tttgaatatt taaaatatga acagaattg agttcttttt gtattgcatc    14280
taaggatcat ttgagatgga tgtcatcatt tatcatccaa aatagaagcc ttcttgccta   14340
acaaagaatt gtaattagat catcaaagat gaaatttata gtaattgaaa agttagctca   14400
tttgactgct tctttcatag actgtgtttt tgtaattaca ctacctttct aaagatagga   14460
aaaatcagag tctctgaaat gtaatactat aagtgaaata tgtattttt aaaataaagg    14520 atcttttccc aagagctaaa ccaagcacca aatctgtttt tgggggtttt tttggtttgt   14580
tggtttgttt gtttgtttgt ttttgacaga gtctccctct gtcgcccagg ctggagtgaa   14640
gcggagcgat ctgggctcac cgcaacctcc gcctcctggg ttccagcaat tctctgcctc   14700
aggcttcgga gtagctggga ttacaggcac tcgccaccac gcccggctaa ttttgtatt    14760 tttagtagag gcggggtttt accatcttgg tcaggctggt tttgaactcc tgacctggtg   14820
atccactcgc ctcagcctcc caaagtgctg ggattacagg tgttttcctt taagtaatac   14880
ttggtataag agaactttat atctggaata atttaaatat tatctgaccg aatctattat   14940
tcacatatag aaactcaggt tttagccatt taacatctaa agctgttctc atttagagga   15000
aattaccaaa agagtgactt atttaactaa caataaaatc taaggataga tatttttca    15060 ttctgttgca gagcaaaagc agccttctgg atatgaaaag atattacttc tttagtgttt   15120
attacttata atttattgta catttctgat acactgaatt aagatgcgat gagagtaggt   15180
tgtagatttt taaagttct tatttgcgtg atttatctac ttgctttttt agtgtcggac    15240
tataaatgat gtatttctct caattatcct cggcctaaat agtaaaagct tgggtgaaat   15300
tacttatgag tatactttc ctgcacagag cagagccatt actgaacact ctcgagcttt    15360
aacaaaaatc atcctatctt atattagaat attaatattt tccctctttc tcggaccttt   15420
gtttcacagt aaatcatata tggatataag ctgcaagtgc tcagaatttg attaaggcta   15480
taagttaatt tctactaaaa aagggattca aatagaactt tcatttggct gtactgtagt   15540
ttcacttgaa ggggcaagca tgcaataaac attgacttat tcaatgcata ggctgtcttc   15600
ataaagatga gactgagtga cagttgtctg tgtattataa aatatcagaa tggtagattg   15660
aatctgatgc ataccaagga gcaatgtgga aattttaggc tgttcgtctt ttttcagtta   15720
ctactaagtg tgtgtatgtg gtgtgtatgt gttttgaact tttcatattt aagctgaatc   15780
ctctttggta gaaatggtta aatagactat agtaaaagtt tctgtctata aatataaaat   15840
gaaaaaatac tgatatcttg catttcccct aatatgttga aagtgcacag aatccttggg   15900
```

```
gtcttttgta taaactgttt ttatatggtt cctgtagaag acagctgagg caccaaacac  15960
acacacaaaa caaacagctt gcttggtgat gataacattc gtgcaaggga gttctctctt  16020
gcataggagt cccaggttac cctaatgcct tcccacatgg tcaaacacat ggagctttca  16080
tatttacaca cagctccaga attctgaagc ctgcagttgt ttatcagtgg gatacaggga  16140
gaaagagtgg tgtctatctt actaactgtt taatgacctg gatcatgaat actgatacag  16200
aataagaaag cactggcctg actgcagggg aaacatggta gatgcctaaa ggaggctttt  16260
ccctgcccca cactgtttat tttaaactat cattatcacc tgaaaggagc ttttcacttt  16320
gaacttaaaa tagtagcttt taaccctgac aagcaagtag gcactttagt attcaagaac  16380
tgaaggtgac aagccctgag gagtgttact ctctttcata accaagctga ctcaaactct  16440
tttagaagct agtgtagtaa cttaaccatc tctaataatg ttgctgcatg ccttcataga  16500
aacagttgga gcaagagctg cattttcttt tttttaagtg tttattattt acattttatt  16560
tttgaaaaca tgccattcct attacatata gaaatacttc ccaaaatcac tgtttgtata  16620
gaactatttt gcttaacatt aggattctat tgaagagcct atatctgcaa taatacgggg  16680
agaaaatccc cttttgtgtg atagattaat gataaagaga aagaaaaggt gagaagtaat  16740
tttgggaaat atgcaatgat aaactagtgg tatttattga actaaacacc agcagctgtg  16800
cttagcatgg ataattgcct aaaaggatga gaaaaaaaag taaaaatcag gagactataa  16860
atttttcagt gaagaataaa ttttctgtca caaattatga acatttaaaa tatgtatttt  16920 aaacttttc ctacttgtaa caaattatca gacttttaa tctaccttttt ttgagctttt  16980 catcttttc cctgaattat agatttaatt ctgtgtatgt atgtgtgtgt ttgaatatat  17040
ttttatattt tagatctaga tttgtaaact agagctgttt ctaactgctt ataagacatt  17100
gccacctgga ttgccaccac tttcactcca gtatttcaat aaacacttca tcaaaaacat  17160
agtttatttt caaacataga atcatggatt gctacaagct gaaaggactt tagagactca  17220
gtaaccccat tccttgcatt tacagatgag aaaatggagg catgggaaag taaagtcagt  17280
tgcctcaaat agcgtaacaa gctatgtata tttctaataa tagctactat tgattaagtt  17340
cttatgttgg gttaagtacc atgctaagca cttttccaaag attatctaat tcttatgtca  17400
tctatatttt tgttggtgct attactctcc tcactttact aaggaagaaa ccaagacatg  17460
gggttaaata acttccctat aaattttgaa ttatctttgg catcatctcc ctatttgcaa  17520
atctccattg tctctttgtt cgtaatcaat gtaaatcaac tcttaaacag ttggatgcca  17580
acaagcagtc tggtgtttgg agctcgaaag tttcgagaga gagagagaga gagagagaga  17640
gagagagaga gagagagaga gagtgtgtgt gtgtgtgtgt gtgtgtgtgt gtgtgttcca  17700
gctttgttga ggtataattg acaagtaaac agtccacaaa actgtacaca tttaagagat  17760
acagtgtgat gttttaatat acattgtgaa gtgattatta ctatcaggct aattcacatg  17820 tccatcaccct ctcagtcatt ttttgtgttt acggtgagaa cacttaagag ctactcaaat  17880
gtagtcaagg ataccataca gtactaactg tagtcaccat gctgtacatt agatctccag  17940
aatgtattaa atattcatct ggcataactg aaactgtgta tcctttgaca aacctatttc  18000
ccctactacc cagcccatgg caaccaccat gttactctct gcgtttatga gttcgacttc  18060
tttagattcc acatataagt gagatcatgc aataggaaga tctaatttag catcctgact  18120 ttcctttta ttagctgtgt atgtcatatt caggttgcct tagcatttgt gaatctgctt  18180
ctctacctgt aaaatgagaa caactaataa ttccttatctc atggattact gagaggatca  18240
gatgaagtaa cataaataaa acatccagca tgttacttgg caaaattgta gtgattgaat  18300
```

```
aaatatttgt ttattcttca agcatgtgtt gagcatctat gtatcaggca agaagagagc   18360
catcatcttt acccttctgg aatatacagg ctcataggaa ataatcaatg ctttgatctt   18420
tttttaaagc ataatgagat gaaaattata ggactcatag actggtcagt tgaggaattt   18480
cccaggatgc ttccagcctc tgctcaaaag gtgtgaattc ccagttgcct gaataggcgc   18540
cagagttggc atagctttct cagtattggg acctgacagg gagattgcac aagtgtaaca   18600
gcacagcctc tgaagattgg ctcaaggggg aagagatgaa ggattacttc catcccttt   18660 attgtttcaa tcaagatata tattatgagc tcatagtacc atcctttcat gatcatcctt   18720
tattgtcttt attagataca atgaaaagat acaaatttgt ccatagaaat attaaatgat   18780
agcaggcatg atttaaaaag tactaaggac tatagatatt actgttttt ctctattttg   18840 tatcatattt tcaggaagaa gagacaacat tttggcatac cttgcttaaa gatagatgat   18900
agccgggtgt ggtggctcag acctgtaatt ccagcacttt gggaggccga ggcgggcaga   18960
tcacctgagg tcaggagttt gaaccaacc tggccaacgt agagaaaccc cgtctgtacc   19020
aaaaaataca aaaattagcc aggcgtggtg gtgggcgcct gtaattccag ccactcagga   19080
gactgaggca cgagaatcac ttgaacccag gaggcagagg ttgcagtgag ctgagatcgt   19140
gccattgcac tccagcctgg gtgacagagg gagacttcgt ctcccaaaaa ataaaaataa   19200
aaaataattg tcttggtgtg ctaatcagga gcttcctgtg agagtggaaa ttccttacat   19260
ggcagtgtca tgaaattta ggcccatgtg aaagatgttt ttgagtgtct caaaatagtt   19320
aacggtttaa aaatacatta tttatgtgtc agaaactgct ttcattgaaa ttgaagtttc   19380
tttgagaact aggatcatat catgtatatc tattgaattt cccacaacaa ttatcacgca   19440
agcaaatgaa tagcagaccc tcaataacac ttactgatga ttattgccat gtataagttg   19500
ggatactctt gagtaccttt ctaagtctgc atttagggaa atacagaaca caaatgaaa   19560 tgtttgattg gttgcttagt ttccacagtg acttttcaaa atgtatagga gcatggtaac   19620
aaaactattt taaatactac aatcttaagt atgcctttat tattcttacc cacaataatg   19680 cattgctta aaaaattgtt tatcagtgtc agaccatacc tttctgagtc tctactatgt   19740
aagatgtgaa agttaatatt cttcaattcc agctactttt cttttcctgc cttctgtcaa   19800
ctcctgtatt ccatatcatt acttcttatt gctaaattta taatatttat attctggttt   19860
gcatctatag ttaattctct tgtgcttcat ttctcagtgc taattgaaaa agaaaacaca   19920
tcacttacaa tgccatgatt gtaataaata aaattcactg taacacctag cagtatggtt   19980
gaacatgtag aaaaggaaaa agtgatcctg tgacactaaa atttagcttg ttctaaggat   20040
gctactttaa gcattagggt aaaatggatt ccctttgct aaattctttc agttcctcaa   20100
aattatgcca catttttgtt tctttcacat ttggactag attttcctgt aagcattcaa   20160
tttttcttga aaattttaat tgcatttttt tattcttgtt gacagaagaa acattttcat   20220
catatcacaa tttttttca gatttcttaa ttataccatt tgatgaatga atacactttt   20280
cttcttgaag tctgattttt ctgttctaat ttagagtttc ttctcatttt tctcctggct   20340
atgtctatta ttgctttagt ctcatgtctt tgtatttgat tattatttt ctttttacta   20400 ctgttttct tcttacagaa aaaaaagaa aaaaaacag gggtttttac aaatattgtg   20460
ctgagtcttt acatgtccaa aatgccttat attttttcctt atagtacatt cataaattat   20520
tgtgattaga accataaatt caaagtaatt ttctctcaga gctgggaaa cattggtacg   20580 ttgttaccct tcatctagga ttgcttatga gatagatatc tgatgccagt ctgattctgt   20640
```

```
cttttttaga taacttttttt ccctattcat atgtttatta ggatctttat cttttcactt    20700
ctgaaattcc tccagatatg gctctgttaa aatgtattct tctcagcact tgatgattct    20760
gtacaatctg gaaacaactg cctttatttta gcttaaggta cttttcttcc attgtacctt    20820
tgattatttc ttccttcttt ttttcaccct atctttatga aactcatgtt aatggtgcat    20880
tagaacttgt gaactgattt ttcttattta ttaaattcca tcacatattt ttcatctgtt    20940
tatctctgta tattttattt tctcaacttt tgatatttttt gttaattgaa atttaatttc    21000
caagaagtcc attttctatt ctctgattga ttcttttttaa tggtagccta tttcgtggct    21060
caaatcatat aaaatgtatt aaattttgtg ggaaaattag gcaaacaaag aaaattaaat    21120
tttacctaac tatatctaaa aacaatacaa ctaaacttaa gaaaagtgcg tatatgtgta    21180
cacatataca tatgcgtgta tatgtgtaca catatgctac atatacatgt atatgtagta    21240
tatgtacatg tagtatatgt gtgtatgtat gtatatacac atgtagtata tctatataca    21300
tgtatatgta caaagaaaaa atatgtatat aatagtttca ctgtacttta tttgctcccc    21360
ttttaaaaat aacagtgcta gagttcatga ctgactaatt ttcagaactt ggtgtgtatg    21420
gttgtttatt aagccctcaa taataatgct ttagtattac agtgcccagg catagtcagt    21480
gactgtgcta atagtcctag cagtagcagt tcatcctgta cagatctaag gtgtaactat    21540
tttcatttct gggcccttgg agattctttg gttgtcttca tatcttttac ctatcttgct    21600
gttcaataac aggtaataga aaaggagata aaacttaaat gtcatcattt cccactgctt    21660
aacagtcttt aaaaataaat gtgaaacccg taaggacgta atcttgccta gctttaagga    21720
atgaaggaaa cactagaaac aacagagaga aaggaataa ctgatcctcc aacatgttct    21780
gttgactcta cctgtaaagt atattcagga tctgactact tcacaccatt tcaccaattt    21840
ccatctccat tcaaaccacc ttcatgtgtt actttgaaaa gtgcagtttc cctgtcatgg    21900
gtttccctgt ttctagcttt gctccccctt cttacctcac cgtgggtttt tacccaaaca    21960
aaaattcaag tgatcattta aaattaagt caggtcatgc ctctcctctg cttaaaacca    22020
ttaatgggtc tctgtttcac tcagaatata agccaaagcc cttttcatga cccaccagtc    22080
ctcaagtgaa ttggctgcta tttgtgtttc tgattccatt tcttgccact attctccctc    22140
attctattct aatttccttg gttttcttgc tgtcctggca acaagaagag catccttttt    22200
cctccaggcc tttgcacttg ctgttccctc ttcctggagc acccttcctt cagagagcca    22260
caggtattgt ttctatcttt ccttctaatc tctccttgag tgttacttttt tcagagataa    22320
attccctaac cattctatct aacagaactc tgactattga ccttgcttta ttttctctct    22380
ttttttttaa aatttttattt ttttattccc ataggttatt ggggaacagg tggtatttgg    22440
ttacatggga aagttctttta gtggtgattt gtgagatctt ggtgcaccta tcacccgagc    22500
agtatacact tcaccctatt cgtagtcttt tattcctcac cccttccca ccttttccc    22560
ctgagtccct agagtccatt gtgtcattct tatgcctttg catcctcata gcgtagctcc    22620
cacttatgag tgagaacata tgatgtttgg ttttccatcc ctgagttact tcacttagaa    22680
taatagtctc cagtcttatc caggtcactg caaatgccat taattcattc cttttttatgg    22740
ctgagtagta ttccatcttta taaatatacc acagtttctt taactactca ccgattgacg    22800
agcatttggg ttggttccac attttttgcaa ttgcaaattg tgctgctata aatgtgtgtg    22860
caagtatctt tttcatataa tgactttttt cctctgggta gatacccagt agtgggattg    22920
ctggatcaaa tggtagttgt actttttagtt atttaaggaa tctccacact gttttccata    22980
gtggctgtac tagtttacat tcccaccagc agtgtagaag tgttctctgt tcaccatatc    23040
```

```
catgccaacg tctactattt tttgattttt tattgccgtt cttgcaggag taaagtattg   23100
cattgtggtt ttgatttgca tttccctgat cattagtgat attgaacatt ttctcatatg   23160
tttgttggtc atttgtatat cttcttttta aaattgtcta ttcatgtcct tagcccactt   23220
tttgatagga ttgtttgttt ttttccttgc taatttgttg gagttccttg tagattctag   23280
atattagtcc tttgccggat gcatagattg tgaagatttt ctcccactct gtgggttgtc   23340
tgtttacgct gctgactgtt cctattgctg tgcagaggc cttttgttta attaagtctc    23400
acctatttat ctttgttttt gttgcatttg cttttgggtt cttggtcatg aagtctttac   23460
ctaagccaat gtctagaagg ttttttctga tgttatcttc tagaattttt atagtttcag   23520
cacgtagatt taagttttg atccatcttg agttgatttt tatataaggt gagagatgag    23580
gatctagttt cattcttcta tatgtggctt accagctatc ccagcaccat ttgttgaata   23640
gggtgtcctt tacctactaa tttatgtttt tgtttgcttt gtcaaaggtc agttggctgt   23700
aagtatgtgg gtttctttct tggttctcta tcccccatt ggtctctgta cctatttta    23760 taccagtacc atgctgtttt ggtgtctatg gccttctagt ataaagtcag gtaatgtgat   23820
tctgcccaat ttgttcttg tgcttagttt tgctttggct ctgtgggttc ttttttgttt    23880
tcatatgaat tttaaaattg ttttttcctaa ttctgtgaag aatgatggtg gtattttgat  23940
gggaattgca tagtttatca acccttggca aagtgtttct gcttttctta aacaatttt    24000 attgtctgct ttctccagta gatgtgagtt ctatgagatg aggaacattg tttgggtcac   24060
tgacatgtat tgtcagcata ccaaacagtg gctagcacat ggtgagcact caataaaatat 24120 ttggtgaaag ttgcagtgaa tgaaaatggt ttctaaaatg gcaatgacta tagtcccagc   24180
tactctgaag gctgaggcag gaagattgcc tgagtctcaa aagtttgggg ttgtagtgca   24240
ctatgattgt gcctgtgaat agctgctgca ttgtagcctg gtcaacacag tgagaaccca   24300
tctctttaaa aaaatggcaa tgaaataatc ttatttttac tgcttttctc tttaaggctg   24360
ccagtgttgt ctttctctg ctgatttatc ctcattggaa attgaagata gataaaatat    24420
ccattgatta tttataggtg aaattaggct tttggatcca tgaggaatag ctgagacaat   24480
cttccaggag cttctggagc cgaggaaaca ttggtcacta aaataccatt tatattggca   24540
actgtactct tttccgatgc tagtgtttca attacattgt gcatttaaaa ggctgttgcg   24600
gctacctcaa aatataaaca tgatgtgcga cactacttgt tagttttgaa caactgattt   24660
ataaatagac ttagggtgct caagcctcct gcaagatgag cactgcctgt gttcttcctt   24720
ctgcttcctt tatttcagct gtgtgtctac caacttcctc ctccttctac actaggagaa   24780
attgcactgt ttccaatatc tttaacatct gctatcatga tgagaaaata tcttttctgg   24840
atttgaaata ccttcttcat tctttttttt taaatggcgg aaataaattc atagtgtttt   24900
gagtgcagtt ttcttcctgc tgttattgct ggctcaaaat ccaggagcat ttcagtgtta   24960
tttctgagct ccatgatggg agttccattt ctgtttatt caaagtgtta tctccagtgt    25020
ctagcacagt gcctggcaca ttataagcct ataatgttta tctagtggat gtagaccaat   25080
actattaaag aattatcatt gcaaagattt agtggcatga aaaatgata atgattaatg    25140 ctctactcca tgctaaggaa atgaagtgca aatcgttctt tatttttctt ccaagtatag   25200
agaactttct gaaattaaag aagcattgat taataagttt taatatatgt tattgatcat   25260
aataatatgt aatcatataa ccaaataaga taacacaggc catctttgt tctttaaaaa    25320 atgacaggaa gattagaata agagaaaaaa ttagaggtca aaacagtttt cttcaaacca   25380
```

```
gtagtgtaac ttactgagat atcttctgta atccttaaat tctgtattga tgctaccaag   25440
atgcaactct tgagctacaa ctgcctcttg ataaaggatg ctggtccctg ctgccagtgt   25500
aatgtttgct catttacagt ggaatgtaca atatagtacc tgggatggtg aagaaggtga   25560
agcaacaaat ttaaaatagc tgtgggtaaa cctacagaaa cagactattc tctttcttcc   25620
agattgcatt attcattttc atatgcctgc ctttatctgc tttggaagcc tatttcctaa   25680
tcttccaaga tttatcatca ccttcatatg tccatagcat gcatttctca gacaggtaag   25740
atagaattgg tatatatttg gtatagcaaa aagtcaaggt tgtctttaga ttatatcctt   25800 ggttttcat gtggtactgg ggagaaagcc tactgtttct tcatctataa aatgaaggac   25860
ctgggcaaga taacattctg tgaaatttca ctgaactttg agctcagcaa agtagggatg   25920
cgtgtgtgtg tgtctatttg caatgcatca cagaccttaa ataaatacag ttgacccttg   25980
aataacatgg aggttaagag caccaacccc ctgcactgtc aaaaatccac atgtaatttt   26040
tgactcccca aaaacttaac tactaatagc ctgctgttgt ctggaggccc tgctgataac   26100
acacacagtt gactaacaca tattttctat gatatgtatt gtgtactata ttcttacaat   26160
aaactaagct agagaaaaga aactgttatt aagaaaatcg taaggtaaag aaaatatatt   26220
tactatttat taaatggaag tagatcatca taaagatctt catcctttgt tgtcttcacc   26280
ttgagtatgc tgaagaagag gaggaaaagg atgggttggt cttgctgttc caggggtggc   26340
agaagtggaa gaaaattcac atataagcag tccatgcagt tcaaacctgt attttaaggt   26400
caacggtatt tgttacattg cattttgtaa gtgaccttgt taattttttt caatgaaaaa   26460
aatagtgttc cattcaaatg cctgtatgtt tatgagaaac atttcagaac tatgaaagtt   26520
gaattcaagg tttcttgcag attgtttgta tactttctgt aatgtttgtc atataatgag   26580
aatactaatg gtcttacaac ttgaaactga ttaactgatt aactctttaa gcaacttaaa   26640
aagaaaatct ttcagtgagg aaagagtatt catcagaagt attctagtag atgacatatt   26700
tttggtaatg aaattgatat gggcaattaa cagcttttc caagttggct atgctgctac   26760
tctcttatta tacaatgata ctattttca gagcagaaag caaattagtt ttattttat   26820 aaaccaaatt ttaaatatcc ctttagagaa tagaaaatat gaaaaagtat ttgcttctca   26880
gacctctcaa caatataaat tttcttctta agaggaaatt tattcttgca tgccaacaca   26940
aaggataaaa agtttaccta tccttagttt ctaagaggaa aatgtgcata aaatttccat   27000
ctgctgtgtg ccagttacca aaacgataag ttccaactca atcttggttg ggtgtggtgg   27060
ctcacgcctg tgatcccggc actttgggag gccgaggtgg gcagatcacg agctcaggag   27120
tttgagacca gcctggccaa tatggtgaaa acccgtctct actaaaaata caaaaaaaaa   27180
aaaaaacaaa actagcccgg catggtggtg tgctcccgta gtcccagcta cttgggaggc   27240
tgaggcagga gaatcgattg aacccaggag gtggaggttg cagtgagcca agattgcacc   27300
actgcactcc agcctgggca aaagagggag actctctctc aaacaaacaa aaagactca   27360 atcttactaa aaaactgcag agaagaatga gtcattttag tcaataaagg aaataaagaa   27420
attctagttt tgaaaatgac ataatttgct acaagaatgc aaaggtgatg acatgaggaa   27480 aaaagggggtt tgctgatttg ttttctctac tactcagcaa atgcaggcca ggaacccatt   27540
tattcaaata tttattacat ggtaaattaa acatttata aaattaggct catattctta   27600
gaattcctgt taacaaagtg acatataaac aagattataa tctaatggag attaatattg   27660
gttgagaaaa atcttgagac ttcctttaaga cttcagttta ataaaatatt gacttaggta   27720
gatatatgtg aggaaatata tattttaccc atgcatgcaa aaatgatgta tgtatttctt   27780
```

```
aaaagagtag gtagcaatga cttcaaagga ccatagctgt ccctatcaac atatatatta    27840
acaaaacaat tagaaacatg agcttagtat gctaattata tttctaccca aagcctcaat    27900
ttgttctata gctatactgt tcatatataa gtaaaatttt aggggtatca gagagagtta    27960
gaaaagagca aatacatgta tgaatttgat aagcctatcc cttaatttga tagatcttaa    28020
aagatatttt atcactgcat tcttctaaag aaatgtattt gtacattgca aaacaaccct    28080
ttttgagaag tagactatga tcacagattt tcttgccact agtatttcct aagatttatt    28140
tggaatagaa gatcgatatt tttctgggat gacatatggt taaaaagtaa aaacaaaac    28200 aaaacaaaaa actcttttaaa aacacaacaa gtaaaaagct gaatgaattg gaaaattaac    28260
gaatcttctt agatctgtca gaaaaatgag attatagggc aaaccactgc atcaaatatt    28320
agagaagcag acaggtagat agaaagaatc acaacttagt ggggcaaaaa cctacaagga    28380 aaattttttgt gggaaccggt gccaggtagg aaaacatgaa ctgtaattga aaaattgttc    28440
agtgtgggcg gttgttcagt gtggcaagtc tgagggttaa aaactccagg aggactcact    28500
tacggaaggg cctgtacttt tgtgagttta acctccagga gtgttcacag tgactactgg    28560
agaaaattcc ctaagggag aagaaaagga accatcttga aatatgtcag agcattttgt    28620
tggactcaag cctgctctca agtgaaacta ttttaccaga gcctaaactt tgggatttt    28680 ataagagtgt aacctcccaa agggaaggga aatacctaag ttcagccccc ttttagcttt    28740
ccacataggg aaaggaaaat atataactct ggacaactca aaccatcctg tccacgttag    28800
ggggcctagg ggaactgaga aaactggtga agttcatagt ccatgggtac agtttcacca    28860
aagagggaga ccaaattata aggctacaga atgcttccct ttcccacacc ttttactatc    28920
atattactaa aagcctattt gcagcagttt cttttactga gtatatcatg tctgtcattc    28980
aaccaaaaaa ttataaggca tgctaaaagg caggaaatgc agtttgaaga cactgaataa    29040
gcatcagaag cagagtcaaa tatggcagtg acattggaat tatcagacca gaaactttat    29100
aaaaaactat ggttaatatg gtgagggatt aaaaaaatga catacaagaa cagatggata    29160
atgtaaatat agagacgaa attttaggaa agaaccaaag agaaatgcca agtatcaagc    29220
atagtgtaca gaaatgatta aaatgtcttt gataggctca taagtagatt gaacatagcc    29280
gaggaaaaaa tctttgaagt taaggatatg ataataggaa cttcaaaact aaaatgcaaa    29340
gagaaaaaag actgtgaaaa aaacagaaga gattattcaa gaactgcagg agaactacaa    29400
aaggtataat gtacgtgcaa tgggcatact agaaaaagaa agaaaggatt agatgcaata    29460
tttgaagaaa tagtgtgtga aaatctcccc caattaatgt cagacaccaa actacttctc    29520
cagagagctc aaagaacacc aagcaggata aatgtcccaa aactactcat gggcatatta    29580
tattcaaact tcagaaaatc aaagattaaa aaaatatcga aagaatccag aaggaaaaaa    29640
cacctataga ggagcaaaaa taataaattt tatctgacat atcctcataa accatacaaa    29700
taagagagta gagtgagaca tttaagatgt tgaaagaaaa atccggcagt gtacgattct    29760
ggaccttgca aaattgtcct tcagaagtta agaaataaag tctgtcttaa agaaacaaaa    29820
atttcaggaa tttgttgcca gtggaccacc cttgcaaaaa atgtttaaag ttcttttagag    29880 agaggtaaaa tgatacaggt tagaaactca gatccacata aggaaaataa aattagggat    29940
atagtagtat tccccaactt gataaagaaa atacacaaaa aacctacagt ttacatcata    30000 cttaatttttt agaaactcaa agctttcctg ctaagatcaa gaacaagaca aaggtgtctc    30060
ctcttaccac tttgtttcct actggaagtg ctacctaatg caataagaca aaggaaagaa    30120
```

```
aatgaaaagc atacagattc cggaggaaga aatcaaactg tctttgttca cggatgacag    30180
ttgtttatat ggaatatcca aaggatcaga aaaagaaaaa ctggaactaa taatgatta    30240
ttgtaaggtt acagaataca aacttaatat aaagaaagcc aatcactttc ctgtatacca    30300
gcaataaaca agtgtaattt gaattaaaaa cacattacca tttacattag caccccaaga    30360
aatgaaatac ttttgtataa atctaacaga atatgtacat gatctatatg aagaaaacta    30420
caaaagtgta atgaaaaata ccagtgaact aaataatgaa gagatgttac atgttcattg    30480
tcaagatgtc agttcttccc aacttgatct atagattcag tgcaatgcca ttaaaaaaca    30540
cagcacgata ttttatggat atcaacaaaa ggattctaaa gtttatatgg agaggcaaaa    30600
gagcagaata gccaactcag tatttgagga gaacaacaaa gtcagaggac tgacactacc    30660
tggctttaaa gcttactata aagctcagat aatcaatgta gtgggtactg gtgaaagaat    30720
attcaaatag accaatggaa tagaataaag agcccaaaca aacccatgta aatataatca    30780
aatgatcttt gacaagggag caaaggcaat acaatggagc aaagatggtc ttttcaacaa    30840
ataatgctgg aaaaactaca cattaacata caacaacaaa aatttttttaa atccaaattg    30900
agtgtaaaca cagatcttat acccttttgca aaaattaact tgaatcatag acctaaatgt    30960
aaaatgcaga actataaaac tcccagaaga taacacagga aaaatcctag atgactttgg    31020
tatggcagtg gcatttttta gatacagctc caaaggcacg atacatgaag gaaatgattg    31080
acaagctgga cttaactaaa atttaaaact tctgctctgt gaaagacaat attaagagaa    31140
tgagaagaca agccacagat ggaaaaatta tttgcaaaag atacttctca taaggacta    31200
ttgttcacaa tgtgcaaaca actcttacaa ctcaacagtt tgaaaatgaa caactcaact    31260
taaaaaatga gcaaaaaacc tgaacagaca actcaccaaa gaagatacac aagtgtcaag    31320
aaagcatagg aaaagatgtt aaacatcata gtcattaggg tattgaaaat taaaacaaca    31380
atgagatacc gctacatacc tgttagaatg gctgaagtca gaacactgat gaaaccaagt    31440
gctggtgaga atgtggagca acaggaacct tcattcattg ctggtaagaa ttcaaaatgg    31500
catagtcact ttggaagaca gtttggcagt ttcttacaaa ataaacatac tcttcccata    31560
tgattcagca atagcgctcc ttggtatgga cttgaaaact tatgtcctgg ccgggcacag    31620
tagctcacgc ctgtaattgc agcactttgg gaggcccagg caggtggatc atttgaggtc    31680
aggagttcaa gaccagcctg gtgaaatccc atggtgaaac cccagctcta ctaaagatac    31740
aaaaaagtag ctgggtgtgg cagtgtgcgc ctgtaatctc agctactagg gaggctgagg    31800
caggagaatc acttgagccc aggaggcgga ggttgcagtg agctgagatc atgccattgc    31860
actccagcct gagtgacaga gcaaaactcc atctcaaaaa aaaagcaaa acaaaaaaca    31920
aacaaacaaa acttatctcc acataaaaac ctgcacacat tgtttaacag ctttacataa    31980
ttgccaaaac ttgggtgcaa tcaagatatc ctttaatatt tgagtggata aactgtggta    32040
catccagatg taagaatatt attcagcact aagaaatgag ctatcacatc ataaaacgac    32100
atggatgaaa cttaaatgca tattataaag tgaaagaagc taatccgaaa aggctaaata    32160
ctgtatgatt ccaactatat gacattccgg aaaagccaaa attatggaga cagtaaaaag    32220
agcagtgttt tccagaggga ggaatgtata ggcaaatttt tagtgcagtg aaatgaatct    32280
atgtaatact atagtggtgg atccatgtca ttatacattt gtccaaacac gtaggatgta    32340
accaccaata gtgaacccta atgtaaacta tggggtttgg gtatcaaaat gcatcaatgt    32400
aggtttatca gttgtaacaa atataccact ctggtatggg atgttgataa tggggaaggt    32460
tgtgggtctg tggggacagg ggtatatggg aactttctac tgttttactg tgaatcaatt    32520
```

```
ttactgtaaa gtttattaat gttaaaaaat ttaatgcaca tgtaccctaa aacttaaagt   32580
ataataataa taaaataaat ttaggcaatc tgaaaaaatg ttaataaaaa agaaaataaa   32640
ctagttgaat gtatcagttc attttcatac tgctataaag tactgcctga gactgagtaa   32700
tttataaagg aaagagattt aattgactca cagtttagca tggctgggga ggtctcagga   32760
aacttaacag tcatggcagg tgacttcaca aagtggcagg aaggagaaat gaacgcagaa   32820
gcaactacca aacacttata aaaccatcag atctcatgag aactcactcc ctatgatgag   32880
aacagcatgg gggcaactgc ccccatgatc caattacttc cacctggtct ctgccttgac   32940
acatgggtat tatggagatt atggggatta taattcaaga tgagatttgg gtggggacac   33000
aaagcctaac catatcagtg ataaaactat gtcttttctt ttatggggtg ctatagtgtt   33060
tcatttcaag ttgtcttttt gacctccatt ttccaatttc tggttaggaa aaataacttt   33120
gtctcctcct taattgaccc acaaccttgt ttgcaatgaa gaatcaacac aaatctttca   33180
ttaaaagaaa taggggaggt gatggggat atccatgagt gtccatgggc ataattcagt   33240
tgccttcatt caatgccaat gatactgcaa agcctacaag gcaaattcat gtacctacag   33300
acagactcca tccttttttct caaactattc aagataaaaa atcttgtttc attttatgtg   33360 aggattttt tcaccatcta tcctcaaaaa atgaaaaata tcctcttcat ttgggaaatg   33420
agtgcttata atagaaagta atttgtagtc agctgttaca cttagatgat ttgtgtcacc   33480
tctgacctgc tttctgataa tgcatgactt cattcatggc tctctaggtg acctgtgtac   33540
cctgacctgg cataaaccac tagagtatta agtcatttca gtggcacatg tttgagggaa   33600
gattgacatc ccactggaag actatctaca gtgagatcct ctaaagcagc tgcattccta   33660
gtgaggcatg attaagttta tcccactatt aggttctgga gtattacttg tcatgcccaa   33720
gaggaaagtt tttctagcat gcagagtatc tggttttttaa tggctactga gctgaaataa   33780
aatgtgccta ctaagggttg ttcatttgtc tgtctcccctt cttcactgt ttttttttcttt   33840 ggaggttaca gtagttatgc ctttctggtc agctggctgt tgacctatca tagaaatgac   33900
actttcacat cttcaagtgt aaggaattag atgttccagc cttcactttg tttctcatcc   33960
aaaatcaatg acaaaacttt cagtattgat ttctcatggc ctatgaacct gagtcaactt   34020
ggcataaagg acttttcaga caagcttctc taaatgcaga gtcagtggct tcttttttgcc   34080 aaactccact ttgctcagtg ataacattaa aatggtgatt tgattcattc ctagtctaaa   34140
aatacttcct catattccaa aatctcagtc attaatacat ggaggaaaat acaaattatt   34200
acatgcctgt gcttctcggc tgttgtagat agataaaata tatacaattg tgttctataa   34260
ttattgagtt cttttaagtt ttatcttttt ttgttttacc aggaagcaaa attatgttta   34320
tttcagagct tatttactgc atttagaatc tcatgacact taaaaaaccct ttctaaaacg   34380 taaatattct ccatgatctc catggtcaca aacagtattt cacgttctaa ttgatattgc   34440
cattttatca tttttttttt ttctttggag acagtctcac tctgttgccc aggctgggat   34500
gcagaagcac gatcttgcct cactgcaacc tccacctcct gagttcaagc gattctcctg   34560
cctcagcctg ccgggtagct agaattacag gcatgtgcca ccacacctgg ctaattctgt   34620
atttttagta gagacagggt ttcacgatgt tggccagact ggtcttgaac tcctgacctc   34680
aggtgatcca cccaccgcag cctcccaaag tgctggaatt acaggcgtga ggcactgcat   34740
ctggcccttt tatctttctt ttaactcaaa tcctcaaata tatccctcca tgtgaagttg   34800
ccttccctaa ttatgtactg tcctagttta atcttcattc cttgtttgcc tctataaaac   34860
```

```
caagtttaaa aatagtctct gattctgtaa atcatcactc ttatgctcat ttatatttct   34920
atctagaata ttttaaatcc tttgtaacaa agtttctact atgcagtcta cctttctcag   34980
ctacgatcta tatactcctt ggccatgtct tttgttattg tgtgtgtttg tctttgtgtg   35040
tgtctgtata gtagtggttt gtaaattctc catttagtca caatatgctt tttgaggatt   35100 ttcctttttcc tgggaatttc ttgatgattt ttattttgtc atgtgatgaa gaatgtatgt   35160
caaagcacca ctgcagaaat agtgcttttc tatttacttg cactcttcca tcttagaaga   35220
gctggtgata gacaaccgac tcttcttttta tcttggtttc tacaacacag aggttgctaa   35280
gcgactttaa tcccttttaa cacaggacaa tcaacaacaa attccttctt tctttagatt   35340
cagatatttc acttagaaaa tctagcaaat aaaaaatggt ttaaaacttc tttaaaatgt   35400
gtaattctgt acaatctcct acatctgtaa cccctgcccc aaatattttt tacttatgct   35460
atttcttgag cattatgata tgcttattca taggcaatca acttgtaagt agcaatagtg   35520
tagccccttc taggaaatcg aagatgtgaa atccagttt aatgtgataa tgagttactt    35580 tgatgaaaaaa tactatgtca caatttgtta taaaaatact catttggatt tctgattcac   35640
ttatattacc ctccaacctt aagtatgatt gaatttatag cttttttatac tactttcttt   35700 atttagggag gagtgtattt aaattctgtt atctcggtta ttacttgaaa gttcaacctc   35760
atactttcat ttttatataa ttttaatatt atgaaaatat tttatgtaat tttatgtata   35820
attcgaaaac attttttaaat attgcatctt taaatttta tttcttttat caaatttttcc    35880 ctatcatttg ttctctggct acaaccaaag ttaatagtta catttttttc cagtgacaaa   35940
tggtaatttg caaagacttg taacagttgc ttaaactttt tttatccctt atttaagaat   36000
catgcaaaca accagagctg ataggcagca ggtgcacatg agtgtggctg tgctgatggt   36060
tactgaaaga tttccaaggt agctagtaat tctgctaccc taagccacta tagctccttc   36120
cccattactc cctgggtcta cccaccatcc tgcagctaga ataataaatg gcatgtaggt   36180
tcctctagga tcctcctcca gcactatgtc tcatgcctgg acatatgagc tgttaaatat   36240
tttgattatc actcctgtgt ggtaagggag acgtctactt gtcgtaactt gatgtttact   36300
aaactacttt taagattacc ttatgataaa agtagacact tgcaattttg cagaatgcat   36360 agtttgttttt taacaaacca ggtaaacata actgcagagt tttcctatac gttttgaaat   36420
ctttaaaaaa gtattttta tttgcctttc tattagaaat agattagata aaaatttcct    36480
tgtttcaatt tttagaatga acattagaga atattgttac tgaaggaatt ttttttaaaaa   36540 tagtgactga tcaaatgtca gcagctttat actatagtgt aaaatttat tttgtagttt    36600 gccatcccat taagcattag aattttttata attgatcctt tgatgtttat attcatgata   36660
ttaatgtaat gtctttaaac cttagctcat ataggtcata tgacttaaag catccttaga   36720
tgaagatatt tgggctataa ataatttatg acataagtga tttaaaaatt cattctttcc    36780 atccatttttg aagaaattgt aaggtagggt tcatgtatac ctaatactta tcccccccaaa   36840 atacgaaaaa taaaatcatt tttaaaatat ctgggttaat gctatagatt ggaagcagtt   36900
tttaaaaagc acttaaagtc taccagttta ttgatcctca atctgtggct gttttaaatg   36960
gatgcaatta gcagttcagt ctaagagaac catggtagta gactcattac tccccagaaa   37020
ccattacatc atttttgtaat attaaattac taaatataag gaatagaata tatattgtaa   37080
aaattgcttt ggaatcaata ataagtattg tggctatcaa ttatagttat atattacaat   37140
gtaagggata tccttttata aacttaatat cacacaagta gacttagaat aattccatta   37200
atataatttt gcttgtgttt ttataccctat tcatttcaat aactcttttt cctatatata   37260
```

```
tttttatct caaattcgat agtatctaaa tcatggaatc ataaaacctt aaagctgggt    37320
tggaacagaa ataatacaat ttaacatctt ataggctctc tagtcctcag tttccctaag    37380
tgatcggctc aagatcatga atttatggag gattagagtc agaattagaa cccaagatta    37440
atttatactt tgttatctct tctacagcct accccttag tttgcctgtg ggtttatgga    37500
agttacagga gagacattct gagattcagc taaaaaccta gctcccaata gaattattgc    37560
cctgtagtca gccgcgcaaa tacaatcaca aatacctgaa gttccttgtg tgaagaaaaa    37620
gaaaatgact attaaagcat caaaatcaat gcaagttacc tttctttgcc cctttcttcc    37680
cctttcactc ctttcttctc ctatactact tgaaatttct agcggggatc tctaaaatgc    37740
ctggatgtta ggaatggtaa gtctattgta gagaattata ttttctattt tagtggatga    37800
aaaataaacc atacccttaa gaggcttttc aaagttaaga ttttgagcac atccttcatt    37860
ggcccagtct ctgaccagtg aggtcaagta ttagccagtg tcagaatgtc gtgaaaagtt    37920
tgtgtttcag atgcagaatt ttttttttgca ttttctgtgt gatgtttata gggtattttc    37980
ttctgaaatg ttttccatct tggttttaa aaatatctat tattttaaaa aatattccct    38040
cataacttct tttatttc ggaaactata taaattgatc tgataatcta tacacaatgc    38100
cttgtgaatt tatacctgta cctctcatgt tccagtgttt ggttcttaaa taatcacttt    38160
gtataatgga aatactatgt taaattgttt ataactggtg gttgatattt cagccttgtt    38220
tggctatcgt agttatataa agactgttaa ttagaaacaa cctcatatgg tgtatgcttg    38280 ttttatctt catggaattt gttctgcaaa cactgagttc tttactggga gtcaccactt    38340
tgtctatgtt aggaggagca ggaagtgaat acatttaagg tctttaattt tcttcttaaa    38400
actttgacta ctgtagtggt tttttaaagc attaacagga gaatagccat cactgccaag    38460
tagctgacat tctgaaatag cacttccctt taggcactgt acagttggaa tcatttactt    38520
gcagagaggt gtgtgtgtgt gtgtgtgtat ttatgtgtgt actcatgtgt ataagaatag    38580
gagaaacact ttgtgggcat atcctgctga ggtgagtaac gtgctgatta gtgaactcca    38640
gtctcatccc atttaaacct ggaggagaac cacatcaagc acagaagcag ccaaagcagc    38700
atttcaacag gaaggaaaca tctattactg gggctttgaa gaaacatgcc atgaaggtgt    38760
actaatatca caagggaag ggaaggacta aattcagcat gataaacaaa gtcccttttt    38820
tgtaacggaa gtgtttgatg atgtttgatc aatggtggat ctatctcttg aaaggaaaat    38880
gcatttaaac cccaaatgga ggattcttat ataaggtgcc tagcttgtaa tgatatattc    38940
atgtttatag gtagagtgac tggttttag agaagaggtt ttttttttc cttcatttt    39000 gaacgaaaac ttgtctgtct ctaggctttg aaatgtagaa ttatttacct ttccccaaaa    39060
tgaaatgttt cactgaatct cctacaagct tgtggaggcc atgaagcatg ttgaataaga    39120
gcacaggctc tggaggccct gccacccaca aagggtgtgc taaggtaaac aactgatagt    39180
attttgaaaa ttagatgact tagaatccat tcaataaatt ttagctattt ttattgtctt    39240 tttttctaa atctatttgg aaaatattgc agataaagta gataatacct ttctaaaaca    39300
cagtgagacc aggcgcagtg gctcatgcct gtaatcccag cactttcgga ggccgaggta    39360
tgcggatcac gaggtcagga gatcgagacc atcctggcta acacggtgaa atcccgtctc    39420
tactaaaaat acaaaaatta gccaggcgtg ggggcatgcg cctgtaatcc cagctactca    39480
ggaggctgag gcaggagaat ggcgtgaacc ggggaggcgg agcttgcagt gagccaagat    39540
cgcaccactg cactccagcc tgggctacag agcaagactc tgtctctaaa aataaaaaaa    39600
```

```
taaaaataga acagtgaata gtttataaag ataaaataga ataggcttca atttagggaa   39660
caaaggaaaa tatgtttagg aatgatatta tgctcaaaat gattgcaact ttgatggtga   39720
agtgtatttt attcaattaa aaatgtagat atggctgggc gtggtggctc acacctgtaa   39780
tcccagcact ttggaaggtt gacgcaggtg gatcacttga ggttaggagt ttgagacctg   39840
cctgggcaac atagtgagac ctcatctcta caaaaaataa acaaaaaatg tgctgggtgt   39900
ggtggtacat gcctgtagtc ctagccactt gggagactga gatggaagga tagcttgagt   39960
ctgggaggtc agtgctgcag tgagccgaga tcgtgccact gcacttgagc ctgggtgaca   40020
gagcaagacc ctgtctcaag aaaacaaaca aaaaaacaaa aacaacagta gatatgtgtg   40080
tgggaatgag aacatttaaa tgtgctcatc ggcttagatt tttctttaac ccccttcatg   40140
gcccttatct taacctctgt cttcagcact acccttcata tgtttgttcc gttttatctt   40200
ctaagtgatt tttttataac tctcaatgta tcatggcaga aggaaaactc agtgtataag   40260
ctgactgtat tttgcatttt ctttttttt tttttttttt tgagatggag tctcactctg   40320
tcacccaggc tggagtgcag tggtgcgatc tcagcttatt gcaacctccg cctcctggag   40380
gcgattctcc cgcctcagcc tccccagtag ctgggactac aggcttgcac caccatgcct   40440
ggataatttt tatattttta gtagagacgg ggtttcatca tgttgtctag gcaggtctca   40500
aactcctgac ctcaagtgat ccacccacct tggcctccca aagtgctggg attgcaggca   40560
tgagccaccg cggcctggct tcatgatcca aaatagcatc attaagcttc tctttcaaaa   40620
catgtatata agcctgtgag tcatcactgt atttatcaga atattatcat attggagact   40680
ttgcaaagct gaacaaagcc agaattattg gctactgagg aactatattc tagcaagaga   40740
ctattctatt tgttggggat cacctctttt tactaaaggg gactgttttg ggcatataaa   40800
actagaattc atggtttctc cttgatagtt tgccagcttg attcccagtc aaccagataa   40860
ctgctggtag tgacactcat gtcctccagg actcccaatc ttgtgccagc tcagagaggg   40920 aaatcccccct agaactgctc acaccattcc aagaaccaca agcaccacct tggtatagtt   40980
aaaaatgtga taccaactca aattctgata aaaacaagtt ctataaagct taataaagtt   41040
atatttttta ctttttaagt tttgtttttac tattttaaac agaaaacaga aggtaaaaac   41100
tcctctgcct tcctcagtat ttggtttgtc agttgctgaa ctcagattta agagtctaat   41160
catatacagg caataaccct cttctaatct taataatgtt tctttgatca tttcttttaaa   41220 aagaaaaatg aaatagccta ttgactccaa ccctgacctc ctgtacttca cctgcctgat   41280
gaatatttat ttggaataca taagttttt caaatgcatc atgtcaagaa tttgtcattt   41340
cagattcctt tctagaatta tctatttatc tcattagtag catcattctt tcagacaacc   41400
aaactcaaaa gctttatcac tataattgaa tttcttttt cttcttacat ttaaaatgtt   41460
actaaatgcc attcatttct ttatcagtaa tatttctgtt tgatcatttt atttcattta   41520
ttctgccacc ctctcattcc aactattgct tatacttgag tactgcaata agccaatatc   41580
ttgcatatga ttatttataa cacctaaatc ttctaccact tcacactcac tgggatggat   41640
ataattttta aaacatacaa taacaggtgt tagtgcggat atggaaaaat tggaaccctg   41700
acacattgct agtggaatgt aaaaaggtgc agccactttg caaaacagtt tggcagttca   41760
tcaaaagatt aagcatggaa ctaccataag acccagtagt ttcgctctta gggattccac   41820
tctcaagaga attgaaaaca tatgcccata caaaaactta taaacattgt atatccatgt   41880
ttgttgcagc attattcaca atagcctaaa ggtagaagca acccaaatgc ctacagatgg   41940
atgaatggat aaacagaatg tggtatagac atacaatgga ctattattca accttaaaga   42000
```

```
ggaagaaaat tctgacacat gctagaaaat aaatggatct tgtatacatt ctactaagtg   42060
gaataagcca atcacacaaa gaaaatatt atgattccac ttacatgagg tacttagaat    42120
agtcaaatta atagaggcat acagtagaat aatgattgcc aggggctggg aggaggagca   42180
aatgggaagt tattgtttaa tgagtataga atttctgttt aggaagatga aaagttctg    42240 gagatgggtg gcagtgatgg ttgcacagca atgtgaatgt acttaatgcc acagaatagt   42300
atacttaaat atggtttgaa tggcaaactt tgttacatac attttatcac aattaaaaag   42360
tttgaaatga atatccaaag aagcattatt tatgaggcta aaagtggaag taacccaaaa   42420
gttcatcatt gatagctaaa ggaaacatgg catatcaaaa cagtagaata ttagtcatac   42480
aaaggaataa agtacagaca catgctgcaa tacagatgca ccttaaaaac attacactaa   42540
gtgaaagaaa ccagacgtaa aaggccaaat tttgtatggt tttatatata taaagtcgtt   42600
caaaatagga aaacccataa agactgaaag ttgattagtg gtcaccaagg cccgggggag   42660
gaatgaatga aaactggctc ctaatgggta ctgggttttt tggggcgagg gggacagagt   42720
gatgaaaata ttgtagaatt tgatagtaat gataggtgag agtggcataa ttttttttaa   42780
tatactaaaa cccactgact catatacttt acaaggatgt attttatggt atgtgaatta   42840
tatctcaaaa caccccttaa attttaacgt atggctttta tgatgccatg tttctaaaga   42900
agcaacgtgt cccagtctca gcttactatt tctaggcatg tgactttgag aaaaaattaa   42960
gagacctccc ttcttactct gtaaaatggg aataataata atgatgataa tgataataat   43020
aatgatctta ccagattttt ttgagtgtta aatgaggtaa catatgtagt gcatctagca   43080
tagtgtctgg catttaccaa gaaccccggg aacctgagct tcaactgctt ctgatactat   43140
tccagatact atttcaggat attccaatac tgtttccata tattcaggac aatggaccaa   43200
ctcctttagc cattttatca aaactctttta gattctgttt caaatcggtc tttccaaagt   43260
cttcttgtgc tcctttgtag acactcttca gtcagagaga gcttttttaat ctcctccaat   43320 ttgctgcagc tgtatctgtg cctcaaaaca acgctttctc cccattcctc ttttctctct   43380
gcccttggaa ctctgtggac ttctctcatg ttttttaacct actccctttt atcagtgcat   43440
gtcatctcca cttatttgta gcacccaata tttttactac atctttgacc aattaagtct   43500
tacttgggtt atgttttttaa agtaggtatc ttattaggtg gtccttttaa agtatatgtc   43560
cagtctctcc agctaaatta aaaccctga gcacagagac cacatgttat aatgttttac   43620
cttttccata gcacttagca tgttaccttg acatggcata tactgaatga atgcttgcta   43680
tttatgagtt tagttagtgc cacatctcat gaagtacagg gacttaatga ttctcaatcc   43740
tgacttcatc ttacagtcac ctggagaata aagtttcctc ttagctcaac aagtcagaat   43800
ctctgagcaa aatcctcaac ttcttaccta ggtgatactc ttgtaagcca cactgtgaac   43860
cactggattc aacagatgaa gtaatataag ccactggctc ttaagcctca ttgattattg   43920
cggtgaagat gtgaagacta aagatgcttt gggcatggca aagtgttcta cagatattag   43980
aattgttatt atggtacatt tgagagtgtc attgctttga gaaagattct ctaagttttt   44040
taacagccac actgtaatgg aaatatccaa ttataggtat ccaaaacctt ttaaactctt   44100
tatatcaggt gtatataccc tgttcctttt tgctaactta aaaatgttca aactctgtct   44160
tctctaggct ggcaaacatt cagcagcaca ccctctcaag attgtttact tgcctttgct   44220
cctgttgagt tacaacgctt ggaagcagga gatgggctca gcagcagcca ataggacatg   44280
atccaggaag agcagtaagg gactgagctg ctggtaagac agtggagaca gttgacactt   44340
```

```
gtttgtcaag tatgaatttta ttcctaatgt aatggtaatc tctctcccaa acttcaactt    44400
caagttaccc tgcaccctct caaatacttt tctttattgt ctatgcttag gacacatgga    44460
ttagattgtt aagatttgtg aatttactaa agttgtgtac tgacttatgt atagctgtat    44520
ttttctggag aaagatagat ttttatcaat tctcaatgtc tatggagttt ttaaaaagag    44580
gtaaggatta ttcaaatgta actataaaca taagaaaatg tgatatctat aaccagttgt    44640
tagagtattt atcgcctcca ttttgcttca cttgtagcca cttcgtctca atcttgttaa    44700
ggaccaaata aatggtattt gtggttactt gctgatctga aaagtgagta cctcctgcac    44760
ctggctagtc agtcttgtga caatttggtg ccatagaact agcagagaac taaattatgg    44820
aatggcagat ctcaggagca gctatgtgat tttacatacg gtttgttttt aatggataga    44880
gacagagtct ggctatgttg cccaggctgc tctgaaactc ctgggttcaa gccatcatcc    44940
tgccttagcc tcttaaggag ctgggattac aggtgcatgc ccccaggccc agttcatatg    45000
attttctgaa aatacaaaag aaagagggag atacaaaata cttttttaat catgttctta    45060
taattatctt aataaaaatc aatttgctct gaatgccatg acctgctgag tgtcccaacc    45120
taagggttgt cagaccattt tctcatatat gcatgtatag aagtagggaa ctaatatatt    45180
tttgtctaaa atgtttaaga tgaagatgag aatgaattct acaatatata attttgcctg    45240
aactatataa gacagttaaa attatagaga cattgcagga gagactctgg attagataga    45300
aaaaaggaag aattaggctt tttttttgtc tataatcctt ttagtaggta attcagcttc    45360
agtttcacta aatcttgttt atgcattcag cataacaaat cttctaataa gcctgtatag    45420
ctctaatctc tgccttactg cagacacctg aggatataag tatccactct gccacttgat    45480
acttctcaga gactgttctg gtgctgagaa atcctttcca gtgtgtcctc agttgaactc    45540
ccatgattcc tggatgttgc cattttcaag acacagggca agcgcatctg tctagattac    45600
ctctctacct tgggaatttt aagtcactct gtgagggaaa gagaactcag tatagtagta    45660
actctcagaa tgaaaatttt cccctttgcat gttaatattt ttagagtaat cattgtcact    45720
gaaaatagac ttcctctttc ccctctcatg ctggaaaatc ttaggtaatt atgaataaag    45780 cattcttttac ttttcccctc ctcccttgat gattgcttta cctcactctg tgagaactgt    45840
gactactcat tctgctcttg tcttttacat gagaactgag agcgcatttt taagatggaa    45900
ttttcctcct taatgaagtc ataacattag tcagaagatt ttctcttctt gaacgttaag    45960
cctgggtaag gaataaagtg cagaagttta tggaaaatta aagataact taaaaaaaaa    46020 acgaagacaa caaattaaaa tattagccat tgagggaaaa ggttttacag gtagctctct    46080
gaggagttct tccctcatat ctcctcaaaa atcttgtttt gcatttaatt ttttacagtt    46140
ggataagctc agcccttgac atattttcaa tagcaaataa gcctagagtt tattttttagt    46200 acatttatta ggaatgtgtt cttgggaaaa ttatttaacc tctgtaagcc ctgctttaaa    46260
tggcaaagaa gaaagtaggt aataatagat aataacagga ttattttatg cattacctgt    46320
acattgccca acatatagta agttctcaat tttatattgg tatttgtttt attattaacc    46380
acttttatta atgttgcttt tagttttttga aatatgaatt cattcaaaaa tatttcttga    46440
gcacctgcca aataccaggc actcttctag gaactagagt ggcattaatg agtaagaggc    46500
aaaaatctct tcccttgttg agcttagaat ccattagagt aagagacaga cacatacaaa    46560
ataaaatgta taatatagta aataccaaga agtgctaagt tttaaaaatg taaagcagaa    46620
aaaggaaatt gagtggcagg gttaggtagt aattgaagat atagtagtca agtaaggcag    46680
cttcaagaga agattatgtc ttaaataaaa atctgataaa gatataaaaa caagccatga    46740
```

```
agttatctga aggaattgca ggtagtggag aacagccaaa agacctggag tagtaaaagg   46800
ttttatgcag agtgatttaa aaagaatcac agtatcttat acatcagtaa atatttacac   46860
atacacttaa gtaagtgata tggacaagaa cttttggaagt tgaatagcaa ggtccatctg   46920
gactataaca gaggaggctt cacaaaggaa ggtgacaggg catggcctgg atcctgaagg   46980
acaggaagaa ttgggatcga taacaaagaa tgacatccca gtggagagaa gtggagggga   47040
aacagcatga aatggagtga aataagaatg ttggccttta gggcaggaat gggccaggca   47100
gagggcaagt gggaagcagg aaaaaggcga ccttgtataa agttcatgtt ggcaaataga   47160
gagaagatgg gaaagcaggg taaggccaaa tttagtaaaa tcctaaagtc aagctaaaga   47220
ttattgcatg ctatcctgaa atattgggg aataattaga gcagatgagt agaaaggtga   47280
attcttgtat ttagctatat cattattttt acaaatttaa acaaataagg aaatggaggc   47340
agtagttgga gtaatttagg agataaattg aaaatggatt ttgttaagag agaagggaag   47400
atagatttta tatattttaa ggaaaaatca tgaggattta tttgctgact gcacgtaaga   47460 gataaagag aggagtcaaa gatttctcta aaattttcaa aatgattaat tacgtgttgg   47520 tattaaaga aataggggaag ttgggacata tgagtttgaa ttcagcatga gtcagttaag   47580
acaatcagat gcagatattc ttaaggcaac taaagttcat ttgatatttg tcatataggc   47640
tgaattaagt ttctaagagc tgtttttact atgcattaaa tccgtgtaat actaacatag   47700
tacaaaagtt gtttgctatc caaattttgt atttttataa taagttggag agacagagaa   47760
tcaaaaaatt attgatttgg aaccattaga catcagctag tccaattagt tcattttgtg   47820
gaaggaaaaa ggatacccag agatgttaca tgactttata gccatgcctc tagctagtat   47880
ctaacttggt ctagcccagg tctccatact gagactctcc tcctgctaat aaaaaaataa   47940
taaaaaagta ttagtggttt gtattttgct ggcttgcttg tggagaatag gattagaagg   48000
tttgacttgc ctgttagcac tctccttgtag ccatttttct aattaacata cacatttttac   48060 cctttctcat gaaacagatc taacttgttt agaagcttca gtcttcttga tttaattaat   48120
cactttctcc caccttttagt cattgttgaa gtttcctgat ttacaatgtt atcttttat    48180 cttttcagta gtataaggag gaatgatatt tctactgttg tactattttt ctgtttatct   48240
ttcagaagaa aaatagcttt tcttattggc ccaaaaaacc atcaccctac aggaaataaa   48300
tcacactctt tgcttgattt tcctgatctg gctactgatt tctcttcaaa tttaagccaa   48360
tacttagact ttaagacttc attgttactt ccttacaggt cattcttatg aactaaaatc   48420
catagtcatt gttctagcaa gcctgagcag tttattcttt gagtcacagg attataaaag   48480
aaaaaataga ccttagagat cataatacag tgctcttcaa actgtactct tcaattttc    48540 tactacttat cagttgtttt ttattctaat aaaatataat tacctagcaa gtgagcagac   48600
atgtatttac agtagcttta caattcttta tacacttctt tactctctcc attacacatg   48660
ccacatggta tgatacaagt cataactcaa ctatgtgaaa gcaaaccac tcttatacat    48720 ggtgtcttgc atatatatta aggcccagag tggtatcagt agtctctgtg tcccaagaga   48780
ctgaattaaa caagactgtt gaccttcttg tggcatttat ctgacaacct tggcaatccc   48840
taaattcaca aatagctgta tagcattttt tgcatttaat gcatatccac atatgatgtg   48900
tcctttgatt ttagaacaag taaagcatgc taaaatagac tgcaccttat gaaagtcatt   48960
ttcactattc ttgtgtttca gtttcctcat caaaaggtga aatatcagct gcctctgttg   49020
atctcaggat cttttaagta gaaatggaag agtcttagtg aaaacagttt gtattctgaa   49080
```

```
agaaaattgc aatgtaaata caggcactaa aaacgtttat tcatctttac agatgttaat   49140
ctgaccagac atttttctca aaatgtgaaa atagtatgga ttttcttagc tcatttaata   49200
ttgaaagact agaaaaacaa gtaatgatgt tctagaagaa tctatgatca tataattaca   49260
gttgtccttc agtatctgtg ggagattggt tccaggaccc cccatggata tcaaaatctg   49320
tggatcctca agtctcttat ataaaatagt gcagtatttg cacatgattt acatataccc   49380
tcccatatac ttcgaatcat ctctcgatta tttataatac tacaatgtcc atgctatgta   49440
agtagttatt acactgtatt gtttagggaa tagtgacaag aaaattaatc tgtacatgtt   49500
cattacaaac acagcaatcc atttttttc tgagtatttt gatctgtgat tgattgaatc    49560
cacagatgct ggaatccatg aatacccatg gggggctgac tataatgttg tctatgtgcg   49620
tagcaatttt gtaattctca accaaggaca cgtatagtcc ttgaatcttg gtaggagtct   49680
tggggacttt tcttaaaata ttttgaccat cttctcaaga tcttgactcc taccccact    49740 tgtacacgtg cacatacttg tgcacactca cacacaatac ccttccttaa gtcctgctca   49800
ccagcttgct tcctattgca ttgagagcat tcaacctgta gaccaagaac ttctaccata   49860
tttttccacc tctaccccaa aacacagttt agacatatcc attcttttca ttcttcagag   49920
tcatctcacc acttccataa attatttcct aattgttccc tctgcctctg ttctttttt    49980 tttttctgat gatcagttca aagtacctct gtatgcccat tcttaagtgc aaatctgacc   50040
atctataccc cttcttaata tcctttcttt tatggatacc catttcagac tttattaaag   50100
gagtggaagc ttcccctcc ccacctcacc acttgaagtt tttgcaatta gaatggagtt    50160
tatttggtta atgcaaaaat agatgtgatg tagaattctt ggggacacct acttatcccc   50220
ttttcagagt ggccctgaat agctctgtga acccaggaat ctgaagaact cagtacagaa   50280
aaccatcagc ctacagaaag tagatcaaac tctatgcttg atattcctga tctggctcct   50340
ggttactctt caaattcctc cttactatat tgtcccttca gatttgtaaa tcttaccgt    50400 gacatcgtat tttacacact gaacctttgt accgctgttc ctctcctgat gaacttccct   50460
tttctcttaa ctacacagct cagatttctc ataagggaag cttcatattt gttgtggcac   50520
tgttgttcct caaacatcct acttactgta gtcatttgtt tatgcttgtc tcctttgcag   50580
attctgaaat tcctagggca aaggctgcat cttgtcttct tattactaat attttacaca   50640
gtatctggtt acatagtagg cattcaatca tacaatttaa aagaagaggt tgactttgtg   50700
atctttttca tatgttttat ttccctctcc ccctactggc aacttcttcc tacttcttaa   50760
aatagataca gcacttgccc actaagtgga gggaagaggt gtgggagtcg agtagttgga   50820
acttcaagtg tcaaaacatg ataatctcat ttgcaaagtt acattatatc ggagcttgaa   50880
cctcagagat acttaattat aagcaacact tgtggaacat tgatacccta catttttttc   50940
actaaagtat cctatcaaaa ttaaatgtgt tgcagttgag atttgtgagg ttttagctat   51000
ttagagactt tagggatatg tttagtgttc taattctaat agtattgatg aatataaatg   51060
tttcactgta gaaagagaag tttgagagct gttgtgaatg atatttgatg tctattaggt   51120
gataatttct gatgactaaa catgctcaag accttagtga gaaatacatg aatacagaaa   51180
atattttgaa aattatgaga agtttatcat tgattataga ttttcttatc cagcagtttt   51240
tggttgtgtt ctgttttca ctgtcagaga agcagaaagt ggtcagtgga ctttagaatg    51300
taggctcttg taggaggcca tatgtttgag agtgctgtcc aggtgctttg tgatgtggct   51360
gagaatggat gcaggcttgc agggaaaaac taatactgta gatctctaga gagcatttta   51420
ggaaagactt ctaagcttta ggttccctga ccaaagagta aaaagtgatt cttaatatcc   51480
```

```
atagctatag aggaaagtaa atacacttcc cacatcaaat gtagaattaa atatttaggc    51540
atttcaagtg tatttcattt agaacaaaat aaaatcatat attcactaat gaaatataaa    51600
accagatggt ctctgaaagg ttttcccctt tactcacttt cagagtaagg caaggaagag    51660
tagttttgtt ttttaattta tattttaatt gtccctttct gttttccaa aagttttatt     51720 ttttgaaagt gagtcacctt ttagacattt gaaaaattag aattactatg atgtttattt    51780
tattagtaag tcttcctaga gtagcaacgt agaaaagcat ctctgaatgc ctacatagta    51840
agtatttaat aaatgttttt tgggccaggt gaggtagctc actcctgtaa tcccagcaat    51900 tgggaggcc gaggcgggtg gatcacctga ggtcaagagt ttgagaccag cctgaccagt      51960
atggtgaaac cccatctcta ctaaaaatgc aaaattagct gggggtggtg gtgcatgcct    52020
ataataccag ctactcggga ggctgaggca ggggaatcgc ttgaactcag gaggtggagg    52080
ttgcagtgag ccgagatcgt gccgttgcac tccagcctga gcaacaagag tgaaactctg    52140
tctcaataaa taaataaata aataaaatac ataaataaat gcttttttgat ttaacgaagg    52200 tgtcattgtc ctatgaaaag gaaaactatc aaaatatatt ttttaaaact tagcttttga    52260
taatgatatg gaagatattt ctcttaatta acctaagtca gaaactaaaa tatgttataa    52320
aatgctaaca tcaaatattt gagaccagtt aaaggagaca gaaggaagtt atggagaaag    52380
aagcagtagc cagaaaataa gggcaagaaa atgttttcta aatttatgag aatcagaatg    52440
tttacaaaat tgctattatt atcatctgga aaaaatatgc cttgtaggct gaaaaaatga    52500
acattccctt tccataccat gcaggaacct tctttactgc attcctaaga ggactagtct    52560
agcacctaat tggatacttg tggtaatatt tgggaactca ctgatctggt acatcagtgt    52620
gggagtcgag tagtcagaac ttcaagtgtc aaaacatgat agtctcattt gcgaagttac    52680
actatattag agcttgaacc tcagagatac ttaattataa ttaacacttg cagaacattt    52740
gatacttaca ttttttttttc actaaagtgt cctaccaaaa ttaaatgtgt tgcagttgag    52800
agttgtgagg ttttagctat ttggaaactt tagggatatg tttagtgttc taattccaat    52860
agtattgatg aacataaatg ttttactgta gaaagagaag tttgagagca agttgagcaa    52920
gaatctgtca ctctaggtct tctactcttt attaaagaat gttggattca tttataactt    52980
actggtccct taaatattaa agtttggtgt ttggtatctt aaacatgatt acatccttat    53040
agggctctct tctaattgcc tggatactgc acatctatta atacagtctc aaagcacact    53100
tgcttttttg atagtaagag cgtacgattt aatcacattg aagttagtcc gcaaaggttt    53160 ttgtctttt ttcaggcaag cagctgatga atgaatctct actatccttc actttgtgac     53220
tgtgattttc taaataaatg ttggagattt aacttacaa tttattaatt tccatcttgt     53280
ttcttcaagt ccctccttta aggaaattta tggaaatctt tttccatacc atcaagtggc    53340
ttatttcttt ttaactttt tccttaagtt caggagtaca cgtgcaggtt tgttgcatag     53400
gcaaccttgg gtcatgggag tttgttgtac aggttatttc atcacccagg tattaagcct    53460
agtacccatt agttattttt cctgatcctc tccctcctcc caccctccac cctctgatag    53520
gccccggtgt gtgttgttcc cctctgtgtc catatgtcct catcatttag ctcccactta    53580
taagtgagaa catgcagtat ttggttttct gttcctatgt tagtttgcta tggataatgg    53640
cctccagctc catccatgtc catgcaaaaa acatgatctt attctcttat atggctgcat    53700
gttattccat ggtgtatata taacacagtt ttttttatc cagtctatta ttggtgggca     53760
tttaggttga ttccatgtct ttgctattgt gaataggact gcagtgaaaa tatgtgtgca    53820
```

```
tgtgtcttta taatagaata atttttttt  cctttggtat  atacccagta gtggggttgc  53880
tgggttgaat agtatttctg tcttgaggtc tttgaggaat cgctacactg tcttccacaa  53940
tggttgaact aatttacatt cccaccaata gcatataagt gttccttttt ctccgcaacc  54000
tcactaacgt gttattttt  gacttttaa  taatagccgt cctgactggt gtgagatggt  54060
atctcattgt ggttttgatt tgcatttctc taatgatcag tgatgttgag ctttatttca  54120
tatgtttgtt ggccgcatgt atgtcttctt ttgtaaagtg tctgttcatg tcctttgccc  54180 acttttcaa  tggggatgtt tgtttgtttg tttgttttt  ctgtaaattt aagatcctta  54240
tagatgctgg atactattgt cagatacata aattgcaaaa tttttctccc attctgtagg  54300
ttgtctgttt tctctgttga tagtttattt tgctatgaag aatgtcttta gtttaattag  54360
atcccatttg tgaattttg  ctatgaactg gatctgatat aagcatatgt ttaatttaa   54420 ctcccaggtc acactgtttt tttgtttg  ttttgttttt gttttgttt  ttgtttttgt   54480 ttttttggag atggagtctc acgctgtcac cagtctggag tgtggtgata caatcttggc  54540
tcattgcaac ctccacattc cgggttcaag caattcttct gcctcagcct cctgagtagc  54600
tgggactaca ggcacacacc accatgccca gctaattttt gtatttttag taaagatggg  54660
gtttcaccat gttggccagg atggtctcta tctcttgact tcatgatctg cccgcctcag  54720
cctcccaaag tgctgggatt acaggcttga gccaccacac ctggcccag  gtcatacttt  54780 taatcaaaat gagaaaaaag attgacttca ctggagtgct tatgtcttgt tttatattca  54840
agttttaaat ttatgttctt gagattatta catcttgagt tacttgataa taccacggtt  54900
gaaatccatg ttgttgaatc cttcaacccc ttgaggactg agaattccct ttaattatct  54960
gtctgaatca ttaaatactt gtaaatcaag agttcaattt agaaatgtta tacttgatac  55020
attttttaaa gctggataaa ttaacctatt aaacaaaatt atctcttctt caaaaaaaag  55080
gcatcacttc ccccacaaat gtgtaattta ggaattgttt tctattggag tggttcacgc  55140
ttatatattt tagttgctct aatgcaaggt gtttcctaaa aagtttaagg aaagtataac  55200
tttattttca tgtatgatag taaataatac aataggggt  gcatttgtgc tatgcttgtt  55260
tttgttccca tttcagtgct caattactgt agcttctaat aaataaaatt atcagttgct  55320
aacatttaaa tcaaacagtt ccacaagtgg aagtattgct tatttgtgag agttgtgttt  55380
ttttaaactt aaccttactg agggttttta aggactgcta attatagatt gtactaagca  55440
aagtataaag taatagaagg ttaccaagtt gaggctagaa ttcaattagt gccaatacag  55500
ttaaaatggt atcattaaca gaacatcttc atccaggacc tttttttttt tttttttt   55560 ttttttcaga cagggtttca ctcctgttgc ccagactgcg gtgcagtggc ctgattgagg  55620
ctcactgcag cctcaacttc ccaggctcag gtgatcctcc cacctcagct tccagagtag  55680
ctgagaccac aggggcatgc caccacccct ggctaatttt ttgtattttt tgtagagaca  55740
gggttttgcc atgttgccca ggctgttcgc aaactcctgg cctcaagcaa tccacctgcc  55800
tcggcttccc aaagtgctgg aattatggga atgagctgcc acaccagcc  cctccggaat  55860 ctttagatta ccaacttctg tcttccaggt ttttatgtcc ttggaaattt atgcatattt  55920
ttagaggtaa gacccatcct catcttcttc ctaatccttg acatattgtg aacacagata  55980
tatatacaat taagtagttc cctgagttac aaatatactt aaatatactt taacttatta  56040
tagaaggctt acaaaaactg tggataaata acatatattt atcttagtta atgaataact  56100
gatgctgaaa ataatgtgaa tgtcaaatta gttctctttt tttctagccc tcaccttga   56160 aaagcctgag cctctgagat gtgagatgac tgctgtaaag tgaagcagcg aatttctaga  56220
```

```
ggctgggttc acgcttcagg tcctctaaat cctaggtcgc ttcccactac tacatactac   56280
cctaaaaaat ctgtaattcg caaatttatt ttttgatctt tttcataact tattaaattt   56340
ttattgaaca aatacaggaa acagttttaa attactcatt gctcttgaat acattggtga   56400
ttattttcct tctctgaaat tctgttttcc ttaaaggcag tcattttttg gtctcttcta   56460
aatgacactt agtatttta gtaacatcat aacttcagtg ccacagtga gccctcattt    56520 tgcaacatat gcctactttt catatctggc ttgcctttta ttatttataa tttaatgaaa   56580
agaaagtacc actctttcca tagttttgta atagaattgc tgtcaacaaa gtagtggatg   56640
cactatgtta taaagatttc attgtgaaaa catgaaatgg ctgttaacta tacatcaggc   56700
aaaataaaaa caggaaatat aaacatttcc tggaacaggg cagagtatga gtaataaggt   56760
atcaaatata attggatacc tgaccaaata tttttaaatg tcttaagaaa tgtcactgga   56820
aagactggag tacttggatt tgtctcttat tcttattttg attcctaaca ctgtgcttgg   56880
cacatggtag gtaattaata aatgtgtgat ggatgaataa tgattgtcat tcaattagtg   56940
actaagagag ttggaaaggg ctatcaattt caaattggtt cctttaagac attttacgt    57000 aagatttggg agaaaagtaa aagagcacca tatgattatg ctttactaag agctgcttcc   57060
attcctacat tgaccatgtg gactcatatt tggcctatat aattacatta gaataaacaa   57120
agcaccaaaa gttggaaaag gaagtagtag taggagaggg ttttaagcta tgtatttact   57180
gggaaaaaaa gtcatgtttt cttttttaaa aatgttctaa acagtactgt aatcacttgg   57240
gaattgaatg tgcttttgtgt cagacaaagg tctttgtata caatacatta catttttgtat  57300 accaatacat tacattacac agaagggagt gcctggcttt gtatacaata cattacatttt  57360 tgtataccaa tacattacat tacacagaag ggagtgcctg gctttgtata caatacatta   57420
cgttttgtat accaatacat tacattacac agaagggagt gcctggcttt gggaaacaca   57480
tctacctaaa ctcttaacat agcacaatgc tgccatacgg taggtaatac caagacaaat   57540
cagggccgtt attacaacc ttgaggaaat gtcttgggaa atatttaaat aattttttgtt   57600 taattataat aaggaatcta cagcctctgt gaagtcatcc caaactcttc gaggcaaatt   57660
tagtctcctc ccacccctgt tttttaatgt ttctaaagga tgttatgtat aatctattag   57720
aaaactggcc aagtgcagtg gctcatgcct gtaatcgcag cactttggga ggccaaggcg   57780
ggtagattac ctgaggtcag gagtttgaga ccagcctagc caatatggcg aaaccctctc   57840
tactaaaaat acaaaaatta gccaggcgta gtggcaagtg cctgtaatcc cagctactca   57900
ggaggctgag gcaggagaat ctcttgaacc cgggaggcga ggttgcagtg agttgagttc   57960
gcgtcactgc attccagcct gggcgacgga gtgagactcc gtctcaaaaa acaaaaacaa   58020
accaaaaaaa aaaaaatat atacacacac acacacacac acacacacac acacatac     58080 atacatacat tagaaaacta attacattgt tttcttaaaa tgttttaagc atctctcttc    58140
ctcaaggaca agaatcttga atccttagtg catatgaggt acttaataga tatttaaatg   58200
aatagtgagc tactattgcc taaaaatatt agacatcatg taatatcagg cctacagttg   58260
atagaaaaag tattctcaac taagaataat ttaccaatgg agaaaactgt tagttttccc   58320
ttctttttct ttgctttata aaatttaaat gacattaaga gttacgtttc ttggaaaatt   58380
gaaaagaata tctgtggcac aatgggctct gggtataatt gcaggataat ttgaaaagtt   58440
taaagaatat tttcaatagg tataagttta tttaggctct gtgtctcctc ttgagatgac   58500
tttagcagta tatatttccc tggaacacca tgcactctag gttttctaat ttattggttt   58560
```

```
aaaatacatg gcattttact acgtaaatat tctctgtatc tgtaggtaca gcacctctgt   58620
gtacactaag ttagtgtatg tattttttta aaattgcctt agttttgcta ttcactagat   58680
tattttccaa ggaacctact cttagattta ttaagcctac tatatatatt ttgttattaa   58740
ctaattctct tattttaaaa aattacttttc cctttctttg cttaaatttg ctttgttttc   58800
ctaaattagt gatttggaat acttaattgt ttttatttttg ttttgttttg tcaataaaag   58860
agttttaaga ctctagttat actatagcta tagccaatgc attttgagag gtgcttacat   58920
attacaatta ttttcagaaa ttccttattt caaagctttg ctttctttga caaagagtt   58980 atttaggaaa agaaaggaat aaaaatctca acttattctc cacttgacta gctttattat   59040
ttgcagtatt ctgttttta cttgttctaa tacttcttta tattttgttg tggaattatg   59100
tcacctaaca atattttcct taacttctta attttagcct gttttccaag ttaatcattt   59160
atctgttgtt tcaatgaata cctaagaaaa ttttctttgt caggataagg cacatgaggt   59220
ctaagattta tttctagaac agtaagcaaa tcatttctga aagtgtgttc ttctactatt   59280
aagtaacatg tttattttttg tcttttagtt gaagtccccc ccaacccaat aggtactatt   59340
ctgatttgtt ctcctattca cacattcttg aaggagagct gatttatctg tacccacaaa   59400
attataatat aattttctca gagtattcaa aacattgtct ttttatttt tcttttttt   59460 gagtttttca ctcttgttgc ctaggctgga gtgcaatggc aggatctcag ctcactgcaa   59520
cctccgcctc ccggtttcaa gagattctcc tgcctcagcc tcccgagtag ctgggattat   59580
aggcatgcac caccactcct ggctaatttt tttctatttt tagtagagac ggagtttctc   59640
catgttggtc aggccggtct caaactccca acctcaggtg atccacctgc ttcagcctcc   59700
taaagtgcta ggattacagg cgtgagccac cacacccagc cgaaaacatt atcttaatgg   59760
agcatttaga acgttatcac tgacaaactt ttttctattg aaaatactgc ttaaaagatc   59820
aggtcatgcc caccccacaa cccacaccct ttgtatttct cttttacttg tcttggcctc   59880
tagttcagat ttatagtttg gtaatgtctg attttctttg ttagtgcttc agcccatctg   59940
gttggggaac agctctatcc cactgggacc tctcccttc tcatgagtg acgccagggt   60000 cctgctgccc ataagcattc tgtttgctga gtttgtatat atttcctttc cccagcttcg   60060
ctgcctttgg ctgctttgtg attaagtaag acatacccat gtttcctaaa gcctccttcg   60120
cctttagtcc ttgatgctgg ggacctttg gttgggaaga cagcttcctt atgtcagggt   60180
gagcctgcta cacaggtatg taactcagac agtgacctac tgttgagttt ctgtttagtg   60240
tttctttgtc tccctcaaat ggtacaaacg tggagggctt caactgcagt ctaccttgt   60300 cctgttagtt ttgtctatca cagcccatgc cctccaaata agagatgatg gagcagtctg   60360
cttattttct gtagcactcc acaactgact ttaaaagagg gactgggatt gggctcttag   60420
tgatgacttt taatgtggat tcatctgcat tttctctaga aattctttaa actctctgcc   60480
tctcagctgg cactattcca tggtattta gtgctaatgg gggatctttt ctaattttg   60540 ttttctttg actgtttaaa tcatttactg gaaagagggc ttagatatct gctcatatgc   60600
tcctgctagt ctacaagtcc tccagcctga ttttgttcat gaacatgatg gaaataagct   60660
tcttaaatgc ctttaatatt ggatactgct ttcaaggaaa tttaaaatag caagcaggct   60720
ttcaagaaga gagaataaat tatcagccag tctcgcaaga acaaaaataa gccaagtcat   60780
ataaaacaag tttggagtaa acttgttttt acatttcaaa ttcgagttga actcttcaag   60840
tgaagcttca gagatataaa aaactttaac tgataaagat tccaaacatt aatatatgga   60900
aatgtatgag ctcactgaaa attttacata aattttacta gaagaggtga ctgaccagtt   60960
```

```
gcttttataa gattctcaaa aagatctcaa atcttaggga ctaatattgt aagtatacgg   61020
ggaaattaag acaaagattt actatcttgt gagtttttag tttggataat gaacttaatt   61080
tcacaagaaa ttgctttagc acaaacatga aaaccttaag catgagaact ctccttttga   61140
agtacaaagg gagactaaag tgaataactc aaactggaaa tgtagaaaat tgaatttgct   61200
atgatttgaa gtcctttcag aatagccaac agattttaaa caagagtttt attgcatagt   61260
ttctttggga tatacattga aggagaaagg aggagggagt tttaaaagac aagtggaaag   61320 cccttctgc ttgttttggc tatggcttcc atttcagtgt ctgtatttaa gggatcataa    61380
aaggaactgg aaagactggt cacaatggca gctctgtacc tgtatgattt cggatgtgaa   61440
aagagtttag cgatttcctt gttaacctat actgctgtgg aagtcattca ttatgcagtt   61500
aggcattagc agaacaaata aagttcacag ctctaggaac caaatttaac tttatcactc   61560
ttctgattta gaatattttc atatgctttc atatgtccta cagacgataa aagatagaa    61620 tcaatacttg gtgattgata ggttatttt taaaagggaa gaaagaatta aacatccatg    61680
gtttcttctt aagtaactgg ggggatgata gtatccctca caccaatggg gagtatagat   61740
gacaggtttg gagtgaaaga cagtgaattc cattttggat aagttgaatt tgaagtgcct   61800
atgggacata caggtacaga tgactaggag acaattgaaa atccaaattg tgaactctgc   61860
tgaagattag aagtacagat ctgagattaa attgctactt gagttcatgg gaataaaata   61920
ggtcattctg caaatggtta tctcaatatc ttcctggcca tctcttgggt caccttgcca   61980
acttttcatt ctcttacaa tctctaaatt ctcatgtttt taaggctctc atcttaggcc    62040
aacttatctt gggtcacctt gctaactttt cattctcttt acagtctcta aatttgtgct   62100
tttaaggccc cattctcaag ctggcttctc tgttttggtg ggaactggta gcaaacattc   62160
atttgtaaac aacccaaatg gctagcattg agcaggactc cccaacatac tcctctgaat   62220
tacattttga gttatctgaa ggatcaatat ctcaaactag gaaactgtag ctttctcatt   62280
tattttcatc atctaattat ttttcttgcc tttaagtata agggatagag acttgattga   62340
tttttatgta caacaagtta aaaaatttaa ttaggcgtct ttgccattta atcagtttat   62400
acttcttgaa tcttttccag tcatcaaaaa gttgctgagc atgcgcagct ttacttacta   62460
gcttatagca tgaagaagag taaaatagga gtggataaag gcacagtggt gagtagtcag   62520
tgtttccaat taatctcaaa gtttaggatt aatttagcgt gaattctgtt cttttgtgtc   62580
ttcctgcttt ttgacgtggt aacctgccat aacaaaagga aacagcagga aacttggtac   62640
caattaaaac agtcttcttc ccccaaagaa cgaactgtca gcaaacaatc tcaaattcaa   62700
agtgataagt gttttagagt gaaacaagga taaagagaca aggctattaa attttaacat   62760
ctgctggaac acaaagcgca tgccagtaga attaagtttg gcatttaata agatacaatt   62820
tgcacatcag aaatgaaata gatgcctcaa ggcatggtat atatatatat atatatatat   62880
atatatatat atatatatat atatatgttt gagcgagggg cacttctagc aaaactgaat   62940
acactggtat aaatgtctgc gtgaaaattt ttttatccat tcactttggg tgtgtattcc   63000
agctgtgagt tattcaacca ggctcactaa gtttgagtct gattaataac gtttaaggtc   63060
acatctgatt aacagtattt gaagtttgaa tttgttctaa gatgactcaa gcgcaataac   63120
attttctata tcaaaatgaa tttccatcca aatagggagg aaatctgaaa tttcagttcc   63180
agtgttgact gagatgctct ggatgagcct ggactcagag ctcaccaact ttggatcttt   63240
atgttaagta gtcagtgggg ttgacttcta gactagagat caaaatgttc tacacctctt   63300
```

```
gatataggtc agtggctgat gtaatgtgct tccaacaact ttcttttaac taaaacagta   63360
catataccaa gttggtttgt cacaatggga acaaaacaga aatctgacaa cagatttctc   63420
taattttttg tgtgtatgtt tctgaatggg ctaaaataca taattttact cttccttggt   63480
gaagatgctt ttataagagg acgtgtttaa gaaaattaag aaatgttgta ggtagccatg   63540
aaagaattat tttaaacaga attagtatag aggtgtgaag atctactgaa gggtgataag   63600
taagtgtgga agagatggtg ttcagcattg ggcttcagta tgaataggta gaagatgagc   63660
aaggcttaga gacaagaagt tcattcaata ggctgttgcg gttatccagc aatgagatgg   63720
tgacagcatg agccatggta gtaaaagtaa ggacatggat aatttgtggg ttctacagac   63780
aataagaaca tagaaccgat aggttatttt ttaaacggga agaaagaatt aaacatccat   63840
ggtttcttct taagtaactg cgtggatgat agtacccctc acactgatgg ggaatgtaga   63900
tgacaggttt ggagtgaaag aatgaattcc attttggata agtagagttt gaagtgccta   63960
tgggacatac aggtacagat gactaggaga cgattgaaaa tccaaattgt gaactctgct   64020
gaaggttaga agtatagatc tgagattgaa ttgctacttg agttcatggg aataaaatag   64080
gtcattcagt aaattgttat ctcaatatct tcctggccat ctcttgggtc accttgttga   64140
cttttcattc tctttacaat gtcaaaattc tggtgttttt aaggccccaa tctcaggctg   64200
gcttctccaa ctgtactctt acttgggatg atcttatcta gtcatggggc attaaatacc   64260
attggtaggt taacacagtt cacaattttc tccagcttag accccttgct gatttcctga   64320
cttgtacact caactgcctg cctaatatac ccacttaat gataatgtac atctcaaact   64380
gagcttattc gaaatagaag ccttaatttt tctgtcagtc atattgttcc catttaccca   64440
tcctaacaaa tagcaccatc atcaaccttt tagctcaaga caaaactcta ggcattatct   64500
tgctttcatt cctttcatgt actttctcac atctaatcca ttaccaagtt gttctgtttc   64560
tgccttcaaa atgtgtccta aatttatcca tttctctgcc actgctattc tctagttcag   64620
gacattctat cctttctctt gtattactgc ggtctctaaa cttcatgtat ctatgtttta   64680
tacttttaat tcattgtcta tacagctacc agagtgatct tttaaaggtc taaatcagtt   64740
catgtcactg ctttatatat aatgcaccta tggcttccca ctggatttaa ataataatct   64800 taacactta ctcctccatg gcctttacat acttctagcc gcacctcaaa acactcctct   64860
tgttcactga gaactaacta gaccagtttc tcttctcctc agctatatca tgctaattta   64920
tgcttcagtg ccttttgtac ttttgttccc tctagctgaa tcattcttcc aggtcattct   64980
atcattggct ttttcattca gttcagatag atatcagcaa atcaagagag tctttcctta   65040
cctgctctat ctaaatagtc ctgttttagt cctctttatc tcatcactca gatttatttc   65100
cctcatagca ctcatcagtc tgaaattgtt tgtttatttg gctacttgtt tgtctagata   65160
aacttcactg gtgaaggaat ccagactatc ttgttcatcc ctacatccct agaacctaga   65220
acaatatgtt aaagataaat aaataaatag atgaaagaat gttgaagaga agagggtcca   65280
gtccagcccc ctgaggtgac cagcatttag ggaataagcc gaggcagagg agggccatta   65340
agaaggagca atgagagata gaggaaaact aagaacaagg tgtccctaaa gtgagagtgt   65400
cctaacacag gtctaaatga aaggatagtt cagaagaggg cactgcagct ggctgaaaga   65460
gaacaagaaa ggctgtaagg tggaggtgaa ttttaattg agccgtgaaa gatagggaaa   65520
ttctgtatga aggagtaaat ggaggcatag aggcatagag gcagaagatg catgcctgtt   65580
tggggaatag tcatcccatt tgtctttcac atatctcatt taatacttct catttaatcc   65640
ttttagtgtt aatgttgtca ctagattaaa aaacaaaggc tccatcagga tcacacagta   65700
```

| | | | | |
|---|---|---|---|---|
| aacagaagaa | tatggattta | aatggagatc | tatctgactg | caaagactac ttactgtaac | 65760 |
| ttaagtcatt | gagattcctt | atggccacct | catattcacc | ctgcatataa cagtatgcca | 65820 |
| atgtaggaat | gaggcgtgaa | taagcagggt | aacaatagaa | acatattctc accttgatta | 65880 |
| ttcctttggt | agcttcaagg | gaaattgagt | ttgaggataa | agtaactctt cccatgtcag | 65940 |
| cactttatct | gtcctgaaac | atgagaaatt | ccaaatgttc | aagccatgca gtttttatct | 66000 |
| agtcagatgg | ttgagaagtc | caggttaccc | atagttgtaa | tgaatacctc ctctttatct | 66060 |
| tcttaatgtt | ctgctttgcc | aaatgatcta | taaagattac | tcagtgtacc tttcagattg | 66120 |
| aggtccagca | gactttcaga | acactacatt | taattacaga | acccaacta ataaaataat | 66180 |
| aagctcatgt | tagtttcagg | tgttgatttg | tttttaatgt | agtcaataat atttacatat | 66240 |
| aatgactggc | aacttaacag | agttataata | gattattcac | ctgtatttgc ctttatttgt | 66300 |
| gggtatacac | acatatatac | atgccttaaa | ctagagtaaa | atcatttatg catactaaat | 66360 |
| caaatttgag | agtcccaaaa | ttttcaaatt | gtgtatggct | ggtctatatt ttctaggact | 66420 |
| gtcctttctg | gtttaaatga | aattaaaaat | tgaattaatg | atattagtct cttttaattt | 66480 |
| tctattttt | tcatgattaa | aaaatattaa | tttccagcca | ggtgcggtag ctcacgcctg | 66540 |
| taatcccagc | actttgggag | gctgaggcgg | gtggatcacc | tgaagtcagg agttcaaaac | 66600 |
| cagcctggcc | aacatggtga | aaccctgtct | ctactaaaaa | tacaaaaact agccaggcat | 66660 |
| ggtggcacgt | gcctgtagtc | ccagatactt | ggatggctga | ggcaggagaa tcacttgaac | 66720 |
| ccaggaggcg | gaggttgcag | tgagctgaga | ttgtgccact | gcactctagc ctggtcgaca | 66780 |
| gagtgagaat | ctgtctcaga | ggaaaaaaaa | aaattaattt | tccccattcc cccacccacc | 66840 |
| caccaaaaga | ctccattgga | gttttatttt | acaaatgcat | ctgctcatct acttcttttt | 66900 |
| aagtgcataa | actagttta | caagcttgag | tttaaatctt | aactcctcaa ttcttttct | 66960 |
| gacatagaaa | tatacaggtg | cattatgaaa | tagctaatag | tgactatttt ctagggctgt | 67020 |
| aactcaatat | ttataagcat | aatgatataa | cctgctgaag | tttgacacgt cagtatagtt | 67080 |
| cttttgttat | tctaagtcat | aaaggcagaa | tttggaaaaa | ttcacagctt tcaaatatg | 67140 |
| cagaagagga | aaaattgaga | ggaagcatac | taaaatttct | ttagccaatt ttaatcaaat | 67200 |
| tgagtttgaa | acttacagga | ttatgcttca | aagcttgtaa | tgatcgtcaa aagtagcctt | 67260 |
| attcaaaatg | acacactaat | ttctaccaca | tctgtattct | tctcattgta agatgttaca | 67320 |
| tataccatg | cttgaccaaa | tggacttcct | gctatttaa | gatatttttc tgtgttttaa | 67380 |
| gtctttctac | aaatttctc | aagcatttcc | ctttacctag | gatgttcttc tttcactgca | 67440 |
| agtgaagaca | ttctaaaaat | tcctaaagca | cactaccaaa | agcccttcat ttggatgacc | 67500 |
| caccttccta | tgagtctcca | tagttgcatg | tctgatggca | tttatttaa ctctatgatc | 67560 |
| tgcttctaaa | ttagataaaa | gctctcagag | agaactatga | ccaattgtca ttctgtttcc | 67620 |
| catggcacct | agtacagtac | tctgctcaca | ggctcaataa | gtaatgagtt gagctacgtt | 67680 |
| tttttaaggc | agagtctccc | tctgtcgccc | agggtggagt | acagtggtgc aatctctgct | 67740 |
| cactgcaacc | tctgctgctg | ggttcaagtg | attctcctgt | ctcagactcc cgagtagctg | 67800 |
| ggactatacc | accatgccac | catgcctggc | taacttttta | tagaaacaag gtttcaccat | 67860 |
| gttggccagg | ctggtctcca | actcctggcc | tcaagtgatc | cacctgcctt ggcctcataa | 67920 |
| agtgctagga | caaagttttg | ccattgtcat | gttacgatat | atattggttt ttgtccatgg | 67980 |
| tttctggttc | atagctccaa | tatccctttt | tacagtcttt | tgttagaatg tggggtgtgt | 68040 |

-continued

```
tggacctcgg ggcaggcctt agaaaacaga atctctcctg ccttcctttc acttgtcccc    68100
cgagggagat ttttttttt tttttttttt ttgagacaag acttccctgt gtcacccagg     68160
ctggagtgca gtggtgtgat catagctcac cgcagcctca gcctcctagg ttcaagcaat    68220
cctcccatct cagcctccca agtacctggg actacaggca catgccacca cacctggcat    68280
tttttttttt ttttttttt ttgtagagag gtttcgccat gttgcccagt ctggcctcca    68340
gctcctgggc tcaagtgatc cacccacctt ggctcaaacc accacaccca accctgaggg    68400
agattctaat cttccccacc cttctgattt tgagtcttaa aaccccagag aaggtcccac    68460
cctttgcact ggggaaagga atgctgatga tcatgaagcc tccataaaaa ctcaggagga    68520
ttgagtctgg ggagcttctg gatagctgaa ccagtggagg ttcctggaag gtggctcatc    68580
cagggaggac ttagaagctc cgtgcacttt ccttatactt caccctaagc atctcttcat    68640
ctgtatcctt tgataaacca gcaaatataa gtaagtgttt cttgagttat gtgagctgct    68700
tgaccaaacg tattgaaccc aaagagggtg ttgtgggaac cccaactcga agctggttgg    68760
tcagaagttc tggaggcctg gatttgtgac ttgtgtctgt ggcaggagca tcttgggaac    68820
tgagcgttta atctacgggg tctgacactg tctccgggaa ttaaattgga ggacacccag    68880
ctagtgtctg ctgcttgtta tgggggagaa accctcacac atttggtcac aagagagaag    68940
ttttctgttt tgaatattgt tgtgatgtga gagcagagga aaaatgcatt ttggagaggt    69000
tttttcctac acagccatag gcagtgataa gaatatgatg ctttttttcca gaaaatgcta    69060 catgagacct ttttataaaa tctaattttc ttcaactgag tagcatttaa actaaaaaga    69120
ataggttatt tcagtgtctc tctgtaataa catcttacaa tcacttgtca gaccatgaaa    69180
taatgttcta gaaaatcagt gaaagagctt tttaaacttt gtgacatttg acttatattt    69240
attaccaaaa agcctgaatt attattcagc acattataat tttatttaaa atttaaatta    69300
gagatgaaat acttgtaaat gtttataaga ttggtagctg tgtgggcttc cagagttaga    69360
aatgcctctg agaaaagatt tagagttttg aaagtatttt gaaaaaagaa acagaaagga    69420
atacaacatt tttcccagca ctgcttcaat aatgcagtct tcagcatcat ctcaaagcaa    69480
taactgcagt acagatgaga tcagccagtt ttttttttccc ccttatctgc agtgatttta    69540
ccatctcttc atgctacatc ttaccacaaa gagaacattg aaacatggga aagagtttgc    69600
tttgatttca accagaatgc caactcattt ctggggttct aaaccataac cttttttagc    69660
agagcagtgt agaattttta tacgatacca taaatggtcg gcctgagtaa cattttaact    69720
gtaagtcaat acctttgaag agacatgtct gacaactcag agttctattt tctccatgtg    69780
tgactaaagt acctttcta ttaagagatc aaccaccatt tccttctact ctttgttctc    69840
cccttaaata aagttaattc agcttcaaaa tattttatga tcttgattac taactgtggg    69900
tctttagaag acaatgtaaa acatttccat gctgtgaata ttagagctag tatacttgga    69960
gtttggctag tatttctggg ggaggtagaa gaggagacat agagtacaaa tgagtatttt    70020
taaagccacg ctgactaaaa caaaggaat gttttataca tgtttatttc atagtacttc     70080
tttgaaacag gtcgggggga ggagagttaa atattgctt tgaatttaa tcaaagttct      70140 ttcatggaat tgttggtgct tctggtaata acagttctat aatctttgtg agttaatctg    70200
aaatgctctt tttcttcatc gtaattcagt gcttgtctta actggtggac ttattttatg    70260
gtattatgtt tataagatgg caactaaaat cagatttttt atactcctaa aagatggata    70320
cgatagaggg gaaggggggt aagctacaac tttttaggttg ttggtgatat ttgaagtgtt    70380
tattgcttct gatttacatt tatatattat attcaaatat aaactttaaa agtaatgatt    70440
```

```
tgccacaggt taaagcagaa catttatatg atatttccta gatgttttcc tctacaatcc   70500
tgtttttgtt ctatgaaaaa tgccataaac ttggatcatt cactaattaa tttgaagctg   70560
ttttcaaaca aaaagctaat tcatctttta gcggatttag ttataatcgt gataacagat   70620
gtatagctaa gtctgttgga caaactgttg gtcacatcaa tcttaaatgc atcatacagc   70680
gtgatgtgaa tttatgatat ttcctaggta atgttaaggt tatatggaaa tttctttgca   70740
ggtagttaag tcttattttg aattcaaatg ttattttcaa tacatacgtg gaagtgtatt   70800
ttttgtttgt cctaaatgtt tagattttt gagtttacaa tttttttgtg tgttctttct   70860
ttgttcttgc ccctccctgc attctctatg aagatacatg tcagcactat gcaacactaa   70920
aataacaatc aaccaaatta tatcctatga acagaccttt ctcttcattt caaaggcata   70980
acttggatgg tctgtttagc tcatggtgaa aaaaaaagt tatgattttg tatttgggca   71040
aagtacaggt gaagagcgtg aatcattaga acagcaatat aactggaaga agatagttta   71100 gttttttacaa gttaaatttg aagctaaagc aaaacttgca taggtatgtg tcctttgctc   71160
ttgaaaatga actcagaact ctacatctga gtggttttat gaatttatac tctcctagtc   71220
cacaggttct catcagtgcc tcaagatcta tgcacagatt aaaattacat aagatatcat   71280
atactacatc tgaattaggg ttttccaaag tatgctattc catggaaata ctgtttattc   71340
agggtgctcc ataaacaatg atcctgtgtt tcattatgtc caggaaatgc cacacagcac   71400
ctttccagac atcctatcat catattaaag actttgaggc catgcattaa agaaagtttt   71460
aaattagaaa aaaataagt tttcttgctt gagcacagaa ctttattttt tctcaggctg   71520
gttctccttt tttaaaatta cacgttaata tcccaaagaa ccagtcccat agatagatat   71580
cacatatgat aagaatctgt ttcaatggtg ttggtgtaca tgtgtgttca ggtacctaca   71640
cattaggaca catctctagt ttattaatac tgcacttata aagagacatg gtagagacat   71700
caagaagaca tcattttagg gtggacacca ttgcctagga cctgcttctt aatgtcaaaa   71760
attcagaaac ccaattttat ctctcccgca gagttgactc gagtgaagga aattgagttg   71820
ttttaattaa actcacatga gattgatgtt taaacaaaat tgtaagttta tcaattaata   71880
atcaagaatt ctgattttta attttcaaaa tattatttat gtccactgtc cagggtactt   71940
gctttaaggg cacccagtga ttcttgaaga tgaagagtct taggaatatt tattttctag   72000
acctcaatga agaaagcttt ttaatcatcc tgccccatag aagaatttat gttcctagtg   72060
atgtgatcat attggccaat ccagtgtttc ttttccaagg acagtactga taaggagcac   72120
caaatctacc tctttgtcct gaacagatca tctccatcta ttcatagttt ggctcagaag   72180
ttggacaagg ctgcatttta tatctacttc ttcctcatgt cggctatgcc atgccgtttc   72240
gttcttttag cttgtttact tatgtgtaaa atgaggtaaa aattcacccc ttcaaaccga   72300
aagtggtctt cgtgatgagt tatttaattg aagccccagt agatatttat cattgccagt   72360
tttagagaat catagcattt tagaacacaa gatgacctta gatgtaatca tgttcattcc   72420
cctcgtatta taaatttta aaaattgaga tgtggggtgg ttgtgacttg ctcacaaacc   72480
cacatttaga accaaaactc agcattcttg ttctgactgt gtctatgtcc tgtaggtata   72540
tgtcttgtct tctcagttaa ataattaaag attcttaaag atagagacca tattttatgc   72600
aacttctgga tcccataaat tatgtttcca gaagaacctt ttgtaatgaa aaatatata   72660 taatgtctat attatatata tagtctatta ctattttgat aatctaaaac atgctatata   72720
attttaggcg atcttaacct atttatcaga gcttttcaga tcaaagaaaa ttagagtaat   72780
```

```
cttcatcatg tatgggaaca ttgatgtatt tttctgatga acacatggtt atatgatact   72840
cttttaaagc atctgtatta ctcttcttc tgatagactg gttatttgt ttatgttatg     72900 aaataatgtt ggcagctttt cattagaact gatacatatt gaaatttctt aaattgatag   72960
ctcatggatg tgcagttggt ttaatggcat ctccattatt aatctttaag aagatcttca   73020
tcttactctc aaaaataacc gtaatatcct acaaattaac taaaacatga tcattgctag   73080
ttgttccaaa ataggaagaa taaaaatgac cagattgtta tggtaaccag ttgattaaga   73140
ctagatcaat aggaaaacga atttattcaa gtctgtacaa aacttctcca aaacatagat   73200
ggcatgcctt ttgaggcaat ggtagggaac aaaatatttt tgagaaggag cagattttag   73260
ggatacagta cagtacataa ttgccaaaat gcttgtgtta caaggattcc tggtacagag   73320
tttttaaata aaatgctagg tatgtcatgt ttgtttcaca ttaatattgt agagtcccct   73380
ggggatgtga caatttagtt gaccaactct aatatagtta atttctacct tttgatagct   73440
ttgtggggtt ttgtttgttt gttttttgtt ttgccattct tgattttagg gctgaagata   73500
tgagacaatg tatcaaacag taaagaatta tgcattgatt aagatcatct tggtgaatta   73560
gatgtttatt atataactcg actttaagac tttgttcaga tctcactatc ttaatgagat   73620
ttaccctcat tatatagtat ttaataggc aaccactccc cgatactctt gattcctcgt     73680
tagctgccct attatttctt tgttttccc ttagcactca acatttctt accacaccac      73740 ataatttact ttcttattgt gttattgtt tttctcctca ttagaatatc aggtccaaga     73800
agacaggagt atttatctct tttgttcagt ggtgtgttac tggtgactac tagagtgcct   73860
gacacataga atatgttcaa taaatattcg ttgcatgaaa gaatgaatac cttgacagat   73920
tatttttata actctaccag tgtcattata taactacact gaatgattat gagccctcct   73980
agaaattaca taaagttctt atatattatt agaacccatt tgttggcctt atgtaatggt   74040
tctattggaa aaatcatacc tccgtatata aaaatgaaag tatttttttt ctacaattgc   74100
ccctcatata tactattata gtctccttca ccccattcag ccattaatgt cttcttgacc   74160
aggtaacata atttttacag cacctttgg ttattagaac aattttattt gtctttcaaa    74220
ctcagtccta ttcattttaa aactcccaac tcaagcctga gtcagtgttc ttctcccagc   74280
acaaacttaa acactggctc caacccttgg agttgaaagt aggggagcct cactcctgat   74340
acctcccctc cccctctacc gtgagcacca gtgcctagga gattgggcag gactgaggaa   74400
ggatgaaaag gagctcaggg ctccttaagc acctgaacaa gactggagga ctttggatgt   74460 tgctatttt ctgcctggca ttgactggct attggacgcc ctctgtgagg caggcatccg     74520
aatactggct ttcttgacat atatggagcg ttctttagag aggcctacaa gggctctcac   74580
tgcacagtac cctgatagga gagatctgtc cttatttctt ctatcaccat agctacttca   74640
gctttgcctg ctgagtccac cccacagtct cttctgctg gggcatcctt gccctggaca     74700
gattcttaga gcatgaccaa gcctaaacaa cttctgcaat ttttctaagt acacttttat   74760
ttaattgaaa gtttcaagca ttggataata taaatgtatc ctagacagtg ttccagtaag   74820
gacaaccagc tcacaattat ccattctaat aatgggagtc aactgaaata gaaaatata    74880 gattttaaa ataatttatg agaaacaaat atttgtgaca cagtacattt ctaattatgt    74940
ttatctttat tattattatt atcgtttcct tcagtacaca ctagtttggt gagacttga    75000 gaaaggccag gaataagccc aaattcaaaa aacaattcca ggattaacag ataagtggat   75060
aatagagaat tgcaaaaga tcatgctcat tttaccaata agaaactggt tggttaactt     75120
gggttgcaaa ctgaaagcag atttatacta aactggcagg tgtctccaga tcttaaatgc   75180
```

```
agatctctat ctctgagtta atctgcctct catcttcaat ggcattcctc tgaatttttc   75240
tccctcaaat aatctatata ttattaaatt ttgtttatac tgccatttta agaaacagat   75300
tttaaaactt taaacatggg aattaaatag gccctactga ggattatgaa aaacctgaca   75360
aaacctccta tgcacatgat ttagattagg agcagtgcac acgctgtatg tgtatgtgca   75420
gctacttgtc caattaacac cttttcagaa atggaggaac tttctctgag gactttgaca   75480
tatttgtgtg ttcagcagtc cttttctttt tttttattt tttatttttt tattattata   75540
ctttaagttt tagggtacat gggcacaatg tgcaggttag ttacatatgt atacatgtgc   75600
catgctggtg cgctgcaccc actaactcgt catctagcat taggtgtatc tcccaatgct   75660
atccctcccc cgtcccccca ccccacaaca gtccccagag tgtgatgttc cccttcctgt   75720
gtccatgtgt tctcattgtt caattcccac ctatgagtga aatatgcgg tgtttggttt   75780 tttgttcttg tgatagttta ctgagaatga tgatttccaa tttcatccat gtccctacaa   75840
aggacatgaa ctcatcattt tttatggctg catagtattc catggtgtat atgtgccaca   75900
ttttcttaat ccagtctatc attgttggac attagggttg gttccaagtc tttgctattg   75960
tgaatagtgc cgcaataaac atacgtgtgc atgtgtcttt atagcagcat gatttatagt   76020
cctttgggta taaacccagt aatgggatgg ctcagtcaaa tggtatttct agttctagat   76080
ccctgaggaa tcgccacact gacttccaca atggttgaac tagttacag tcccaccaac   76140 agcgtaaaag tgttcctatt tctccacatc ctctccagca cttgttgtgt cctcactttt   76200
taatgatcgc cattctaact ggtgtgagat gatatctcat tgtggttttg attttcattt   76260
ctctgatggc cagtgatggt gagcattttt tcatgtgtct tttggctgca taaatgtctt   76320
cttttgagaa gtgtctgttc atgtgcttcg cccactttt gatgggattg tttgttttt   76380 tcttgtaaat ttgtttgagt tctttgtaga ttctggatat tagccctttg tcagatgagt   76440
aggttgcgaa aattttctgc cattttgtgg gttgcctgtt cactctgatg gtagttcctt   76500
ttgctgtgca gaagctcttt agtttaatta gatcccattt gtcaattttg gcttttgttg   76560
ccattgcttt tggtgttta gacatgaagt ccttgcccgt gcctatgtcg tgaatggtgt   76620
tgcctaggtt ttcttctagg gtttttatgg ttttaggtct aacgtttaag tctttaatcc   76680
atcttgaatt gattttttgta taaggtgtaa ggaagggatc cagtttcagc tttccacata   76740
tggctagcca gttttcccag caccatttat taaatagggca atcctttccc catttcttgt   76800
ttttctcagg tttgtcaaag atcagatagt tgtagatatg tggccttatt tctgagggct   76860
ctgttctgtt ccattgatct atatctctgt tttggtacca gcaccaggac catgctcagc   76920
agtccttttt caagagatgt gaagtacatc ttcacagatt tttaaatatt tagatagaaa   76980
gttcttacag aatgagaaat aaaaagttag ctttgcctta aaaatattaa ttcaccttat   77040
attctccata cttaatccat ataggaaaca ttatattcca ggtctaacat gtggcttgct   77100
tacattaatt ttgctgttga aaatatatg ttttggatta tgtttttaaa attttagctt   77160
taatatttaa atattaaata atgttaactt taaattaacg aagaatagtt tttaattta   77220 taagaaatgc cctataaaaa acactttctt tacctcaaga gtgagacttg gcaaccatac   77280
caatattaca tagtaatttt aaagtcaaac gaaatggaga gaacttaata gatacagaag   77340
ataagaattt aaactaacat tttgctcggg attttagaac actatacaga gggaaattta   77400
gtagacaata atgaagtcca tagcattgca cacatcttga aataagtgta taattgacac   77460
aagctatgtc ccatgttgat aggaagaatc caaaatagtt ttggagaata atgccatcta   77520
```

```
tgcaggaggt gtggccatat acatcatctt tactcagtgt ttttcatgtc aataaatatt    77580
taattcctaa cactctgaat tactaataga ggtgaagcct gtcagtggaa gtgacagaga    77640
gatacacagt gattcccgta agtttgatcc tgaaacacag tgcctttagc agatatagtt    77700
cccataagca agcagtctga agtatttacc ctcagtaatc tgaatgtata aataaacagg    77760
attcatgatg gtagagtaat ttatatatac ttgtagtatt aggacatgca aaacttattt    77820
tatggaaaaa aataatttac taccttatag tatggcaact atacaaatct ataaattgac    77880
tcttttgtcc ccttgaaaaa aagctgacat aaaatttaaa tgatgtgtat tttttcttag    77940
agcaataaaa gatataccec cacctagaaa agcaataaac caaaaaataa aacaaaaaca    78000
aaatcaagcc ctcttcacaa atttgagcat atctacagct ttatgtggtg agagatacag    78060
ctaccattct tgagtaatcc gaagagtcaa atggtatgga gcaaaattac agtcctaaat    78120
gcatattggt gaaatgagat gctgatccat ttgcacacta atgtgctatt tttaagtcat    78180
gcatcatagc atcttcaaag aggcctgtca taattatgat ggattagact gcagagtcag    78240
tcctagatgc agtaattgtt tcacagatgc tgccaatgcg actagaattt ataataaatt    78300
attttcagag aggcgggaga aggaacaaaa tcaaggaaaa actgctgtgg ctaaaacctg    78360
ttttggtctt aggaaaccaa aatgttagct agtagtcaaa aggccagtat tttcaactga    78420
gataaacatg cttcattaat acatgcctct gacatagaag ataaaggtta acataattga    78480
catatcagcc agtctctctc tctctctctc tctctctctc tctctctctc tctctgtctc    78540
gtagcttatg aaaatttatt ctggggcatt agctgaaatt attgagtggc catataattg    78600
ttgcatgttt ctatttatgt taaattgcct ggttataatt tgacctttag aatttctgaa    78660
aaaaatggtg gtatttatag taaatagaaa tattcttttt ggttccttgg aagcccatgc    78720
attacaaaga acattagatt attggaataa aaggatagac atacataata tgactagtgg    78780
gatctaaatt ataaccttt aaaattgtaa tttaattagt ctgtcattta ggcaaatgat    78840
aatttctaaa actgccttt tagacttaaa aaaataccaa agttcttata actttagcat    78900
tatgttttgt tcattcttaa agtttaattc actttgttgc cttttggta aacctatgaa    78960 gaaatctcat gctgcaccat atagtaaaaa atcgtgtgtg tgtgtgtgtg tgtgtgtgat    79020
ttgaataatg agctatgtgt tatattttga taagcaaaga taagtttata gtgaagcaga    79080
taaacatgcc atgtattttc ctaggttaag ggttcaataa tcagaagagc ttctacaact    79140
catttgcctt ctcactagtt ttttttgaaat tgcgctctat gagttttta tgtggtgttc    79200 tctgtacttg ctgactactg atgcacattt ctccttaggt cactggttct cctccctcag    79260
caatgttgta ggtagctttg atgaacattc gttgtcagcc ttttacctt gacttagtgt    79320 ttttctctca tactacggca agaagaaatg aagttaaatt ttacaagagt gacttgggtg    79380
gctgatatgc ccacattgac agggacaaga gctctagtct tcccctctcc tgtattccca    79440
tggcacttca gtagtctcat tgcctcaaca taaccacagt tcagggcagt agaggatgtt    79500
tgcatctttg tgttagctcc atgccatggc aactgcactg agtgaggatt caactcagtg    79560
cagcaggact gaaaaaataa atgaactaat gtgtcttgag ctccaattct ctgagtgaca    79620
ttatcagggg agattcataa atcatcctca aatattctag agaaaaatca tcagcagtcc    79680
agcattgcaa agataatctg ggaaggtggc aaagaaggga tcagaataac tctgtggcag    79740
cttcaaattc catgtcctaa aagtttacgt tttctttttt attctatccc aaaccacata    79800
aagaaatgat ttgttggcaa aagacatgca aaatgcccct aatcatctta ataattcag    79860 acctacagat acgtagccaa aatacttgtt ttttaatcct aaaccttaaa aaaaaagctt    79920
```

```
aaattgttgg ctaaatgtga atttaataac aaaacttact cctttaatta tgcacttgtc  79980
ttagtattgt gtggtgggaa gagctttaga gagctgccag agtgcttagg cctagtccct  80040
gtgggagcct ctgttttggt gcttcaccat gggcagattc ctcagttttc acatctttaa  80100
aatgagaaaa tggtactaga tccttgctgc tactctgaaa tgtttataca ttgttaggac  80160
cattgttaca tattattact tatatttgag tgtcaccttg aatttctta gccgtgtgat  80220 atggtttggt tgttggctcc tctaaatctc ctgttgaaat ataatcccca gtgttggagg  80280
tgggggcctg gtgggaagtg tttggattat tggggcagat ccctcatggc atggtgctgt  80340
cctcctgata gtgagttctc aagagatctg gttaagggtg tgtggcacgt cccctccct   80400 gtctccttcc ctccctctct ccttccctcc ctctgtcctt ccctccctct tcctccctct   80460
tcctctctct ttttctccca ctccagccat gttagatgcc tgctcccctt ttgctttctg   80520
ccatgattat aagttttgta aggcctcacc caaagcagat gccagtgctt tgcctcctat   80580
acagcctgca gaaccatgag ccaattaaac ctattttctt ataaattacc cagacagcta   80640
tttctttata gcaactcaaa aacagcctaa cataccttc aaaaggttaa aatgctattt   80700
agtcattcca gaagcaagat ctcttttgtcc agaattctgg aaataaagat gccaaaataa   80760
tatggcatgt atttgatctc agggaatttt catttttca aaaggaggaa aaaagagtaa   80820
tataattttt taatatttg gtagctctaa cagtgcttag aaccagttct caagagcaca   80880
ttgtgaaact ttcaggaatt gcatgagctg taggttgata acatgatgcc agctataacc   80940
cataagagca tctcctgagg aatatgttaa aaactgtatt cattcttaaa ttttaactaa   81000
atgcaatgag tgaagtattg acatcatgaa aatcatccct gggtaaacaa ttagtcactc   81060
caggttttcc caaaggttct tctgtctctg ttcttgtata taaacttcgt aaccagttta   81120
acaaccccaa aaaaggcctt aattttgatt ggccagcatc ctcttaggaa agacattgcc   81180
atcctcttgt aaagttgctt ctcattctaa aataagaatt gtttccatct agggaatgat   81240
ttttataggt agaatcttat ttggcatgga ctcttttgca tacagtgaat tacaatgtgt   81300
agaccttcaa tagcaaggtg tttgaatatt tagttgcaca atagagcagt atcttaatat   81360
tgtataccat attaattttg tgttctctgg tgtaagaaaa aatagaagga tgtttaattt   81420
caactaaaaa atcaatcatg ataattcaaa atatttctga tgagtcattt ataagagcag   81480
atatgaatta aaattatatt tttgttctta gtctctgaga agcaaaaatc acacaaataa   81540
tctccatagc aaaaatttat atttatctga aaaacagttt aactttgaaa aacttttctt   81600
tgcaatcatt taaattcata aaaaaaattc attaactcta ctttcactga atagcaggtg   81660
aatagcaggt caatatctac aaaaattcat ctttgaagat tttttatct tacgcaaaaa   81720 ttattgactt catgtagact ttttatgcaa gcttgaaaac actgtgtaaa tgaccccata   81780
aaaactacag catgaaagct ttttcagtat ttctacaatg agcaaaatgc ataggtctca   81840
tttccttctc ttttattaag caaaataata ctttatcaac atcagtatgc aagcactaag   81900
agcttgaaag agtactgtgc aagtgggtta ctggatcata atattccagg gtatgtatat   81960
aaaaagtgtg atttagcaca tattaaagta aaagaaaata ttgcatttt ctccttctaa   82020 aatggcagtt tattagttta aatttcctga aataagattt aaagaccaat aacaaatttt   82080
cctcattcta acatataact ttcctgccct tcttgtgaaa aagttaacca ttaaactttt   82140
cacacaaatg gttgtataaa ggacttgctg tcacagacaa aatagttctg tataatgttt   82200
aaaaatggcc attgtgttta aaactccata ttgaaataca tttctttttt agtcaccttc   82260
```

```
atttcttagt agctattatt atactcaaag gatttgccct tgacactttta aagaatgtcc    82320
aaaattatgt ggaatggatt ataataaaag ataatatatt aaatgcttaa aatattttat    82380
accttagaaa gtagaaaaac atgtattatg tacagatcct acaaatttta tataatttat    82440
cataaatgta cacatgtata tacatgtaaa taccttttga ttgctctgta tatgaattgg    82500
tgttttacag ttaccaaaag aaaagtgcct ttttttggta gtatctggac aggtaattga    82560
ctttctttct gcaggattta tttagattta tgtctatgct ccttaatttt tgaaaagtga    82620
tagtgtcctg attttggaga agcctctcat atcaaagact acaaatcaat tttcatgatt    82680
ttaaaaccta aagtttcttt attaggtgtt attgatgatt aaaagccatt gtctcaccca    82740
aattttctac ttgttcaata gaaacataat gtaagccaca tggaatttta cattttctag    82800
tactcacatt aaaacaagtg aaaaagaaac aaattgatga tacgtttgat ttaacccaat    82860
acatttaaaa tagttcaaca tgtattaaat attttttgag tattttttgtg ttttttttaac   82920
actaaatctt tgaaatccaa actaaatgtt ttcatagata ccacatctca atttggacta    82980
gacacatttt aagggctcaa tagctatatg tgactagtca ctgttggatg atgtatatct    83040
agaccatctc ttaatgtatg gaaggaagta atctagcag aaataaaaac atcactttgt     83100
tttctttgtc caatatgagt tataacttta tttttttgag acagagtctc gctctgttgc    83160
caggctggag tgcagtggcg cgatctcggc tcactgcaac ctccgcctcc tgggttcaaa    83220
tgattctcct gcctcagcct cccaagtaac tgggactaca ggcatgcgcc accatgccca    83280
gctactttt gtattttag tagtggcggt gtttgaccac gttggccaag atggtctcga     83340
tctcttgacc tcgtgatctg cctgcctcag cctcccaaag tgctgggact acaggcgtga    83400
gccaccgtgc ctggcctttt attttattta ttaagtaata cacatgcttg gaagttattt    83460
aaaaaaaaaa aaaggaata gttaaaagta atcccctcc cagtgctttt ctccagctgc      83520
cccattcctt ttcctggagg caaattatta tggccagttc attatatatt ctccagagat    83580
gattttttt tattttacaa aggtataggt tgtagcattc ttatataaac tgttgtgtag     83640
cttcctttat tccatttaat tactgggaga tacttccatc tgaaaatata gagatactaa    83700
ttttaatagc tacatggtat tatattgtgt ggctgtacca taaattattt aacataaccc    83760
ttattgatgt aggttgtttc taacctttta ttactgcaaa agattgtgcc tacatcattt    83820
aatgtatata tgagcatatt tgtcagatat atatatatat attttttgag acagtgtctc    83880
actctgtcac ccaggctgga gtgcagcatc acaatctcac ctcactgcag tgtccacctc    83940
ctgggttcag gtgattcttc ttcctcagcc tcccaagtaa ctgggattac aggtgcctac    84000
caccatgccc tgctaatttt tgtatctttt taggagagac gggatttcac catgttggcc    84060
aggttggtct agaactcctg gcctcaggtg atccactggc cttagcttcc caaagtgctg    84120
ggattatagg cgtgagctac cacacccagc ctgtcagata aattcttaaa agggtcaagg    84180
aaagtgtttc tgaaatttta tacatattgc caaattgtca tcctacatga tatttgtggc    84240
agttttgact ctcaaaagcc acatgagaga gtatctgttt cccacatgc ttgccaaaca     84300
tagtatagta tcaagcttac tgatcttcac taattggaga agagaaaaaa actgtacctt    84360
gttgcagttt taatttgcat ttcttttat gagcaatagt agatatcttc ttaaatactt     84420
aagagccatt cacatttcat tttctatgaa ctgtccatgt cccttgtcca ttttttagta    84480
tgtggttatt catttatttg taggcgtcct atatgttaag aaaagtttta tacaacttt      84540
aactcttttt acatgtttat tttggcacat ataaattta gcaaactttc ccatctttta     84600
tgacttctag attttgtttc acaaaaaaag agcttagcca gtcattagat ttttttaagt    84660
```

```
tttctcagat tgttttaac ttttgggggg gttttattc ctgtattcaa atattaaatt    84720
catctagaat ttatcttaaa gtgtaaggga atgatcccac tttatcattt ttcaggaga    84780 ttacccagtt gttctaatat caagtatgtc tttgaaatcc catccttatc ttgtagcata    84840
tttctgtggt ttgggtctat ttttgaacat tctgttttat tccattgatc atattaatat    84900
tatatgtgca aacacaaact attttaagta tagtagcttt gttgctttta aatatctttt    84960
aatttggcta ctaggcccca tacaattctt tttcagaata ttcctggcta cccaatttgt    85020 ttattttcc aaatgaactt tggagtcaac ttccttaatt cctcaaaata ttctgcaagt    85080 actttagta agagtatatt aagtgaataa tttgacaact atctaagaac atattatagc    85140
ttttcccttg ttttgttttt gtacttatat attagtatag ttttaaagtt atattaaaat    85200
aggtcttcca cattttaaaa acttattcct agtgtattaa ttcttctat tataactaca    85260 gtatttatt ccagtaaaac ttctgactgg ttgatgctct tataaatcaa ggctataaat    85320
ttttcttcag ctactttgct gaattctcac aaactgtaac cattttttac ttgattctct    85380
aggttgacca gtatataatc ttttatctg taaacaataa ctttagcgtt gctttcaaca    85440
tctatattct tattctattt cattttcctt gtttatcaag aaatagctgt tttaatagag    85500 ttgttttcg cccaaaaaga aaatagtctt tctttttcta cttatatctt taaaataaat    85560
gtaatgagaa agactgtggg aaaataaagc agacaccta tacaatggat taatttttt     85620 agtgccattt cttctggctt tctctattat tgggactctg aaatcttcgt tagtactact    85680
ctcaaaaatg ttcgaatgaa tgcaatcaga ttcaagggta caagtgcagg ttatataggt    85740
gaattgcatg ccttgggggt ttggtgtaca gactattttg tcacccaggt aataagcgta    85800
gtacttaata ggtagttttt tgatcctctc ccttctccca tcctcaaagt atccctgctg    85860
tctgttgttc cccctctttg tgtccatgtg ttcttgctgt ttagctgcca cttaagagaa    85920
catgtggtat ttttctgttc ctttgttagt ttgtttagga taatggcctc cagctccatc    85980
catgttgctg cacagaacac gattttgtgt ttctttatgg ctgtgtagta ttccatggtg    86040
tatatgtaac actttcttta tccagtctac tacttacgga catttaggtt gattccatgt    86100
cttcgctatc attaatagtg ctgtgatgaa catacgtgtg caatatgcct ttatggtaga    86160
atgatttata tccctttggg taatatgccg aataatggga ttgctcggtc agatggcaat    86220
tctaagtcct ctgaaattac cgcactgctt tccacaacag ctgaactagt ttacattccc    86280
acaagcaata aggggataag tgttcccttt tctctgcagg aatgattaat tctttagag    86340 agtcaaagat ggaatcctag ggaagatgat atctgaggca ggtttagagt cattgggcaa    86400
ataaggggat taagaaggca ttctaggcag acagaaaacc aaaggcatga agctctgaaa    86460
cagcttacta tgtttggata tttataagct gttgttattg ttggagtata aactgtaaga    86520
gagagtagga ggacagaaaa aacagcctgt atgcgggggg aagaaaacat ttaaacagaa    86580
attctcaaaa gatttgggca gccagcccct ctagagaaaa acatagaatc acctagaaag    86640
ggtttttcat aaagtacact tttcatcacc cctattctgt cacctggaat attgataaca    86700
ctgaagggag tgtgccttat ctctcaggtg tatttggatg aaatagtttg agaaccatgc    86760
aggcaagttt aagccagtgt gttaaagaga atatgacatc agatttgcat tttacaatct    86820
tccttttgat aacaaaggga accttaaagg gctggagggg aagggcagac ggggctaggg    86880
gaggagaacc cttttaaaaa gctactgcag gtggggtgcg gtggctcaca cctgtaatcc    86940
cagcactttg ggaggccaag gcaggcagat cacctgaggt caggagttca agaccagcct    87000
```

```
ggccaacata gtaaaacccc atctctacta aaaatacaaa aattagctag gcatggtagc    87060
aggcacctgt aatctcagct acttgggagg ctgaggcagg agaattgctt gaacctggga    87120
ggcagaggtt gcagtgagcc aagattgtgc cgctgcactc cagcctgggc aagagagtga    87180
gactccatct caaaaaaaaa aaaaaaaaag ctactgcagt agatcaggag gaggcacagt    87240
gataaagaga agatctgagc tatgaagtgg cagtcaagat gattaaagga atatatagga    87300
agtacagttg atagaactta gcaagtgatt aggtaaatga agtgctagag aaaataaagg    87360
ggatattttt caattgtttt tagcattttg gcaaaaaatt atttaggaat gaaattgatg    87420
ctagtaacta agagtatgaa cttcccacat tagctggtaa ttttgatcac ccttgttctc    87480
catgaccata aatattttag agttgctatg aagacaagaa tgtttatttc ctgagtagct    87540
gtcagttgtc actatgaaac atgaaaataa atatcagttt gctatgtcta ggtattccga    87600
tatttatcca caattattcc ttaagatata ttagtatttt tatagataga tagatagata    87660
gatagaaata aacacatttt aattttttgtt tccatgctct ttagaattca actagagggc    87720
agccttgtgg atggccccga agcaagcctg atggaacagg atagaaccaa ccatgttgag    87780
ggcaacagac taagtccatt cctgatacca tcacctccca tttgccagac agaacctctg    87840
gctacaaagc tccagaatgg aagcccactg cctgagagag ctcatccaga agtaaatgga    87900
gacaccaagt ggcactcttt caaaagttat tatggaatac cctgtatgaa gggaagccag    87960
aatagtcgtg tgagtcctga ctttacacaa gaaagtagag ggtattccaa gtgtttgcaa    88020
aatggaggaa taaaacgcac agttagtgaa ccttctctct ctgggctcct tcagatcaag    88080
aaattgaaac aagaccaaaa ggctaatgga gaaagacgta acttcggggt aagccaagaa    88140
agaaatccag gtgaaagcag tcaaccaaat gtctccgatt tgagtgataa gaaagaatct    88200
gtgagttctg tagcccaaga aaatgcagtt aaagatttca ccagttttttc aacacataac    88260 tgcagtgggc ctgaaaatcc agagcttcag attctgaatg agcaggaggg gaaaagtgct    88320
aattaccatg acaagaacat tgtattactt aaaaacaagg cagtgctaat gcctaatggt    88380
gctacagttt ctgcctcttc cgtggaacac acacatggtg aactcctgga aaaaacactg    88440
tctcaatatt atccagattg tgtttccatt gcggtgcaga aaaccacatc tcacataaat    88500
gccattaaca gtcaggctac taatgagttg tcctgtgaga tcactcaccc atcgcatacc    88560
tcagggcaga tcaattccgc acagacctct aactctgagc tgcctccaaa gccagctgca    88620
gtggtgagtg aggcctgtga tgctgatgat gctgataatg ccagtaaact agctgcaatg    88680
ctaaatacct gttcctttca gaaaccagaa caactacaac aacaaaaatc agttttttgag    88740 atatgcccat ctcctgcaga aaataacatc cagggaacca caaagctagc gtctggtgaa    88800
gaattctgtt caggttccag cagcaatttg caagctcctg gtggcagctc tgaacggtat    88860
ttaaaacaaa atgaaatgaa tggtgcttac ttcaagcaaa gctcagtgtt cactaaggat    88920
tccttttctg ccactaccac accaccacca ccatcacaat tgcttctttc tccccctcct    88980
cctcttccac aggttcctca gcttccttca gaaggaaaaa gcactctgaa tggtggagtt    89040
ttagaagaac accaccacta ccccaaccaa agtaacacaa cacttttaag ggaagtgaaa    89100
atagagggta aacctgaggc accacctccc cagagtccta atccatctac acatgtatgc    89160
agcccttctc cgatgctttc tgaaaggcct cagaataatt gtgtgaacag gaatgacata    89220
cagactgcag ggacaatgac tgttccattg tgttctgaga aaacaagacc aatgtcagaa    89280
cacctcaagc ataccccacc aatttttggt agcagtggag agctacagga caactgccag    89340
cagttgatga gaaacaaaga gcaagagatt ctgaagggtc gagacaagga gcaaacacga    89400
```

```
gatcttgtgc ccccaacaca gcactatctg aaaccaggat ggattgaatt gaaggcccct    89460
cgttttcacc aagcggaatc ccatctaaaa cgtaatgagg catcactgcc atcaattctt    89520
cagtatcaac ccaatctctc caatcaaatg acctccaaac aatacactgg aaattccaac    89580
atgcctgggg ggctcccaag gcaagcttac acccagaaaa caacacagct ggagcacaag    89640
tcacaaatgt accaagttga aatgaatcaa gggcagtccc aaggtacagt ggaccaacat    89700
ctccagttcc aaaaccctc acaccaggtg cacttctcca aaacagacca tttaccaaaa    89760
gctcatgtgc agtcactgtg tggcactaga tttcattttc aacaaagagc agattcccaa    89820
actgaaaaac ttatgtcccc agtgttgaaa cagcacttga atcaacaggc ttcagagact    89880
gagccatttt caaactcaca ccttttgcaa cataagcctc ataaacaggc agcacaaaca    89940
caaccatccc agagttcaca tctccctcaa aaccagcaac agcagcaaaa attacaaata    90000
aagaataaag aggaaatact ccagactttt cctcaccccc aaagcaacaa tgatcagcaa    90060
agagaaggat cattctttgg ccagactaaa gtggaagaat gttttcatgg tgaaaatcag    90120
tattcaaaat caagcgagtt cgagactcat aatgtccaaa tgggactgga ggaagtacag    90180
aatataaatc gtagaaattc cccttatagt cagaccatga aatcaagtgc atgcaaaata    90240
caggtttctt gttcaaacaa tacacaccta gtttcagaga ataaagaaca gactacacat    90300
cctgaacttt ttgcaggaaa caagacccaa aacttgcatc acatgcaata ttttccaaat    90360
aatgtgatcc caaagcaaga tcttcttcac aggtgctttc aagaacagga gcagaagtca    90420
caacaagctt cagttctaca gggatataaa aatagaaacc aagatatgtc tggtcaacaa    90480
gctgcgcaac ttgctcagca aaggtacttg atacataacc atgcaaatgt ttttcctgtg    90540
cctgaccagg gaggaagtca cactcagacc cctccccaga aggacactca aaagcatgct    90600
gctctaaggt ggcatctctt acagaagcaa gaacagcagc aaacacagca accccaaact    90660
gagtcttgcc atagtcagat gcacaggcca ttaaggtgg aacctggatg caagccacat    90720
gcctgtatgc acacagcacc accagaaaac aaaacatgga aaaggtaac taagcaagag    90780 aatccacctg caagctgtga taatgtgcag caaaagagca tcattgagac catggagcag    90840
catctgaagc agtttcacgc caagtcgtta tttgaccata aggctcttac tctcaaatca    90900
cagaagcaag taaagttga atgtcaggg ccagtcacag ttttgactag acaaaccact    90960
gctgcagaac ttgatagcca caccccagct ttagagcagc aaacaacttc ttcagaaaag    91020
acaccaacca aaagaacagc tgcttctgtt ctcaataatt ttatagagtc accttccaaa    91080
ttactagata ctcctataaa aaattattg gatacacctg tcaagactca atatgatttc    91140
ccatcttgca gatgtgtagg taagtgccag aaatgtactg agacacatgg cgtttatcca    91200
gaattagcaa atttatcttc agatatggga tttttccttct tttttaaat cttgagtctg    91260 gcagcaattt gtaaaggctc ataaaaatct gaagcttaca ttttttgtca agttaccgat    91320
gcttgtgtct tgtgaaagag aacttcactt acatgcagtt tttccaaaag aattaaataa    91380
tcgtgcatgt ttatttttcc ctctcttcag atcctgtaaa atttgaatgt atctgtttta    91440
gatcaattcg cctatttagc tctttgtata ttatctcctg gagagacagc taggcagcaa    91500 aaaacaatc tattaaaatg agaaataac gaccataggc agtctaatgt acgaacttta    91560
aatatttttt aattcaaggt aaaatatatt agtttcacaa gatttctggc taatagggaa    91620
attattatct tcagtcttca tgagttgggg gaaatgataa tgctgacact cttagtgctc    91680
ctaaagtttc cttttctcca tttatacatt tggaatgttg tgatttatat tcattttgat    91740
```

```
tcccttttct ctaaaatttc atcttttga ttaaaaaata tgatacaggc ataccctcaga   91800
gatattgtgg gtttggctcc ataccacaat aaaatgaata ttacaataaa gcaagttgta   91860
aggacttttt ggtttctcac tgtatgtaaa agttatttat atactatact gtaacatact   91920
aagtgtgcaa tagcattgtg tctaaaaaat atatacttta aaataatttt attgttaaaa   91980
aaatgccaac aattatctgg gcctttagtg agtgctaatc ttttgctgg tggagggtcg    92040
tgcttcagta ttgatcgctg tggactgatc atggtggtag ttgctgaagg ttgctgggat   92100
ggctgtgtgt gtggcaattt cttaaaataa gacaacagtg aagtgctgta tcaattgatt   92160
tttccattca caaagatttt ctctgtagca tgcaatgctg tttgatagca tttaacccac   92220
agcagaattt ctttgaaaat tggactcagt cctctcaaac tgtgctgctg ctttatcaac   92280
taagttttg taattttctg aatcctttgt tgtcatttca gcagtttaca gcatcttcat    92340
tggaagtata ttccatctca acattctttt gttcatccat aagaagcaac ttcttatcaa   92400
gttttttcat gacattgcag taactcagcc ccatcttcag gctctacttc taattctggt   92460
tctcttgcta catctccctc atctgcagtg acctctccac ggaagtcttg aactcctcaa   92520
agtaatccat gagggttgga atcaacttct aaactcctgt taatgttgat atattgaccc   92580
cctcccatga attatgaatg ttcttaataa cttctaaatg gtgataccctt tccagaaggc   92640
tttcaatgta ctttgcccgg atccatcaga agactatctt ggcagctgta gactaacaat   92700
atatttctta aatgataaga cttgaaagtc aaaagtactc cttaatccat aggctgcaga   92760
atcaatgttg tattaacagg cacgaaaaca gcattaatct tgtgcatctc catcggagct   92820
cttgggtgac taggtgcctt gagcagtaat attttgaaag gaggttttgg ttttgttttt   92880
tgttttttt tttgttttt tagcagtaag tctcaacact gggcttaaaa tattcagtaa    92940
actatgttgt aaaagatgt gttatcatcc agactttgtt gttccattac tctacacaag    93000
cagggtacac ttagcataat tcttaagggc cttggaattt tcagaatggt aaatgagtat   93060
gggcttcaac ttaaaatcat caactgcatt agcctgtaac aagagagtca gcctgtcctt   93120
tgaagcaagg cattgacttc tatctatgaa agtcttagat ggcaccttgt ttcaatagta   93180
ggctgtttag tacagccacc ttcatcagtg atcttagcta gatcttctgc ataacttgct   93240
gcagcttcta catcagcact tgctgcctca ccttgtcctt ttatgttata gagacagctg   93300
cgcttcttaa actttataaa ccaacttctg ctagcttcca acttctcttc tgcagcttcc   93360
tcattctctt catagaactg aagggagtca aggccttgct ctggattaag ctttggctta   93420
aggaatgttg tggctgacgt gatcttctat ccagaccact aaagcgctct ccatatcagc   93480
aataaggccg ttttgctttc ttacctttca tgtgttcact ggagtaattt ccttcaagaa   93540
ttttcctttt acattcacaa cttggctaac tggcatgcaa ggcctagctt tcagcctgtc   93600
ttggcttttg acatgccttc ctcacttagc tcgtcatatc tagcttttga tttaaagtgg   93660
caggcataca actcttcctt tcacttgaac acttagaggc cactgtaggg ttattaattg    93720
gcctaatttc aatattgttg tgttttaggg aatagagagg cccagggaga gggagagagc   93780
ccaaacggct ggttgataga gcaggcagaa tgcacacaac atttatcaga ttatgtttgc   93840
accatttacc agattatggg tacggttgt ggcaccccc aaaaattaga atagtaacat     93900
caaagatcac tgatcacaga tcgccataac ataataata ataaacttta aaatactgtg    93960
agaattacca aaatgtgata cagagacatg aagtgagcac atgctgttga aaaaatgac    94020
actgatagac atacttaaca cgtgggattg ccacaaacct tcagtttgta aaagtcacag    94080
taactgtgac tcacaaaaga acaaagcaca ataaaacgag gtatgcctgt attttaaaa    94140
```

```
aaagcttttt gttaaaattc aggatatgta ataggtctgt aggaatagtg aaatatttt    94200 gctgatggat gtagatatat acgtggatag agatgaagat cttaattata gctatgcagc   94260
atagatttag tcaaagacat ttgaaaagac aaatgttaaa ttagtgtggc taatgaccta   94320
cccgtgccat gttttccctc ttgcaatgag atacccaca ctgtgtagaa ggatggaggg    94380
aggactccta ctgtccctct ttgcgtgtgg ttattaagtt gcctcactgg gctaaaacac   94440
cacacatctc atagataata tttggtaagt tgtaatcgtc ttcactcttc tcttatcacc   94500 caccccctatc ttcccacttt tccatctttg ttggtttgca acagccccctt ctttttgcct  94560 gactctccag gattttctct catcataaat tgttctaaag tacatactaa tatgggtctg   94620
gattgactat tcttatttgc aaaacagcaa ttaaatgtta tagggaagta ggaagaaaaa   94680
ggggtatcct tgacaataaa ccaagcaata ttctgggggt gggatagagc aggaaatttt   94740 attttttaatc ttttaaaatc caagtaatag gtaggcttcc agttagcttt aaatgttttt  94800
tttttccagc tcaaaaaatt ggattgtagt tgatactaca tataatacat tctaattccc   94860
tcactgtatt ctttgtttag tttcatttat ttggtttaaa ataatttttt atcccatatc   94920
tgaaatgtaa tatattttta tccaacaacc agcatgtaca tatacttaat tatgtggcac   94980
attttctaat agatcagtcc atcaatctac tcattttaaa gaaaaaaaaa ttttaaagtc   95040
acttttagag ccccttaatgt gtagttgggg gttaagcttt gtggatgtag cctttatatt  95100
tagtataatt gaggtctaaa ataataatct tctattatct caacagagca aattattgaa   95160
aaagatgaag gtccttttta tacccatcta ggagcaggtc ctaatgtggc agctattaga   95220
gaaatcatgg aagaaggta attaacgcaa aggcacaggg cagattaacg tttatccttt    95280
tgtatatgtc agaattttc cagccttcac acacaaagca gtaaacaatt gtaaattgag    95340
taattattag taggcttagc tattctaggg ttgccaacac tacacactgt gctattcacc   95400
agagagtcac aatatttgac aggactaata gtctgctagc tggcacaggc tgcccacttt   95460
gcgatggatg ccagaaaacc caggcatgaa caggaatcgg ccagccaggc tgccagccac   95520
aaggtactgg cacaggctcc aacgagaggt cccactctgg cttttcccacc tgataataaa  95580 gtgtcaaagc agaaagactg gtaaagtgtg gtataagaaa agaaccactg aattaaattc   95640
acctagtgtt gcaaatgagt acttatctct aagttttctt ttaccataaa aagagagcaa   95700
gtgtgatatg ttgaatagaa agagaaacat actatttaca gctgccttt ttttttttt     95760 tcgctatcaa tcacaggtat acaagtactt gcctttactc ctgcatgtag aagactctta   95820
tgagcgagat aatgcagaga aggcctttca tataaattta tacagctctg agctgttctt   95880
cttctagggt gccttttcat taagaggtag gcagtattat tattaaagta cttaggatac   95940
attggggcag ctaggacata ttcagtatca ttccttgctcc atttccaaat tattcatttc   96000
taaattagca tgtagaagtt cactaaataa tcatctagtg gcctggcaga aatagtgaat   96060
ttccctaagt gccttttttt tgttgttttt tgttttgtt tttaaacaa gcagtaggtg    96120 gtgctttggt cataagggaa gatatagtct atttctagga ctattccata ttttccatgt   96180
ggctggatac taactatttg ccagcctcct tttctaaatt gtgagacatt cttggaggaa   96240
cagttctaac taaaatctat tatgactccc caagttttaa aatagctaaa tttagtaagg   96300
gaaaaaatag tttatgtttt agaagactga acttagcaaa ctaacctgaa ttttgtgctt   96360
tgtgaaattt tatatcgaaa tgagcttcc cattttcacc cacatgtaat ttacaaaata    96420
gttcattaca attatctgta cattttgata ttgaggaaaa acaaggctta aaaaccatta   96480
```

```
tccagtttgc ttggcgtaga cctgtttaaa aaataataaa ccgttcattt ctcaggatgt    96540
ggtcatagaa taaagttatg ctcaaatgtt caaatatttt gattgcctct tgaattcatt    96600
tgctaattgt atgtgtgtgt gtttctgtgg gtttctttaa ggtttggaca aagggtaaa     96660 gctattagga ttgaaagagt catctatact ggtaaagaag gcaaaagttc tcagggatgt    96720
cctattgcta agtgggtaag tgtgacttga taaagccttt ggtcttaaat cttgggcatt    96780
ttgatttgta aatctgaccc tgagaattgg gttacccaga tcaaagactc atgccagtta    96840
aaaagaacat tacctgtatt ttttatcatg tgttatctct taagaagagg cagattagtt    96900
ctaaaatcaa caaattgtat ttaattgaaa taatttagtg atgaggaaga ggtccattct    96960
agtgcctgct aaatgtataa tccttcttag aatgtgaagt tgtccttaaa cttttaaata    97020
ccttcagtta atctttatat tgtcatttat gaaaaccttg aactaagact tatgtatctt    97080
tcatctagct ctggttttaa tgcaggtagc atttaattgt ccccactgta ctgggtatag    97140
tctgctaaac attaaggagt agttttgcat ctctccttgt tctgatacta gggtcaaagc    97200 ccactttta tagatgggca gcaaaaggca cattggacat gctgataaat gttgccctaa     97260
ttgtgatcta aacatgataa aatatacata cataagtgcc cttatctgct gcaagtgacc    97320
cttgttttgt tttggttggg gtgggggtg tttgggatgg aatggtgatc cacgcaggtg     97380
gttcgcagaa gcagcagtga agagaagcta ctgtgtttgg tgcgggagcg agctggccac    97440
acctgtgagg ctgcagtgat tgtgattctc atcctggtgt gggaaggaat cccgctgtct    97500
ctggctgaca aactctactc ggagcttacc gagacgctga ggaaatacgg cacgctcacc    97560
aatcgccggt gtgccttgaa tgaagagtaa gtgaagccca gggcctctcc cctctttgcg    97620
gccactgata ggaaagccca atctttggtt gaaggaaga gagttcagcg tgcacttta     97680 catttataaa atgggcatca aaatgcctgt ttggcagtca tgcgataaga agttgtattt    97740
gctaatgtga ataacttgag atgatttcat tatctgaatt gtacagttta gccattaatt    97800
aggagcagtc agagtgtctg taaccacatg gcctcagtta taccataaac ttgaaattgt    97860
ttatgtgctc acatgctaca agtgacggct cctgtgtgcc tggccactat attagtatgt    97920
attgactcca cttccatgtt gcagtatctg aaacagaaag taagtctaat gagaaacttt    97980
gggattccca ggtcaaatac cttccatatg tatgtagcaa aaacaaaata caaagcctag    98040
aagttctgta gaaatagaac tgattttac tttcattcaa actattcatt atttccacaa     98100
tagtaatcaa aactgcttct acttttactg ctgctaaatg atcagcaaat tactggatat    98160
ggatatatat tattttccag gaatataaga atttagaata gaactgcaag agtatgcact    98220
taaatatatt tagtgcatcc agttgctaat gttttgtttt aaacaccatc cactttgcat    98280
gaagtctaaa ccttcagttg gaaaaagcct cattttaat attcctctac tgtgctgata    98340
atcctgtata acactaaaag aatagatgaa tgttcacggt gctacacaga aatgtttttt    98400
tttttttttt tttttttttt gagatggagt ttcgctcttg ttgcccaggc tggagtgcaa    98460
tggcgcgatc ttggttcacc gcgacctcca cctcccaggt tcaagagatt ctcctgcctc    98520 agcctccta gtagctggga ttacaggcat gtgccaccac acccggctaa ttttgtattt     98580
ttagtagaga cagggtttct ccatgttggt caggctggtc tcgaactccc gacctcaggt    98640
gattgcccac ctcggcctcc caaagtgcct tacaggcatg agccgccgcg cctggccaga    98700
aatcttacaa gttattttgc ccacgattgg ttttaaaata attttaattt tgcactattt    98760
cctttagtgt cttttttctct gcatccacca aactatagaa tcatttgctg agcttataag    98820
aaatgctcat actgctcatt gcaacagcta gccaaatttg tcctttgctg tttaaaactc    98880
```

```
taactagcat ggttttacta aatttatgtt aacacagttt ctctctctgg gttgtggga    98940 gacaaatcaa ttataaataa tctctttaga aaagttactc tttctatatg aaagtgtgac   99000
ttgactttct atgataatta tgatccaaaa attttatggt gtgtacctga ccactttac    99060 aaatgattaa ttggaaggta gaaattgctg attcataaca tgtaacttat aaacttatga   99120
tggactactt taagcataaa tttttttttt tttttaaga cagagtttca ctctgtcacc    99180
caggctggag tgcaatggtg cgatctcggc tcactgcaac ctccatctcc tgggttcaag   99240
caattctcct gcctcagcct cccgaatagc tgggattaca ggcatgcact accacaccca   99300
gctaattttg tattttagt agagacaggg tttctccatg ttgatcaggc tggtctggaa    99360
ctcctgacct cgggtgatcc gcccgcctcg gcctcccaga gtgctgggat tacaggcatg   99420
agccactgtg cccagcctga aatattttt taatctaccc tgactcctct tgctcttct    99480 gaagaaaaat ttttaaaaat gtatgtaggt gcctttaatt agaaaaaaaa ttaaaaatta   99540
aggcaacttg tgctcatatt ggtaatagca tttctttcaa gaactcagta atactgcatt   99600
gtctttaaag cataatatct cttagacttg acggtttgag attctaaatc actgaagaac   99660
ctcttgtgaa aatgatagtt ttaaaatttc ttttcaaaaa tagtcctatt gcaaaatgtt   99720
tgattttctt gaagtttcct ggaaactata tttcattcat tgtaatgaat ttaattttca   99780
ttaacataga tctctaatat ttttctcagc tcaccacaac ctccacctcc cgggttcaag   99840
tgattctcat gccacagcct cccgagtagc tagaattaca ggcacccacc cggctcattt   99900
ttgtattttt agtagagaca gggtttcacc atgttggcca gattgatctc gaactcctgg   99960
cttcaggtaa cccacccacc ctggcctccc aaagtgctgg gattacaggt gtaggccacc  100020
atgcccagcc agcttttcca taattcttat aaatgccaat gcctgaaatg gaatctgaca  100080 tataaaaat tacatgaaga acttttatta ttttgcattt gaaaaccatg aaaaatagtt   100140
ggaccagagt ctcagaaagc ttgtagtttg ttagtttaac tgctctaaat gtcaggcaga  100200
tacaaaacta ttaaaagaca tgcttcaaat atgaagacaa tttaaaagca cagctgtaca  100260
cttttgcttt ttgtctagtt tcaaggtaaa gatgaataat catttagata atgcttaagc  100320
tatgcttatg catacttaga gcaattctcc aaaataaaaa attttaatac ttaaatacat  100380
gattaaaata gacacgtatc caatgtcaat acagacttta ctcagaaata gcttttgaag  100440
tttcttctac cccataaata gatttatttt tatggctggc agaaatgaaa attacaactt  100500
tttgccaaga acagagaata gaataatctc aaattggggc tgcggactca gttttatgtt  100560
caaagctgtg tgaacctcat cactgagttc ttacaaatcc ctgtgtccac atgctccaaa  100620
ccacccactg tgagttcaga aaagaactct gagtgcatct ttcagtagga aagtaaaaac  100680
tgatttttac atttccttg agccaaacca gctgttctt ctttaaagat ttcccttga    100740 gatttccatt ttatgactaa gtctaaccag tattttttg gcaagtaaga gttgtgggag   100800
tgtatctgtc atcataagga aatcaaagcc agaaatgcct tctgccatgg tgggtgatgt  100860
taaacatttc aaggaacttt atattataaa aattgtcaaa cataaaagga aaagtgcaat  100920
ataatgaatt ccatggaccc atcacacagc atcaatattt atcaacattt tatcaatatt  100980
ttttcatata ttttcccac atccactccc actagtgttt gaaagcagaa gacagataac  101040
ttaccatctt acctgttaac atttcaggat gtatttctaa caggtaaaga ctttatcatt  101100
taatatttag actgtgtttg ttcaaattat ctgattagat tctatttcag aaaacacaca  101160
cataaacaaa aatgataatg agaaaagaa agcccttcca catgattgac acttctgagt    101220
```

-continued

```
agtgtgatcc cagttcatgt ccattgtctg ggatagctat taaataaaac ttcctctcat   101280
aaaattctct ccatttagaa gataaattct gtgattcaca agcctctttt tatttataat   101340
agcccttccc ctttctttat gaatttgaat ttgtttttta aagaaactgt gattttctct   101400
gtaaaattcc ccacattctg gatttggccg atttcatctt ggttcttttg tttacttaa    101460
cctattcctc tatccccagt atcttctgtg gactggtagt ttgactggtt cttttctt     101520
tcttttttt tttttttttt tttttttgag acaggctctc gctctgtcgc ttaggctgga    101580
gtgcagtggc ccaatctcag ctcactgcaa cctccacctc ccaggttcaa gctattctca   101640
tgcctcagcc tcctgagtaa ctgggactgc aagcatgtgc cacctcatcc tgctgatttt   101700
tgtactttta gtagagacgg ggtttcgcca tgttggccag gctggtctgg aactcctggc   101760
ctcaagtgat ccgcccacct tggcctccca aagtgctggg attacaggca tgagctatca   101820
cgcccagctg attttaagt aatataagta tgtgtgcatg tatagtatac attggcaaaa    101880
acacttcata agtagtgcta aaatcatctt atttatatac atcaggagac acataatgtc   101940
tgtttgtttc ccattttagt gatattaaga gtgtttagca tgtttagttg tcagcctgat   102000
ccatcattat gttcttcatc aaactttcac cagatagttt cacatcaatt gatgatcatt   102060
gcctgttct attatttgt tttcaagttg acagttttct ctcacttgat gttgtgtaaa     102120
tttagttata taaagttaaa ttattttgct attttttcta tgctgtatac atttgaataa   102180
ctgacctaat ttttacttta aaaatatttt acaattagaa gtccaaatag taaatcaaag   102240
gttaagaatt tttgcagaaa tctgttatat agatgacatt ttaatatttg ccctttatat   102300
catttaccat gagccaaatt tcaagtcata ttaaaatgac tgtcatgtgc taattctaac   102360
aatatttgaa agaccctat caaaataaat atccttta gtagccactt tattagaaaa      102420
tcaacttaa gttattcccc catgttttt tctaattgag atataattca cataccataa     102480
aatttaccct tttaaagtat acaattcagt tgtttcagta cattcacaaa gctatgcaaa   102540
tgtcacctct acctagtttc agaacgtttt catcattccc agaaggaaac cctgtattta   102600
ttaggcagtc acttcccctt ctccccttct tccttcctct aagtggcaac cacaaataaa   102660
cattcagttt ctctggattt acctattctg ggcattttgt attagtgaaa tcatgtattt   102720
ggcctttctc tctggcttct ttcatgtacc tcaatgtttt caagtctcat tcattttatt   102780
aaaaaaaaaa agtacctttt ttcttttct tttttttttt tttgtccacg tatatattca   102840
caccacattt tttgagacag agtctcgctc tgttgcccag gctagggtgc aatggtgcaa   102900
cctcagctca ctgcaacctc tgtctcccgg gttcaagtga ttctcatgcc tcagccccca   102960
agtagttggg attacagttg tgcaccacca cacccagcta attttgtat ttttagtaga    103020
gacagggttt caccatgttg gctaggctgg tctcaaactc agcctcaagt gatccttcta   103080
ccttagcctc ctaaagtgct gggattacaa gcatgagcca ctgtgcccag ccacattttc   103140
tttttccatt tattagttaa ttgacatttg gatcgtttct acttttggc gattataaat    103200
tatgctgcaa tgaacatcgg tgtacaagtt tttgtgtgaa catgtttca gttaccttgg    103260
gatatacacc taggagtgac attgttagta atatggtaac tttatgttta acttttgaa    103320
gaactgccaa actgttttcc aaagtagctt tatgctttta catttctgcc aacaatgtat   103380
gaaggttcca gtgtatctcc acatcctcaa gaaaatgtta ttgtcttttt aattgtaacc   103440
atccaagtgg gtatgaagtt tatctcgtga ttttgatttg cattttccta atggctgata   103500
ttgggcatct tttcacgtgt gtattgacca tgtatttttt tgagaaaagt ctacttatat   103560
gttttaatt gtattattt tagagttgta agaatatgtt atgttgatac ttgaactttg     103620
```

```
tcaaatgcct ggtttgcaga tattttctcc tatcccacag gttgtcgctt cactttgata   103680
atgtccttaa agtacaaaag ttttaaattg attttgatga aactcaattt cttttttaatt  103740 ggcagcttgt gcatttgggg tcatatttaa gaaatcattg cctcattcaa gatctgaaag   103800
atttacacct atgctttctt ctcagagtat tataacttta gttcttacat ttagattttt   103860
aattaatgtt gagttaattt gatggtgaga gataagagtc caacttcatt cctttgcaag   103920
tagctgtcca gttttctcag caccatttgt taaaagactg ttttttttca attaactgac   103980
caagatgtat gggtttattt ctggactctt aattctgtta atctgcatga cttttcttat   104040
gccagtacca cactgtgctg attcctgtag ttttgtagta aattttgaaa tcaagacagg   104100
taagtcttcc aactttgtac ttttgcctac catgttcttt gggtttccat atgcattta    104160 agatcagctt ctccgtttcc tttctggatt tttttttttt tttttttttt tttttttttg   104220
gtggagctgg agtcttacta tattacccaa gctggttttg aactcctggc taaagagatc   104280
ctccctccta ggcttcccag agagctgggg ttacaggcat gagccaccac atccaacccc   104340
cttctgggac tttgactggg gttctgttga atctgttggt caatttggag agtattgata   104400
tcttaacatt aaagcttcca atttatgaac acaggctatt ttccCattta ttcttaaatt   104460
tctttcagta atgttttgga tgaaacatgt acaaagtcct gcactttta ttttttttaa    104520 gacagagtct tgctctgctg cccagtccag agtgcagtgc tgccatctca gctcactgca   104580
acctccacct ccgggttcaa gtgattctcc tgcctcagct ggaactacag gtgcgcgcca   104640
ccatgcctgg ctaattgttt tgtgttttg gtggagacag ggtttcacca tgttggccag    104700
gctggtctca aacacctggc tcaagtgac ctgactgcct tggcctccca aagtactggg     104760
attacaggca tgagccacca cgcctggcct gtacttctgt taaaatttt tctatgtatt    104820 ttttttatcc tattgcaaaa tcaaattttt tgttgataat atatggtcat aaatttcatt   104880
tttatatatt ggtctcatat cctaccaact tgctgaacta gcttattagc actaactttt   104940
tttggtagat tccttaggat ttgctgcata caagattatg tcatctacaa gtagagatag   105000 ttttgttttct tcacttccaa tctgggtggc tttatgtttt tttcttgcct gattacccag   105060
ttagaacttc cagaaaatgt caggtacaat taacaactgc aaacatcctt gtcttattca   105120
ttttagaaag aaattttag tttttcacca ttaagtatga tactagttgt aggttttgtt    105180 taaaaaaga ctgtgtcaag ttcagaagtt cccttctgtt gctagtttgt tgaataattt    105240
tatcacgaaa gggtgttgaa cttttctcaa atgctgtggc tacatctaat gaaatgatca   105300
tgcgttcttc tccttattc tattaatatg gtatattata ttgattcatt tttatacatt    105360
agattaacat tatatttctg gaataaatcc cacttggcct cagtgtgtat tactttttat   105420
atattgctgg agtctgtttg caggtatttc attgaggact ttcgcatctc tgttgataag   105480
gtatactgat ctttagttct cttgtgatat ctttggtttt ggtgtcagag taattctgag   105540
ttcacaaaat gcattgggaa atgttccctt ctctatcttt tggaagagtt tacaaaggat   105600
tggtttaact ctttttttaaa tgtttgagga aattctctac ccctgggctt tcctttgtgg  105660
gaatttttaa acattttaa aatagattat ttttaaagca attttagggt aaaagcacat    105720
tgaatgaaag gcacagagct tccttaagta catgctgccc ctgtatgtgc atagcctccc   105780
tcattatcaa catcctttac cagaatggta catttgttgc agtcaatgaa cctgcattga   105840
caattgtcga tgaaagttca tagtttagag ttcacctttg gtgttatgta ttctgtgagt   105900
ctggatccat gtttaatgat actcattcac cattacagta tcattcagag taatttcact   105960
```

```
gccttaaaag tcctctgtac cctacctatt tttctctcct accccactaa cccttagcaa   106020
ccaatgatct ttttatctca ataattttgc ctattccaga atgtcatata gttggaatga   106080
tacagtatat ggagccttttt cagactggtt tttgtcactt agtaataagc ttttaaattt   106140
tccaccatgt catgatcgtt catttctttt cagcattgaa taatattcca ttgtctggtt   106200
tatcacagtt gatttatcca ttcacatagt gaaagacatc ttagttgctt ccaagttttg   106260
acaattatga ataaagctgt tataaaagta tgtaggtttt tgtgtggaca aaagttttca   106320
gctcctttga gtaaataaca cagagcacag tagcttgatt gacagtaaga gtaagaaata   106380
ttttttctca gtctgtgtct tattttttca ttcacttgac agtgccattt gcagaacaaa   106440
cagaaagttt taattttaat gaagtctagg ttatcagtta attcatgaat aatgtttttg   106500
gtattgtatc taaaaagtca acaccaaggt catctatatg ttctgtgtta tcttccagaa   106560
attttatagt tctgcatttt acatttaggg ctgtgaccca ttttgcatta attttgcaaa   106620
agctataaag actatgtata gattcacttg tttgcatgtg gagttgtcca gttgttcccg   106680
taccatttct taaagactat ctttgcttta ttgtattacc tttgctactt tgtcaaagat   106740
cagttgatta taattaagtg gtctgtttct ggactcttta ttctgttcca ttgatatatt   106800
tgtctagact ttcaccaata ccacactatc ttgttaactt aggctttaga gtaagtcttg   106860
caatcatgta gtgtcagtcc tctgacattg ttttttctcct tcagtattga gttggctatt   106920
cttttgccta ttactaagta aaaaaagcag tctgaaaagg ctatatatac agtcatttat   106980
tggtcttttg cctcttgata taaactttaa aattactttg tcagtatcct caaaatcttg   107040
caggaattttt datagattgc actgcatttc tagattgagt tagaaatact gccatcttga   107100
caatacacat cttcctatcc atgaacatgg aacatctctt tcttggatat ccttcattag   107160
aattttgcat tttccccata tagaccatgt acatattaga tttatacata aatatttcat   107220
ttggggggt gctaatggta atgtattttt atctcagatt ctgcttgtac attgctggta   107280
tgcagaaaag tgatcaactt ttgtatatta aacttgtttc ctgcaaccat gttatataat   107340
cactttagat ccagtttttt tttttttggt cattctttca tattttctag gtgatcatgt   107400
catctagcaa agacaacttc tttctaatct gtataccttt tattttcttg tcttaatgta   107460
ttagctagca tttccagtat gatgttgaaa ggcattggtg agaggcaaca tacttgcctt   107520
gttcctgatc tcagcaggaa atcttcaatt ttatgttagc tctatggttt tgtagatatt   107580
ctttatttac attaaatatg ttagctgtat ggttttgtat atattcttta tcaggttcag   107640
gtagttcccc tcttttccta gtttactgag aggcttttga aaatcattaa tcagtgttgg   107700
attttgtaaa tacttttttt ccacctattg atattaccat atgattttc tttagcttat   107760
taacgaaatg gattacatta attgattttc aaatttgaa ctagactggc atacctggag   107820
caaatcccac atggttgtga tacattattt atgaatgcat tcatggtcat ggttgctatt   107880
agtctgtagt tatcttttat tgtaaagact ttggtgttgg tattaaggta atgctgccct   107940
catagaataa gttatgaagt atttttctctg cttctgtctt aattgagatt gtagagaatt   108000
catataattt cttccttaaa actttggtag aaatcagaat gaaccatctg tgtctggtac   108060
tttgttttga aaagttattg ctgattcaat ttctttcata gatataggcc tatttagatt   108120
attattttgc ataaatattg gtagttgtgt ccttcaagga attggtccat ttcaccttga   108180
ttattaaatg tgtgggcaca tttgttcata atatttcttt attatccttt gttttttgaga   108240
cagggtctca ctctgttgc ccaggctgga gtgcagtagt atgatctcag ctcactgcag   108300
ccttgacttc ctgggctcaa gtgatttacc cacctcagcc tcccaagtag ctcggactac   108360
```

```
aggcacatgc caccatgcct ggctaatttt tttattatta ttagagatgg agttttccta 108420
tgttgcccag tgtggtcttg aactcctgga ctcaagcaat ctgcctgcct cagcctccaa 108480
agagtgatgg gattgcaggc atgagccatc acacctagcc tgatggcaga acttttaggg 108540
aacaatagaa tggtatatgg cattttcaaa aattgttttc ccctcctcct atggaagcat 108600
gaagggattt ttctctagta ttcattgtga gaacctcatc tggctcctga atgtagaaaa 108660
ctcacaaaac tgtgaggaac ctattatgac tggatgcctt tggagttgtt cacactgaac 108720
ctccagcaat tcatcaatta tatttcagat tttcctatcc caacactggt tcctacagag 108780
gtttctgctc cagtaagctg taattctttt tatccatctg cttccttggt tgtgagggca 108840
gtgattttcc ctgtgacctc atttctctga cagatctaag tagtcttgat tacatctttt 108900
aacctgttgt aggtatattc agattttcta tttcttcttc agtcaatttt agtagtttgt 108960
gttttctag aagtttgttc tctagctctg ctttagctcc atccaataaa atatgagtat 109020
gtcgagtttt catttacaac aaggtatttt ctaattccta tcatgttttt ttgattcctg 109080
actgtatagg agtatatttt tacctattac ccaaatttgc ttgttattca tgtataattt 109140
tatcagaaaa cacactttgc acaatttttg cagtgttaca tttatttaga cttgttttat 109200
aacttgacat acagtccatc ctggagaatg tttcacgtgt gcttgagaag aatgtgtata 109260
ttcagctgtt ggtgggtggc atgttttata gatgtctgtt agacctagtt ggtttatagt 109320
gttttttaca acttctgttt tcttttaat cttctatcta cttttagcca ttattgaaag 109380
tggattagta aattatctat ttattccttt aattctgcca ttttttgctt catgtatttt 109440
ggtgctctgt tgcttattac atgtatgttt acatttgtta catcatttta atggcttgaa 109500
cttttttatta taaatgtgt atatcttgta gatatcgtat agttaaatct tttaaaaat 109560
tgatattgct agtctttgcc ttttaatttt tcaatttata tacatttaac ataattattg 109620
ataaggtagg atttgtctgc cattttgtct gtatcttgtc tttttttgtg ttcaatagat 109680
attttctagt gtactgtttt aattcccttg tcttttacta aattttttga tgttcttaat 109740
ggtttccctg gggattacaa ctaacttata acagctagtc tgaagtaata ccaatttcat 109800
tacaatataa ggaaactttg ttcccatata gctacattcc ctcttttttac tctgtgctat 109860
tatacaaatt acatttttatt ttatgcccat taacacagat tatgtttttt cttttaaatc 109920
agattgatat tgtcatttaa atcaaatatg agaaaaatag ttacaaaaaa atacatatat 109980
gatttcatat ttacctatgt aattatcttt actggtgctc tttaagttct taggtgtatt 110040
tgaggtactg tctagtgtcc tttccttttca gcctgaagta tacatttagt attttttgta 110100
ggacatgcct gaaaacaata aactcttatt tatcagagaa tgtcctaatt tattatataa 110160
tacatttctg aaagatagtt ttgcaaaata cagaattctt ggttggcagt cttttttcttg 110220
tggttctatg tcattctact gccttctggt cttcattgtt tctgatcaga gatcagctat 110280
taatcttatt gggaatcctg catacatgat aatcatacag ttttcatgat tttcttgtgt 110340
tggctttcag cagtttggtt atgatgttta tatgtatgca tatctttggg tttatgttac 110400
atggagttag ttgagcttct tggacatgta gattgatgtt gttcatcaaa tttgagaagt 110460
tttcggccat tattttttcaa atattcttcc tattctttat tcttcatcct ctactttggg 110520
gacctgcatt atgtctatgt tggtatgctt tatggtcttc cacagatctc tgaggttctg 110580
tttatgtttt catttttcag actgaataat ctcaattgac ttatcttcaa gtccctttt 110640
cccctccttt tcaactctgc tattgaaccc ctctaatttt tactgcagtt attacacttt 110700
```

```
cagctttaga attctattta ataatatctt tttcttgagt ttatctcatg tatttaataa  110760
aatgctgtag tcttacttta gttatttaaa tacagttttc tttcattatt tgggcataca  110820
tgaaatagct gacttaaagt cttttgtccag tggcctaaca tctggacttt ttcaggaata  110880
gcctctattg actactttat aggggccata ctttgtttct gtttctctta attgtttaga  110940
cattttaaac taatgtaatg ctgagagca gtggctcgtg cctgtaatcc cagcacgttg  111000
agaggccaaa gcaggagcat cacttaagcc caggagttca agactagcct gggcagcata  111060
gtgagaccct gtctctacaa aaataaaaat aaataaaata atataatctg gtaaatctga  111120
aaatcagatt ctaccccctg cccagaatat gttactgttt ctggtggttg ttgtttattt  111180 cttttttaact actcctataa agtttgtatt gtttctcata gatagccatc gaagtctttg  111240
cttggttaac ttagaggtca gctaaggatt agacagaatt ccttaggtgc ctgagatcaa  111300
taagtcagtc tttgacaaag gggtctgtat gtgtgttggg gcatgcattc aacactcagc  111360
caggctattt gcagctctgg attagccttt attccctgct tgtgcagagt ctcaaggtta  111420
gactgtggtg agagtttagg gctttctgag gtcttttgtg ggccctacag ttgcatgtgg  111480
ctttctaaat tcccaggaat atattttcaa agcctcctgt ggatcatctc atttcccagg  111540
taatttactt ttaagctttt ttagttatct tatgttttgc tccagttatt agctacacct  111600
gagtcagtga caatattcaa cagctgccta tgattatttg acaaatgcct ctgtggaaaa  111660
ggtggttcac actaggtgaa ctccaagtta gataaagtaa agataacctt actagtggga  111720
tcttccagga aactaccaaa caggtcaaat aatgtaaggt ctctgtgaat gggactttag  111780
agtatatcca accagtctag agtatatcca accaatctgg cctcctctag tggcagcctg  111840
gctgctgctt ttcataataa atgtgggctg ttttgatttg aaggctacca tagagctgtg  111900
gggaaagtta aaataccaca gagctcactc ttctcactga aatcctgtct ttttttccct  111960
tgaacaaatt ctccctatat tgctgcaagc ttttttgctaa tttccagatc tgaaaaagct  112020
gattctgaca atatttatca gtactttat tgcttttatg gaggataaaa ttttcagaga  112080
tccttattct gccatttttg ctgacatgtg taaagtgatc atttctaatt gtaaaattcc  112140
ttttgcattt attagctgga atactttaca ggactttcc tcatcaaccg ttagttacca  112200
tttaatatag tttgtaagaa tgatagaata aatgcatggc aagaatcttt acttctcaaa  112260
tttcagagat tttgatggga aattatattt agagatcaca atcagtgtct agatgtgctc  112320
cctgctatgg aggtgtcatt acttttaggc ttttttaatg ggcaaataca tgaagtaatt  112380
attttttaga aagaaaatct gagattaact caaatcatta attcatactg attttttccta  112440 ttcatagttg acagagtatt attatctttt gttctgcttc tcttgtacac tgaaattctt  112500 ggttttgat attaacaatt atttacttat atcacaatat acatacatta atttaaaaat  112560
aatttacagt gctacctgaa tatttttctct tgtaagttgt tttatctctc tttgcttact  112620
tgtatgtttg tttattgtca ttagaatgta tcaaactagg gctataaagc tgtaatacta  112680
tattttagcc agaaactagg acctagcact caaatgccca tcaatggtag aataattcat  112740 cacatttta taagatggaa tatggtactc aatgaaaatg aataaagtac aactacatgc  112800
agtgatttgg atggatatcc caaacataat ggaaaaagca cacacaaata agcttatatt  112860
atataattcc atataccat gtatatatca agtataaaag taggcaaaac aagctactga  112920
tggtggcaca cacctatagt tccagctatt tgggaggctg aggcgggaag atcacttgag  112980
cccagaagtt caggttcaac ctgagcaaca tagcaagacc ccatctgtaa aaagaaagc  113040 attattaaca taaaaatagg cagaactact atattcttag agaagttact gttagggaga  113100
```

```
cagacagtga gtgactgaaa ggcaaaatga ggggaaattc caggggatag taaatatttt  113160
gtttcttagt gtgggttcta cttaactggg tattttccat ttgtaaactg taaaattatg  113220 tgcactttc tgtatgtgta ttacattgca ataaaattgt ttaaaagtca attgaaatag   113280
ttctgtgtgt ggttatgcca cagcttaata cagagttaga ttagacttct tttcaaactc  113340
attttgcata tagacaccta taatatcagc tgcacagcct atataatgct atccatagca  113400
atgaatttgg tcttttgatt tttcaggaga acttgcgcct gtcagggggct ggatccagaa  113460 acctgtggtg cctccttctc ttttggttgt tcatggagca tgtactacaa tggatgtaag  113520
tttgccagaa gcaagatccc aaggaagttt aagctgcttg gggatgaccc aaaagaggtt  113580
tgtttacttc ctgatgtata atcgctttat ttttcataga gaattcatta gcttagatga  113640
agtgaacaat atgacatatc ttggtaagct cttattaatc aaagttttc ccaaactgta   113700 gatacacact atttttaag ttggcataat aatcatatta tgccaaaata atagataaaa   113760
tttgagcaac aaaaacttcc tctttggtct tttatgttaa ttccaaagtt ttaaaggggg  113820
gtcacttcat tgttaaaact aaatgagaat tggtgatgtt tttcatattt tgactctgaa  113880
ttatggaagt tacataagta ctacattcag aaaagaccat ttttagtcac atttatgtgc  113940
aatgagattc aaataattta aagtcactgt aatgaatgca tttaataaag tcactgtaat  114000
gaatgcattt aagtaactaa aacatttaga ttttaatata actctgtaat ggaaataaat  114060
ggacactaat ttctcactga agtcattggt ttttgtcttg tctgtagaat acgtatttct  114120
tataatttgc aaattgataa atttaacaac ttttgggtgg catgtagtct agagtataga  114180
tacttcttga cttatgagga gactacattc ctataaatcc gttgtaaaat gaaaatccat  114240 ttaataccc caataaaccc atcctaaagt aaaaaaaaaa cgaagccatt ataggtcagg   114300
gactgtctcc gtactaattg aatgatgaga aaacctcagt atatttagca tttagctatg  114360
accacatttt cagtcattct atacacttac aattatcttt tgaatttcga atacaattaa  114420
aatatttcca tactatagat attataacat tgatgagtcc ctttaaatga agaatttgtt  114480
aaccttatta agcttccact tactattata gtcacagtta ataaagcaag tgcaaaaact  114540
cctgaaatca cagtataagt ttttttaaagg atgttttcaa taattaaagt ttacttaaat  114600
gtgcgagaca tcatttcata agacaagaat atgaatatta ataacttaat gaaaagtact  114660
gattttgctt gctgtcattt taattttcta cagataactt ttttttttaac cactgttta   114720 tcaagtgata aatgtttatc actttcacga ggtttcatgt aaaccaaatc cagaggatac  114780
caagtaactt attgcctctg ttgggtagga gagctctgtt cagaaacctc ctcaccttct  114840
aaaatttaca tctctgccag gtggttatgt ctcacaactt ttttttttta gagaaatatc  114900
aatctgaaat gaagacttct aagtataaat ggagcagcta aatatgatca cctaccttt   114960 tttaacagta tattacttgg aaaatctgtt cttcatgagc agggcaggtg ggggtgtaac  115020
tgagcatttc ccctttcaag taaattctgc aaaggttttc atgtatcctg cattctagtt  115080
ctgaagcatt ttatccatat ttgaagtgtc cagtaaattt tagttgctct atggagagat  115140
cattccaaat tatttaaata ctatctttat aaacataaaa tgtaaagatt agaaatagac  115200
aaattaagct aaagaagttc ttttaatagt tcatcttcct tggtagctaa aaaatgtgac  115260
ctctttaaga ccatacggct taattcccct aaccctactc ctggcacagg cttgtgtgta  115320
taaaatgcaa aatatctgca tgcagttaga aaatcaatct tatgaaaaaa acaaatagct  115380
agatatttac tagcacatat gaaattaaat gatagtcatg ttttaaagat gctttattta  115440
```

```
gtaataaagg caccatatat tgtgtttggg attcaaaatg taaggggaat aatctaactg   115500
atagtctctt ttacatagag aaaatggact tagaatttaa tatgtagaat tattcacttt   115560
atacaggaag agaaactgga gtctcatttg caaaacctgt ccactcttat ggcaccaaca   115620
tataagaaac ttgcacctga tgcatataat aatcaggtaa gtttaaataa tcattggcag   115680
caattgtaac aacttacttg ttactaatga cctatgtcca aaaatatttt tgaaacaatg   115740 attttaaat attattctaa cttttcctct taattgttga aaccactgca gtgttcagtt   115800
tcgagtatat aaaaattata ccatacaaaa gtacattttt tttgtctttt agctgtaaag   115860
acatgcgctt ctaaaagtca caggctgttc tatctactaa tcttgttctc atatgaataa   115920
ttttgtttct gtaaacagac tatggagatt acatcaaaat tatgtggccc aagctatagg   115980
ttctaactac ctatttttac tgcaagtcta taagtataaa tgagtattca taagaattta   116040
tagacttaca aatattcaca taaagctatg catatactaa cattgtaagt atatatattt   116100
cggtccagat gtgtcagatt ttgctgatct tcctttttg tttgaccttg acttcataca   116160
ccaagcaaaa acatttttt tttctatttt acatgtgtat tctaaactat agctagttaa   116220
gacaggtaga tgatttggtc agaaatctct catcatgaag gcaaaaaact aaaatcttca   116280
ctgtttcagt aacatcaaca acaaaagcat taagtgaaag tctattacaa actaaacact   116340
gtgtttagtc actgggaaca taaaggtgag cagtgccatc tctgtctgtc tttaagaatt   116400
ccgtctttgc tgggtacggt ggctcacacc tttaatccca cactttggg aggccaaggc   116460 aggtggatca cctgaggtca ggagttctag accagcctga tcaacatgga gaaaccctgt   116520
ctctactaaa aatacaaaat tagctgggtg tggtggcagg cacctgtaat cccagctact   116580
cggaaggcta aggcaggaga atagcttgaa cctgggaggt ggaggttgca gtgagccgaa   116640
gtcaaaccat tgcactccag cctaggcaac aagagcgaaa ctccatctca aaaaaaaaa   116700 aaaattcatc tttaactggg tgcggtagtt tatgcctgta atcccagcta cccaggagac   116760
caggagtctg aggctgcggt gagccatgat tgcatcactg tgctccatcc tgggtgacaa   116820
agatgaccca gattctaaaa aaaaagcaaa aaacaaaaga attccttctt tagtggagac   116880
agagacatat aaaataaata gcaattttag aattacacag ttccagctgg aatagaagaa   116940
tgtgcacatt tctaaaaaaa tttaaaaaca aaacccaaaa gtagactaga tgtcacaagc   117000
agccttagac gctaaataaa gatctttgaa ctttattctg taggtaacca ttgggctgtt   117060
tcaagtgtgt gttggggatg aagggtaaa gtgatgtaat tcgtattttg aaaaatttac   117120
ttaaaagcca agtaagggaa atataactta aatctatgta agattagaga gagaagaaag   117180
ctattgcaat cattgggcaa gagattttaa ggacctaaag aaatggcagg aattaagtat   117240
gtacactaac taaggtggag cttagagaac ttggtgacta gatgtatgga tgagaaaaga   117300
atttggagat acaacaaatt tccagtttgg acaggtagtt ctattaacta gtatcagaaa   117360
ttggtaagaa atagtaagtt ttgggatggg gagaagatat caaaattttg gacatgctag   117420
gcttctaggt taattagatg gagaatcagg agaaaaattc aggctagcac tgtagatttg   117480
agagtcagaa tgctggcagg acttaaagtt gaatacatag gaatgaaagg aggttttcaa   117540
agtagagatt ataaagagga caagggctg atgatggat tctggagcca tcaatcattt   117600
taggcatgag tggaggaaga gaagccaatg aagtaagaac tggggaggg agtagaagaa   117660 atgtagtagg aaaagtgaaa gagggagatg gatggatgga ggaaagctgg aatgatgaga   117720
agacacccag agcagagtat acaggagcaa taggtatggg gctctgggat gggtgctctg   117780
tcatttactt gataatatta aagactctcg tgggattaga ttagtttaca cagcagacat   117840
```

```
ggacaaggga ctaatcctaa aatgatttag ctactcttct tttccactgt ggactttaac  117900
gtcccaaaca ttttttttttt ttttggttc gaacaataga ggcaaattaa acgatggtct   117960
atttgtaagt tattttatgt caaattatgt ttttagaaat gtgtatgaat atctatgaaa   118020 agttttttaaa cactattaat agttggatta atactgttat tttgtttagc tagtatcaca  118080
aagtataagg agtgctttga tactgtcgta aaagtttaat tctcagcaag aacttctgaa   118140
ataaatcaag ctataaaaat aaataaatga atgagtctat gttgctagat ttaaagttgg   118200
gtcattttct attaaatgaa tttttaatag gtgctgttaa tcaaatggct ttacttgagg   118260
cagaataaca aagcattgat gttctttttg ctcccttgat tcttattatg gaccgtctca   118320
tacttgaaac tattttatac atttcctaaa acttaagtac ccaaaatatg aagccatcaa   118380
atatgttcaa gttttaatat ttatatatga aaatgtgttg atgtaatgtc tagataaatt   118440
aagtcaatta atagttgtaa atggatgaga tgcttctgaa tggataaaat attttttatat 118500 tgcatggtag gtactattgg taatattcat ccatgtatgt taatatgctt tagagatcaa  118560
aataatagcc atgtgatgtt tccacacagt acacgggaag accatttgat gttatagatg   118620
ctgtcataaa acctactatt tgatctttac ctcctttccc caactgagtg tcgtatctct   118680
atttctcaca tctgaatatt cttccttgct ttattccttg atttcatgaa gtcttattgc   118740
taaagtttag ttggctctcc acagcatctc ttctgtcagt cccatggaat tagagcttca   118800
gttttctcaa cttaaatgtc ctttcttcgt gtctatccag tagacatata tttggctctg   118860
tcttttctat gcctgcctta caatttaaca gtagacctga aatagcaggt gtcaatctca   118920
aaatcgtgtg ctatttatca tacatgaaga tgacatttta gacaaatgct tctaagagag   118980 cttttctatga agatggaaat attctctatt tatgctgttc agtgtaatag gcactagcca   119040
catgtggtta ttatttaaca gttgatacgt ggctagtgta attgagttta aattaatgta   119100
aaaattaaca caaacagcca catgtggata atggttacca tagtgaacag cacaaccttta  119160 gaccatgaga aagttatgca tttagaattg tcttccagac atttagatgg atttccagta   119220
attcattcac aaaatcctgc atggtatttt ttaggagatg gcataagtgt aatttctagc   119280
tgattgtata tctgtttttg ttcaagaaac agaataaagc taactagacc acagcatgaa   119340
ctgaacggcc acaaagcaca catctatgtt aaagagtagt tggtaccttc attttccttt   119400
ggccaaagtt ttatgaggtt agatagacaa atacatatat gaatccaaca gtaaataata   119460
tgaagccacc acaaactttt atcctaatgc aagttcatct tctagccatg atggagtaaa   119520
cagagactac atatgccgtt acacatttaa gaaaaaactg acaaaatata tgaaacaatg   119580 gttttttagac atagaataag aaattcaaga gacagtggca ccagagagaa aggaagtaaa   119640
aaggtgaacc tataaatacc ccagtttact tcctgaagag agtattaggc tccagtgtag   119700
ccagtaggaa cccaaacaca cccagcctta tctctgtatt aaggagacaa agttcaaaat   119760
ttggagaggc caaggtgacg agagttcact attcagaata tcagagagga gagagtgtta   119820
ttgagaaaag ctccagagac ctgcagaggg ttctgatcca gtcttcagct gagtattaaa   119880
cagcacatgc atgtgaaaaa actgccaagg ctaggtaggg aaagaaccat cagaagaagc   119940
aggcagaata atcccttgat ctcacacagg acctggaata gttcttgatc ataccagcca   120000
gacggagaag acttcataat actattcata attgtattgc cttggtagta gaagtaaatt   120060
tggcagttct gacctcatct aaaaatgctt aaaatgaaaa catagaaggg ccaaactgat   120120
tctaagtaat ttaactgcat cacagtacaa aaattaaaaa aaaaatctac caacaaggta   120180
```

```
aaatttatag tctagcattc catcagaaaa tacaaggcat acaaagaaaa aagaaaatat   120240
aacctttact ggggaacagg cagaaatcaa tcaataaaaa tagtcccaga actgacatat   120300
gtgatacaat atgtaaataa gttcattaaa atggctatca tatttcatat gttaaaatgc   120360
cagaggaaag catgagagtg ataaggaaag atcagaagat attaaaatac cctacaatga   120420
ccttctagaa gtgaaaaata tatatctaga ttaaaaatac actaggcgga attaacagat   120480
taaggaactt gaagacatag taatagaaat ttttcagtat aaagaaaaaa ctgaaaaaaa   120540
tgaatatata aaagacctat tagccaatat tgttacacta atatatgtgt aattggagta   120600
ccagaaggag gtgggagaca gaaaaatatt taaagaaaca atggccaaat ttttttcaga   120660
tttgttcaaa actgtgaacc cacagatctc agcagctcag caaacccag attaaaaaac    120720 aaagacataa aaaagacta tcaaaaattt ataatcaact tgcttacaat ctgtgataaa    120780
gagaaactca gaaaggcaaa tggagaaaaa aggacatatt acactaggtg ggaaaaaata   120840
agacaggaga cttcattcag aaaaaggcaa gagagaagat gtaagagaaa catctttaac   120900
atactaaaag aaaaaagact ctccacccag aaatatataa ccaatgaaaa caactctcaa   120960
aaaagacagc aaaataaaga atattttttc agacatacat acaaaagctg aaagaattca   121020
ccaccaacaa actagcactt taaaaatgtt aaacgaaatc cttcaggaag aaagaacatg   121080
ataccagaca gaaatccaga tcaacataat gaaatgaaca gtatcaaaaa tagtaaacat   121140
ggttaaaaga cttttaaaaa aatgataact tgctatctta aaaatatatt aacaatgtat   121200
tatgaggttt ataacacgta gaagtagcac agaggctgag gaattgaaag tatattattg   121260
taaagtactt atacgatatg tggactgggt atattacttg gctgtaaact gtgagacgtt   121320
agagtacact gtgtacctta aaccactaaa aaaaaaaaaa aaagtatata gctaatcagc   121380
cagtaaagac agaaaaatga aatcaatcca aaaatgtttt taaaaatata taggaccaaa   121440
aaaagataaa tataaaaata aaacaaatag caagatggtt tatttaaacc caactgtatc   121500
aacaaccaca ttaaatgtaa atggttttaa cacccctaat tataaggcag agcttgtgat   121560
attgaaaaaa aagcaaaaac caagaaaacc actttaaata taaagataca aataaattaa   121620
aaagatattt ttaacataaa aaatgatgtt gaaaagacat aacaggaaaa aatatgatta   121680
ttgcagtagg tacagaaaaa ccatttgata atattcaaca ttcataaaag gaaactttct   121740
caacctatta aatacataaa tggaaagcca aaagctaatg ctatacttag tggtgaaaga   121800
ctaatacttg acccctaaga taaggaacaa gacaacaatg tccattttta accaactgct   121860
tctattcaac atcaaactgt aaattttaga aagtgcagta aggcaataaa taaagcagtc   121920
aagattgggt aggaaaaaat aaaactgtac ttatttgcag atgacatgtt tgtctacata   121980
agaagtctca aaaatctac cagaaaatga aattaatata tgaatttagc aaagttgtga    122040
aatacaaaat tcaagtgtat ttttatatac tagcaataaa taaatcaaaa taaaccatta   122100
aaatagcatc aaaatataaa attcttagac atacatttga caaaaatgta taagattata   122160
tactggaaac taaaacattg ctgagataaa ttatagaaaa cttcagtaac tggagagata   122220
cactatgtta atggatcaaa agactaaata ttattaagat gtcagttctc cccaaactaa   122280
tcaatatgtt caatcatga tgtttcaaaa ccccagcagg ttttttgaaa gaattggaca    122340
agatggctgt aaaatatata tacttggaaa tgcaaaggac ttggaatagt caaataatat   122400
tttaaaataa gggcagaatt tgagactata tattgcatgg ttttcagatt tactgaaatc   122460
tataattgct actgtctgtc aagacagttt gatattgccc aggcgcagtg gctcacgcct   122520
gtaattccag cactttcgga ggccgaggtg ggtggatcac ttgaggccag gagttttgag   122580
```

```
accagcctgg ccaacatggc aaaactctat ctctaataaa aatacaaaaa attactgggg   122640
catggtggcg cgtgcttata gtcccagctg cttgggaggt tgaggcctga gaatcgcttg   122700
aatccaggag gcagaggttg cagtgagccc agatcgtgcc actgcactcc agcctgggtg   122760
acagagtggg actctgtctc aataaataaa taaaattttt aaaaagtttg atattgacat   122820
acctacatac acaccattat acacaagtgg atcagaatag agaatcctta agtagaccca   122880
acatatataa tatggtcaat tgattttttaa caaagatgat tcaattggga agggataacc   122940 atttatcca gtagtatctg aacagttgga aagccataag ggaaaaaagg taatcttgac   123000
ccttaatttc acaccattta taaaaattaa ctccaaataa atccatttat atgaaattct   123060
agaaaatgaa aatctgtagt gatagattag tagttgtctg agaacaaagc aggaagcatg   123120
aattatacag gggcatgagg aaattttttaa gagtaatgaa tatgtacttt attttggttg   123180
tgacaaatat atatcaaaac tcaaatagca tactttatgg cctcaataac actataaaat   123240
aaaaatttta ccatgtcaag atatttgctc tattttgtgt cattccattt tgtttctgga   123300
tatatattta agttcaaaac attttttttaa agttctaaat ggtctaaata ctagtgagtt   123360
ttcggtgtaa gagtaaaact aactactttc gcattcacac acacttttat ttttcagatt   123420
gaatatgaac acagagcacc agagtgccgt ctgggtctga aggaaggccg tccattctca   123480
ggggtcactg catgtttgga cttctgtgct catgcccaca gagacttgca caacatgcag   123540
aatggcagca cattggtaag ttgggctgag gacagcttag cagctgttga gtctgttctc   123600
acactgctaa taaagacata tgcaagactg ggtaatttat aaaggaaaga gatttaattg   123660
actcacagtt ccacatggct gtggaggcct cacaatcata gctgaaggca aatgaggagc   123720
aaagtcacat cttacatggc ggcaggcaag agaacatgtg caggggaact cccctttata   123780
aaatcatcag atctcatgag acttactctc ctgagaacag catgggaaag atctgccccc   123840
atgattcaat tacctcccac tgggtccttc ccaaaacaca tgggaatttt gggagctaca   123900
attcaagatg agatttaggt agggacacag ccagaccata tcagcagcat ctcatgttga   123960
ggagcagaac actggaattt agtagcattc ggttagagta atatgttgtc tgcaggtttc   124020
actggacagc aatattttca tgaatgaatt cctgttgcaa agtgacctgc tttggcataa   124080
ctagcactct catgataggt tggcacatta gtttcctgtc aattgtgttg acaagcacat   124140
gagaatcatg gaaatccttg gtgttaatct aaaccagtga ctatgcattg ccagttacag   124200
ttaacttcca ggaaaatctc aaaattcagt gccagttacc tggtagattg taatcagtta   124260
agcaaaaagc caaatacaag ccattcacct tacagagaga gaagcatatt caccttacag   124320
agagagaagc ataaatgaga aacacatcat cattgtcaca gtaactgtgg taacctattg   124380
taaaagattc acagtgcaaa agagcctgac tacatattac agtgggtaaa atggatcggt   124440
cttgtaattg gaggcagtgg tgaggggaaa atagatacat gttatatata tatatatata   124500
tatatatgtt ctataccaac aaagggttca gggtataatt ttgcatgtaa aggggtgacc   124560
cagagtagag ataaagaaca aaatattctg ttgaaaaaac tatgaatcaa tcaacctaat   124620
gaattatcaa catggatgta ggtgtagttg aagaagatgg tcagtgagaa tatggaaaca   124680
gatatcagga attaaagtca tattctaggg cagaaaagca ttcatggagg tattagatga   124740
tagctgaagt aatttgaaga agctggtgtg aagttttgt tgagaagcag agaagatatt   124800
aatttaatgt tctagatcag agattggaaa actcttctct ataaagggca agatggtaaa   124860
tattttaggg actgcaggcc acataggatt tctgtcacat tgtttggtgg ggttttttg   124920
```

```
tttattttgt tttttaaaaa ctccttgaaa atgtaaaaac cattcttagt ttactggcca    124980
tacaaacaca agctgtgagg cacattagcc gtaggttctg gtttcctaac ttctgatcca    125040
gaagaacaaa cacaaggcct accaaccacc ccaacatcta aaatcatcac taatcatgta    125100
ctcagcacct gctcattatt aggaggctat gctagtttct gaaaagcaga agtagtaaat    125160
gataactggg gctatagtgc atcctaatat aaccatgttt cattccagga aggtgacaga    125220
gagtaagatg atgagaagga tgtttagaat caagaagaat ttgcctctga tagagcatgg    125280
gttctgtgaa gtaaaatgga aaggagcact agataagaac tgaatagggt taaatatgta    125340
tgggaaaagt aacaaggtgc tcagagacat gaatttgaag acttctgtgc agaaagtgac    125400
aggctcatta ataccatctc atgttgaagt tatttctaaa gtcagtccat tgtgatcaca    125460
tttctctcaa gaatatcttc taattttatt ttagatcaca ttagatcaca ttgtctccat    125520
tgatcaaaaa cactaaatac taaaaagtta gtatttaaaa accacaaata atcttttacc    125580
aaagctagtg taattgtagt aactaaagca aaaagtacca tttaattatc aaagcaacag    125640
aggtagcttt cctccctcca ccccttaccc ttttcagagt acccacttat atggtcatat    125700
ttcagaaaag aaatgaagaa aagagaaagt taggtttgac agagtacaaa ggaggagaga    125760
caagagagtg aaaatagtat taagttgcat attacctgta tcagccaaat ctttacctttt   125820 tcatttttta tattttttact tcagttatct tatggaaatt tcttaaacag agagagttag    125880
gtgtcaggta tgtgaaaaga catgaaattt gtgttcagaa gtatgagatg aggcaaatgt    125940
gatactacca aaaacagagg aagtcatttc gtagaaaaaa cttttagcct gtttttgaag    126000
aggcttcaca tctagcacat ctattttga agtgtgaaaa gcaagagagt gcttcatttt     126060
gggggagtgt tgcttcttcc catagacaga aacatatgtg aagaacaagg gtcaccacag    126120
ctaactgttc ctgatagact cagagaaagg gtgggtgggc aatgtcaatt tgtcttatct    126180
ccctgtacca ttttgttgct attttcatta ataacaggta ggatggtttt atggtaatat    126240
atatgtcact gatctggatc aactaggcca ccaacacaaa tctgaatact gagaggagaa    126300
agatacacac acacacacac gttttctttg ggacctgtag ttgaggctgt aatgtcttac    126360
ttccctacca ggtatgcact ctcactagag aagacaatcg agaatttgga ggaaaacctg    126420
aggatgagca gcttcacgtt ctgcctttat acaaagtctc tgacgtggat gagtttggga    126480
gtgtggaagc tcaggaggag aaaaaacgga gtggtgccat tcaggtactg agttcttttc    126540
ggcgaaaagt caggatgtta gcagagccag tcaagacttg ccgacaaagg aaactagaag    126600
ccaagaaagc tgcagctgaa aagctttcct ccctggagaa cagctcaaat aaaaatgaaa    126660
aggaaaagtc agccccatca cgtacaaaac aaactgaaaa cgcaagccag gctaaacagt    126720
tggcaggtaa atttaatgta aagcatttgt agataaatgt gttgtgtggt atattaaaaa    126780
tgaaaattat tttggttttg cccccatcaa cttgtaagtt ctggggtaca catgcaggat    126840
gtgcaggttt gttatacagg taaacatgtg ccatggtgat ttgctgcaca gatcaaccca    126900
ttacctaggt attaagccca gcatcttcct gatgcacccc taccaatagg cgccagtgtg    126960
tgttgtcccc actcccccac catgtgtcca tgtgctctta ttgtaaaatg aacattgtta    127020
attttggaaa gttatatcaa tcatggtctt agttctgtgc cagagtcttc tctaaagtag    127080
caagggccag gctttgttct cagagatggt aatgagatat tgcaccatca acatggaaaa    127140
catggaaaag tctggatttt attctataat aaacagcaac ttttttttaac aggtaagtga    127200 tacgatgaaa ttcattgtaa tttggcagta ggccaaatta gtagaggagc taatagtttg    127260
gagataaaca cagtaaacca gaactgaggt aacaagacct tgaatttttgt tggttagtag    127320
```

```
caaagatata gcaaaatgat gcaaatgagc tcttccaaaa tgggaaaaag aaaatacatt  127380
ggtgacaaaa cactggaatg aaagagaaga aaagtttaaa gatgacccca aagttttaaa  127440
cctaaactta acctactgtt ttaggtttct aaaacagtac tatttattga aataagtaag  127500
tttgaaaata tgattgagag agagagaggg gagaatgaaa catttttcct tagacatgtt  127560
gagtctgtgg tttaggaggg gttctacatg tagattatgc tacaaaactt ttacccatca  127620
aaatagatta cagctgtagt aataacaata gaacattatt catgaatact aagttattgt  127680 cttccatag cctcctgctt tatgtctgca gtttgtaaaa agaaaaaaaa tccaaaattt  127740
gggatggtat tggcctggcc attaacaaaa gcaaaccagt ttgcttaaaa ctagccatct  127800
ttgctgcttc atgaagtcaa atttctctac tgattcattt ccaagctcag aggaactaag  127860
ttaaataatt tagaatatgc taaagatgct tgataagtgt ttattgactg gttgacttaa  127920
cactaagtaa atactgttca cttaggttag ctgtgaaata taattagata gaaccttgtc  127980
tctgctccct tttaactggc ttctgcaggt aataatccct tctgttctca gaactgccat  128040
tgcagtttca tctatttgtt cttaactcat atgactttt aaagtgaggt caaaacagaa  128100
gtatgacttt taaagtttc atttacaaag ctgaaagttt cttaaagtg ttatctacaa  128160 ctgtgttaac ttcctttctg gaaagcctgc ttataaagta gcacttgttg attatataag  128220 atgcttttg tgtttaaata cgtgtcattc ttttttttca caacattccc gaatcttaca  128280
taataaatct tatttaatt atttagcaaa ttccattgca tgccaggcaa tgaagaagta  128340
agtaaaataa acattttcc ttcccattta ggaatttact taccagtggg ggtgaagaga  128400
gggctaaaaa cataactata atacattgtg agtattgctt tatcagatct atctttgcag  128460
ttgagtatta caaaagcact agaagatgag gtcaaagcgg tcccttgagg aagggatgac  128520
tacaccaagg aaggataggg agagagggag gaaaagggag gcacttcaag cagaggcatg  128580
ttcagaagtt ccaaagaaca ttttgctctc aatggaatgg ctttggatgt ttattacatt  128640
ttttttttca ctaagttttg tatttctaat gccttagaca aaaaattgtg ctggacaatg  128700
atcagaaccc tgactttgct cttatctttg cttaatgggt gtcgtatatc actagtggag  128760
tttcttacct acatttaagt atcctcacta gccttcataa aataatcatc aacatcaaag  128820
atacctgttt ctgttctctc ttaccctgtc cacagaactt ttgcgacttt caggaccagt  128880
catgcagcag tcccagcagc cccagcctct acagaagcag ccaccacagc cccagcagca  128940
gcagagaccc cagcagcagc agccacatca ccctcagaca gagtctgtca actcttattc  129000
tgcttctgga tccaccaatc catacatgag acggcccaat ccagttagtc cttatccaaa  129060
ctcttcacac acttcagata tctatggaag caccagccct atgaacttct attccacctc  129120
atctcaagct gcaggttcat atttgaattc ttctaatccc atgaacccctt accctgggct  129180 tttgaatcag aatacccaat atccatcata tcaatgcaat ggaaacctat cagtggacaa  129240
ctgctcccca tatctgggtt cctattctcc ccagtctcag ccgatggatc tgtataggta  129300
tccaagccaa gaccctctgt ctaagctcag tctaccaccc atccatacac tttaccagcc  129360
aaggtttgga aatagccaga gttttacatc taaatactta ggttatggaa accaaaatat  129420
gcagggagat ggtttcagca gttgtaccat tagaccaaat gtacatcatg tagggaaatt  129480
gcctccttat cccactcatg agatggatgg ccacttcatg ggagccacct ctagattacc  129540
acccaatctg agcaatccaa acatggacta taaaaatggt gaacatcatt caccttctca  129600
cataatccat aactacagtg cagctccggg catgttcaac agctctcttc atgccctgca  129660
```

```
tctccaaaac aaggagaatg acatgctttc ccacacagct aatgggttat caaagatgct   129720
tccagctctt aaccatgata gaactgcttg tgtccaagga ggcttacaca aattaagtga   129780
tgctaatggt caggaaaagc agccattggc actagtccag ggtgtggctt ctggtgcaga   129840
ggacaacgat gaggtctggt cagacagcga gcagagcttt ctggatcctg acattggggg   129900
agtggccgtg gctccaactc atgggtcaat tctcattgag tgtgcaaagc gtgagctgca   129960
tgccacaacc cctttaaaga atcccaatag gaatcacccc accaggatct ccctcgtctt   130020
ttaccagcat aagagcatga atgagccaaa acatggcttg gctctttggg aagccaaaat   130080
ggctgaaaaa gcccgtgaga aagaggaaga gtgtgaaaag tatggcccag actatgtgcc   130140
tcagaaatcc catggcaaaa aagtgaaacg ggagcctgct gagccacatg aaacttcaga   130200
gcccacttac ctgcgtttca tcaagtctct tgccgaaagg accatgtccg tgaccacaga   130260
ctccacagta actacatctc catatgcctt cactcgggtc acagggcctt acaacagata   130320
tatatgatat cacccccttt tgttggttac ctcacttgaa aagaccacaa ccaacctgtc   130380
agtagtatag ttctcatgac gtgggcagtg gggaaaggtc acagtattca tgacaaatgt   130440
ggtgggaaaa acctcagctc accagcaaca aaagaggtta tcttaccata gcacttaatt   130500
ttcactggct cccaagtggt cacagatggc atctaggaaa agaccaaagc attctatgca   130560
aaaagaaggt ggggaagaaa gtgttccgca atttacattt ttaaacactg gttctattat   130620
tggacgagat gatatgtaaa tgtgatcccc ccccccgct tacaactcta cacatctgtg    130680 accacttta ataatatcaa gtttgcatag tcatggaaca caaatcaaac aagtactgta    130740
gtattacagt gacaggaatc ttaaaatacc atctggtgct gaatatatga tgtactgaaa   130800
tactggaatt atggcttttt gaaatgcagt ttttactgta atcttaactt ttatttatca   130860
aaatagctac aggaaacatg aatagcagga aaacactgaa tttgtttgga tgttctaaga   130920
aatggtgcta agaaaatggt gtctttaata gctaaaaatt taatgccttt atatcatcaa   130980
gatgctatca gtgtactcca gtgcccttga ataatagggg taccttttca ttcaagtttt   131040
tatcataatt acctattctt acacaagctt agttttttaaa atgtggacat tttaaaggcc   131100
tctggatttt gctcatccag tgaagtcctt gtaggacaat aaacgtatat atgtacatat   131160
atacacaaac atgtatatgt gcacacacat gtatatgtat aaatatttta aatggtgttt   131220
tagaagcact ttgtctacct aagctttgac aacttgaaca atgctaaggt actgagatgt   131280
ttaaaaaaca agtttacttt cattttagaa tgcaaagttg attttttttaa ggaaacaaag   131340 aaagctttta aaatatttttt gcttttagcc atgcatctgc tgatgagcaa ttgtgtccat   131400
ttttaacaca gccagttaaa tccaccatgg ggcttactgg attcaaggga atacgttagt   131460
ccacaaaaca tgttttctgg tgctcatctc acatgctata ctgtaaaaca gttttataca   131520
aaattgtatg acaagttcat tgctcaaaaa tgtacagttt taagaatttt ctattaactg   131580
caggtaataa ttagctgcat gctgcagact caacaaagct agttcactga agcctatgct   131640
atttatggat tcataggctc ttcagagaac tgaatggcag tctgcctttg tgttgataat   131700
tatgtacatt gtgacgttgt catttcttag cttaagtgtc ctcttttaaca agaggattga   131760 gcagactgat gcctgcataa gatgaataaa cagggttagt tccatgtgaa tctgtcagtt   131820 aaaagaaac aaaaacaggc agctggtttg ctgtggtggt tttaaatcat taatttgtat    131880 aagaagtga aagagttgta tagtaaaatta aattgtaaac aaaacttttt taatgcaatg    131940
ctttagtatt ttagtactgt aaaaaaatta aatatataca tatatatata tatatatata   132000
tatatatata tgagtttgaa gcagaattca catcatgatg gtgctactca gcctgctaca   132060
```

-continued

```
aatatatcat aatgtgagct aagaattcat taaatgtttg agtgatgttc ctacttgtca 132120
tatacctcaa cactagtttg gcaataggat attgaactga gagtgaaagc attgtgtacc 132180
atcatttttt tccaagtcct ttttttttatt gttaaaaaaa aaagcatacc ttttttcaat 132240
acttgatttc ttagcaagta taacttgaac ttcaacctt ttgttctaaa aattcaggga 132300
tatttcagct catgctctcc ctatgccaac atgtcacctg tgtttatgta aaattgttgt 132360
aggttaataa atatattctt tgtcagggat ttaacccttt tattttgaat cccttctatt 132420
ttacttgt                                                          132428
```

<210> SEQ ID NO 2
<211> LENGTH: 2002
<212> TYPE: PRT
<213> ORGANISM: Homo sapiens

<400> SEQUENCE: 2

```
Met Glu Gln Asp Arg Thr Asn His Val Glu Gly Asn Arg Leu Ser Pro
1               5                   10                  15

Phe Leu Ile Pro Ser Pro Ile Cys Gln Thr Glu Pro Leu Ala Thr
                20                  25                  30

Lys Leu Gln Asn Gly Ser Pro Leu Pro Glu Arg Ala His Pro Glu Val
            35                  40                  45

Asn Gly Asp Thr Lys Trp His Ser Phe Lys Ser Tyr Tyr Gly Ile Pro
        50                  55                  60

Cys Met Lys Gly Ser Gln Asn Ser Arg Val Ser Pro Asp Phe Thr Gln
65                  70                  75                  80

Glu Ser Arg Gly Tyr Ser Lys Cys Leu Gln Asn Gly Gly Ile Lys Arg
                85                  90                  95

Thr Val Ser Glu Pro Ser Leu Ser Gly Leu Leu Gln Ile Lys Lys Leu
            100                 105                 110

Lys Gln Asp Gln Lys Ala Asn Gly Glu Arg Arg Asn Phe Gly Val Ser
        115                 120                 125

Gln Glu Arg Asn Pro Gly Glu Ser Ser Gln Pro Asn Val Ser Asp Leu
    130                 135                 140

Ser Asp Lys Lys Glu Ser Val Ser Ser Val Ala Gln Glu Asn Ala Val
145                 150                 155                 160

Lys Asp Phe Thr Ser Phe Ser Thr His Asn Cys Ser Gly Pro Glu Asn
                165                 170                 175

Pro Glu Leu Gln Ile Leu Asn Glu Gln Glu Gly Lys Ser Ala Asn Tyr
            180                 185                 190

His Asp Lys Asn Ile Val Leu Leu Lys Asn Lys Ala Val Leu Met Pro
        195                 200                 205

Asn Gly Ala Thr Val Ser Ala Ser Ser Val Glu His Thr His Gly Glu
    210                 215                 220

Leu Leu Glu Lys Thr Leu Ser Gln Tyr Tyr Pro Asp Cys Val Ser Ile
225                 230                 235                 240

Ala Val Gln Lys Thr Thr Ser His Ile Asn Ala Ile Asn Ser Gln Ala
                245                 250                 255

Thr Asn Glu Leu Ser Cys Glu Ile Thr His Pro Ser His Thr Ser Gly
            260                 265                 270

Gln Ile Asn Ser Ala Gln Thr Ser Asn Ser Glu Leu Pro Pro Lys Pro
        275                 280                 285

Ala Ala Val Val Ser Glu Ala Cys Asp Ala Asp Ala Asp Asn Ala
    290                 295                 300
```

```
Ser Lys Leu Ala Ala Met Leu Asn Thr Cys Ser Phe Gln Lys Pro Glu
305                 310                 315                 320

Gln Leu Gln Gln Gln Lys Ser Val Phe Glu Ile Cys Pro Ser Pro Ala
                325                 330                 335

Glu Asn Asn Ile Gln Gly Thr Thr Lys Leu Ala Ser Gly Glu Glu Phe
            340                 345                 350

Cys Ser Gly Ser Ser Ser Asn Leu Gln Ala Pro Gly Gly Ser Ser Glu
                355                 360                 365

Arg Tyr Leu Lys Gln Asn Glu Met Asn Gly Ala Tyr Phe Lys Gln Ser
370                 375                 380

Ser Val Phe Thr Lys Asp Ser Phe Ser Ala Thr Thr Thr Pro Pro Pro
385                 390                 395                 400

Pro Ser Gln Leu Leu Leu Ser Pro Pro Pro Leu Pro Gln Val Pro
                405                 410                 415

Gln Leu Pro Ser Glu Gly Lys Ser Thr Leu Asn Gly Gly Val Leu Glu
                420                 425                 430

Glu His His His Tyr Pro Asn Gln Ser Asn Thr Thr Leu Leu Arg Glu
                435                 440                 445

Val Lys Ile Glu Gly Lys Pro Glu Ala Pro Pro Ser Gln Ser Pro Asn
450                 455                 460

Pro Ser Thr His Val Cys Ser Pro Ser Pro Met Leu Ser Glu Arg Pro
465                 470                 475                 480

Gln Asn Asn Cys Val Asn Arg Asn Asp Ile Gln Thr Ala Gly Thr Met
                485                 490                 495

Thr Val Pro Leu Cys Ser Glu Lys Thr Arg Pro Met Ser Glu His Leu
                500                 505                 510

Lys His Asn Pro Pro Ile Phe Gly Ser Ser Gly Glu Leu Gln Asp Asn
                515                 520                 525

Cys Gln Gln Leu Met Arg Asn Lys Glu Gln Glu Ile Leu Lys Gly Arg
530                 535                 540

Asp Lys Glu Gln Thr Arg Asp Leu Val Pro Pro Thr Gln His Tyr Leu
545                 550                 555                 560

Lys Pro Gly Trp Ile Glu Leu Lys Ala Pro Arg Phe His Gln Ala Glu
                565                 570                 575

Ser His Leu Lys Arg Asn Glu Ala Ser Leu Pro Ser Ile Leu Gln Tyr
                580                 585                 590

Gln Pro Asn Leu Ser Asn Gln Met Thr Ser Lys Gln Tyr Thr Gly Asn
                595                 600                 605

Ser Asn Met Pro Gly Gly Leu Pro Arg Gln Ala Tyr Thr Gln Lys Thr
                610                 615                 620

Thr Gln Leu Glu His Lys Ser Gln Met Tyr Gln Val Glu Met Asn Gln
625                 630                 635                 640

Gly Gln Ser Gln Gly Thr Val Asp Gln His Leu Gln Phe Gln Lys Pro
                645                 650                 655

Ser His Gln Val His Phe Ser Lys Thr Asp His Leu Pro Lys Ala His
                660                 665                 670

Val Gln Ser Leu Cys Gly Thr Arg Phe His Phe Gln Gln Arg Ala Asp
                675                 680                 685

Ser Gln Thr Glu Lys Leu Met Ser Pro Val Leu Lys Gln His Leu Asn
                690                 695                 700

Gln Gln Ala Ser Glu Thr Glu Pro Phe Ser Asn Ser His Leu Leu Gln
705                 710                 715                 720
```

```
His Lys Pro His Lys Gln Ala Ala Gln Thr Gln Pro Ser Gln Ser Ser
            725                 730                 735

His Leu Pro Gln Asn Gln Gln Gln Gln Lys Leu Gln Ile Lys Asn
            740                 745                 750

Lys Glu Glu Ile Leu Gln Thr Phe Pro His Pro Gln Ser Asn Asn Asp
            755                 760                 765

Gln Gln Arg Glu Gly Ser Phe Phe Gly Gln Thr Lys Val Glu Glu Cys
            770                 775                 780

Phe His Gly Glu Asn Gln Tyr Ser Lys Ser Ser Glu Phe Glu Thr His
785                 790                 795                 800

Asn Val Gln Met Gly Leu Glu Glu Val Gln Asn Ile Asn Arg Arg Asn
                    805                 810                 815

Ser Pro Tyr Ser Gln Thr Met Lys Ser Ser Ala Cys Lys Ile Gln Val
            820                 825                 830

Ser Cys Ser Asn Asn Thr His Leu Val Ser Glu Asn Lys Glu Gln Thr
            835                 840                 845

Thr His Pro Glu Leu Phe Ala Gly Asn Lys Thr Gln Asn Leu His His
        850                 855                 860

Met Gln Tyr Phe Pro Asn Asn Val Ile Pro Lys Gln Asp Leu Leu His
865                 870                 875                 880

Arg Cys Phe Gln Glu Gln Glu Gln Lys Ser Gln Gln Ala Ser Val Leu
                885                 890                 895

Gln Gly Tyr Lys Asn Arg Asn Gln Asp Met Ser Gly Gln Gln Ala Ala
            900                 905                 910

Gln Leu Ala Gln Gln Arg Tyr Leu Ile His Asn His Ala Asn Val Phe
        915                 920                 925

Pro Val Pro Asp Gln Gly Gly Ser His Thr Gln Thr Pro Pro Gln Lys
    930                 935                 940

Asp Thr Gln Lys His Ala Ala Leu Arg Trp His Leu Leu Lys Gln
945                 950                 955                 960

Glu Gln Gln Gln Thr Gln Gln Pro Gln Thr Glu Ser Cys His Ser Gln
                965                 970                 975

Met His Arg Pro Ile Lys Val Glu Pro Gly Cys Lys Pro His Ala Cys
            980                 985                 990

Met His Thr Ala Pro Pro Glu Asn Lys Thr Trp Lys Lys Val Thr Lys
        995                 1000                1005

Gln Glu Asn Pro Pro Ala Ser Cys Asp Asn Val Gln Gln Lys Ser
    1010                1015                1020

Ile Ile Glu Thr Met Glu Gln His Leu Lys Gln Phe His Ala Lys
    1025                1030                1035

Ser Leu Phe Asp His Lys Ala Leu Thr Leu Lys Ser Gln Lys Gln
    1040                1045                1050

Val Lys Val Glu Met Ser Gly Pro Val Thr Val Leu Thr Arg Gln
    1055                1060                1065

Thr Thr Ala Ala Glu Leu Asp Ser His Thr Pro Ala Leu Glu Gln
    1070                1075                1080

Gln Thr Thr Ser Ser Glu Lys Thr Pro Thr Lys Arg Thr Ala Ala
    1085                1090                1095

Ser Val Leu Asn Asn Phe Ile Glu Ser Pro Ser Lys Leu Leu Asp
    1100                1105                1110

Thr Pro Ile Lys Asn Leu Leu Asp Thr Pro Val Lys Thr Gln Tyr
    1115                1120                1125

Asp Phe Pro Ser Cys Arg Cys Val Glu Gln Ile Ile Glu Lys Asp
```

-continued

```
                    1130                1135                1140
Glu Gly Pro Phe Tyr Thr His Leu Gly Ala Gly Pro Asn Val Ala
            1145                1150                1155
Ala Ile Arg Glu Ile Met Glu Glu Arg Phe Gly Gln Lys Gly Lys
            1160                1165                1170
Ala Ile Arg Ile Glu Arg Val Ile Tyr Thr Gly Lys Glu Gly Lys
            1175                1180                1185
Ser Ser Gln Gly Cys Pro Ile Ala Lys Trp Val Val Arg Arg Ser
            1190                1195                1200
Ser Ser Glu Glu Lys Leu Leu Cys Leu Val Arg Glu Arg Ala Gly
            1205                1210                1215
His Thr Cys Glu Ala Ala Val Ile Val Ile Leu Ile Leu Val Trp
            1220                1225                1230
Glu Gly Ile Pro Leu Ser Leu Ala Asp Lys Leu Tyr Ser Glu Leu
            1235                1240                1245
Thr Glu Thr Leu Arg Lys Tyr Gly Thr Leu Thr Asn Arg Arg Cys
            1250                1255                1260
Ala Leu Asn Glu Glu Arg Thr Cys Ala Cys Gln Gly Leu Asp Pro
            1265                1270                1275
Glu Thr Cys Gly Ala Ser Phe Ser Phe Gly Cys Ser Trp Ser Met
            1280                1285                1290
Tyr Tyr Asn Gly Cys Lys Phe Ala Arg Ser Lys Ile Pro Arg Lys
            1295                1300                1305
Phe Lys Leu Leu Gly Asp Asp Pro Lys Glu Glu Lys Leu Glu
            1310                1315                1320
Ser His Leu Gln Asn Leu Ser Thr Leu Met Ala Pro Thr Tyr Lys
            1325                1330                1335
Lys Leu Ala Pro Asp Ala Tyr Asn Asn Gln Ile Glu Tyr Glu His
            1340                1345                1350
Arg Ala Pro Glu Cys Arg Leu Gly Leu Lys Glu Gly Arg Pro Phe
            1355                1360                1365
Ser Gly Val Thr Ala Cys Leu Asp Phe Cys Ala His Ala His Arg
            1370                1375                1380
Asp Leu His Asn Met Gln Asn Gly Ser Thr Leu Val Cys Thr Leu
            1385                1390                1395
Thr Arg Glu Asp Asn Arg Glu Phe Gly Gly Lys Pro Glu Asp Glu
            1400                1405                1410
Gln Leu His Val Leu Pro Leu Tyr Lys Val Ser Asp Val Asp Glu
            1415                1420                1425
Phe Gly Ser Val Glu Ala Gln Glu Glu Lys Lys Arg Ser Gly Ala
            1430                1435                1440
Ile Gln Val Leu Ser Ser Phe Arg Arg Lys Val Arg Met Leu Ala
            1445                1450                1455
Glu Pro Val Lys Thr Cys Arg Gln Arg Lys Leu Glu Ala Lys Lys
            1460                1465                1470
Ala Ala Ala Glu Lys Leu Ser Ser Leu Glu Asn Ser Ser Asn Lys
            1475                1480                1485
Asn Glu Lys Glu Lys Ser Ala Pro Ser Arg Thr Lys Gln Thr Glu
            1490                1495                1500
Asn Ala Ser Gln Ala Lys Gln Leu Ala Glu Leu Leu Arg Leu Ser
            1505                1510                1515
Gly Pro Val Met Gln Gln Ser Gln Gln Pro Gln Pro Leu Gln Lys
            1520                1525                1530
```

```
Gln Pro Pro Gln Pro Gln Gln Gln Arg Pro Gln Gln Gln Gln
    1535            1540                1545

Pro His His Pro Gln Thr Glu Ser Val Asn Ser Tyr Ser Ala Ser
    1550            1555                1560

Gly Ser Thr Asn Pro Tyr Met Arg Arg Pro Asn Pro Val Ser Pro
    1565            1570                1575

Tyr Pro Asn Ser Ser His Thr Ser Asp Ile Tyr Gly Ser Thr Ser
    1580            1585                1590

Pro Met Asn Phe Tyr Ser Thr Ser Ser Gln Ala Ala Gly Ser Tyr
    1595            1600                1605

Leu Asn Ser Ser Asn Pro Met Asn Pro Tyr Pro Gly Leu Leu Asn
    1610            1615                1620

Gln Asn Thr Gln Tyr Pro Ser Tyr Gln Cys Asn Gly Asn Leu Ser
    1625            1630                1635

Val Asp Asn Cys Ser Pro Tyr Leu Gly Ser Tyr Ser Pro Gln Ser
    1640            1645                1650

Gln Pro Met Asp Leu Tyr Arg Tyr Pro Ser Gln Asp Pro Leu Ser
    1655            1660                1665

Lys Leu Ser Leu Pro Pro Ile His Thr Leu Tyr Gln Pro Arg Phe
    1670            1675                1680

Gly Asn Ser Gln Ser Phe Thr Ser Lys Tyr Leu Gly Tyr Gly Asn
    1685            1690                1695

Gln Asn Met Gln Gly Asp Gly Phe Ser Ser Cys Thr Ile Arg Pro
    1700            1705                1710

Asn Val His His Val Gly Lys Leu Pro Pro Tyr Pro Thr His Glu
    1715            1720                1725

Met Asp Gly His Phe Met Gly Ala Thr Ser Arg Leu Pro Pro Asn
    1730            1735                1740

Leu Ser Asn Pro Asn Met Asp Tyr Lys Asn Gly Glu His His Ser
    1745            1750                1755

Pro Ser His Ile Ile His Asn Tyr Ser Ala Ala Pro Gly Met Phe
    1760            1765                1770

Asn Ser Ser Leu His Ala Leu His Leu Gln Asn Lys Glu Asn Asp
    1775            1780                1785

Met Leu Ser His Thr Ala Asn Gly Leu Ser Lys Met Leu Pro Ala
    1790            1795                1800

Leu Asn His Asp Arg Thr Ala Cys Val Gln Gly Gly Leu His Lys
    1805            1810                1815

Leu Ser Asp Ala Asn Gly Gln Glu Lys Gln Pro Leu Ala Leu Val
    1820            1825                1830

Gln Gly Val Ala Ser Gly Ala Glu Asp Asn Asp Glu Val Trp Ser
    1835            1840                1845

Asp Ser Glu Gln Ser Phe Leu Asp Pro Asp Ile Gly Gly Val Ala
    1850            1855                1860

Val Ala Pro Thr His Gly Ser Ile Leu Ile Glu Cys Ala Lys Arg
    1865            1870                1875

Glu Leu His Ala Thr Thr Pro Leu Lys Asn Pro Asn Arg Asn His
    1880            1885                1890

Pro Thr Arg Ile Ser Leu Val Phe Tyr Gln His Lys Ser Met Asn
    1895            1900                1905

Glu Pro Lys His Gly Leu Ala Leu Trp Glu Ala Lys Met Ala Glu
    1910            1915                1920
```

```
Lys Ala Arg Glu Lys Glu Glu Cys Glu Lys Tyr Gly Pro Asp
    1925                1930                1935

Tyr Val Pro Gln Lys Ser His Gly Lys Leu Lys Arg Glu Pro
    1940                1945                1950

Ala Glu Pro His Glu Thr Ser Glu Pro Thr Tyr Leu Arg Phe Ile
    1955                1960                1965

Lys Ser Leu Ala Glu Arg Thr Met Ser Val Thr Thr Asp Ser Thr
    1970                1975                1980

Val Thr Thr Ser Pro Tyr Ala Phe Thr Arg Val Thr Gly Pro Tyr
    1985                1990                1995

Asn Arg Tyr Ile
    2000

<210> SEQ ID NO 3
<211> LENGTH: 311
<212> TYPE: PRT
<213> ORGANISM: Homo sapiens

<400> SEQUENCE: 3

Arg Cys Val Glu Gln Ile Ile Glu Lys Asp Glu Gly Pro Phe Tyr Thr
1               5                   10                  15

His Leu Gly Ala Gly Pro Asn Val Ala Ala Ile Arg Glu Ile Met Glu
                20                  25                  30

Glu Arg Phe Gly Gln Lys Gly Lys Ala Ile Arg Ile Glu Arg Val Ile
            35                  40                  45

Tyr Thr Gly Lys Glu Gly Lys Ser Ser Gln Gly Cys Pro Ile Ala Lys
        50                  55                  60

Trp Val Val Arg Arg Ser Ser Glu Glu Lys Leu Leu Cys Leu Val
65                  70                  75                  80

Arg Glu Arg Ala Gly His Thr Cys Glu Ala Ala Val Ile Val Ile Leu
                85                  90                  95

Ile Leu Val Trp Glu Gly Ile Pro Leu Ser Leu Ala Asp Lys Leu Tyr
                100                 105                 110

Ser Glu Leu Thr Glu Thr Leu Arg Lys Tyr Gly Thr Leu Thr Asn Arg
            115                 120                 125

Arg Cys Ala Leu Asn Glu Glu Arg Thr Cys Ala Cys Gln Gly Leu Asp
        130                 135                 140

Pro Glu Thr Cys Gly Ala Ser Phe Ser Phe Gly Cys Ser Trp Ser Met
145                 150                 155                 160

Tyr Tyr Asn Gly Cys Lys Phe Ala Arg Ser Lys Ile Pro Arg Lys Phe
                165                 170                 175

Lys Leu Leu Gly Asp Asp Pro Lys Glu Glu Glu Lys Leu Glu Ser His
            180                 185                 190

Leu Gln Asn Leu Ser Thr Leu Met Ala Pro Thr Tyr Lys Lys Leu Ala
        195                 200                 205

Pro Asp Ala Tyr Asn Asn Gln Ile Glu Tyr Glu His Arg Ala Pro Glu
    210                 215                 220

Cys Arg Leu Gly Leu Lys Glu Gly Arg Pro Phe Ser Gly Val Thr Ala
225                 230                 235                 240

Cys Leu Asp Phe Cys Ala His Ala His Arg Asp Leu His Asn Met Gln
                245                 250                 255

Asn Gly Ser Thr Leu Val Cys Thr Leu Thr Arg Glu Asp Asn Arg Glu
            260                 265                 270

Phe Gly Gly Lys Pro Glu Asp Glu Gln Leu His Val Leu Pro Leu Tyr
        275                 280                 285
```

```
Lys Val Ser Asp Val Asp Glu Phe Gly Ser Val Glu Ala Gln Glu Glu
    290                 295                 300

Lys Lys Arg Ser Gly Ala Ile
305                 310
```

<210> SEQ ID NO 4
<211> LENGTH: 80
<212> TYPE: PRT
<213> ORGANISM: Homo sapiens

<400> SEQUENCE: 4

```
Asn Asp Glu Val Trp Ser Asp Ser Glu Gln Ser Phe Leu Asp Pro Asp
 1               5                  10                  15

Ile Gly Gly Val Ala Val Ala Pro Thr His Gly Ser Ile Leu Ile Glu
                20                  25                  30

Cys Ala Lys Arg Glu Leu His Ala Thr Thr Pro Leu Lys Asn Pro Asn
            35                  40                  45

Arg Asn His Pro Thr Arg Ile Ser Leu Val Phe Tyr Gln His Lys Ser
        50                  55                  60

Met Asn Glu Pro Lys His Gly Leu Ala Leu Trp Glu Ala Lys Met Ala
65                  70                  75                  80
```

<210> SEQ ID NO 5
<211> LENGTH: 22
<212> TYPE: DNA
<213> ORGANISM: Artificial sequence
<220> FEATURE:
<223> OTHER INFORMATION: Primer

<400> SEQUENCE: 5
tgaacttccc acattagctg gt                                            22

<210> SEQ ID NO 6
<211> LENGTH: 24
<212> TYPE: DNA
<213> ORGANISM: Artificial sequence
<220> FEATURE:
<223> OTHER INFORMATION: Primer

<400> SEQUENCE: 6
gaaactgtag caccattagg catt                                          24

<210> SEQ ID NO 7
<211> LENGTH: 25
<212> TYPE: DNA
<213> ORGANISM: Artificial sequence
<220> FEATURE:
<223> OTHER INFORMATION: Primer

<400> SEQUENCE: 7
caaaaggcta atggagaaag acgta                                         25

<210> SEQ ID NO 8
<211> LENGTH: 25
<212> TYPE: DNA
<213> ORGANISM: Artificial sequence
<220> FEATURE:
<223> OTHER INFORMATION: Primer

<400> SEQUENCE: 8
gcagaaaagg aatccttagt gaaca                                         25

```
<210> SEQ ID NO 9
<211> LENGTH: 25
<212> TYPE: DNA
<213> ORGANISM: Artificial sequence
<220> FEATURE:
<223> OTHER INFORMATION: Primer

<400> SEQUENCE: 9
gccagtaaac tagctgcaat gctaa                                         25

<210> SEQ ID NO 10
<211> LENGTH: 23
<212> TYPE: DNA
<213> ORGANISM: Artificial sequence
<220> FEATURE:
<223> OTHER INFORMATION: Primer

<400> SEQUENCE: 10
tgcctcatta cgttttagat ggg                                           23

<210> SEQ ID NO 11
<211> LENGTH: 22
<212> TYPE: DNA
<213> ORGANISM: Artificial sequence
<220> FEATURE:
<223> OTHER INFORMATION: Primer

<400> SEQUENCE: 11
gaccaatgtc agaacacctc aa                                            22

<210> SEQ ID NO 12
<211> LENGTH: 26
<212> TYPE: DNA
<213> ORGANISM: Artificial sequence
<220> FEATURE:
<223> OTHER INFORMATION: Primer

<400> SEQUENCE: 12
ttgattttga atactgattt tcacca                                        26

<210> SEQ ID NO 13
<211> LENGTH: 24
<212> TYPE: DNA
<213> ORGANISM: Artificial sequence
<220> FEATURE:
<223> OTHER INFORMATION: Primer

<400> SEQUENCE: 13
ttgcaacata agcctcataa acag                                          24

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
attggcctgt gcatctgact at                                            22

<210> SEQ ID NO 15
<211> LENGTH: 23
<212> TYPE: DNA
<213> ORGANISM: Artificial sequence
<220> FEATURE:
<223> OTHER INFORMATION: Primer
```

```
<400> SEQUENCE: 15
gcaacttgct cagcaaaggt act                                            23

<210> SEQ ID NO 16
<211> LENGTH: 24
<212> TYPE: DNA
<213> ORGANISM: Artificial sequence
<220> FEATURE:
<223> OTHER INFORMATION: Primer

<400> SEQUENCE: 16
tgctgccaga ctcaagattt aaaa                                           24

<210> SEQ ID NO 17
<211> LENGTH: 34
<212> TYPE: DNA
<213> ORGANISM: Artificial sequence
<220> FEATURE:
<223> OTHER INFORMATION: Primer

<400> SEQUENCE: 17
atactacata taatacattc taattccctc actg                                34

<210> SEQ ID NO 18
<211> LENGTH: 24
<212> TYPE: DNA
<213> ORGANISM: Artificial sequence
<220> FEATURE:
<223> OTHER INFORMATION: Primer

<400> SEQUENCE: 18
tgtttactgc tttgtgtgtg aagg                                           24

<210> SEQ ID NO 19
<211> LENGTH: 26
<212> TYPE: DNA
<213> ORGANISM: Artificial sequence
<220> FEATURE:
<223> OTHER INFORMATION: Primer

<400> SEQUENCE: 19
catttctcag gatgtggtca tagaat                                         26

<210> SEQ ID NO 20
<211> LENGTH: 23
<212> TYPE: DNA
<213> ORGANISM: Artificial sequence
<220> FEATURE:
<223> OTHER INFORMATION: Primer

<400> SEQUENCE: 20
cccaattctc agggtcagat tta                                            23

<210> SEQ ID NO 21
<211> LENGTH: 29
<212> TYPE: DNA
<213> ORGANISM: Artificial sequence
<220> FEATURE:
<223> OTHER INFORMATION: Primer

<400> SEQUENCE: 21
agacttatgt atctttcatc tagctctgg                                      29

<210> SEQ ID NO 22
<211> LENGTH: 25
```

```
<212> TYPE: DNA
<213> ORGANISM: Artificial sequence
<220> FEATURE:
<223> OTHER INFORMATION: Primer

<400> SEQUENCE: 22
actctcttcc tttcaaccaa agatt                                            25

<210> SEQ ID NO 23
<211> LENGTH: 27
<212> TYPE: DNA
<213> ORGANISM: Artificial sequence
<220> FEATURE:
<223> OTHER INFORMATION: Primer

<400> SEQUENCE: 23
atgccacagc ttaatacaga gttagat                                          27

<210> SEQ ID NO 24
<211> LENGTH: 30
<212> TYPE: DNA
<213> ORGANISM: Artificial sequence
<220> FEATURE:
<223> OTHER INFORMATION: Primer

<400> SEQUENCE: 24
tgtcatattg ttcacttcat ctaagctaat                                       30

<210> SEQ ID NO 25
<211> LENGTH: 28
<212> TYPE: DNA
<213> ORGANISM: Artificial sequence
<220> FEATURE:
<223> OTHER INFORMATION: Primer

<400> SEQUENCE: 25
gatgctttat ttagtaataa aggcacca                                         28

<210> SEQ ID NO 26
<211> LENGTH: 35
<212> TYPE: DNA
<213> ORGANISM: Artificial sequence
<220> FEATURE:
<223> OTHER INFORMATION: Primer

<400> SEQUENCE: 26
ttcaacaatt aagaggaaaa gttagaataa tattt                                 35

<210> SEQ ID NO 27
<211> LENGTH: 25
<212> TYPE: DNA
<213> ORGANISM: Artificial sequence
<220> FEATURE:
<223> OTHER INFORMATION: Primer

<400> SEQUENCE: 27
tgtcattcca ttttgtttct ggata                                            25

<210> SEQ ID NO 28
<211> LENGTH: 26
<212> TYPE: DNA
<213> ORGANISM: Artificial sequence
<220> FEATURE:
<223> OTHER INFORMATION: Primer

<400> SEQUENCE: 28
```
aaattaccca gtcttgcata tgtctt                                       26

<210> SEQ ID NO 29
<211> LENGTH: 22
<212> TYPE: DNA
<213> ORGANISM: Artificial sequence
<220> FEATURE:
<223> OTHER INFORMATION: Primer

<400> SEQUENCE: 29
ctggatcaac taggccacca ac                                           22

<210> SEQ ID NO 30
<211> LENGTH: 33
<212> TYPE: DNA
<213> ORGANISM: Artificial sequence
<220> FEATURE:
<223> OTHER INFORMATION: Primer

<400> SEQUENCE: 30
ccaaaattaa caatgttcat tttacaataa gag                               33

<210> SEQ ID NO 31
<211> LENGTH: 25
<212> TYPE: DNA
<213> ORGANISM: Artificial sequence
<220> FEATURE:
<223> OTHER INFORMATION: Primer

<400> SEQUENCE: 31
gctcttatct ttgcttaatg ggtgt                                        25

<210> SEQ ID NO 32
<211> LENGTH: 27
<212> TYPE: DNA
<213> ORGANISM: Artificial sequence
<220> FEATURE:
<223> OTHER INFORMATION: Primer

<400> SEQUENCE: 32
tgtacatttg gtctaatggt acaactg                                      27

<210> SEQ ID NO 33
<211> LENGTH: 24
<212> TYPE: DNA
<213> ORGANISM: Artificial sequence
<220> FEATURE:
<223> OTHER INFORMATION: Primer

<400> SEQUENCE: 33
aatggaaacc tatcagtgga caac                                         24

<210> SEQ ID NO 34
<211> LENGTH: 26
<212> TYPE: DNA
<213> ORGANISM: Artificial sequence
<220> FEATURE:
<223> OTHER INFORMATION: Primer

<400> SEQUENCE: 34
tatatatctg ttgtaaggcc ctgtga                                       26

<210> SEQ ID NO 35
<211> LENGTH: 23
<212> TYPE: DNA
<213> ORGANISM: Artificial sequence

```
<220> FEATURE:
<223> OTHER INFORMATION: Primer

<400> SEQUENCE: 35
cagagctttc tggatcctga cat                                       23

<210> SEQ ID NO 36
<211> LENGTH: 25
<212> TYPE: DNA
<213> ORGANISM: Artificial sequence
<220> FEATURE:
<223> OTHER INFORMATION: Primer

<400> SEQUENCE: 36
gcccacgtca tgagaactat actac                                     25

<210> SEQ ID NO 37
<211> LENGTH: 28
<212> TYPE: DNA
<213> ORGANISM: Artificial sequence
<220> FEATURE:
<223> OTHER INFORMATION: Primer

<400> SEQUENCE: 37
tctaagctca gtctaccacc catccata                                  28

<210> SEQ ID NO 38
<211> LENGTH: 25
<212> TYPE: DNA
<213> ORGANISM: Artificial sequence
<220> FEATURE:
<223> OTHER INFORMATION: Primer

<400> SEQUENCE: 38
tgctcgctgt ctgaccagac ctcat                                     25

<210> SEQ ID NO 39
<211> LENGTH: 6869
<212> TYPE: DNA
<213> ORGANISM: Homo sapiens

<400> SEQUENCE: 39
ccgtgccatc ccaacctccc acctcgcccc caaccttcgc gcttgctctg cttcttctcc      60
caggggtgga gacccgccga ggtccccggg gttcccgagg gctgcaccct tccccgcgct     120
cgccagccct ggcccctact ccgcgctggt ccgggcgcac cactccccc  gcgccactgc     180 acggcgtgag ggcagcccag gtctccactg cgcgccccgc tgtacggccc caggtgccgc     240
cggcctttgt gctggacgcc cggtgcgggg ggctaattcc ctgggagccg gggctgaggg     300
ccccagggcg gcggcgcagg ccggggcgga gcggaggag  gccggggcgg agcaggagga     360
ggcccgggcg gaggaggaga gccggcggta gcggcagtgg cagcggcgag agcttgggcg     420
gccgccgccg cctcctcgcg agcgccgcgc gcccgggtcc cgctcgcatg caagtcacgt     480 ccgcccctc  ggcgcggccg ccccgagacg ccggccccgc tgagtgatga aacagacgt     540 caaactgcct tatgaatatt gatgcggagg ctaggctgct ttcgtagaga agcagaagga     600
agcaagatgg ctgcccttta ggatttgtta gaaaggagac ccgactgcaa ctgctggatt     660
gctgcaaggc tgagggacga gaacgaggct ggcaaacatt cagcagcaca ccctctcaag     720
attgtttact tgcctttgct cctgttgagt tacaacgctt ggaagcagga gatgggctca     780
gcagcagcca ataggacatg atccaggaag agcaaattca actagagggc agccttgtgg     840
```

```
atggcccega agcaagcctg atggaacagg atagaaccaa ccatgttgag ggcaacagac    900
taagtccatt cctgatacca tcacctccca tttgccagac agaacctctg ctacaaagc    960
tccagaatgg aagcccactg cctgagagag ctcatccaga agtaaatgga gacaccaagt   1020
ggcactcttt caaaagttat tatgaatac cctgtatgaa gggaagccag aatagtcgtg    1080
tgagtcctga ctttacacaa gaaagtagag ggtattccaa gtgtttgcaa atggaggaa    1140
taaaacgcac agttagtgaa ccttctctct ctgggctcct tcagatcaag aaattgaaac   1200
aagaccaaaa ggctaatgga gaaagacgta acttcggggt aagccaagaa agaaatccag   1260
gtgaaagcag tcaaccaaat gtctccgatt tgagtgataa gaaagaatct gtgagttctg   1320
tagcccaaga aaatgcagtt aaagatttca ccagttttc aacacataac tgcagtgggc    1380
ctgaaaatcc agagcttcag attctgaatg agcaggaggg gaaaagtgct aattaccatg   1440
acaagaacat tgtattactt aaaaacaagg cagtgctaat gcctaatggt gctacagttt   1500
ctgcctcttc cgtggaacac acacatggtg aactcctgga aaaaacactg tctcaatatt   1560
atccagattg tgtttccatt gcggtgcaga aaaccacatc tcacataaat gccattaaca   1620
gtcaggctac taatgagttg tcctgtgaga tcactcaccc atcgcatacc tcagggcaga   1680
tcaattccgc acagacctct aactctgagc tgcctccaaa gccagctgca gtggtgagtg   1740
aggcctgtga tgctgatgat gctgataatg ccagtaaact agctgcaatg ctaaatacct   1800
gttccttca gaaaccagaa caactacaac aacaaaaatc agtttttgag atatgcccat    1860
ctcctgcaga aaataacatc cagggaacca caaagctagc gtctggtgaa gaattctgtt   1920
caggttccag cagcaattg caagctcctg gtggcagctc tgaacggtat ttaaaacaaa    1980
atgaaatgaa tggtgcttac ttcaagcaaa gctcagtgtt cactaaggat tccttttctg   2040
ccactaccac accaccacca ccatcacaat tgcttctttc tccccctcct cctcttccac   2100
aggttcctca gcttccttca gaaggaaaaa gcactctgaa tggtggagtt ttagaagaac   2160
accaccacta ccccaaccaa agtaacacaa cacttttaag ggaagtgaaa atagagggta   2220
aacctgaggc accaccttcc cagagtccta atccatctac acatgtatgc agcccttctc   2280
cgatgctttc tgaaaggcct cagaataatt gtgtgaacag gaatgacata cagactgcag   2340
ggacaatgac tgttccattg tgttctgaga aaacaagacc aatgtcagaa cacctcaagc   2400
ataacccacc aatttttggt agcagtggag agctacagga caactgccag cagttgatga   2460
gaaacaaaga gcaagagatt ctgaagggtc gagacaagga gcaaacacga gatcttgtgc   2520
ccccaacaca gcactatctg aaaccaggat ggattgaatt gaaggcccct cgttttcacc   2580
aagcggaatc ccatctaaaa cgtaatgagg catcactgcc atcaattctt cagtatcaac   2640
ccaatctctc caatcaaatg acctccaaac aatacactgg aaattccaac atgcctgggg   2700
ggctcccaag gcaagcttac acccagaaaa caacacagct ggagcacaag tcacaaatgt   2760
accaagttga aatgaatcaa gggcagtccc aaggtacagt ggaccaacat ctccagttcc   2820
aaaaaccctc acaccaggtg cacttctcca aaacagacca tttaccaaaa gctcatgtgc   2880
agtcactgtg tggcactaga tttcattttc aacaagagc agattcccaa actgaaaaac   2940
ttatgtcccc agtgttgaaa cagcacttga atcaacaggc ttcagagact gagccatttt   3000
caaactcaca ccttttgcaa cataagcctc ataaacaggc agcacaaaca caaccatccc   3060
agagttcaca tctcccctcaa aaccagcaac agcagcaaaa attacaaata aagaataaag   3120
aggaaatact ccagacttt cctcaccccc aaagcaacaa tgatcagcaa agagaaggat    3180
cattctttgg ccagactaaa gtggaagaat gttttcatgg tgaaaatcag tattcaaaat   3240
```

```
caagcgagtt cgagactcat aatgtccaaa tgggactgga ggaagtacag aatataaatc    3300
gtagaaattc cccttatagt cagaccatga aatcaagtgc atgcaaaata caggtttctt    3360
gttcaaacaa tacacaccta gtttcagaga ataaagaaca gactacacat cctgaacttt    3420
ttgcaggaaa caagacccaa aacttgcatc acatgcaata ttttccaaat aatgtgatcc    3480
caaagcaaga tcttcttcac aggtgctttc aagaacagga gcagaagtca caacaagctt    3540
cagttctaca gggatataaa aatagaaacc aagatatgtc tggtcaacaa gctgcgcaac    3600
ttgctcagca aaggtacttg atacataacc atgcaaatgt ttttcctgtg cctgaccagg    3660
gaggaagtca cactcagacc cctccccaga aggacactca aaagcatgct gctctaaggt    3720
ggcatctctt acagaagcaa gaacagcagc aaacacagca accccaaact gagtcttgcc    3780
atagtcagat gcacaggcca attaaggtgg aacctggatg caagccacat gcctgtatgc    3840
acacagcacc accagaaaac aaaacatgga aaaggtaac taagcaagag aatccacctg    3900
caagctgtga taatgtgcag caaaagagca tcattgagac catggagcag catctgaagc    3960
agtttcacgc caagtcgtta tttgaccata aggctcttac tctcaaatca cagaagcaag    4020
taaaagttga aatgtcaggg ccagtcacag ttttgactag acaaaccact gctgcagaac    4080
ttgatagcca caccccagct ttagagcagc aaacaacttc ttcagaaaag acaccaacca    4140
aaagaacagc tgcttctgtt ctcaataatt ttatagagtc accttccaaa ttactagata    4200
ctcctataaa aaatttattg gatacacctg tcaagactca atatgatttc ccatcttgca    4260
gatgtgtaga gcaaattatt gaaaagatg aaggtccttt ttatacccat ctaggagcag    4320
gtcctaatgt ggcagctatt agagaaatca tggaagaaag gtttggacag aagggtaaag    4380
ctattaggat tgaaagagtc atctatactg gtaaagaagg caaaagttct cagggatgtc    4440
ctattgctaa gtgggtggtt cgcagaagca gcagtgaaga gaagctactg tgtttggtgc    4500
gggagcgagc tggccacacc tgtgaggctg cagtgattgt gattctcatc ctggtgtggg    4560
aaggaatccc gctgtctctg gctgacaaac tctactcgga gcttaccgag acgctgagga    4620
aatacggcac gctcaccaat cgccggtgtg ccttgaatga agagagaact tgcgcctgtc    4680 agggctgga tccagaaacc tgtggtgcct ccttctcttt tggttgttca tggagcatgt    4740
actacaatgg atgtaagttt gccagaagca agatcccaag gaagtttaag ctgcttgggg    4800
atgacccaaa agaggaagag aaactggagt ctcatttgca aaacctgtcc actcttatgg    4860
caccaacata taagaaactt gcacctgatg catataataa tcagattgaa tatgaacaca    4920
gagcaccaga gtgccgtctg ggtctgaagg aaggccgtcc attctcaggg gtcactgcat    4980
gtttggactt ctgtgctcat gcccacagag acttgcacaa catgcagaat ggcagcacat    5040
tggtatgcac tctcactaga gaagacaatc gagaatttgg aggaaaacct gaggatgagc    5100
agcttcacgt tctgccttta tacaaagtct ctgacgtgga tgagtttggg agtgtggaag    5160
ctcaggagga gaaaaacgg agtggtgcca ttcaggtact gagttctttt cggcgaaaag    5220
tcaggatgtt agcagagcca gtcaagactt gccgacaaag gaaactagaa gccaagaaag    5280
ctgcagctga aaagctttcc tccctggaga acagctcaaa taaaaatgaa aaggaaaagt    5340
cagccccatc acgtacaaaa caaactgaaa acgcaagcca ggctaaacag ttggcagaac    5400
ttttgcgact ttcaggacca gtcatgcagc agtcccagca gcccagcct ctacagaagc    5460 agccaccaca gccccagcag cagcagagac cccagcagca gcagccacat cacccctcaga    5520 cagagtctgt caactcttat tctgcttctg gatccaccaa tccatacatg agacggccca    5580
```

```
atccagttag tccttatcca aactcttcac acacttcaga tatctatgga agcaccagcc    5640
ctatgaactt ctattccacc tcatctcaag ctgcaggttc atatttgaat tcttctaatc    5700
ccatgaaccc ttaccctggg cttttgaatc agaataccca atatccatca tatcaatgca    5760
atggaaacct atcagtggac aactgctccc catatctggg ttcctattct ccccagtctc    5820
agccgatgga tctgtatagg tatccaagcc aagaccctct gtctaagctc agtctaccac    5880
ccatccatac actttaccag ccaaggtttg gaaatagcca gagttttaca tctaaatact    5940
taggttatgg aaaccaaaat atgcagggag atggtttcag cagttgtacc attagaccaa    6000
atgtacatca tgtagggaaa ttgcctcctt atcccactca tgagatggat ggccacttca    6060
tgggagccac ctctagatta ccacccaatc tgagcaatcc aaacatggac tataaaaatg    6120
gtgaacatca ttcaccttct cacataatcc ataactacag tgcagctccg ggcatgttca    6180
acagctctct tcatgccctg catctccaaa acaaggagaa tgacatgctt tcccacacag    6240
ctaatgggtt atcaaagatg cttccagctc ttaaccatga tagaactgct tgtgtccaag    6300
gaggcttaca caaattaagt gatgctaatg gtcaggaaaa gcagccattg gcactagtcc    6360
agggtgtggc ttctggtgca gaggacaacg atgaggtctg gtcagacagc gagcagagct    6420
ttctggatcc tgacattggg ggagtggccg tggctccaac tcatgggtca attctcattg    6480
agtgtgcaaa gcgtgagctg catgccacaa cccctttaaa gaatcccaat aggaatcacc    6540
ccaccaggat ctccctcgtc ttttaccagc ataagagcat gaatgagcca aaacatggct    6600
tggctctttg ggaagccaaa atggctgaaa aagcccgtga gaaagaggaa gagtgtgaaa    6660
agtatggccc agactatgtg cctcagaaat cccatggcaa aaaagtgaaa cgggagcctg    6720
ctgagccaca tgaaacttca gagcccactt acctgcgttt catcaagtct cttgccgaaa    6780
ggaccatgtc cgtgaccaca gactccacag taactacatc tccatatgcc ttcactcggg    6840
tcacagggcc ttacaacaga tatatatga                                     6869
```